(12) United States Patent
Mezes et al.

(10) Patent No.: US 7,179,899 B2
(45) Date of Patent: Feb. 20, 2007

(54) COMPOSITE ANTIBODIES OF HUMANIZED HUMAN SUBGROUP IV LIGHT CHAIN CAPABLE OF BINDING TO TAG-72

(75) Inventors: Peter S. Mezes, Old Lyme, CT (US); Ruth A. Richard, Midland, MI (US); Kimberly S. Johnson, Gales Ferry, CT (US); Jeffrey Schlom, Potomac, MD (US); Syed V. S. Kashmiri, Gaithersburg, MD (US); Liming Shu, Gaithersburg, MD (US); Eduardo A. Padlan, Kensington, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 308 days.

(21) Appl. No.: 10/255,478

(22) Filed: Sep. 25, 2002

(65) Prior Publication Data

US 2003/0165498 A1    Sep. 4, 2003

Related U.S. Application Data

(60) Division of application No. 08/961,309, filed on Oct. 30, 1997, now Pat. No. 6,495,137, and a continuation-in-part of application No. 08/261,354, filed on Jun. 16, 1994, now Pat. No. 5,976,531, which is a continuation-in-part of application No. 07/510,697, filed on Jul. 17, 1990, now abandoned, and a continuation-in-part of application No. 07/964,536, filed on Oct. 20, 1992, now abandoned.

(60) Provisional application No. 60/030,173, filed on Oct. 31, 1996.

(51) Int. Cl.
*C07H 21/04*   (2006.01)

(52) U.S. Cl. .................. 536/23.53; 530/387.7; 530/388.8; 424/133.1; 424/155.1; 435/326

(58) Field of Classification Search ............... 536/23.1; 435/320.1; 530/387.3
See application file for complete search history.

(56) References Cited

U.S. PATENT DOCUMENTS

| 4,642,334 A | 2/1987 | Moore et al. |
| 4,656,134 A | 4/1987 | Ringold |

FOREIGN PATENT DOCUMENTS

| AU | 8943540 | 4/1990 |
| WO | 8900692 | 6/1988 |
| WO | 8901783 | 3/1989 |
| WO | 9004410 | 10/1989 |

OTHER PUBLICATIONS

Janeway et al., Immunobiology, 3rd edition, Garland Publishing Inc., 1997, pp. 3:7 to 3:9.*
Jones et al. (1986), Nature, 321:522-525.
Brown et al. (1987), Cancer Research, 47:3577-3583.
Marsh et al, Nucleic Acids Research, 13:6531-6544, (1985).
Polke et al, Immunobiol., 163:95-109, (1982).
Klobeck et al., Nucleic Acids Research, 13:6516-6528, (1985).
Clackson et al., Nature, 352:624-628, (1991).
Huse et al., Science, 246:1275-1281, (1989).
Whittle et al., Protein Engineering, 6:499-505, (1987).
Brady et al., J. Mol. Biol., 219:603-604, (1991).
Riechmann et al., Nature, 332: 323-327, (1988).
Colcher et al., Cancer Research, 49:1738-1745, (1989).
Sheer et al., Cancer Research, 48:6811-6818, (1988).
Harris et al., Tib Tech, 11:42-44, (1993).
Waldman, Science, 252:1657-1660, (1991).
Primus et al., Cancer Immunol Immunother, 31:249-257, (1990).
Neeleman and Wunsch, A General Method Applicable to the Search for Similarities in the Amino Acid Sequence of Two Proteins, J.Mol. Biol. 48:443-453 (1970).
Pearson and Lipman, Improved tools for biological sequence comparison, Proc. Natl. Acad. Sci, USA, 85:2444-2448 (1988).

* cited by examiner

*Primary Examiner*—G. R. Ewoldt
*Assistant Examiner*—Michael Szperka
(74) *Attorney, Agent, or Firm*—Jarett Abramson

(57) ABSTRACT

Novel composite and humanized anti-TAG-72 monoclonal antibodies, antibody fragments, and derivatives thereof using human subgroup IV kappa light chain framework regions.

6 Claims, 71 Drawing Sheets

FIG.2A

```
VH αTAG                                                                                              CCT
CC49                                                                                                 ...
CC83                                                                                                 ...

VH αTAG    TCTCTTCCTC CACCACCAAA TCCACCATTT GTAAATCAAC
CC49       .......... .......... .......... ..........
CC83       .......... .......... .......... ..........

VH αTAG    ATGTTAACAT ATCACAGAGT GGAGCAACAG AATCAGGGCA
CC49       .......... .......... .......... ..........
CC83       .......... .......... .......... ..........

VH αTAG    AAAATATGCT GAGAGATTTA TCCCTGTGT  TACAACCAAA
CC49       .......... .......T.. .......... ..........
CC83       .......... .......... .......... ..........

VH αTAG    GCATCTGTCT AGAATTCATA AAAACTTTAT GGGATACATT
CC49       .......... .......... .......... ..........
CC83       .......... .......... .......... ..........

VH αTAG    TCCTCAGAGA GGAATAGGAT TTGGACCTGA CGATCCTGCT
CC49       .......... .......... .......... ..........
CC83       .......... .......... .......... ..........
```

FIG.2B

```
VHαTAG   GCCCGAGCCA TGTGATGACA GTTCTTCTCC AGTTGAACTA
CC49     .......... .......... .......... ..........
CC83     .......... .......... .......... ..........

VHαTAG   GGTCCTTATC TAAGAAATGC ACTGCTCATG AATATGCAAA
CC49     .......... .......... .......... ..........
CC83     .......... .......... .......... ..........

VHαTAG   TCACCCGAGT CTATGGCAGT AAATACAGAG ATGTTCATAC
CC49     .......... .......... .......... ..........
CC83     .......... .......... .......... ..........

VHαTAG   CATAAAAACA ATATATGATC AGTGTCTTCT CCGCTATCCC
CC46     .......... .......... .......... ..........
CC49     .......... ......G... .......... ..........
CC83     .......... .......... .......... ..........
CC92     .......... .......... .......... ..........
```

FIG. 2C

```
           TGGACACACT GACTCTAACC ATG GAA TGG AGC TGG
VH∝TAG     .......... .......... ... ... ... ... ...
CC46       .......... .......... ... ... ... ... ...
CC49       .......... .......... ... ... ... ... ...
CC83       .......... .......... ... ... ... ... ...
CC92       .......... .......... ... ... ... ... ...

GTC TTT CTC TTC TTC CTG TCA GTA ACT ACA G
VH∝TAG     ... ... ... ... ... ... ... ... ... ... .
CC46       ... ... ... ... ... ... ... ... ... ... .
CC49       ... ... ... ... ... ... ... ... ... ... .
CC83       ... ... ... ... ... ... ... ... ... ... .
CC92       ... ... ... ... ... ... ... ... ... ... .

GTAAGGGGCT CACCATTTCC AAATCTAAAG TGGAGTCAGG
VH∝TAG     .......... .......... .......... ..........
CC46       .......... .......... .......... ..........
CC49       .......... .......... .......... ..........
CC83       .......... .......... .......... ..........
CC92       .......... .......... .......... ..........
```

FIG.2D

```
VHαTAG  GCCTGAGGTG ACAAAGATAT CACCTTTGGC TTTCCACAG
CC46    .......... .......... .......... .........
CC49    .......... ......G... .......... ..G......
CC83    .......... .......... .......... .........
CC92    .......... .......... .......... .........

VHαTAG  GT GTC CAC TCC CAG GTT CAG GTG CAG CTG CAG CAG TCT
CC46    .. ... ... ... ..A T.. ... ... ... ... ... ... ...
CC49    .. ... ... ... ..A T.. ... ... ..A ..T ... ... ...
CC83    .. ... ... ... ... ..G ... ... ... ..T ... ... ...
CC92    .. ... ... ... ... ... ... ... ..A ... ... ... ...

VHαTAG  GAC GCT GAG TTG GTG AAA CCT GGG GCT TCA GTG
CC46    ... ... ... ... ... ... ... ... ... ... ...
CC49    ... ... ... ... ... ..G ... ... ... ... ...
CC83    ... ... ... ... ... ... ... ... ... ... ...
CC92    ... ... ... ... ... ... ... ... ... ... ...
```

FIG.2E

|  | | | | | | | | | | | |
|---|---|---|---|---|---|---|---|---|---|---|---|
| VH αTAG | AAG | ATA | TCC | TGC | AAG | GCT | TCT | GGC | TAC | ACC | TTC |
| CC46 | . | .T. | . | . | . | . | . | . | . | . | . |
| CC49 | . | .T. | . | . | . | . | . | . | . | . | . |
| CC83 | . | .T. | . | . | . | . | . | . | . | . | . |
| CC92 | . | . | . | . | . | . | . | . | . | . | . |

|  | | | | | | | | | | | |
|---|---|---|---|---|---|---|---|---|---|---|---|
| VH αTAG | ACT | GAC | CAT | GCT | ATT | CAC | TGG | GTG | AAG | CAG | AAG |
| CC46 | . | . | . | . | . | . | . | . | . | . | . |
| CC49 | . | . | . | .A. | . | . | . | . | .A. | . | ..C |
| CC83 | . | . | . | . | . | . | . | . | . | . | . |
| CC92 | . | . | . | . | . | . | . | . | . | . | ..A |

— CDR1 —

|  | | | | | | | | | | | |
|---|---|---|---|---|---|---|---|---|---|---|---|
| VH αTAG | CCT | GAA | CAG | GGC | CTG | GAA | TGG | ATT | GGA | TAT | ATT |
| CC46 | . | . | . | . | . | . | . | . | . | .T. | .T. |
| CC49 | . | . | . | . | . | . | . | . | . | . | . |
| CC83 | . | . | . | . | . | . | . | . | . | . | . |
| CC92 | . | . | . | . | . | . | . | . | . | . | . |

— CDR2 —

|  | | | | | | | | | | | |
|---|---|---|---|---|---|---|---|---|---|---|---|
| VH αTAG | TCT | CCC | GGA | AAT | GGT | GAT | ATT | AAG | TAC | AAT | GAG |
| CC46 | . | . | . | . | .A. | . | .T. | . | . | . | . |
| CC49 | . | . | . | . | .A. | . | . | . | ..A | . | . |
| CC83 | . | . | . | . | .A. | . | . | . | . | . | . |
| CC92 | . | . | . | . | . | . | . | . | . | . | . |

FIG. 2F

```
               ←————CDR2————→
         AAG TTC AAG GGC|AAG GCC ACA CTG ACT GCA GAC
VH αTAG  AAG TTC AAG GGC AAG GCC ACA CTG ACT GCA GAC
CC46     ..G ... ... ... ... ... ... ... ... ... ...
CC49     ... ... ... ..T ... ... ... ... ... ... ...
CC83     ... ... ... ... ... ... ... ... ... ... ...
CC92     ... ... ... ... ... ... ... ... ... ... ...

VH αTAG  AAA TCC TCC AGC ACT GCC TAC ATG CAG CTC AAC
CC46     ... ... ... ..T ... ... ... ... ... .T. ...
CC49     ... ... ... .A. ... ... ... .G. ..A ... ...
CC83     ... .C. ... ... ..T ... ... ... ... ... ...
CC92     ... ... ... ... ... ... ... ... ... ... ...

VH αTAG  AGC CTG ACA TCT GAG GAT TCT GCA GTG TAT TTC
CC46     ... ... ... ... ... ..C ... ... ... ... ...
CC49     ... ... ... ... ... ... ... ... ... ... ...
CC83     ... ..C ... ... ... ... ... ... ... ... ...
CC92     ... ... ... ... ... ... ... ... ... ... ...
```

FIG. 2G

```
         TGT AAA AGA CACAGTGTTG TAACCACATC CTGAGTGTGT
VHαTAG
CC46     ... .CG G.C GGC TAC GGG TTT GCT TTC TGG GGC
CC49     ... ... ... TCC CTG AAT ATG GCC TAC TGG GGT
CC83     ... .G. ... TCC TTC TAC GGC AAC --- TGG GGC
CC92     ... .C. ... TCT CTA TCC GGG AAC TCC TGG GGC
                                    ←——CDR3——→

CAGAAATCCT GGGGGAGCAG AAAGATACAC TGGGACTGAG
VHαTAG
CC46     CAA GGG ACT GTC ACT GTC TCT GCA G
CC49     CAA GGA ACC GTC ACC GTC TCC TCA G
CC83     CAA GGC ACC CTC ACA GTC TCC TCA G
CC92     CAG GGC ACC CTC ACA GTC TCC TCA G

VHαTAG   AAGACAGAAA AATTAATCCT TAGACTTGCT CAGAAATCGT

VHαTAG   AATTTGAAT GCCTATTTAT TTCATCTTGC TCACACCT

VHαTAG   ATATTGCTTT TGTAAGCTT
```

FIG.3A

```
            ───────LEADER PEPTIDE───────
      -19                              -10
VHαTAG  Met Glu Trp Ser Trp Val Phe Leu Phe Phe
CC46     .   .   .   .   .   .   .   .   .   .
CC49     .   .   .   .   .   .   .   .   .   .
CC83     .   .   .   .   .   .   .   .   .   .
CC92     .   .   .   .   .   .   .   .   .   .

↑
VHαTAG  Leu Ser Val Thr Thr Gly Val His Ser Gln
CC46     .   .   .   .   .   .   .   .   .   .
CC49     .   .   .   .   .   .   .   .   .   .
CC83     .   .   .   .   .   .   .   .   .   .
CC92     .   .   .   .   .   .   .   .   .   .

10
VHαTAG  Val Gln Leu Gln Gln Ser Asp Ala Glu Leu
        Phe
CC46     .   .   .   .   .   .   .   .   .   .
CC49     .   .   .   .   .   .   .   .   .   .
CC83     .   .   .   .   .   .   .   .   .   .
CC92     .   .   .   .   .   .   .   .   .   .
```

FIG. 3B

|  | | | | | | | | | | 20 | | | |
|---|---|---|---|---|---|---|---|---|---|---|---|---|---|
| VHαTAG | Val | Lys | Pro | Gly | Ala | Ser | Val | Lys | Ile | Ser | . | . | . |
| CC46 | | Arg | | | | | | | | | . | . | . | . |
| CC49 | | | | | | | | | | | | | |
| CC83 | | | | | | | | | | | | | |
| CC92 | | | | | | | | | | | | | |

|  | | | | | | | 30↓ | | | |
|---|---|---|---|---|---|---|---|---|---|---|
| VHαTAG | Cys | Lys | Ala | Ser | Gly | Tyr | Thr | Phe | Thr | Asp | . . . . |
| CC46 | | | | | | | | | | | |
| CC49 | | | | | | | | | | | |
| CC83 | | | | | | | | | | | |
| CC92 | | | | | | | | | | | |

CDR1→

|  | | | | | 40 | | | | |
|---|---|---|---|---|---|---|---|---|---|
| VHαTAG | His | Ala | Ile | His | Trp | Val | Lys | Gln | Lys | Pro . . . . |
| CC46 | | | | | | | | | | |
| CC49 | | | | | | | Asn | | | |
| CC83 | | | | | | | | | | |
| CC92 | | | | | | | | | | |

|  | | | | | | | 50↓ | | |
|---|---|---|---|---|---|---|---|---|---|
| VHαTAG | Glu | Gln | Gly | Leu | Glu | Trp | Ile | Gly | Tyr | Ile . . |
| CC46 | | | | | | | | | | |
| CC49 | | | | | | | | | | |
| CC83 | | | | | | | | | | Phe |
| CC92 | | | | | | | | | | Phe |

FIG.3C

```
                                        CDR2
                                                           60
         Ser Pro Gly Asn Gly Asp Ile Lys Tyr Asn  .  .  .  .
VHαTAG
CC46      .   .   .   .   .   .   .   .   .   .   .  .  .  .
CC49      .   .   .   .   .  Asp  .   .  Phe  .   .  .  .  .
CC83      .   .   .   .   .  Asp  .   .   .   .   .  .  .  .
CC92      .   .   .   .   .  Asp  .   .   .   .   .  .  .  .

70
         Glu Lys Phe Lys Gly  |Lys Ala Thr Leu Thr  .  .  .  .
VHαTAG
CC46      .   .   .   .   .    .   .   .   .   .   .  .  .  .
CC49      .  Arg  .   .   .    .   .   .   .   .   .  .  .  .
CC83      .   .   .   .   .    .   .   .   .   .   .  .  .  .
CC92      .   .   .   .   .    .   .   .   .   .   .  .  .  .

80
         Ala Asp Lys Ser Ser Ser Thr Ala Tyr Met  .  .  .  .
VHαTAG
CC46      .   .   .   .   .   .   .   .   .   .   .  .  .  .
CC49      .   .   .   .   .   .   .   .   .   .   .  .  .  .
CC83      .   .   .   .   .   .   .   .   .  Val  .  .  .  .
CC92      .   .   .  Pro  .  Asn  .   .   .  Val  .  .  .  .
```

FIG.3D

```
            Gln Leu Asn Ser Leu Thr Ser Glu Asp Ser
VH αTAG
CC46            .   Phe  .   .   .   .   .   .   .   .
CC49            .   .   .   .   .   .   .   .   .   .
CC83            .   .   .   .   .   .   .   .   .   .
CC92            .   .   .   .   .   .   .   .   .   .

90
            Ala Val Tyr Phe Cys Lys Arg
VH αTAG
CC46         .   .   .   .   .   .  Thr Gly
CC49         .   .   .   .   .   .  Thr  .
CC83         .   .   .   .   .   .  Arg  .
CC92         .   .   .   .   .   .  Thr  .

|←――――――――――― CDR3 ―――――――――――→|      105
CC46        Gly Tyr Gly Phe Ala Phe | Trp Gly Gln
CC49        Ser Leu Asn Met Ala Tyr | Trp Gly Gln
CC83        Ser Phe Tyr Gly Asn  -  | Trp Gly Gln
CC92        Ser Leu Ser Gly Asn Ser   Trp Gly Gln
```

FIG.3E

```
                         110
CC46  Gly Thr Leu Val Thr Val Ser Ala
CC49  Gly Thr Ser Val Thr Val Ser Ser
CC83  Gly Thr Thr Leu Thr Val Ser Ser
CC92  Gly Thr Thr Leu Thr Val Ser Ser
```

FIG.4A

```
              Met Glu Lys Leu Trp Phe
  1  5'-GAA TTC ATG GAA AAA CTT TGG TTC

7     Leu Leu Leu Leu Leu Thr Ile Pro
 25     TTG CTT CTG CTG CTG ACC ATC CCT

15     Ser Trp Val Leu Ser Gln Ile Thr
 49     TCA TGG GTC TTG TCC CAG ATC ACC

23     Leu Lys Glu Ser Gly Pro Thr Leu
 73     TTG AAG GAG TCT GGT CCT ACN CTG

31     Val Lys Pro Thr Gln Thr Leu Thr
 97     GTG AAA CCC ACA CAG ACC CTC ACG

37     Leu Thr Cys Thr Phe Ser Gly Phe
121     CTG ACC TGC ACC TTC TCT GGG TTC
                                         ←———CDR1———
 47     Ser Leu Ser │Thr His Gly Val Gly
145     TCA CTC AGC │ACT CAT GGA GTG GGT
        ─────────→│
 55     Val Gly│Trp Ile Arg Xaa Xaa Pro
169     GTG GGC│TGG ATC CGT NNN NNC CCA

63     Gly Lys Ala Leu Glu Trp Leu Ala
193     GGA AAG GCC CTG GAG TGG CTT GCA
                              ———CDR2———
 71    │Leu Ile Tyr Trp Asp Asp Asp Lys
217    │CTC ATT TAT TGG GAT GAT GAT AAG
       ─────────────────────────────────
 79     Arg Tyr Ser Pro Ser Leu Lys Ser│
241     CGC TAC AGC CCA TCT CTG AAG AGC│
```

FIG.4B

```
87      Arg Leu Thr Ile Thr Lys Asp Thr
265     AGG CTC ACC ATC ACC AAG GAC ACC

95      Ser Lys Asn Gln Val Ile Leu Thr
289     TCC AAA AAC CAG GTG ATC CTT ACA

103     Met Thr Asn Met Asp Pro Val Asp
313     ATG ACC AAC ATG GAC CCT GTG GAC

111     Thr Ala Thr Tyr Tyr Cys Ala His
337     ACA GCC ACA TAT TAT TGT GCA CAC
                         ―――― CDR3 ――――
119     |Gly Leu Pro Ser Met Val Lys Asn|
361     |GGG CTG CCA TCT ATG GTT AAG AAC|

127     Trp Gly Gln Gly Thr Thr Val Thr
385     TGG GGC CAA GGG ACC ACG GTC ACC

135     Val Ser Ser Gly Ser
409     GTC TCC TCA GGG AGT-3'
```

FIG.5A

MOUSE GERMLINE J-H GENES
FROM pNP9

```
5'-GGATCCTGGC CAGCATTGCC GCTAGGTCCC
   TCTCTTCTAT GCTTTCTTTG TCCCTCACTG
   GCCTCCATCT GAGATAATCC TGGAGCCCTA
   GCCAAGGATC ATTTATTGTC AGGGGTCTAA
   TCATTGTTGT CACAATGTGC CTGGTTTGCT
   TACTGGGGCC AAGGACTCT  GGTCACTGTC
   TCTGCAGGTG AGTCCTAACT TCTCCCATTC
   TAAATGCATG TTGGGGGAT  TCTGAGCCTT
   CAGGACCAAG ATTCTCTGCA AACGGGAATC
   AAGATTCAAC CCCTTTGTCC CAAAGTTGAG
   ACATGGGTCT GGGTCAGGGA CTCTCTGCCT
   GCTGGTCTGT GGTGACATTA GAACTGAAGT
   ATGATGAAGG ATCTGCCAGA ACTGAAGCTT
   GAAGTCTGAG GCAGAATCTT GTCCAGGGTC
   TATCGGACTC TTGTGAGAAT TAGGGGCTGA
   CAGTTGATGG TGACAATTTC AGGGTCAGTG
   ACTGTCAGGT TTCTCTGAGG TGAGGCTGGA
   ATATAGGTCA CCTTGAAGAC TAAAGAGGGG
   TCCAGGGGCT TTTCTGCACA GGCAGGGAAC
   AGAATGTGGA ACAATGACTT GAATGGTTGA
   TTCTTGTGTG ACACCAAGAA TTGGCATAAT
   GTCTGAGTTG CCCAAGGGTG ATCTTAGCTA
   AAAACCCACT ATTGTGATTA CTATGCTATG
   GACTACTGGG GTCAAGGAAC CTCAGTCACC
   GTCTCCTCAG GTAAGAATGG CCTCTCCAGG
   TCTTTATTTT TAACCTTTGT TATGGAGTTT
   TCTGAGCATT GCAGACTAAT CTTGGATATT
   TGCCCTGAGG GAGCCGGCTG AGAGAAGTTG
   GGAAATAAAT CTGTCTAGGG ATCTCAGAGC
   CTTTAGGACA GATTATCTCC ACATCTTTGA
   AAAACTAAGA ATCTGTGTGA TGGTGTTGGT
   GGAGTCCCTG GATGATGGGA TAGGGACTTT
```

FIG.5B

```
GGAGGCTCAT TTGAGGGAGA TGCTAAAACA
ATCCTATGGC TGGAGGGATA GTTGGGGCTG
TAGTTGGAGA TTTTCAGTTT TTAGAATGAA
GTATTAGCTG CAATACTTCA AGGACCACCT
CTGTGACAAC CATTTTATAC AGTATCCAGG
CATAGGGACA AAAAGTGGAG TGGGGCACTT
TCTTTAGATT TGTGAGGAAT GTTCCACACT
AGATTGTTTA AAACTTCATT TGTTGGAAGG
AGCTGTCTTA GTGATTGAGT CAAGGGAGAA
AGGCATCTAG CCTCGGTCTC AAAAGGGTAG
TTGCTGTCTA GAGAGGTCTG GTGGAGCCTG
CAAAAGTCCA GCTTTCAAAG GAACACAGAA
GTATGTGTAT GGAATATTAG AAGATGTTGC
TTTTACTCTT AAGTTGGTTC CTAGGAAAAA
TAGTTAAATA CTGTGACTTT AAAATGTGAG
AGGGTTTTCA AGTACTCATT TTTTTAAATG
TCCAAAATTT TTGTCAATCA ATTTGAGGTC
TTGTTTGTGT AGAACTGACA TTACTTAAAG
TTTAACCGAG GAATGGGAGT GAGGCTCTCT
CATACCCTAT TCAGAACTGA CTTTTAACAA
TAATAAATTA AGTTTAAAAT ATTTTTAAAT
GAATTGAGCA ATGTTGAGTT GAGTCAAGAT
GGCCGATCAG AACCGGAACA CCTGCAGCAG
CTGGCAGGAA GCAGGTCATG TGGCAAGGCT
ATTTGGGGAA GGGAAAATAA AACCACTAGG
TAAACTTGTA GCTGTGGTTT GAAGAAGTGG
TTTTGAAACA CTCTGTCCAG CCCCACCAAA
CCGAAAGTCC AGGCTGAGCA AAACACCACC
TGGGTAATTT GCATTTCTAA AATAAGTTGA
GGATTCAGCC GAAACTGGAG AGGTCCTCTT
TTAACTTATT GAGTTCAACC TTTTAATTTT
AGCTTGAGTA GTTCTAGTTT CCCCAAACTT
AAGTTTATCG ACTTCTAAAA TGTATTTAGA
ATTC-3'
```

FIG.8A

HUMVL (+), 26-MER:
(Cla I)
5'- GAAGAGTATC GATAAAATTT ATTGAG-3'

FIG.8B

HUMVL(-), 98-MER:

(SPLICE SITE)
(Hind III)
5'-CATTAAGCTT AGAAAAGTGT ACTTACGTTT
GATCACCACC TTGGTCCCTC CGCCGAAAGT
GAGAGGATAA CTATAATATT GCTGACAGTA
ATAAACTG-3'

Leu Thr Phe Gly Gly Gly Thr Lys
CTC ACT TTC GGC GGA GGG ACC AAG

Val Glu Ile Lys A↓(rg)
GTG GAG ATC AAA C GTAAGTGCAC

TTTCCTAA

FIG. 10A

```
      Cla I
5' ATCGATAAAA TTTATTGAGA ATTTGTTTAT TATGATTAAC  3418
3' TAGCTATTTT AAATAACTCT TAAACAAATA ATACTAATTG

AGAGGTAAAA GCCAGTATAT TACTGATTAA TATAGGTAAA   3458
   TCTCCATTTT CGGTCATATA ATGACTAATT ATATCCATTT
           *
   AGGCAGTTAA GAAATTGGGA ATGCTTTCTC TTCTGCTTTC   3498
   TCCGTCAATT CTTTAACCCT TACGAAAGAG AAGACGAAAG

TTCTACGATG CACAAGGCGT TTCACATTTA TGCCCCTATG   3538
   AAGATGCTAC GTGTTCCGCA AAGTGTAAAT ACGGGGATAC

AAAATTACTA GGCTGTCCTA GTCATTAGAT CTTTCAGCAG   3578
   TTTTAATGAT CCGACAGGAT CAGTAATCTA GAAAGTCGTC

TTTGTAGTTT TAGAGCTTCT AAGTTGACTT CTGTCTTTTC   3618
   AAACATCAAA ATCTCGAAGA TTCAACTGAA GACAGAAAAG

TATTCATACA ATTACACATT CTGTGATGAT ATTTTTGGCT   3658
   ATAAGTATGT TAATGTGTAA GACACTACTA TAAAAACCGA
                        HUMLIN1 (-)
```

FIG. 10B

```
CTTGATTTAC ATTGGGTACT TTCACAACCC ACTGCTCATG   3698
GAACTAAATG TAACCCATGA AAGTGTTGGG TGACGAGTAC

AAATTTGCTT TTGTACTACT GGTTGTTTTT GCATAGGCCCC   3738
TTTAAACGAA AACATGATGA CCAACAAAAA CGTATCCGGG

CTCCAGGCCA CGACCAGGTG TTTGGATTTT ATAAACGGGC   3778
GAGGTCCGGT GCTGGTCCAC AAACCTAAAA TATTTGCCCG

CGTTTGCATT GTGAACTGAG CTACAACAGG CAGGCAGGGG   3818
GCAAACGTAA CACTTGACTC GATGTTGTCC GTCCGTCCCC

Met Val Leu Gln Thr Gln Val Phe Ile  -10
CAGCAAG ATG GTG TTG CAG ACC CAG GTC TTC ATT   3852
GTCGTTC TAC CAC AAC GTC TGG GTC CAG AAG TAA

Ser Leu Leu Leu Trp Ile Ser G Intron
TCT CTG CTC TTG CTC TGG ATC TCT G GTGA GGAATTAAAAA     -4
AGA GAC GAG AAC GAG ACC TAG AGA C CACT CCTTAATTTT   3888

AGTGCCACAG TCTTTTCAGA GTAATATCTG TGTAGAAATA
TCACGGTGTC AGAAAGTCT CATTATAGAC ACATCTTTAT
            ─────────
            HUMLIN2 (-)
```

FIG.10C

```
AAAAAATTA AGATATAGTT GGAAATAAATG ACTATTTCCA
TTTTTTAAT TCTATATCAA CCTTTATTAC TGATAAAGGT
          BamHI
ATATGGATCC AATTATCTGC TGACTTATAA TACTACTAGA
TATACCTAGG TTAATAGACG ACTGAATATT ATGATGATCT

AAGCAAATTT AAATGACATA TTTCAATTAT ATCTGAGACA
TTCGTTTAAA TTTACTGTAT AAAGTTAATA TAGACTCTGT

GCGTGTATAA GTTTATGTAT AATCATTGTC CATTACTGAC
CGCACATATT CAAATACATA TTAGTAACAG GTAATGACTG

TACAG
ATGTC
                    +1
ly Ala Tyr Gly Asp Ile Val Met Thr Gln Ser
GT GCC TAC GGG GAC ATC GTG ATG ACC CAG TCT        7
CA CGG ATG CCC CTG TAG CAC TAC TGG GTC AGA     4125
```

FIG.10D

```
Pro Asp Ser Leu Ala Val Ser Leu Gly Glu Arg Ala Thr 20
CCA GAC TCC CTG GCT GTG TCT CTG GGC GAG AGG GCC ACC 4164
GGT CTG AGG GAC CGA CAC AGA GAC CCG CTC TCC CGG TGG
                                        CDR1
Ile Asn Cys Lys Ser Ser Gln Ser Val Leu Tyr Ser Ser 27F
ATC AAC TGC AAG TCC AGC CAG AGT GTT TTA TAC AGC TCC 4203
TAG TTG ACG TTC AGG TCG GTC TCA CAA AAT ATG TCG AGG

Asn Asn Lys Asn Tyr Leu Ala Trp Tyr Gln Gln Lys Pro 40
AAC AAT AAG AAC TAC TTA GCT TGG TAC CAG CAG AAA CCA 4242
TTG TTA TTC TTG ATG AAT CGA ACC GTC GTC TTT GGT
        HUM1CDR1(-)                              CDR2
Gly Gln Pro Pro Lys Leu Leu Ile Tyr Trp Ala Ser Thr 53
GGA CAG CCT CCT AAG CTG CTC ATT TAC TGG GCA TCT ACC 4281
CCT GTC GGA GGA TTC GAC GAG TAA ATG ACC CGT AGA TGG

Arg Glu Ser Gly Val Pro Asp Arg Phe Ser Gly Ser Gly 66
CGG GAA TCC GGG GTC CCT GAC CGA TTC AGT GGC AGT GGG 4320
GCC CTT AGG CCC CAG GGA CTG GCT AAG TCA CCG TCA CCC

Ser Gly Thr Asp Phe Thr Leu Thr Ile Ser Ser Leu Gln Ala
TCT GGG ACA GAT TTC ACT CTC ACC ATC AGC AGC CTG CAG GCT
AGA CCC TGT CTA AAG TGA GAG TGG TAG TCG TCG GAC GTC CGA
```

FIG.10E

```
                                                          ┌─────────────── CDR3 ───────────────
Glu Asp Val Ala Val Tyr Tyr Cys│Gln Gln Tyr Tyr Tyr Ser 93
GAA GAT GTG GCA GTT TAT TAC TGT│CAG CAA TAT TAT AGT 4401
CTT CTA CAC CGT CAA ATA ATG ACA GTC GTT ATA ATA TCA
                           ↑
    ┌──────
Tyr│Pro Leu Thr│Phe Gly Gly Gly Thr Lys Val Val Ile 106
TAT│CCT CTC ACT│TTC GGC GGA GGG ACC AAG GTG GTG ATC 4440
ATA GGA GAG TGA AAG CCG CCT CCC TGG TTC CAC CAC TAG

Hind III                        107
Lys A(rg)                                       4466
AAA C  GTAAGTACAC TTTCTAAG CTT-3'
TTT G  CATTCATGTG AAAGATTC GAA 5'
```

FIG. 15

(A portion of the DNA Sequence of pSV2neo)

◄──── TOWARDS Eco RI SITE 5'-GAG<u>GAGGTTA</u>

<u>GGGTTTATGA</u> <u>GGAC</u>ACAGAG GAGCTTCCTG

G|GGATCC|AGA CATGATAAGA TACATTGATG
  Bam H1

AGTTTGGACA AACCACAACT AGA-3'

FIG. 17

LOST Bam HI
SITE IN
pSV2neo

```
                      Cla I      Eco RV  Spe I
5'-CTTCCTGGGG  ATCATCGATT  GATATCAACT   3394
                     |   FROM HUMAN C
                     | Hind III-Bam HI INSERT
         Hind III
   AGTTGAAGCT  TTTTTTTTTT  CAGTGCTATT   3423

TAATTATTTC  AATATCCTCT  CATCAAATGT   3453

ATTTAAATAA  CAAAAGCTCA  ACCAAAAAGA   3483

AAGAAATATG  TAATTCTTTC  AGAGTAAAAA   3513

TCACACCCAT  GACCTGGCCA  CTGAGGGCTT   3543

GATCAATTCA  CTTTGAATTT  GGCATTAAAT   3573

ACCATTAAGG  TATATTAACT  GATTTTAAAA   3603
                                  TOWARDS
   TAAGATATAT  TCGTGACC-3'   Bam HI    3621
```

DNA SEQUENCING — pRL1001

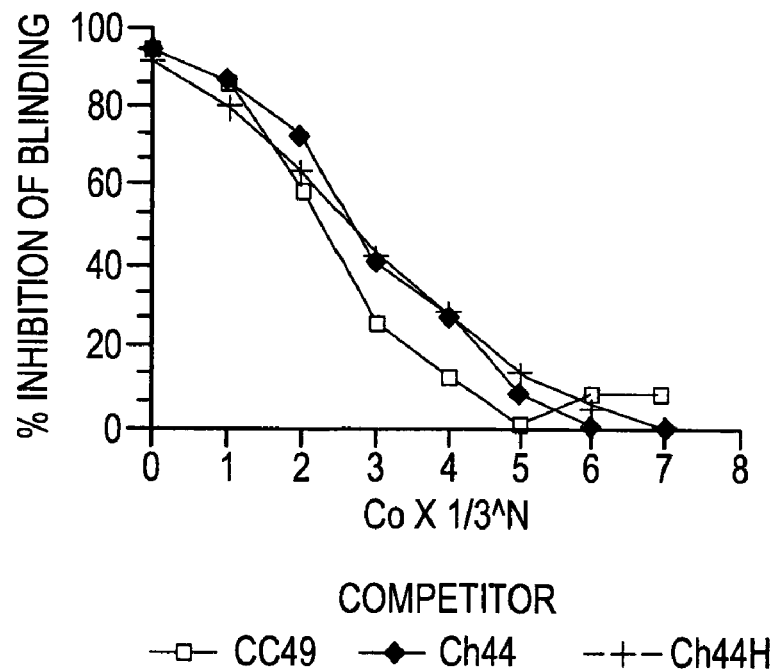

FIG. 22A

```
                                           Met Leu
          AAAAACTAT AAGCTCCATG ATG CTT

Leu Gln Ala Phe Leu Phe Leu Leu Ala
TTG CAA GCT TTC CTT TTC CTT TTG GCT

Gly Phe Ala Ala Lys Ile Ser Ala Asp
GGT TTT GCA GCC AAA ATA TCT GCA GAC

Ile Val Met Thr Gln Ser Pro Asp Ser
ATC GTG ATG ACC CAG TCT CCA GAC TCC

Leu Ala Val Ser Leu Gly Glu Arg Ala
CTG GCT GTG TCT CTG GGC GAG AGG GCC
                                    ├──────── CDR1L ──
Thr Ile Asn Cys │Lys Ser Ser Gln Ser
ACC ATC AAC TGC │AAG TCC AGC TGC AAG

Val Leu Tyr Ser Ser Asn Asn Lys Asn
GTT TTA TAC AGC TCC AAC AAT AAG AAC
─────────────►│
Tyr Leu Ala │Trp Tyr Gln Gln Lys Pro
TAC TTA GCT │TGG TAC CAG CAG AAA CCA

Gly Gln Pro Pro Lys Leu Leu Ile Tyr
GGA CAG CCT CCT AAG CTG CTC ATT TAC
├────────── CDR2L ──────────►
│Trp Ala Ser Thr Arg Glu Ser │Gly Val
│TGG GCA TCT ACC CGG GAA TCC │GGG GTC

Pro Asp Arg Phe Ser Gly Ser Gly Ser
CCT GAC CGA TTC AGT GGC AGC GGG TCT
```

FIG.22B

```
Gly Thr Asp Phe Thr Leu Thr Ile Ser
GGG ACA GAT TTC ACT CTC ACC ATC AGC

Ser Leu Gln Ala Glu Asp Val Ala Val
AGC CTG CAG GCT GAA GAT GTG GCA GTT
                    |————————CDR3L——
Tyr Tyr Cys|Gln Gln Tyr Tyr Ser Tyr
TAT TAC TGT|CAG CAA TAT TAT AGT TAT
——————————→
Pro Leu Thr|Phe Gly Gly Gly Thr Lys
CCT CTC ACT|TTC GGC GGA GGG ACC AAG
           |—
Val|Lys Glu Ser Gly Ser Val Ser Ser
GTG|AAG GAG TCA GGT TCG GTC TCC TCA
   ——————LINKER——
Glu Gln Leu Ala Gln Phe Arg Ser Leu
GAA CAA TTG GCC CAA TTT CGT TCC TTA
——→|
Asp|Val Gln Leu Gln Gln Ser Asp Ala
GAC|GTC CAG TTG CAG CAG TCT GAC GCT

Glu Leu Val Lys Pro Gly Ala Ser Val
GAG TTG GTG AAA CCT GGG GCT TCA GTG

Lys Ile Ser Cys Lys Ala Ser Gly Tyr
AAG ATT TCC TGC AAG GCT TCT GGC TAC
                    —————————CDR1H———→|
Thr Phe Thr|Asp His Ala Ile His|Trp
ACC TTC ACT|GAC CAT GCA ATT CAC|TGG

Val Lys Gln Asn Pro Glu Gln Gly Leu
GTG AAA CAG AAC CCT GAA CAG GGC CTG
```

FIG.22C

```
Glu Trp Ile Gly│Tyr Phe Ser Pro Gly
GAA TGG ATT GGA│TAT TTT TCT CCC GGA
                    ──CDR2H──
Asn Asp Asp Phe Lys Tyr Asn Glu Arg
AAT GAT GAT TTT AAA TAC AAT GAG AGG

Phe Lys Gly│Lys Ala Thr Leu Thr Ala
TTC AAG GGC│AAG GCC ACA CTG ACT GCA

Asp Lys Ser Ser Ser Thr Ala Tyr Val
GAC AAA TCC TCC AGC ACT GCC TAC GTG

Gln Leu Asn Ser Leu Thr Ser Glu Asp
CAG CTC AAC AGC CTG ACA TCT GAG GAT

Ser Ala Val Tyr Phe Cys Thr Arg│Ser
TCT GCA GTG TAT TTC TGT ACA AGA│TCC
──CDR3H──────────────────────▶
Leu Asn Met Ala Tyr│Trp Gly Gln Gly
CTG AAT ATG GCC TAC│TGG GGT CAA GGA

Thr Ser Val Thr Val Ser
ACC TCA GTC ACC GTC TCC TAG TGA
```

AGCTTGGAAC ACCACACAAA CCATATCCAA A

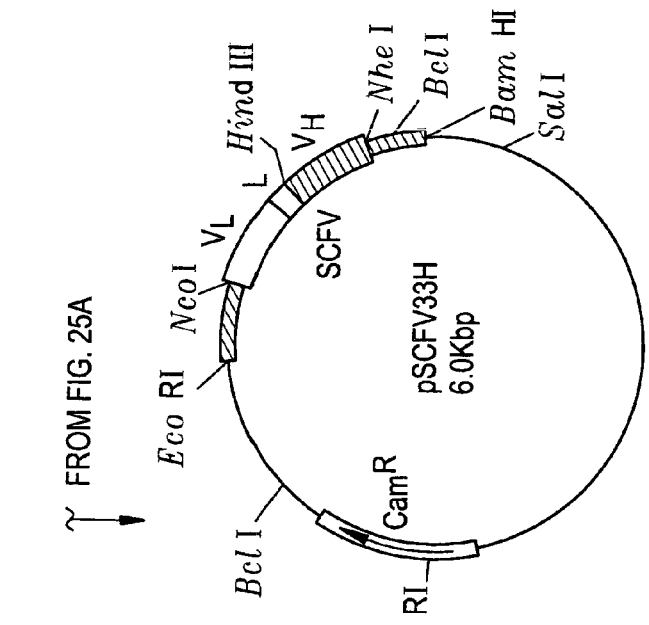
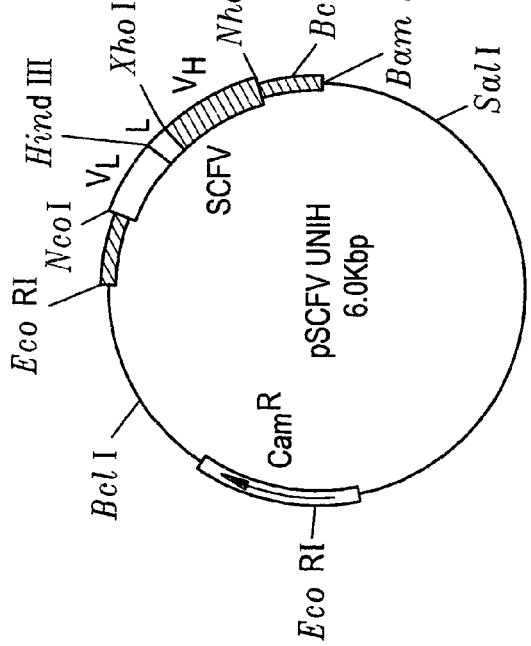
FIG. 25B

FIG. 26A

```
                                    Eco RI
CTCATGTTTG ACAGCTTATC ATCGATGAAT

TCCATCACTT CCCTCCGTTC ATTTGTCCCC

GGTGGAAACG AGGTCATCAT TTCCTTCCGA

AAAAACGGTT GCATTTAAAT CTTACATATG

TAATACTTTC AAAGACTACA TTTGTAAGAT

TTGATGTTTG AGTCGGCTGA AAGATCGTAC

GTACCAATTA TTGTTTCGTG ATTGTTCAAG

CCATAACACT GTAGGGATAG TGGAAAGAGT

GCTTCATCTG GTTACGATCA ATCAAATATT
```

```
                                  ←─── pelB Signal
                                  Met  Lys  Tyr  Leu
CAAACGGAGG GAGACGATTT TG│ATG  AAA  TAC  CTA
Sequence
Leu  Pro  Thr  Ala  Ala  Ala  Gly  Leu  Leu  Leu
TTG  CCT  ACG  GCA  GCC  GCT  GGA  TTG  TTA  TTA
                          Nco I ──→│←── H4V_L
Leu  Ala  Ala  Gln  Pro  Ala     Met  Ala│Asp  Ile
CTC  GCT  GCC  CAA  CCA  GCC     ATG  GCC│GAC  ATC Val  Met  Thr  Gln  Ser  Pro  Asp  Ser  Leu  Ala
GTG  ATG  ACC  CAG  TCT  CCA  GAC  TCC  CTG  GCT Val  Ser  Leu  Gly  Glu  Arg  Ala  Thr  Ile  Asn
GTG  TCT  CTG  GGC  GAG  AGG  GCC  ACC  ATC  AAC Cys  Lys  Ser  Ser  Gln  Ser  Val  Leu  Tyr  Ser
TGC  AAG  TCC  AGC  CAG  AGT  GTT  TTA  TAC  AGC
```

FIG. 26B

```
Ser Asn Asn Lys Asn Tyr Leu Ala Trp Tyr
TCC AAC AAT AAG AAC TAC TTA GCT TGG TAC

Gln Gln Lys Pro Gly Gln Pro Pro Lys Leu
CAG CAG AAA CCA GGA CAG CCT CCT AAG CTG

Leu Ile Tyr Trp Ala Ser Thr Arg Glu Ser
CTC ATT TAC TGG GCA TCT ACC CGG GAA TCC

Gly Val Pro Asp Arg Phe Ser Gly Ser Gly
GGG GTC CCT GAC CGA TTC AGT GGC AGC GGG

Ser Gly Thr Asp Phe Thr Leu Thr Ile Ser
TCT GGG ACA GAT TTC ACT CTC ACC ATC AGC

Ser Leu Gln Ala Glu Asp Val Ala Val Tyr
AGC CTG CAG GCT GAA GAT GTG GCA GTT TAT

Tyr Cys Gln Gln Tyr Tyr Ser Tyr Pro Leu
TAC TGT CAG CAA TAT TAT AGT TAT CCT CTC
                                        H4V_L
Thr Phe Gly Gly Gly Thr Lys Val Val Ile
ACT TTC GGC GGA GGG ACC AAG GTG GTG ATC
Hind III  LINKER
Lys│Leu  Ser Ala Asp Asp Ala Lys Lys Asp
AAG│CTT  AGT GCG GAC GAT GCG AAA AAG GAT Ala Ala Lys Lys Asp Asp Ala Lys Lys Asp
GCT GCG AAG AAG GAT GAC GCT AAG AAA GAC
         LINKER    Xho I  CC49 V_H
Asp Ala Lys Lys Asp Leu│Gln Val Gln Leu
GAT GCT AAA AAG GAC CTC│CAG GTT CAG TTG
```

FIG.26C

| | | | | | | | | | |
|---|---|---|---|---|---|---|---|---|---|
| Gln | Gln | Ser | Ala | Glu | Leu | Val | Lys | Pro | Gly |
| CAG | CAG | TCT | GCT | GAG | TTG | GTG | AAA | CCT | GGG |
| Ala | Ser | Val | Lys | Ile | Ser | Cys | Lys | Ala | Ser |
| GCT | TCA | GTG | AAG | ATT | TCC | TGC | AAG | GCT | TCT |
| Gly | Tyr | Thr | Phe | Thr | Asp | His | Ala | Ile | His |
| GGC | TAC | ACC | TTC | ACT | GAC | CAT | GCA | ATT | CAC |
| Trp | Val | Lys | Gln | Asn | Pro | Glu | Gln | Gly | Leu |
| TGG | GTG | AAA | CAG | AAC | CCT | GAA | CAG | GGC | CTG |
| Glu | Trp | Ile | Gly | Tyr | Phe | Ser | Pro | Gly | Asn |
| GAA | TGG | ATT | GGA | TAT | TTT | TCT | CCC | GGA | AAT |
| Asp | Asp | Phe | Lys | Tyr | Asn | Glu | Arg | Phe | Lys |
| GAT | GAT | TTT | AAA | TAC | AAT | GAG | AGG | TTC | AAG |
| Gly | Lys | Ala | Thr | Leu | Thr | Ala | Asp | Lys | Ser |
| GGC | AAG | GCC | ACA | CTG | ACT | GCA | GAC | AAA | TCC |
| Ser | Ser | Thr | Ala | Tyr | Val | Gln | Leu | Asn | Ser |
| TCC | AGC | ACT | GCC | TAC | GTG | CAG | CTC | AAC | AGC |
| Leu | Thr | Ser | Glu | Asp | Ser | Ala | Val | Tyr | Phe |
| CTG | ACA | TCT | GAG | GAT | TCT | GCA | GTG | TAT | TTC |
| Cys | Thr | Arg | Ser | Leu | Asn | Met | Ala | Tyr | Trp |
| TGT | ACA | AGA | TCC | CTG | AAT | ATG | GCC | TAC | TGG |
| Gly | Gln | Gly | Thr | Ser | Val | Thr | Val | Ser | Ser |
| GGT | CAA | GGA | ACC | TCA | GTC | ACC | GTC | TCC | TCA |

```
         Nhe I
TAA AAAGCTAGCG ATGAATCCGT CAAAACATCA
                       Bcl I
TCTTACATAA AGTCACTTGG TGATCAAGCT

CATATCATTG TCCGGCAATG GTGTGGGCTT

TTTTTGTTTT CTATCTTTAA AGATCATGTG

AAGGAAAAAA CGGGAAAATC GGTCTGCGGG

AAAGGACCGG GTTTTGTCG AAATCATAGG
                                Bam HI
CGAATGGGTT GGATTGTGAC AAAATTCGGA TCC
```

FIG. 28A

```
                                    Eco RI
CTCATGTTTG ACAGCTTATC ATCGATGAAT

TCCATCACTT CCCTCCGTTC ATTTGTCCCC

GGTGGAAACG AGGTCATCAT TTCCTTCCGA

AAAAACGGTT GCATTTAAAT CTTACATATG

TAATACTTTC AAAGACTACA TTTGTAAGAT

TTGATGTTTG AGTCGGCTGA AAGATCGTAC

GTACCAATTA TTGTTTCGTG ATTGTTCAAG

CCATAACACT GTAGGGATAG TGGAAAGAGT

GCTTCATCTG GTTACGATCA ATCAAATATT
```

```
                                   ┌──── peIB Signal
                                   │ Met Lys Tyr Leu
CAAACGGAGG GAGACGATTT TG│ATG AAA TAC CTA
Sequence
Leu Pro Thr Ala Ala Ala Gly Leu Leu Leu
TTG CCT ACG GCA GCC GCT GGA TTG TTA TTA
                              Nco I ──→│←── H4V_L
Leu Ala Ala Gln Pro Ala  Met Ala│Asp Ile
CTC GCT GCC CAA CCA GCC  ATG GCC│GAC ATC Val Met Thr Gln Ser Pro Asp Ser Leu Ala
GTG ATG ACC CAG TCT CCA GAC TCC CTG GCT Val Ser Leu Gly Glu Arg Ala Thr Ile Asn
GTG TCT CTG GGC GAG AGG GCC ACC ATC AAC Cys Lys Ser Ser Gln Ser Val Leu Tyr Ser
TGC AAG TCC AGC CAG AGT GTT TTA TAC AGC
```

FIG.28B

```
Ser Asn Asn Lys Asn Tyr Leu Ala Trp Tyr
TCC AAC AAT AAG AAC TAC TTA GCT TGG TAC

Gln Gln Lys Pro Gly Gln Pro Pro Lys Leu
CAG CAG AAA CCA GGA CAG CCT CCT AAG CTG

Leu Ile Tyr Trp Ala Ser Thr Arg Glu Ser
CTC ATT TAC TGG GCA TCT ACC CGG GAA TCC

Gly Val Pro Asp Arg Phe Ser Gly Ser Gly
GGG GTC CCT GAC CGA TTC AGT GGC AGC GGG

Ser Gly Thr Asp Phe Thr Leu Thr Ile Ser
TCT GGG ACA GAT TTC ACT CTC ACC ATC AGC

Ser Leu Gln Ala Glu Asp Val Ala Val Tyr
AGC CTG CAG GCT GAA GAT GTG GCA GTT TAT

Tyr Cys Gln Gln Tyr Tyr Ser Tyr Pro Leu
TAC TGT CAG CAA TAT TAT AGT TAT CCT CTC
                                      H4V_L
Thr Phe Gly Gly Gly Thr Lys Val Val Ile
ACT TTC GGC GGA GGG ACC AAG GTG GTG ATC
Hind III LINKER
Lys│Leu Ser Ala Asp Asp Ala Lys Lys Asp
AAG│CTT AGT GCG GAC GAT GCG AAA AAG GAT Ala Ala Lys Lys Asp Asp Ala Lys Lys Asp
GCT GCG AAG AAG GAT GAC GCT AAG AAA GAC
           LINKER        Xho I
Asp Ala Lys Lys Asp Leu│Gln
GAT GCT AAA AAG GAC CTC│CAG
```

FIG. 28C

```
        Nhe I      ┌─ Flag Peptide
        Ala   Ser │ Asp  Tyr  Lys  Asp
ACAATGTC  GCT  AGC │ GAC  TAC  AAG  GAC
                ──→│
Asp  Asp  Asp  Lys│
GAT  GAT  GAC  AAA│ TAA    AAACCTAGC GATGAATCCG  TCAAAACATC  ATCTTACATA
              Bcl I
AAGTCACTT   GGTGATCAAG  CTCATATCAT

TGTCCGGCA   ATGGTGTGGG  CTTTTTTTGT

TTTCATCTT   TAAAGATCAT  GTGAAGGAAA

AAACGGGAA   AATCGGTCTG  CGGGAAAGGA

CCGGGTTTT   TGTCGAAATC  ATAGGCGAAT
                                Bam HI
GGGTTGGAT   TGTGACAAAA  TTCGGATCC
```

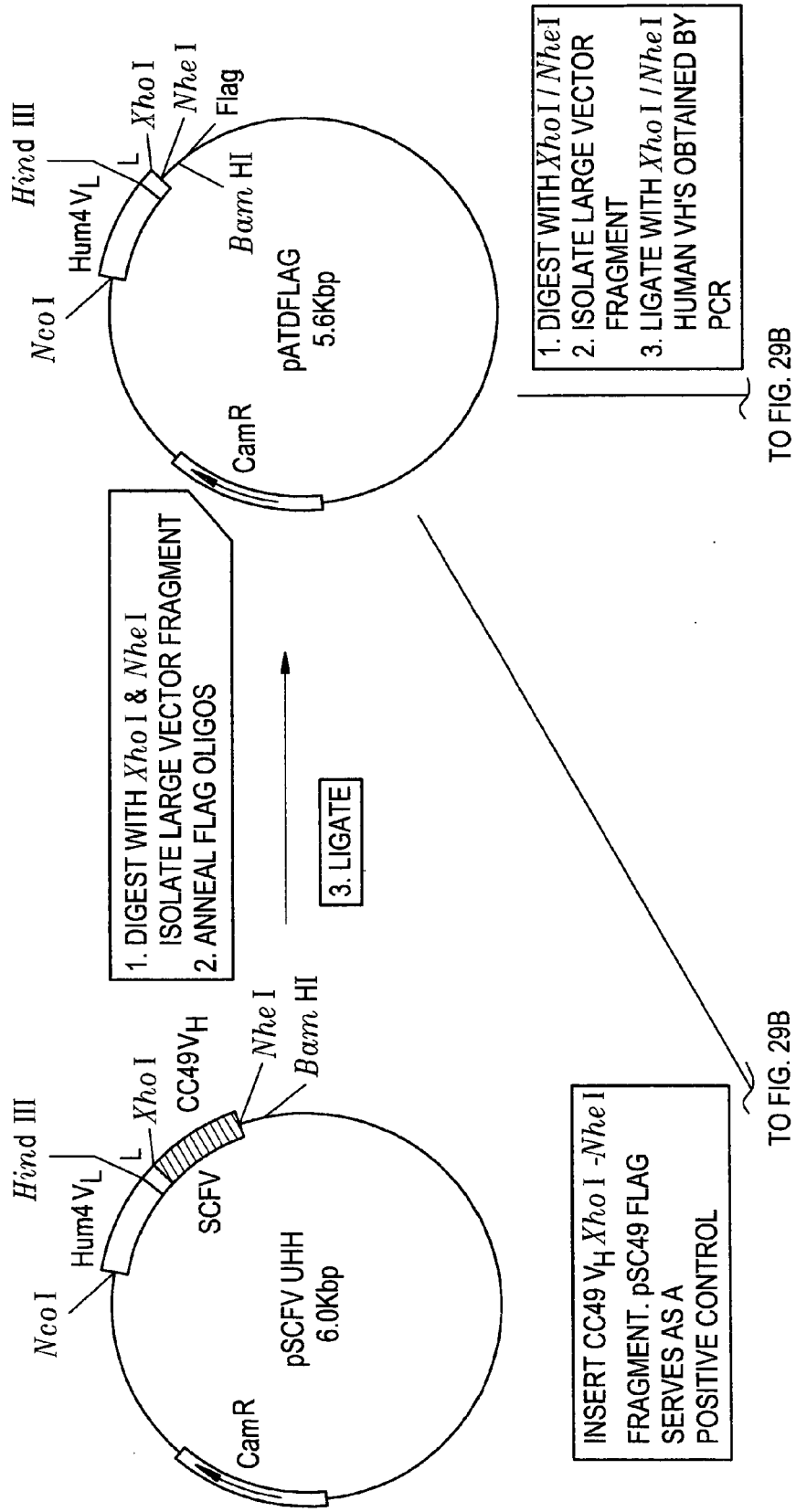

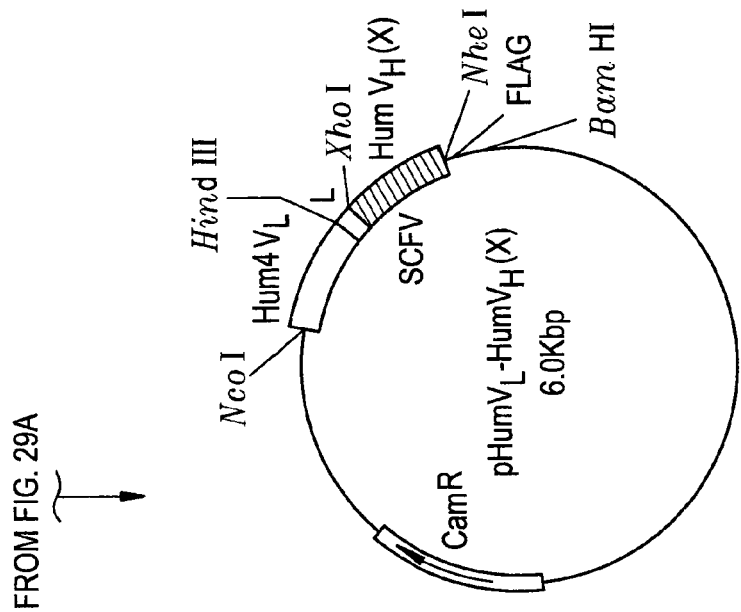
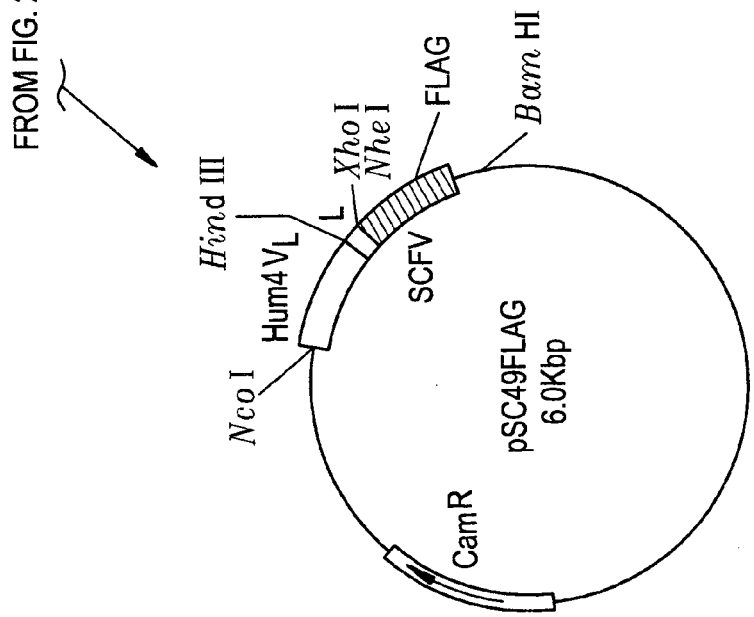
FIG. 29B

FIG. 30A

```
                                    Eco RI
CTCATGTTTG  ACAGCTTATC  ATCGATGAAT

TCCATCACTT  CCCTCCGTTC  ATTTGTCCCC

GGTGGAAACG  AGGTCATCAT  TTCCTTCCGA

AAAAACGGTT  GCATTTAAAT  CTTACATATG

TAATACTTTC  AAAGACTACA  TTTGTAAGAT

TTGATGTTTG  AGTCGGCTGA  AAGATCGTAC

GTACCAATTA  TTGTTTCGTG  ATTGTTCAAG

CCATAACACT  GTAGGGATAG  TGGAAAGAGT

GCTTCATCTG  GTTACGATCA  ATCAAATATT
```

```
                                       peIB Signal
                                 Met  Lys  Tyr  Leu
CAAACGGAGG  GAGACGATTT  TG│ATG  AAA  TAC  CTA
Sequence
Leu  Pro  Thr  Ala  Ala  Ala  Gly  Leu  Leu  Leu
TTG  CCT  ACG  GCA  GCC  GCT  GGA  TTG  TTA  TTA
                               Nco I →│← H4V_L
Leu  Ala  Ala  Gln  Pro  Ala   Met  Ala│Asp  Ile
CTC  GCT  GCC  CAA  CCA  GCC   ATG  GCC│GAC  ATC Val  Met  Thr  Gln  Ser  Pro  Asp  Ser  Leu  Ala
GTG  ATG  ACC  CAG  TCT  CCA  GAC  TCC  CTG  GCT Val  Ser  Leu  Gly  Glu  Arg  Ala  Thr  Ile  Asn
GTG  TCT  CTG  GGC  GAG  AGG  GCC  ACC  ATC  AAC Cys  Lys  Ser  Ser  Gln  Ser  Val  Leu  Tyr  Ser
TGC  AAG  TCC  AGC  CAG  AGT  GTT  TTA  TAC  AGC
```

FIG. 30B

```
Ser Asn Asn Lys Asn Tyr Leu Ala Trp Tyr
TCC AAC AAT AAG AAC TAC TTA GCT TGG TAC

Gln Gln Lys Pro Gly Gln Pro Pro Lys Leu
CAG CAG AAA CCA GGA CAG CCT CCT AAG CTG

Leu Ile Tyr Trp Ala Ser Thr Arg Glu Ser
CTC ATT TAC TGG GCA TCT ACC CGG GAA TCC

Gly Val Pro Asp Arg Phe Ser Gly Ser Gly
GGG GTC CCT GAC CGA TTC AGT GGC AGC GGG

Ser Gly Thr Asp Phe Thr Leu Thr Ile Ser
TCT GGG ACA GAT TTC ACT CTC ACC ATC AGC

Ser Leu Gln Ala Glu Asp Val Ala Val Tyr
AGC CTG CAG GCT GAA GAT GTG GCA GTT TAT

Tyr Cys Gln Gln Tyr Tyr Ser Tyr Pro Leu
TAC TGT CAG CAA TAT TAT AGT TAT CCT CTC
                                        H4V_L
Thr Phe Gly Gly Gly Thr Lys Val Val Ile
ACT TTC GGC GGA GGG ACC AAG GTG GTG ATC
Hind III  LINKER
Lys|Leu Ser Ala Asp Asp Ala Lys Lys Asp
AAG|CTT AGT GCG GAC GAT GCG AAA AAG GAT Ala Ala Lys Lys Asp Asp Ala Lys Lys Asp
GCT GCG AAG AAG GAT GAC GCT AAG AAA GAC
        LINKER         Xho I    CC49 V_H
Asp Ala Lys Lys Asp Leu|Gln Val Gln Leu
GAT GCT AAA AAG GAC CTC|CAG GTT CAG TTG
```

FIG.30C

```
Gln Gln Ser Ala Glu Leu Val Lys Pro Gly
CAG CAG TCT GCT GAG TTG GTG AAA CCT GGG

Ala Ser Val Lys Ile Ser Cys Lys Ala Ser
GCT TCA GTG AAG ATT TCC TGC AAG GCT TCT

Gly Tyr Thr Phe Thr Asp His Ala Ile His
GGC TAC ACC TTC ACT GAC CAT GCA ATT CAC

Trp Val Lys Gln Asn Pro Glu Gln Gly Leu
TGG GTG AAA CAG AAC CCT GAA CAG GGC CTG

Glu Trp Ile Gly Tyr Phe Ser Pro Gly Asn
GAA TGG ATT GGA TAT TTT TCT CCC GGA AAT

Asp Asp Phe Lys Tyr Asn Glu Arg Phe Lys
GAT GAT TTT AAA TAC AAT GAG AGG TTC AAG

Gly Lys Ala Thr Leu Thr Ala Asp Lys Ser
GGC AAG GCC ACA CTG ACT GCA GAC AAA TCC

Ser Ser Thr Ala Tyr Val Gln Leu Asn Ser
TCC AGC ACT GCC TAC GTG CAG CTC AAC AGC

Leu Thr Ser Glu Asp Ser Ala Val Tyr Phe
CTG ACA TCT GAG GAT TCT GCA GTG TAT TTC

Cys Thr Arg Ser Leu Asn Met Ala Tyr Trp
TGT ACA AGA TCC CTG AAT ATG GCC TAC TGG
                            CC49 V_H ─────▶
Gly Gln Gly Thr Ser Val Thr Val Ser Ser
GGT CAA GGA ACC TCA GTC ACC GTC TCC TCA
```

FIG. 30D

```
        Nhe I    ┌─Flag Peptide
     Ala   Ser  │ Asp  Tyr  Lys  Asp
     GCT   AGC  │ GAC  TAC  AAG  GAC
                      ────────▶
Asp  Asp  Asp  Lys│
GAT  GAT  GAC  AAA│ TAA   AAACCTAGC GATGAATCCG  TCAAAACATC  ATCTTACATA
                Bcl I
AAGTCACTT   GGTGATCAAG  CTCATATCAT

TGTCCGGCA   ATGGTGTGGG  CTTTTTTTGT

TTTCATCTT   TAAAGATCAT  GTGAAGGAAA

AAACGGGAA   AATCGGTCTG  CGGGAAAGGA

CCGGGTTTT   TGTCGAAATC  ATAGGCGAAT
                                Bam HI
GGGTTGGAT   TGTGACAAAA  TTCGGATCC
```

FIG. 31B

FROM FIG. 31A

Plate transformation mix onto hydrophilic membranes (137 mm) which are placed on LB CAM 20 agar plates (150 mm) with a colony density of ≤ 50,000 per plate. Grow for 8-16 hours at 37°C.

SCFV is secreted by *E.coli* and may bind to TAG.

Transfer hydrophilic membrane onto fresh LB CAM 20 plate having a TAG-72-coated hydrophobic membrane (137 mm) already placed on the agar surface. Incubate for 24-96 hours.

assay

Process hydrophobic membrane using a prototype biotinylated TAG-competing antibody, e.g. B72.3, CC49, CC83 or biotinylated competing peptide or mimetic. Use streptavidin conjugated with alkaline phosphatase to bind to biotin and suitable substrate for alkaline phosphatase to develop a color reaction.

Co-relate clear zones on membrane assay with colony (ies) on hydrophilic membrane. Isolate/purify correct clone as necessary. Characterize DNA (sequence) and determine binding affinity of SCFV to TAG-72. Purify SCFV and perform *in vivo* animal biodistribution studies.

Determine normal : tumor tissue binding profile by immunohistochemistry.

Utilize Hum4 $V_L$ and $V_H$ in preferred antibody formats e.g. whole Ig (IgGl, IgE, IgM etc.) Fab or $F(ab')_2$ fragment, or SCFV.

FIG. 32A

```
            ******    * *    * * *    CDR1   ****      *******
nCC49                DIVMSQSPSSLPVSVGEKVTLSC KSSQSLLYSGNQKNYLA WYQQKPGQSPKLLIY
LEN                  DIVMTQSPDSLAVSLGERATINC                   WYQQKPGQSPKLLIY
HuCC49     DIVMSQSPDSLAVSLGERVTLNC KSSQSLLYSGNQKNYLA WYQQKPGQSPKLLIY

CDR2   * ***  *  * * **  * * *    *****  *  *  * * *  CDR3   *   *     *
nCC49      WASARES GVPDRFTGSGSGTDFTLSISSVKTEDLAVYYC QQYYSYPLT FGAGTKLVLK
LEN                GVPDRFSGSGSGTDFTLTISSLQAEDVAVYYC           FGQGTKLEIK
HuCC49     WASARES GVPDRFSGSGSGTDFTLTISSVQAEDVAVYYC QQYYSYPLT FGAGTKLELK
```

FIG. 32B

```
           ** *  *       *  *    ***  CDR1  *****    *  *    * * *****   ****
nCC49                QVQLQQSDAELVKPGASVKISCKASGYTFT DHAIH WVKQNPEQGLEWIG
21/28'CL   QVQLVQSGAEVKKPGASVKVSCKASGYTFT               WVRQAPGQRLEWMG
HuCC49               QVQLVQSGAEVVKPGASVKISCKASGYTFT DHAIH WVKQNPGQGLEWIG

CDR2   *      *         * * **   *  * *****  CDR3   *    *  *   *
nCC49      YFSPGNDDFKYNERFKG KATLTADKSSSTAYMQLNSLTSEDSAVYFCTR SLNMAY WGQGTSVTVSS
21/28'CL                     RVTITRDTSASTAYMELSSLRSEDTAVYYCAR        WGQGTLVTVSS
HuCC49     YFSPGNDDFKYNERFKG KATLTADTSASTAYVELSSLRSEDTAVYFCTR SLNMAY WGQGTLVTVSS
```

FIG. 33A

```
     gcaagcttccaccATGGATAGCCAGGCCCAGGTGCTCATGCTCCTGCTGC
  1  ---------+---------+---------+---------+---------+  50
     cgttcgaaggtggTACCTATCGGTCCCGGTCCACGAGTACGAGGACGACG TGTGGGTGAGCGGCACATGCGGCGACATCGTGATGAGCCAGTCTCCAGAC
 51  ---------+---------+---------+---------+---------+ 100
     ACACCCACTCGCCGTGTACGCCGCTGTAGCACTACTCGGTCAGAGGTCTG TCCCTGGCCGTGTCCCTGGGCGAGAGGGTGACTCTGAATTGCAAGTCCAG
101  ---------+---------+---------+---------+---------+ 150
     AGGGACCGGCACAGGGACCCGCTCTCCCACTGAGACTTAACGTTCAGGTC CCAGTCCCTGCTCTATAGCGGAAATCAGAAGAACTATCTCGCCTGGTATC
151  ---------+---------+---------+---------+---------+ 200
     GGTCAGGGACGAGATATCGCCTTTAGTCTTCTTGATAGAGCGGACCATAG AGCAGAAACCAGGGCAGAGCCCTAAACTGCTGATTTACTGGGCATCCGCT
201  ---------+---------+---------+---------+---------+ 250
     TCGTCTTTGGTCCCGTCTCGGGATTTGACGACTAAATGACCCGTAGGCGA AGGGAATCCGGCGTGCCTGATCGCTTCAGCGGCAGCGGATCTGGGACAGA
251  ---------+---------+---------+---------+---------+ 300
     TCCCTTAGGCCGCACGGACTAGCGAAGTCGCCGTCGCCTAGACCCTGTCT CTTCACTCTGACAATCAGCAGCGTGCAGGCAGAAGACGTGGCAGTCTATT
301  ---------+---------+---------+---------+---------+ 350
     GAAGTGAGACTGTTAGTCGTCGCACGTCCGTCTTCTGCACCGTCAGATAA ATTGTCAGCAGTATTATAGCTATCCCCTCACATTCGGCGCTGGCACCAAG
351  ---------+---------+---------+---------+---------+ 400
     TAACAGTCGTCATAATATCGATAGGGGAGTGTAAGCCGCGACCGTGGTTC CTGGAACTGAAAcgggccgcggct
401  ---------+---------+---- 424
     GACCTTGACTTTgcccggcgccga
```

FIG. 33B

```
     ctaagcttccaccATGGAGTGGTCCTGGGTCTTCCTCTTCTTCCTGTCCG
  1  ---------+---------+---------+---------+---------+ 50
     gattcgaaggtggTACCTCACCAGGACCCAGAAGGAGAAGAAGGACAGGC TGACTACTGGAGTGCACTCCCAGGTCCAGCTGGTGCAGTCCGGCGCTGAG
 51  ---------+---------+---------+---------+---------+ 100
     ACTGATGACCTCACGTGAGGGTCCAGGTCGACCACGTCAGGCCGCGACTC GTGGTGAAACCTGGGGCTTCCGTGAAGATTTCCTGCAAGGCAAGCGGCTA
101  ---------+---------+---------+---------+---------+ 150
     CACCACTTTGGACCCCGAAGGCACTTCTAAAGGACGTTCCGTTCGCCGAT CACCTTCACTGATCACGCAATCCACTGGGTGAAACAGAATCCTGGACAGC
151  ---------+---------+---------+---------+---------+ 200
     GTGGAAGTGACTAGTGCGTTAGGTGACCCACTTTGTCTTAGGACCTGTCG GCCTGGAGTGGATTGGATATTTCTCTCCCGGAAACGATGATTTTAAGTAC
201  ---------+---------+---------+---------+---------+ 250
     CGGACCTCACCTAACCTATAAAGAGAGGGCCTTTGCTACTAAAATTCATG AATGAGAGGTTCAAGGGCAAGGCCACACTGACTGCAGACACATCTGCCAG
251  ---------+---------+---------+---------+---------+ 300
     TTACTCTCCAAGTTCCCGTTCCGGTGTGACTGACGTCTGTGTAGACGGTC CACTGCCTACGTGGAGCTCTCCAGCCTGAGATCCGAGGATACTGCAGTGT
301  ---------+---------+---------+---------+---------+350
     GTGACGGATGCACCTCGAGAGGTCGGACTCTAGGCTCCTATGACGTCACA ACTTCTGCACAAGATCCCTGAATATGGCCTACTGGGGACAGGGAACCCTG
351  ---------+---------+---------+---------+---------+ 400
     TGAAGACGTGTTCTAGGGACTTATACCGGATGACCCCTGTCCCTTGGGAC GTCACCGTCTCCAGCgccaaaactacgggcccat
401  ---------+---------+---------+---- 434
     CAGTGGCAGAGGTCGcggttttgatgcccgggta
```

COMPOSITE ANTIBODIES OF HUMANIZED HUMAN SUBGROUP IV LIGHT CHAIN CAPABLE OF BINDING TO TAG-72

CROSS-REFERENCE TO RELATED APPLICATION

This application is a Divisional of prior application Ser. No: 08/961,309 filed Oct. 10, 1997 now U.S. Pat. No. 6,495,137.

The Applicants herein claim the benefit of priority under 35 U.S.C. § 119(e) to U.S. Provisional Application No. 60/030,173 entitled, "Humanized Monoclonal Antibodies Specific to TAG-72, Methods for Their Manufacture and Usage in the Treatment or Diagnosis of Cancer," which was filed on Oct. 31, 1996 by W. H. Kerr Anderson et al. The present application is a Continuation-in-Part of application Ser. No. 08/261,354 filed Jun. 16, 1994, now U.S. Pat. No. 5,976,531, which is a Continuation-in-Part of application Ser. No. Ser. No. 07/510,697, filed Jul. 17, 1990 now abandoned, and Ser. No. 07/964,536, filed Oct. 20, 1992 now abandoned, both now abandoned.

FIELD OF THE INVENTION

The present invention is directed to the fields of immunology and genetic engineering.

BACKGROUND OF THE INVENTION

The following information is provided for the purpose of making known information believed by the applicants to be of possible relevance to the present invention. No admission is necessarily intended, nor should be construed, that any of the following information constitutes prior art against the present invention.

Antibodies are specific immunoglobulin (Ig) polypeptides produced by the vertebrate immune system in response to challenges by foreign proteins, glyco-proteins, cells, or other antigenic foreign substances. The binding specificity of such polypeptides to a particular antigen is highly refined, with each antibody being almost exclusively directed to the particular antigen which elicited it.

Two major methods of generating vertebrate antibodies are presently utilized: generation in situ by the mammalian B lymphocytes and generation in cell culture by B cell hybrids. Antibodies are generated in situ as a result of the differentiation of immature B lymphocytes into plasma cells (see Gough (1981), *Trends in Biochem Sci*, 6:203). Even when only a single antigen is introduced into the immune system of a particular mammal, a uniform population of antibodies does not result, i.e., the response is polyclonal. The limited but inherent heterogeneity of polyclonal antibodies is overcome by the use of hybridoma technology to create "monoclonal" antibodies in cell cultures by B cell hybridomas (see Kohler and Milstein (1975), *Nature*, 256: 495–497). In this process, a mammal is injected with an antigen, and its relatively short-lived, or mortal, splenocytes or lymphocytes are fused with an immortal tumor cell line. The fusion produces hybrid cells or "hybridomas" which are both immortal and capable of producing the genetically-coded antibody of the B cell.

In many applications, the use of monoclonal antibodies produced in non-human animals is severely restricted where the monoclonal antibodies are to be used in humans. Repeated injections in humans of a "foreign" antibody, such as a mouse antibody, may lead to harmful hypersensitivity reactions, i.e., an anti-idiotypic, or anti-mouse antibody (HAMA), response (see Shawler et al. (1985), *Journal of Immunology*, 135:1530–1535; and Sear et al., *J. Biol. Resp. Modifiers*, 3:138–150).

Various attempts have already been made to manufacture human-derived monoclonal antibodies by using human hybridomas (see Olsson et al. (1980), *Proc. Natl. Acad. Sci. USA*, 77:5429; and Roder et al. (1986), *Methods in Enzymology*, 121:140–167). Unfortunately, yields of monoclonal antibodies from human hybridoma cell lines are relatively low compared to mouse hybridomas. In addition, human cell lines expressing immunoglobulins are relatively unstable compared to mouse cell lines, and the antibody producing capability of these human cell lines is transient. Thus, while human immunoglobulins are highly desirable, human hybridoma techniques have not yet reached the stage where human monoclonal antibodies with required antigenic specificities can be easily obtained.

Thus, antibodies of nonhuman origin have been genetically engineered to create chimeric or humanized antibodies. Such genetic engineering results in antibodies with a reduced risk of a HAMA response compared to that expected after injection of a human patient with a mouse antibody. In a chimeric antibody, non-human regions of immunoglobulin constant sequences are replaced by corresponding human ones (see U.S. Pat. No. 4,816,567 to Cabilly et al., Genentech); in a humanized antibody, complementarity determining regions (CDRs) are grafted onto human framework regions (FR) (see European Patent Office Application (EPO) 0 239 400 to Winter). Some researchers have produced Fv antibodies (see U.S. Pat. No. 4,642,334 to Moore, DNAX) and single chain Fv (SCFV) antibodies (see U.S. Pat. No. 4,946,778 to Ladner, Genex).

The above patent publications only show the production of antibody fragments in which some portion of the variable domains is coded for by nonhuman V gene regions. Humanized antibodies to date still retain various portions of light and heavy chain variable regions of nonhuman origin: the chimeric, Fv and single chain Fv antibodies retain the entire variable region of nonhuman origin and CDR-grafted antibodies retain CDR of nonhuman origin.

Such nonhuman-derived regions are expected to elicit an immunogenic reaction when administered into a human patient (see Brüggemann et al. (1989), *J. Exp. Med.*, 170: 2153–2157; and Lo Buglio (1991), Sixth International Conference on Monoclonal Antibody Immunoconjugates for Cancer, San Diego, Calif.). Thus, it is most desirable to obtain a human variable region which is capable of binding to a selected antigen.

One known human carcinoma tumor antigen is tumor-associated glycoprotein-72 (TAG-72), as defined by monoclonal antibody B72.3 (see Thor et al. (1986) *Cancer Res.*, 46:3118–3124; and Johnson, et al. (1986), *Cancer Res.*, 46:850–857). TAG-72 is associated with the surface of certain tumor cells of human origin, specifically the LS174T tumor cell line (American Type Culture Collection (ATCC) No. CL 188), which is line.

Numerous murine monoclonal antibodies have been developed which have binding specificity for TAG-72. Exemplary murine monoclonal antibodies include the "CC" (colon cancer) monoclonal antibodies, which are a library of murine monoclonal antibodies developed using TAG-72 purified on an immunoaffinity column with an immobilized anti-TAG-72 antibody, B72.3 (ATCC HB-8108) (see EP 394277, to Schlom et al., National Cancer Institute). Certain CC antibodies were deposited with the ATCC: CC49 (ATCC No. HB 9459); CC83 (ATCC No. HB 9453); CC46 (ATCC No. HB 9458); CC92 (ATCC No. HB 9454); CC30 (ATCC NO. HB 9457); CC11 (ATCC HB No. 9455) and CC15 (ATCC No. HB 9460). Various antibodies of the CC series have been chimerized (see, for example, EPO 0 365 997 to Mezes et al., The Dow Chemical Company).

It is thus of great interest to develop antibodies against TAG-72 containing a light and/or heavy chain variable region(s) derived from human antibodies. However, the prior art simply does not teach recombinant and immunologic techniques capable of routinely producing an anti-TAG-72 antibody in which the light chain and/or the heavy chain variable regions have specificity and affinity for TAG-72 and which are derived from human sequences so as to elicit expectedly low or no HAMA response. It is known that the function of an immunoglobulin molecule is dependent on its three dimensional structure, which in turn is dependent on its primary amino acid sequence. A change of a few or even one amino acid can drastically affect the binding function of the antibody, i.e., the resultant antibodies are generally presumed to be a non-specific immunoglobulin (NSI), i.e., lacking in antibody character, (see, for example, U.S. Pat. No. 4,816,567 to Cabilly et al., Genentech).

Surprisingly, the present invention is capable of meeting many of these above mentioned needs and provides a method for supplying the desired antibodies. For example, in one aspect, the present invention provides a cell capable of expressing a composite antibody having binding specificity for TAG-72, said cell being transformed with (a) a DNA sequence encoding at least a portion of a light chain variable region ($V_L$) effectively homologous to the human Subgroup IV germline gene (Hum4 $V_L$); and a DNA sequence segment encoding at least a portion of a heavy chain variable region ($V_H$) capable of combining with the $V_L$ into a three dimensional structure having the ability to bind to TAG-72.

In one aspect, the present invention concerns a composite antibody or antibody fragment comprising a DNA sequence encoding at least one chain which comprises a variable region having a heavy chain ($V_H$) and a light chain ($V_L$), (A) said $V_H$ being encoded by a DNA sequence comprising a subsegment effectively homologous to the $V_H\alpha$TAG germline gene ($V_H\alpha$TAG), and (B) said $V_L$ being encoded by a DNA sequence comprising a subsegment effectively homologous to the human Subgroup IV germline gene (Hum$_k$IV).

In another aspect, the present invention provides a composite antibody or antibody fragment having binding specificity for TAG-72, comprising (a) a DNA sequence encoding at least a portion of a light chain variable region ($V_L$) effectively homologous to the human Subgroup IV germline gene (Hum4 $V_L$); and a DNA sequence segment encoding at least a portion of a heavy chain variable region ($V_H$) capable of combining with the $V_L$ into a three dimensional structure having the ability to bind TAG-72.

The invention further includes the aforementioned antibody alone or conjugated to an imaging marker or therapeutic agent. The invention also includes a composition comprising the aforementioned antibody in unconjugated or conjugated form in a pharmaceutically acceptable, non-toxic, sterile carrier.

The invention is also directed to a method for in vivo diagnosis of cancer which comprises administering to an animal containing a tumor expressing TAG-72 a pharmaceutically effective amount of the aforementioned composition for the in situ detection of carcinoma lesions.

The invention is also directed to a method for intraoperative therapy which comprises (a) administering to a patient containing a tumor expressing TAG-72 a pharmaceutically effective amount of the aforementioned composition, whereby the tumor is localized, and (b) excising the localized tumors.

Additionally, the invention also concerns a process for preparing and expressing a composite antibody. Some of these processes are as follows. A process which comprises transforming a cell with a DNA sequence encoding at least a portion of a light chain variable region ($V_L$) effectively homologous to the human Subgroup IV germline gene (Hum4 $V_L$); and a DNA sequence segment encoding at least a portion of a heavy chain variable region ($V_H$) which is capable of combining with the $V_L$ to form a three dimensional structure having the ability to bind to TAG-72. A process for preparing a composite antibody or antibody which comprises culturing a cell containing a DNA sequence encoding at least a portion of a light chain variable region ($V_L$) effectively homologous to the human Subgroup IV germline gene (Hum4 $V_L$); and a DNA sequence segment encoding at least a portion of a heavy chain variable region ($V_H$) capable of combining with the $V_L$ into a three dimensional structure having the ability to bind to TAG-72 under sufficient conditions for the cell to express the immunoglobulin light chain and immuno-globulin heavy chain. A process for preparing an antibody conjugate comprising contacting the aforementioned antibody or antibody with an imaging marker or therapeutic agent.

DESCRIPTION OF THE DRAWINGS

FIG. 2 illustrates the nucleotide sequences of $V_H\alpha$TAG, CC46 $V_H$, CC49 $V_H$, CC83 $V_H$ and CC92 $V_H$.

FIG. 3 illustrates the amino acid sequences of $V_H\alpha$TAG, CC46 $V_H$, CC49 $V_H$, CC83 $V_H$ and CC92 $V_H$.

FIG. 4 illustrates the $V_H$ nucleotide and amino acid sequences of antibody B17X2.

FIG. 5 illustrates the mouse germline J-H genes from pNP9.

FIG. 8 illustrates the entire sequence of HUMVL(+) and HUMVL(−).

FIG. 9 illustrates the human J4 (HJ4) nucleotide sequence and amino acid sequence.

FIG. 10 illustrates the nucleotide sequences, and the amino acid sequences of Hum4 $V_L$, ClaI-HindIII segment.

FIG. 15 illustrates a primer, NEO102SEQ, used for sequencing plasmid DNA from several clones of pSV2neo-102.

FIG. 17 illustrates a partial nucleotide sequence segment of pRL1000.

FIG. 22 illustrates the nucleotide sequence and amino acid sequence of SCFV1.

FIG. 26 shows the DNA sequence and amino acid sequence of Hum4 $V_L$-CC49$V_H$ SCFV present in pSCFVUHH.

FIG. 28 illustrates the nucleotide sequence of FLAG peptide adapter in pATDFLAG.

FIG. 29 illustrates the construction of pATDFLAG, pHumVL-HumVH (X) and pSC49FLAG.

FIG. 30 illustrates the nucleotide and amino acid sequences of pSC49FLAG.

FIG. 32 illustrates the "humanization" protocols used in Example 6 to produce the humanized antibody variable regions derived from CC49.

FIG. 33 illustrates the nucleotide sequences of the humanized CC49 (HuCC49*) variable regions genes.

DETAILED DESCRIPTION OF THE INVENTION

Figure 1:
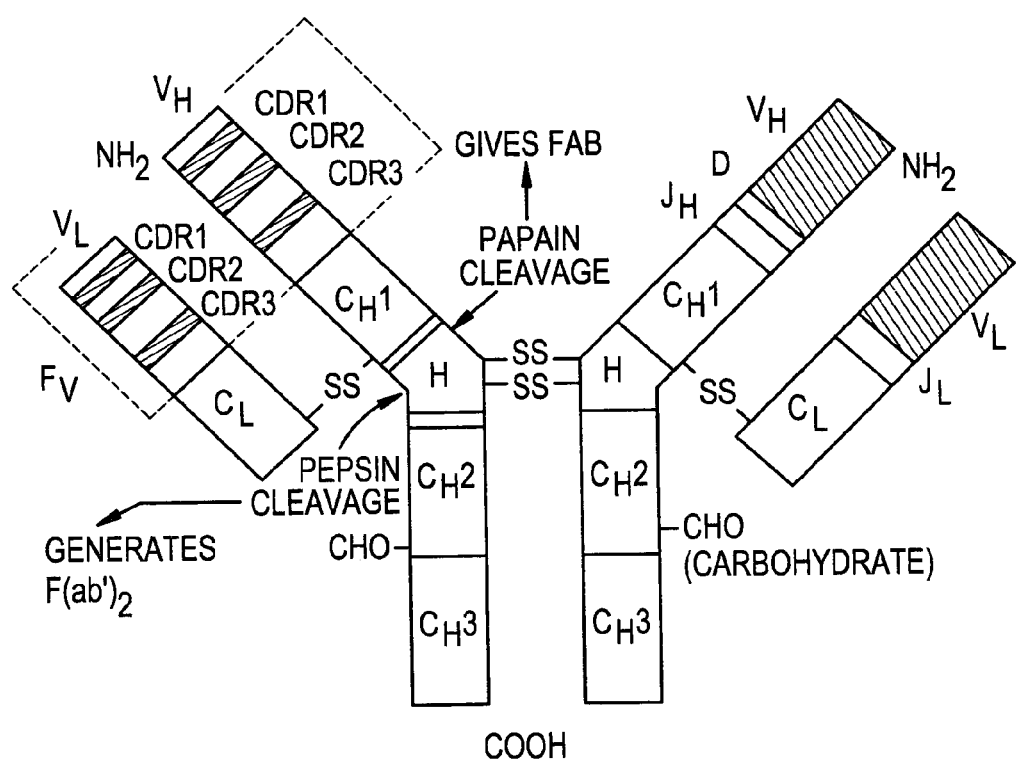
FIG. 1 illustrates a basic immunoglobulin structure.

Prior to setting forth the invention, definitions of certain terms which are used in this disclosure are set forth below:

Antibody—This refers to single chain, two-chain, and multi-chain proteins and glycoproteins belonging to the classes of polyclonal, monoclonal, chimeric, and hetero immunoglobulins (monoclonal antibodies being preferred); it also includes synthetic and genetically engineered variants of these immunoglobulins. "Antibody fragment" includes Fab, Fab', F(ab')$_2$, and Fv fragments, as well as any portion of an antibody having specificity toward a desired target epitope or epitopes.

Humanized antibody—This will refer to an antibody derived from a non-human antibody, typically murine, that retains or substantially retains the antigen-binding properties of the parent antibody but which is less immunogenic in humans. This may be achieved by various methods including (a) grafting only the non-human CDRs onto human framework and constant regions with or without retention of critical framework residues, or (b) transplanting the entire non-human variable domains, but "cloaking" them with a human-like section by replacement of surface residues. Such methods as are useful in practicing the present invention include those disclosed in Jones et al., Morrison et al., Proc. Natl. Acad. Sci. USA, 81:6851–6855 (1984); Morrison and Oi, Adv. Immunol., 44:65–92 (1988); Verhoeyen et al., Science, 239:1534–1536 (1988); Padlan, Molec. Immun., 28:489–498 (1991); Padlan, Molec. Immun., 31(3):169–217 (1994).

Complementarity Determining Region, or CDR—The term CDR, as used herein, refers to amino acid sequences which together define the binding affinity and specificity of the natural Fv region of a native immunoglobulin binding site as delineated by Kabat et al (1991).

Framework Region—The term FR, as used herein, refers to amino acid sequences interposed between CDRs. These portions of the antibody serve to hold the CDRs in an appropriate orientation for antigen binding.

Constant Region—The portion of the antibody molecule which confers effector functions. In the present invention, murine constant regions are substituted with human constant regions. The constant regions of the subject chimeric or humanized antibodies are derived from human immunoglobulins. The heavy chain constant region can be selected from any of the five isotypes: alpha, delta, epsilon, gamma or mu. Further, heavy chains of various subclasses (such as the IgG subclasses of heavy chains) are responsible for different effector functions and thus, by choosing the desired heavy chain constant region chimeric antibodies with desired effector function can be produced. Preferred constant regions are gamma 1 (IgG1), gamma 3 (IgG3) and gamma 4 (IgG4). More preferred is a constant region of the gamma 1 (IgG1) isotype. The light chain constant region can be of the kappa or lambda type, preferably of the kappa type.

Chimeric antibody—This is an antibody containing sequences derived from two different antibodies, which typically are of different species. Most typically chimeric antibodies comprise human and murine antibody fragments, generally human constant and murine variable regions.

Mammals—Animals that nourish their young with milk secreted by mammary glands, preferably warm blooded mammals, more preferably humans.

Immunogenicity—A measure of the ability of a targeting protein or therapeutic moiety to elicit an immune response (humoral or cellular) when administered to a recipient. The present invention is concerned with the immunogenicity of the subject humanized antibodies or fragments thereof.

Humanized antibody of reduced immunogenicity—This refers to a humanized antibody exhibiting reduced immunogenicity relative to the parent antibody.

Humanized antibody substantially retaining the binding properties of the parent antibody—This refers to a humanized antibody which retains the ability to specifically bind the antigen recognized by the parent antibody used to produce such humanized antibodies. Preferably the humanized antibody will exhibit the same or substantially the same antigen-binding affinity and avidity as the parent antibody, e.g., CC49. Preferably, the affinity of the antibody will at least about 10% of that of the parent antibody. More preferably, the affinity will be at least about 25%, i.e. at least two-fold less than the affinity of the parent antibody. Most preferably the affinity will be at least about 50% that of the parent antibody. Methods for assaying antigen-binding affinity are well known in the art and include half-maximal binding assays, competition assays, and Scatchard analysis. Suitable antigen binding assays are described in this application.

In a preferred embodiment, the antibodies and fragments of the present invention will be substantially homologous with those exemplified below and/or presented in the Figures. The phrase "substantially homologous" is used in regard to the similarity of a subject amino acid sequence (of an oligo- or polypeptide or protein) to a related, reference amino acid sequence. This phrase is defined as at least about 75% "correspondence"—i.e. the state of identical amino acid residues being situated in parallel—between the subject and reference sequences when those sequences are in "alignment," i.e. when a minimal number of "null" bases have been inserted in the subject and/or reference sequences so as to maximize the number of existing bases in correspondence between the sequences. "Null" bases are not part of the subject and reference sequences; also, the minimal number of "null" bases inserted in the subject sequence may differ from the minimal number inserted in the reference sequence. In this definition, a reference sequence is considered "related" to a subject sequence where both amino acid sequences make up proteins or portions of proteins which are either αTAG antibodies or antibody fragments with αTAG binding affinity. Each of the proteins comprising these aTAG antibodies or antibody fragments may independently be antibodies or antibody fragments or bi- or multi-functional proteins, e.g., such as fusion proteins, bi- and multi-specific antibodies, single chain antibodies, and the like.

Nucleic acids, amino acids, peptides, protective groups, active groups and so on, when abbreviated, are abbreviated according to the IUPAC IUB (Commission on Biological Nomenclature) or the practice in the fields concerned.

The basic immunoglobulin structural unit is set forth in FIG. 1. The terms "constant" and "variable" are used functionally. The variable regions of both light ($V_L$) and heavy ($V_H$) chains determine binding recognition and specificity to the antigen. The constant region domains of light ($C_L$) and heavy ($C_H$) chains confer important biological properties such as antibody chain association, secretion, transplacental mobility, complement binding, binding to Fc receptors and the like.

The immunoglobulins of this invention have been developed to address the problems of the prior art. The methods of this invention produce, and the invention is directed to, composite antibodies. By "composite antibodies" is meant immunoglobulins comprising variable regions not hitherto found associated with each other in nature. By "composite Hum4 $V_L$, $V_H$ antibody" means an antibody or immunoreactive fragment thereof which is characterized by having at least a portion of the $V_L$ region encoded by DNA derived from the Hum4 $V_L$ germline gene and at least a portion of a $V_H$ region capable of combining with the $V_L$ to form a three dimensional structure having the ability to bind to TAG-72.

The composite Hum4 $V_L$, $V_H$ antibodies of the present invention assume a conformation having an antigen binding site which binds specifically and with sufficient strength to TAG-72 to form a complex capable of being isolated by using standard assay techniques (e.g., enzyme-linked immunosorbent assay (ELISA), radioimmunoassay (RIA), or flourescence-activated cell sorter analysis (FACS), immunohistochemistry and the like). Preferably, the composite Hum4 $V_L$, $V_H$ antibodies of the present invention have an antigen binding affinity or avidity greater than $10^5$ $M^{-1}$, more preferably greater than $10^6$ $M^{-1}$ and most preferably greater than $10^8$ $M^{-1}$. For a discussion of the techniques for generating and reviewing immunoglobulin binding affinities see Munson (1983), *Methods Enzymol.*, 92:543–577 and Scatchard (1949), *Ann. N.Y. Acad. Sci.*, 51:660–672.

Human antibody kappa chains have been classified into four subgroups on the basis of invariant amino acid sequences (see, for example, Kabat et al. (1991), *Sequences of Proteins of Immunological Interest* (4th ed.), published by The U.S. Department of Health and Human Services). There appear to be approximately 80 human $V_K$ genes, but only one Subgroup IV $V_K$ gene has been identified in the human genome (see Klobeck, et al. (1985), *Nucleic Acids Research*, 13:6516–6528). The nucleotide sequence of Hum4 $V_L$ is set forth in Kabat et al. (1991), supra.

It has been found, quite surprisingly, that an immunoglobulin having a light chain with at least a portion of the $V_L$ encoded by a gene derived from Hum4 $V_L$ may, if combined with a suitable $V_H$, have binding specificity for TAG-72. The type of $J_L$ gene segment selected is not critical to the invention, in that it is expected that any $J_L$, if present, can associate with the Hum4 $V_L$. The present invention obviously contemplates the Hum4 $V_L$ in association with a human $J_k$ sequence. The five human $J_k$ sequences are set forth in Heiter et al. (1982), *The Journal of Biological Chemistry*, 357:1516–1522. However, the present invention is not intended to be limited to the human $J_k$. The present invention specifically contemplates the Hum4 $V_L$ in association with any of the at least six human $J_l$ genes (see Hollis et al. (1982), *Nature*, 296:321–325).

An exemplary technique for engineering the Hum4 $V_L$ with selected $J_L$ segments includes synthesizing a primer having a so-called "wagging tail", that does not hybridize with the target DNA; thereafter, the sequences are amplified and spliced together by overlap extension (see Horton et al. (1989), *Gene*, 77:61–68).

The $C_L$ of the composite Hum4 $V_L$, $V_H$ antibodies is not critical to the invention. To date, the Hum4 $V_L$ has only been reported as having been naturally rearranged with the single $C_k$ gene (see Heiter et al. (1980), Cell, 22:197–207). However, the present invention is not intended to be limited to the Ck light chain constant domain. That is, the $C_L$ gene segment may also be any of the at least six $C_l$ genes (see Hollis et al., supra).

The DNA encoding the heavy chain variable region consists roughly of a heavy chain variable ($V_H$) gene sequence, a heavy chain diversity ($D_H$) gene sequence, and a heavy chain joining ($J_H$) gene sequence.

The present invention is directed to any $V_H$ capable of combining with a light chain variable region effectively homologous to the light chain variable region encoded by the human Subgroup IV germline gene, to form a three dimensional structure having the ability to bind to TAG-72.

The choice of $D_H$ and $J_H$ segment of the composite Hum4 $V_L$, $V_H$ antibody are not critical to the present invention. Obviously, human and murine $D_H$ and $J_H$ gene segments are contemplated, provided that a given combination does not significantly decrease binding to TAG-72. Specifically, when utilizing CC46 $V_H$, CC49 $V_H$, CC83 $V_H$ and CC92 $V_H$, the composite Hum4 $V_L$, $V_H$ antibody will be designed to utilize the $D_H$ and $J_H$ segments which naturally associated with those $V_H$ of the respective hybridomas (see FIGS. 2 and 3). Exemplary murine and human $D_H$ and $J_H$ sequences are set forth in Kabat et al. (1991), supra. An exemplary technique for engineering such selected $D_H$ and $J_H$ segments with a $V_H$ sequence of choice includes synthesizing selected oligonucleotides, annealing and ligating in a cloning procedure (see, Horton et al., supra).

In a specific embodiment the composite Hum4 $V_L$, $V_H$ antibody will be a "composite Hum4 $V_L$, $V_H\alpha$TAG antibody", means an antibody or immunoreactive fragment thereof which is characterized by having at least a portion of the $V_L$ region encoded by DNA derived from the Hum4 $V_L$ germline gene and at least a portion of the $V_H$ region encoded by DNA derived from the $V_H\alpha$TAG germline gene, which is known in the art (see, for example, EPO 0 365 997 to Mezes et al., the Dow Chemical Company). FIG. 2 shows the nucleotide sequence of $V_H\alpha$TAG, and the nucleotide sequences encoding the $V_H$ of the CC46, CC49, CC83 and CC92 antibodies, respectively. FIG. 3 shows the corresponding amino acid sequences of $V_H\alpha$TAG, CC46 $V_H$, CC49 $V_H$, CC83 $V_H$ and CC92 $V_H$.

A comparison of the nucleotide and amino acid sequences of $V_H\alpha$TAG, CC46 $V_H$, CC49 $V_H$, CC83 $V_H$ and CC92 $V_H$ shows that those CC antibodies are derived from $V_H\alpha$TAG. Somatic mutations occurring during productive rearrangement of the $V_H$ derived from $V_H\alpha$TAG in a B cell gave rise to some nucleotide changes that may or may not result in a homologous amino acid change between the productively rearranged hybridomas (see, EPO 0 365 997).

Because the nucleotide sequences of the $V_H\alpha$TAG and Hum4 $V_L$ germline genes have been provided herein, the present invention is intended to include other antibody genes which are productively rearranged from the $V_H\alpha$TAG germline gene. Other antibodies encoded by DNA derived from $V_H\alpha$TAG may be identified by using a hybridization probe made from the DNA or RNA of the $V_H\alpha$TAG or rearranged genes containing the recombined $V_H\alpha$TAG. Specifically, the probe will include of all or a part of the $V_H\alpha$TAG germline gene and its flanking regions. By "flanking regions" is meant to include those DNA sequences from the 5' end of the $V_H\alpha$TAG to the 3' end of the upstream gene, and from 3' end of the $V_H\alpha$TAG to the 5' end of the downstream gene.

The CDR from the variable region of antibodies derived from $V_H\alpha$TAG may be grafted onto the FR of selected $V_H$, i.e., FR of a human antibody (see EPO 0 239 400 to Winter). For example, the cell line, B17X2, expresses an antibody utilizing a variable light chain encoded by a gene derived from Hum4 $V_L$ and a variable heavy chain which makes a stable $V_L$ and $V_H$ combination (see Marsh et al. (1985), *Nucleic Acids Research*, 13:6531–6544; and Polke et al. (1982), *Immunobiol.* 163:95–109. The nucleotide sequence of the $V_H$ chain for B17X2 is shown in FIG. 4. The B17X2 cell line is publicly available from Dr. Christine Polke, Universitats-Kinderklinik, Josef-Schneider-Str. 2, 8700 Würzburg, FRG). B17X2 is directed to N-Acetyl-D-Glucosamine and is not specific for TAG-72.

However, consensus sequences of antibody derived from the CDR1 of $V_H\alpha$TAG (amino acid residues 31 to 35 of FIG. 3) may be inserted into B17X2 (amino acid residues 31 to 37 of FIG. 4) and the CDR2 of $V_H\alpha$TAG (amino residues 50 to 65 of FIG. 3) may be inserted into B17X2 (amino acid residues 52 to 67 of FIG. 4). The CDR3 may be replaced by any $D_H$ and $J_H$ sequence which does not affect the binding of the antibody for TAG-72 but, specifically, may be replaced by the CDR3 of an antibody having its $V_H$ derived from $V_H\alpha$TAG, e.g., CC46, CC49, CC83 and CC92. Exemplary techniques for such replacement are set forth in Horton et al., supra.

The $C_H$ domains of immunoglobulin heavy chain derived from $V_H\alpha$TAG genes, for example may be changed to a human sequence by known techniques (see, U.S. Pat. No. 4,816,567 to Cabilly, Genentech). $C_H$ domains may be of various complete or shortened human isotypes, i.e., IgG (e.g., IgG$_1$, IgG$_2$, IgG$_3$, and IgG$_4$), IgA (e.g., IgA1 and IgA2), IgD, IgE, IgM, as well as the various allotypes of the individual groups (see Kabat et al. (1991), supra).

Given the teachings of the present invention, it should be apparent to the skilled artisan that human $V_H$ genes can be tested for their ability to produce an anti-TAG-72 immunoglobilin combination with the Hum4 $V_L$ gene. The $V_L$ may be used to isolate a gene encoding for a $V_H$ having the ability to bind to TAG-72 to test myriad combinations of Hum4 $V_L$ and $V_H$ that may not naturally occur in nature, e.g., by generating a combinatorial library using the Hum4 $V_L$ gene to select a suitable $V_H$. Examples of these enabling technologies include screening of combinatorial libraries of $V_L$-$V_H$ combinations using an Fab or single chain antibody (SCFV) format expressed on the surfaces of fd phage (Clackson, et al. (1991), *Nature*, 352:624–628), or using a 1 phage system for expression of Fv's or Fabs (Huse, et al. (1989), *Science*, 246:1275–1281). However, according to the teachings set forth herein, it is now possible to clone SCFV antibodies in *E. coli*, and express the SCFVs as secreted soluble proteins. SCFV proteins produced in *E. coli* that contain a Hum4 $V_L$ gene can be screened for binding to TAG-72 using, for example, a two-membrane filter screening system (Skerra, et al. (1991), *Analytical Biochemistry*, 196:151–155).

The desired gene repertoire can be isolated from human genetic material obtained from any suitable source, e.g., peripheral blood lymphocytes, spleen cells and lymph nodes of a patient with tumor expressing TAG-72. In some cases, it is desirable to bias the repertoire for a preselected activity, such as by using as a source of nucleic acid, cells (source cells) from vertebrates in any one of various stages of age, health and immune response.

Cells coding for the desired sequence may be isolated, and genomic DNA fragmented by one or more restriction enzymes. Tissue (e.g., primary and secondary lymph organs, neoplastic tissue, white blood cells from peripheral blood and hybridomas) from an animal exposed to TAG-72 may be probed for selected antibody producing B cells. Variability among B cells derived from a common germline gene may result from somatic mutations occurring during productive rearrangement.

Generally, a probe made from the genomic DNA of a germline gene or rearranged gene can be used by those skilled in the art to find homologous sequences from unknown cells. For example, sequence information obtained from Hum4 $V_L$ and $V_H\alpha$TAG may be used to generate hybridization probes for naturally-occurring rearranged V regions, including the 5' and 3' nontranslated flanking regions. The genomic DNA may include naturally-occurring introns for portions thereof, provided that functional splice donor and splice acceptor regions had been present in the case of mammalian cell sources.

Additionally, the DNA may also be obtained from a cDNA library. mRNA coding for heavy or light chain variable domain may be isolated from a suitable source, either mature B cells or a hybridoma culture, employing standard techniques of RNA isolation. The DNA or amino acids also may be synthetically synthesized and constructed by standard techniques of annealing and ligating fragments (see Jones, et al. (1986), *Nature*, 321:522–525; Reichmann et al., (1988), Nature, 332:323–327; Sambrook et al. (1989), supra and Merrifield et al. (1963), *J. Amer. Chem. Soc.*, 85:2149–2154). Heavy and light chains may be combined in vitro to gain antibody activity (see Edelman, et al. (1963), *Proc. Natl. Acad. Sci. USA*, 50:753).

The present invention also contemplates a gene library of $V_H\alpha$TAG homologs, preferably human homologs of V$_H$αTAG. By "homolog" is meant a gene coding for a V$_H$ region (not necessarily derived from, or even effectively homologous to, the V$_H$αTAG germline gene) capable of combining with a light chain variable region effectively homologous to the light chain variable region encoded by the human Subgroup IV germline gene, to form a three dimensional structure having the ability to bind to TAG-72.

Preferably, the gene library is produced by a primer extension reaction or combination of primer extension reactions as described herein. The V$_H$αTAG homologs are preferably in an isolated form, that is, substantially free of materials such as, for example, primer extension reaction agents and/or substrates, genomic DNA segments, and the like. The present invention thus is directed to cloning the V$_H$αTAG-coding DNA homologs from a repertoire comprised of polynucleotide coding strands, such as genomic material containing the gene expressing the variable region or the messenger RNA (mRNA) which represents a transcript of the variable region. Nucleic acids coding for V$_H$αTAG-coding homologs can be derived from cells producing IgA, IgD, IgE, IgG or IgM, most preferably from IgM and IgG, producing cells.

The V$_H$αTAG-coding DNA homologs may be produced by primer extension. The term "primer" as used herein refers to a polynucleotide whether purified from a nucleic acid restriction digest or produced synthetically, which is capable of acting as a point of initiation of synthesis when placed under conditions in which synthesis of a primer extension product which is complimentary to a nucleic acid strand is induced, i.e., in the presence of nucleotides and an agent for polymerization such as DNA polymerase, reverse transcriptase and the like, and at a suitable temperature and pH.

Preferably, the V$_H$αTAG-coding DNA homologs may be produced by polymerase chain reaction (PCR) amplification of double stranded genomic or cDNA, wherein two primers are used for each coding strand of nucleic acid to be exponentially amplified. The first primer becomes part of the nonsense (minus or complementary) strand and hybridizes to a nucleotide sequence conserved among V$_H$ (plus) strands within the repertoire. PCR is described in Mullis et al. (1987), *Meth. Enz.*, 155:335–350; and *PCR Technology*, Erlich (ed.) (1989). PCR amplification of the mRNA from antibody-producing cells is set forth in Orlandi et al. (1989), *Proc. Natl. Acad. Sci., USA,* 86:3387–3837.

According to a preferred method, the V$_H$αTAG-coding DNA homologs are connected via linker to form a SCFV having a three dimensional structure capable of binding TAG-72. The SCFV construct can be in a V$_L$-L-V$_H$ or V$_H$-L-V$_L$ configuration. For a discussion of SCFV see Bird et al. (1988), *Science,* 242:423–426. The design of suitable peptide linker regions is described in U.S. Pat. No. 4,704,692 to Ladner et al., Genex.

The nucleotide sequence of a primer is selected to hybridize with a plurality of immunoglobulin heavy chain genes at a site substantially adjacent to the V$_H$αTAG-coding DNA homolog so that a nucleotide sequence coding for a functional (capable of binding) polypeptide is obtained. The choice of a primer's nucleotide sequence depends on factors such as the distance on the nucleic acid from the region coding for the desired receptor, its hybridization site on the nucleic acid relative to any second primer to be used, the number of genes in the repertoire it is to hybridize to, and the like. To hybridize to a plurality of different nucleic acid strands of V$_H$αTAG-coding DNA homolog, the primer must be a substantial complement of a nucleotide sequence conserved among the different strands.

The peptide linker may be coded for by the nucleic acid sequences that are part of the poly-nucleotide primers used to prepare the various gene libraries. The nucleic acid sequence coding for the peptide linker can be made up of nucleic acids attached to one of the primers or the nucleic acid sequence coding for the peptide linker may be derived from nucleic acid sequences that are attached to several polynucleotide primers used to create the gene libraries. Additionally, noncomplementary bases or longer sequences can be interspersed into the primer, provided the primer sequence has sufficient complementarily with the sequence of the strand to be synthesized or amplified to non-randomly hybridize therewith and thereby form an extension product under polynucleotide synthesizing conditions (see Horton et al. (1989), *Gene,* 77:61–68).

Exemplary human V$_H$ sequences from which complementary primers may be synthesized are set forth in Kabat et al. (1991), supra; Humphries et al. (1988), *Nature,* 331:446–449; Schroeder et al. (1990), *Proc. Natl. Acad. Sci. USA,* 87:6146–6150; Berman et al. (1988), *EMBO Journal,* 7:727–738; Lee et al. (1987), *J. Mol. Biol.,* 195:761–768); Marks et al. (1991), *Eur. J. Immunol.,* 21:985–991; Willems, et al. (1991), *J. Immunol.,* 146:3646–3651; and Person et al. (1991), *Proc Natl. Acad. Sci. USA,* 88:2432–2436. To produce V$_H$ coding DNA homologs, first primers are therefore chosen to hybridize to (i.e. be complementary to) conserved regions within the J region, CH1 region, hinge region, CH2 region, or CH3 region of immunoglobulin genes and the like. Second primers are therefore chosen to hydribidize with a conserved nucleotide sequence at the 5' end of the V$_H$αTAG-coding DNA homolog such as in that area coding for the leader or first framework region.

Alternatively, the nucleic acid sequences coding for the peptide linker may be designed as part of a suitable vector. As used herein, the term "expression vector" refers to a nucleic acid molecule capable of directing the expression of genes to which they are operatively linked. The choice of vector to which a V$_H$αTAG-coding DNA homologs is operatively linked depends directly, as is well known in the art, on the functional properties desired, e.g., replication or protein expression, and the host cell (either procaryotic or eucaryotic) to be transformed, these being limitations inherent in the art of constructing recombinant DNA molecules. In preferred embodiments, the eucaryotic cell expression vectors used include a selection marker that is effective in an eucaryotic cell, preferably a drug resistant selection marker.

Expression vectors compatible with procaryotic cells are well known in the art and are available from several commercial sources. Typical of vector plasmids suitable for procaryotic cells are pUC8, pUC9, pBR322, and pBR329 available from BioRad Laboratories, (Richmond, Calif.), and pPL and pKK223 available from Pharmacia, (Piscataway, N.J.).

Expression vectors compatible with eucaryotic cells, preferably those compatible with vertebrate cells, can also be used. Eucaryotic cell expression vectors are well known in the art and are available from several commercial sources. Typically, such vectors are provided containing convenient restriction sites for insertion of the desired DNA homologue. Typical of vector plasmids suitable for eucaryotic cells are pSV2neo and pSV2gpt (ATCC), pSVL and pKSV-10 (Pharmacia), pBPV-1/PML2d (International Biotechnologies, Inc.), and pTDT1 (ATCC).

The use of viral expression vectors to express the genes of the V$_H$αTAG-coding DNA homologs is also contemplated. As used herein, the term "viral expression vector" refers to a DNA molecule that includes a promoter sequences derived from the long terminal repeat (LTR) region of a viral genome. Exemplary phage include l phage and fd phage (see, Sambrook, et al. (1989), *Molecular Cloning: A Laboratory Manual*, (2nd ed.), and McCafferty et al. (1990), *Nature*, 6301:552–554.

The population of $V_H\alpha$TAG-coding DNA homologs and vectors are then cleaved with an endonuclease at shared restriction sites. A variety of methods have been developed to operatively link DNA to vectors via complementary cohesive termini. For instance, complementary cohesive termini can be engineered into the $V_H\alpha$TAG-coding DNA homologs during the primer extension reaction by use of an appropriately designed polynucleotide synthesis primer, as previously discussed. The complementary cohesive termini of the vector and the DNA homolog are then operatively linked (ligated) to produce a unitary double stranded DNA molecule.

The restriction fragments of Hum4 $V_L$-coding DNA and the $V_H\alpha$TAG-coding DNA homologs population are randomly ligated to the cleaved vector. A diverse, random population is produced with each vector having a $V_H\alpha$TAG-coding DNA homolog and Hum4 $V_L$-coding DNA located in the same reading frame and under the control of the vector's promoter.

The resulting single chain construct is then introduced into an appropriate host to provide amplification and/or expression of a composite Hum4 $V_L$, $V_H\alpha$TAG homolog single chain antibody. Transformation of appropriate cell hosts with a recombinant DNA molecule of the present invention is accomplished by methods that typically depend on the type of vector used. With regard to transformation of procaryotic host cells, see, for example, Cohen et al. (1972), *Proceedings National Academy of Science, USA*, 69:2110; and Sambrook, et al. (1989), supra. With regard to the transformation of vertebrate cells with retroviral vectors containing rDNAs, see, for example, Sorge et al. (1984), *Mol. Cell. Biol.*, 4:1730–1737; Graham et al. (1973), *Virol.*, 52:456; and Wigler et al. (1979), *Proceedings National Academy of Sciences, USA*, 76:1373–1376.

Exemplary prokaryotic strains that may be used as hosts include *E. coli, Bacilli*, and other entero-bacteriaceae such as *Salmonella typhimurium*, and various *Pseudomonas*. Common eukaryotic microbes include *S. cerevisiae* and *Pichia pastoris*. Common higher eukaryotic host cells include Sp2/0, VERO and HeLa cells, Chinese hamster ovary (CHO) cell lines, and W138, BHK, COS-7 and MDCK cell lines. Furthermore, it is now also evident that any cell line producing Hum4 $V_L$, e.g., the B17X2 human cell line, can be used as a recipient human cell line for introduction of a $V_H$ gene complementary to the Hum4 $V_L$ which allows binding to TAG-72. For example, the B17X2 heavy chain may be genetically modified to not produce the endogenous heavy chain by well known methods; in this way, glycosylation patterns of the antibody produced would be human and not non-human derived.

Successfully transformed cells, i.e., cells containing a gene encoding a composite Hum4 $V_L$, $V_H\alpha$TAG homolog single chain antibody operatively linked to a vector, can be identified by any suitable well known technique for detecting the binding of a receptor to a ligand. Preferred screening assays are those where the binding of the composite Hum4 $V_L$, $V_H\alpha$TAG homolog single chain antibody to TAG-72 produces a detectable signal, either directly or indirectly. Screening for productive Hum4 $V_L$ and $V_H\alpha$TAG homolog combinations, or in other words, testing for effective antigen binding sites to TAG-72 is possible by using for example, a radiolabeled or biotinylated screening agent, e.g., antigens, antibodies (e.g., B72.3, CC49, CC83, CC46, CC92, CC30, CC11 and CC15) or anti-idiotypic antibodies (see Huse et al., supra, and Sambrook et al., supra); or the use of marker peptides to the $NH_2$— or COOH-terminus of the SCFV construct (see Hopp et al. (1988), *Biotechnology*, 6:1204–1210).

Of course, the Hum4 $V_L$-coding DNA and the $V_H\alpha$TAG-coding DNA homologs may be expressed as individual polypeptide chains (e.g., Fv) or with whole or fragmented constant regions (e.g., Fab, and $F(ab')_2$). Accordingly, the Hum4 $V_L$-coding DNA and the $V_H\alpha$TAG-coding DNA homologs may be individually inserted into a vector containing a $C_L$ or $C_H$ or fragment thereof, respectively. For a teaching of how to prepare suitable vectors see EPO 0 365 997 to Mezes et al., The Dow Chemical Company.

DNA sequences encoding the light chain and heavy chain of the composite Hum4 $V_L$, $V_H$ antibody may be inserted into separate expression vehicles, or into the same expression vehicle. When coexpressed within the same organism, either on the same or the different vectors, a functionally active Fv is produced. When the $V_H\alpha$TAG-coding DNA homolog and Hum4 $V_L$ polypeptides are expressed in different organisms, the respective polypeptides are isolated and then combined in an appropriate medium to form a Fv. See Greene et al., *Methods in Molecular Biology*, Vol. 9, Wickner et al. (ed.); and Sambrook et al., supra).

Subsequent recombinations can be effected through cleavage and removal of the Hum4 $V_L$-coding DNA sequence to use the $V_H\alpha$TAG-coding DNA homologs to produce Hum4 $V_L$-coding DNA homologs. To produce a Hum4 $V_L$-coding DNA homolog, first primers are chosen to hybridize with (i.e. be complementary to) a conserved region within the J region or constant region of immunoglobulin light chain genes and the like. Second primers become part of the coding (plus) strand and hybridize to a nucleotide sequence conserved among minus strands. Hum4 $V_L$-coding DNA homologs are ligated into the vector containing the $V_H\alpha$TAG-coding DNA homolog, thereby creating a second population of expression vectors. The present invention thus is directed to cloning the Hum4 $V_L$-coding DNA homologs from a repertoire comprised of polynucleotide coding strands, such as genomic material containing the gene expressing the variable region or the messenger RNA (mRNA) which represents a transcript of the variable region. It is thus possible to use an iterative process to define yet further, composite antibodies, using later generation $V_H\alpha$TAG-coding DNA homologs and Hum4 $V_L$-coding DNA homologs.

The present invention further contemplates genetically modifying the antibody variable and constant regions to include effectively homologous variable region and constant region amino acid sequences. Generally, changes in the variable region will be made in order to improve or otherwise modify antigen binding properties of the receptor. Changes in the constant region of the antibody will, in general, be made in order to improve or otherwise modify biological properties, such as complement fixation, interaction with membranes, and other effector functions.

"Effectively homologous" refers to the concept that differences in the primary structure of the variable region may not alter the binding characteristics of the antibody. Normally, a DNA sequence is effectively homologous to a second DNA sequence if at least 70 percent, preferably at least 80 percent, and most preferably at least 90 percent of the active portions of the DNA sequence are homologous.

Such changes are permissable in effectively homologous amino acid sequences so long as the resultant antibody retains its desired property.

If there is only a conservative difference between homologous positions of sequences, they can be regarded as equivalents under certain circumstances. General categories of potentially equivalent amino acids are set forth below, wherein amino acids within a group may be substituted for other amino acids in that group: (1) glutamic acid and aspartic acid; (2) hydrophobic amino acids such as alanine, valine, leucine and isoleucine; (3) asparagine and glutamine; (4) lysine and arginine and (5) threonine and serine.

Exemplary techniques for nucleotide replacement include the addition, deletion or substitution of various nucleotides, provided that the proper reading frame is maintained. Exemplary techniques include using polynucleotidemediated, site-directed mutagenesis, i.e., using a single strand as a template for extension of the oligonucleotide to produce a strand containing the mutation (see Zoller et al. (1982), *Nuc. Acids Res.*, 10:6487–6500; Norris et al. (1983), *Nuc. Acids Res.*, 11:5103–5112; Zoller et al. (1984), *DNA*, 3:479–488; and Kramer et al. (1982), *Nuc. Acids Res.*, 10:6475–6485) and polymerase chain reaction exponentially amplifying DNA in vitro using sequence specified oligonucleotides to incorporate selected changes (see *PCR Technology: Principles and Applications for DNA Amplification*, Erlich, (ed.) (1989); and Horton et al., supra).

Further, the antibodies may have their constant region domain modified, ie., the $C_L$, $CH_1$, hinge, $CH_2$, $CH_3$ and/or $CH_4$ domains of an antibody polypeptide chain may be deleted, inserted or changed (see EPO 327 378 A1 to Morrison et al., the Trustees of Columbia University; U.S. Pat. No. 4,642,334 to Moore et al., DNAX; and U.S. Pat. No. 4,704,692 to Ladner et al., Genex). Once a final construct is obtained, the composite Hum4 $V_L$, $V_H$ antibodies may be produced in large quantities by injecting the host cell into the peritoneal cavity of pristane-primed mice, and after an appropriate time (about 1–2 weeks), harvesting ascites fluid from the mice, which yields a very high titer of homogeneous composite Hum4 $V_L$, $V_H$ antibodies, and isolating the composite Hum4 $V_L$, $V_H$ antibodies by methods well known in the art (see Stramignoni et al. (1983), *Intl. J. Cancer,* 31:543–552). The host cell are grown in vivo, as tumors in animals, the serum or ascites fluid of which can provide up to about 50 mg/mL of composite Hum4 $V_L$, $V_H$ antibodies. Usually, injection (preferably intraperitoneal) of about $10^6$ to $10^7$ histocompatible host cells into mice or rats will result in tumor formation after a few weeks. It is possible to obtain the composite Hum4 $V_L$, $V_H$ antibodies from a fermentation culture broth of procaryotic and eucaryotic cells, or from inclusion bodies of *E. coli* cells (see Buckholz and Gleeson (1991), BIO/TECHNOLOGY, 9:1067–1072. The composite Hum4 $V_L$, $V_H$ antibodies can then be collected and processed by well-known methods (see generally, *Immunological Methods*, vols. I & II, eds. Lefkovits, I. and Pernis, B., (1979 & 1981) Academic Press, New York, N.Y.; and *Handbook of Experimental Immunology*, ed. Weir, D., (1978) Blackwell Scientific Publications, St. Louis, Mo.).

The composite Hum4 $V_L$, $V_H$ antibodies can then be stored in various buffer solutions such as phosphate buffered saline (PBS), which gives a generally stable antibody solution for further use.

Uses While it is possible for an antibody or fragment thereof to be administered alone—i.e. because they bear human $C_H$ regions and will thus exert effector functions including complement mediated cytotoxicity and antibody dependent cell-mediated cytotoxicity—it is preferable to present it as a pharmaceutical formulation. The active ingredient may comprise, for topical administration, from 0.001% to 10% w/w, e.g., from 1% to 2% by weight of the formulation, although it may comprise as much as 10% w/w but preferably not in excess of 5% w/w and more preferably from 0.1% to 1% w/w of the formulation.

The topical formulations of the present invention, comprise an active ingredient together with one or more acceptable carrier(s) therefor and optionally any other therapeutic ingredients(s). The carrier(s) must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

Kits according to the present invention include frozen or lyophilized humanized antibodies or humanized antibody fragments to be reconstituted, respectively, by thawing (optionally followed by further dilution) or by suspension in a (preferably buffered) liquid vehicle. The kits may also include buffer and/or excipient solutions (in liquid or frozen form)—or buffer and/or excipient powder preparations to be reconstituted with water—for the purpose of mixing with the humanized antibodies or humanized antibody fragments to produce a formulation suitable for administration. Thus, preferably the kits containing the humanized antibodies or humanized antibody fragments are frozen, lyophilized, pre-diluted, or pre-mixed at such a concentration that the addition of a predetermined amount of heat, of water, or of a solution provided in the kit will result in a formulation of sufficient concentration and pH as to be effective for in vivo or in vitro use in the treatment or diagnosis of cancer. Preferably, such a kit will also comprise instructions for reconstituting and using the humanized antibody or humanized antibody fragment composition to treat or detect cancer. The kit may also comprise two or more component parts for the reconstituted active composition. For example, a second component part—in addition to the humanized antibodies or humanized antibody fragments—may be bifunctional chelant, bifunctional chelate, or a therapeutic agent such as a radionuclide, which when mixed with the humanized antibodies or humanized antibody fragments forms a conjugated system therewith. The above-noted buffers, excipients, and other component parts can be sold separately or together with the kit.

It will be recognized by one of skill in the art that the optimal quantity and spacing of individual dosages of a humanized antibody or humanized antibody fragment of the invention will be determined by the nature and extent of the condition being treated, the form, route and site of administration, and the particular animal being treated, and that such optima can be determined by conventional techniques. It will also be appreciated by one of skill in the art that the optimal course of treatment, i.e., the number of doses of an antibody or fragment thereof of the invention given per day for a defined number of days, can be ascertained by those skilled in the art using conventional course of treatment determination tests.

The subject humanized antibodies may also be administered in combination with other anti-cancer agents, e.g., other antibodies or drugs. Also, the subject humanized antibodies or fragments may be directly or indirectly attached to effector moieties having therapeutic activity. Suitable effector moieties include by way of example cytokines (IL-2, TNF, interferons, colony stimulating factors, IL-1, etc.), cytotoxins (Pseudomonas exotoxin, ricin, abrin, etc.), radionuclides, such as $^{90}$Y, $^{131}$I, $^{99m}$Tc, $^{111}$In, $^{125}$I, among others, drugs (methotrexate, daunorubicin, doxorubicin, etc.), immunomodulators, therapeutic enzymes (e.g., beta-galactosidase), anti-proliferative agents, etc. The attachment of antibodies to desired effectors is well known. See, e.g., U.S. Pat. No. 5,435,990 to Cheng et al. Moreover, bifunctional linkers for facilitating such attachment are well known and widely available. Also, chelators (chelants and chelates) providing for attachment of radionuclides are well known and available.

The composite Hum4 $V_L$, $V_H$ antibodies provide unique benefits for use in a variety of cancer treatments. In addition to the ability to bind specifically to malignant cells and to localize tumors and not bind to normal cells such as fibroblasts, endothelial cells, or epithelial cells in the major organs, the composite Hum4 $V_L$, $V_H$ antibodies may be used to greatly minimize or eliminate HAMA responses thereto. Moreover, TAG-72 contains a variety of epitopes and thus it may be desirable to administer several different composite Hum4 $V_L$, $V_H$ antibodies which utilize a variety of $V_H$ in combination with Hum4 $V_L$. Specifically, the composite Hum4 $V_L$, $V_H$ antibodies are useful for, but not limited to, in vivo and in vitro uses in diagnostics, therapy, imaging and biosensors.

The composite Hum4 $V_L$, $V_H$ antibodies may be incorporated into a pharmaceutically acceptable, non-toxic, sterile carrier. Injectable compositions of the present invention may be either in suspension or solution form. In solution form the complex (or when desired the separate components) is dissolved in a pharmaceutically acceptable carrier. Such carriers comprise a suitable solvent, preservatives such as benzyl alcohol, if needed, and buffers. Useful solvents include, for example, water, aqueous alcohols, glycols, and phosphonate or carbonate esters. Such aqueous solutions generally contain no more than 50 percent of the organic solvent by volume.

Injectable suspensions require a liquid suspending medium, with or without adjuvants, as a carrier. The suspending medium can be, for example, aqueous polyvinylpyrrolidone, inert oils such as vegetable oils or highly refined mineral oils, or aqueous carboxymethylcellulose. Suitable physio-logically-acceptable adjuvants, if necessary to keep the complex in suspension, may be chosen from among thickeners such as carboxymethylcellulose, polyvinylpyrrolidone, gelatin and the alginates. Many surfactants are also useful as suspending agents, for example, lecithin, alkylphenol, polyethylene oxide adducts, naphthalenesulfonates, alkylbenzenesulfonates, and the polyoxyethylene sorbitan esters. Many substances which effect the hydrophobicity, density, and surface tension of the liquid suspension medium can assist in making injectable suspensions in individual cases. For example, silicone antifoams, sorbitol, and sugars are all useful suspending agents.

Methods of preparing and administering conjugates of the composite Hum4 $V_L$, $V_H$ antibody, and a therapeutic agent are well known or readily determined. Moreover, suitable dosages will depend on the age and weight of the patient and the therapeutic agent employed and are well known or readily determined.

Conjugates of a composite Hum4 $V_L$, $V_H$ antibody and an imaging marker may be administered in a pharmaceutically effective amount for the in vivo diagnostic assays of human carcinomas, or metastases thereof, in a patient having a tumor that expresses TAG-72 and then detecting the presence of the imaging marker by appropriate detection means.

Administration and detection of the conjugates of the composite Hum4 $V_L$, $V_H$ antibody and an imaging marker, as well as methods of conjugating the composite Hum4 $V_L$, $V_H$ antibody to the imaging marker are accomplished by methods readily known or readily determined. The dosage of such conjugate will vary depending upon the age and weight of the patient. Generally, the dosage should be effective to visualize or detect tumor sites, distinct from normal tissues. Preferably, a one-time dosage will be between 0.1 mg to 200 mg of the conjugate of the composite Hum4 $V_L$ antibody and imaging marker per patient.

Examples of imaging markers which can be conjugated to the composite Hum4 $V_L$ antibody are well known and include substances which can be detected by diagnostic imaging using a gamma scanner or hand held gamma probe, and substances which can be detected by nuclear magnetic resonance imaging using a nuclear magnetic resonance spectrometer.

Suitable, but not limiting, examples of substances which can be detected using a gamma scanner include $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re, $^{188}$Re and $^{99m}$Tc. An example of a substance which can be detected using a nuclear magnetic resonance spectrometer is gadolinium.

Conjugates of a composite Hum4 $V_L$, $V_H$ antibodies and a therapeutic agent may be administered in a pharmaceutically effective amount for the in vivo treatment of human carcinomas, or metastases thereof, in a patient having a tumor that expresses TAG-72. A "pharmaceutically effective amount" of the composite Hum4 $V_L$ antibody means the amount of said antibody (whether unconjugated, i.e., a naked antibody, or conjugated to a therapeutic agent) in the pharmaceutical composition should be sufficient to achieve effective binding to TAG-72.

Exemplary naked antibody therapy includes, for example, administering heterobifunctional composite Hum4 $V_L$, $V_H$ antibodies coupled or combined with another antibody so that the complex binds both to the carcinoma and effector cells, e.g., killer cells such as T cells, or monocytes. In this method, the composite Hum4 $V_L$ antibody-therapeutic agent conjugate can be delivered to the carcinoma site thereby directly exposing the carcinoma tissue to the therapeutic agent. Alternatively, naked antibody therapy is possible in which antibody dependent cellular cytoxicity or complement dependent cytotoxicity is mediated by the composite Hum4 $V_L$ antibody.

Examples of the antibody-therapeutic agent conjugates which can be used in therapy include antibodies coupled to radionuclides, such as $^{311}$I, $^{90}$Y, $^{105}$Rh $^{47}$Sc, $^{67}$Cu, $^{212}$Bi, $^{211}$At, $^{67}$Ga, $^{125}$I, $^{186}$Re, $^{188}$Re, $^{177}$Lu, $^{99m}$Tc, $^{153}$Sm, $^{123}$I and $^{111}$In; to drugs, such as methotrexate, adriamycin; to biological response modifiers, such as interferon and to toxins, such as ricin.

Methods of preparing and administering conjugates of the composite Hum4 $V_L$, $V_H$ antibodies and a therapeutic agent are well known or readily determined. The pharmaceutical composition may be administered in a single dosage or multiple dosage form. Moreover, suitable dosages will depend on the age and weight of the patient and the therapeutic agent employed and are well known or readily determined.

Composite Hum4 $V_L$, $V_H$ antibodies, and particularly composite Hum4 $V_L$, $V_H$ single chain antibodies thereof, are particularly suitable for radioimmunoguided surgery (RIGS). In RIGS, an antibody labeled with an imaging marker is injected into a patient having a tumor that expresses TAG-72. The antibody localizes to the tumor and is detected by a hand-held gamma detecting probe (GDP). The tumor is then excised (see Martin et al. (1988), *Amer. J. Surg.*, 156:386–392; and Martin et al. (1986), *Hybridoma*, 5:S97–S108). An exemplary GDP is the Neoprobe™ scanner, commercially available from Neoprobe Corporation, Columbus, Ohio. The relatively small size and human character of the composite Hum4 $V_L$, $V_H$ single chain antibodies will accelerate whole body clearance and thus reduce the waiting period after injection before surgery can be effectively initiated.

Administration and detection of the composite Hum4 $V_L$, $V_H$ antibody-imaging marker conjugate may be accomplished by methods well known or readily determined.

The dosage will vary depending upon the age and weight of the patient, but generally a one time dosage of 0.1 mg to 200 mg of the composite Hum4 $V_L$ antibody-marker conjugate per patient is administered.

EXAMPLES

The following nonlimiting examples are merely for illustration of the construction and expression of composite Hum4 $V_L$, $V_H$ antibodies. All temperatures not otherwise indicated are Centigrade. All percents not otherwise indicated are by weight.

Example 1

Figure 6:
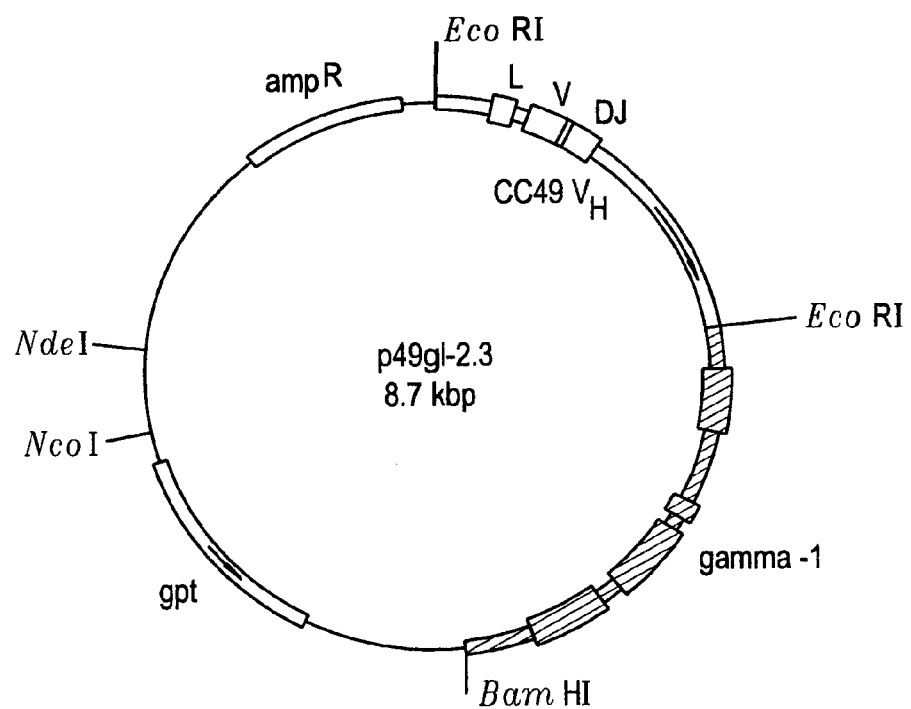
FIG. 6 illustrates the plasmid map of p49 g1–2.3.
Figure 7:
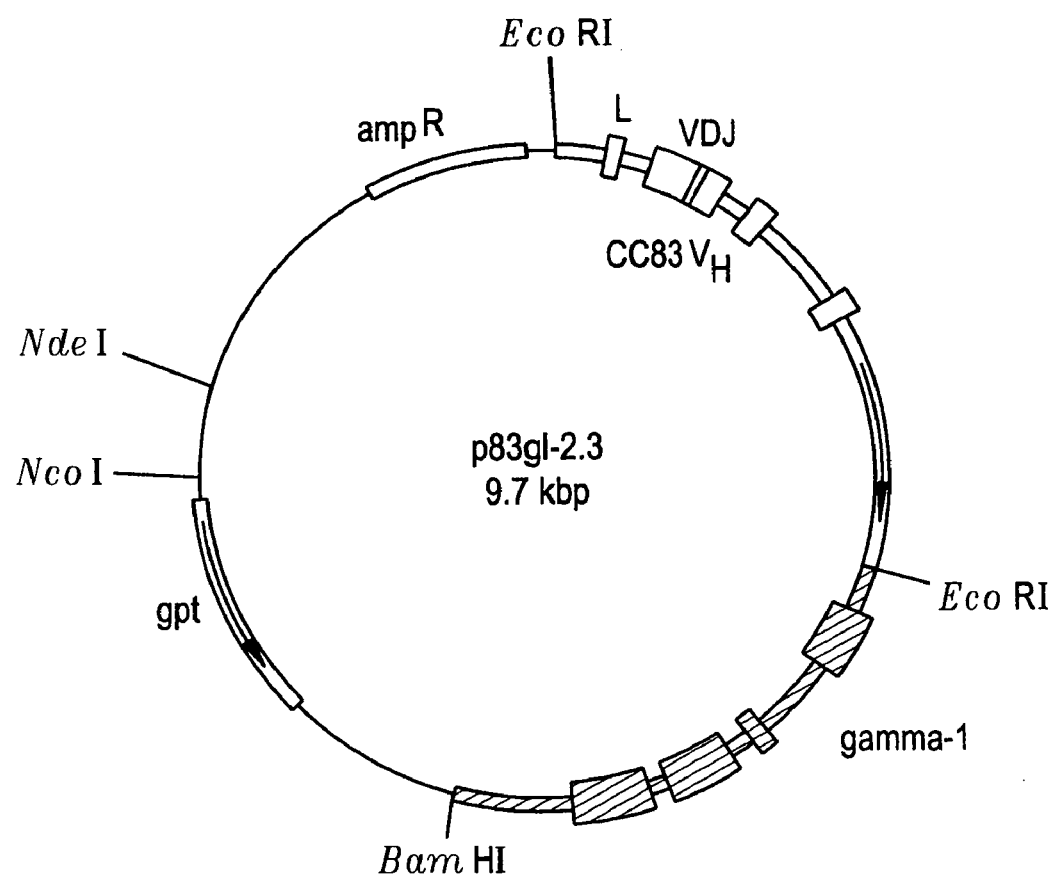
FIG. 7 illustrates the plasmid map of p83 g1–2.3.

CC49 and CC83 were isolated from their respective hybridomas using pNP9 as a probe (see FIG. 5). CC49 $V_H$ was obtained from p49 g1–2.3 (see FIG. 6) and CC83 $V_H$ was obtained from p83 g1–2.3 (see FIG. 7), following the procedures set forth in EPO 0 365 997.

DNA encoding an antibody light chain was isolated from a sample of blood from a human following the protocol of Madisen et. al. (1987), *Am. J. Med. Genet.*, 27:379–390), with several modifications. Two 5 mL purple-cap Vacutainer tubes (containing EDTA as an anticoagulant) were filled with blood and stored at ambient temperature for 2 hours. The samples were transferred to two 4.5 mL centrifuge tubes. To each tube was added 22.5 mL of filter-sterilized erythrocycte lysate buffer (0.155 M NH$_4$Cl and 0.17 M Tris, pH 7.65, in a volume ratio of 9:1), and incubated at 37° C. for 6.5 minutes The tubes became dark red due to the lysed red blood cells. The samples were centrifuged at 9° C. for 10 minutes, using an SS-34 rotor and a Sorvall centrifuge at 5,300 revolutions per minute (rpm) (~3,400×g). The resulting white cell pellets were resuspended in 25 mL of 0.15 M NaCl solution. The white blood cells were then centrifuged as before. The pellets were resuspended in 500 µL of 0.15 M NaCl and transferred to 1.5 mL microcentrifuge tubes. The cells were pelleted again for 3 minutes, this time in the microcentrifuge at 3,000 rpm. Very few red blood cells remained on the pellet. After the supernatants were decanted from the 2 microcentrifuge tubes, 0.6 mL high TE buffer (100 mM Tris, pH 8.0) was added. The tubes were hand-shaken for between 10 and 15 minutes. The resulting viscous solution was extracted with phenol, phenolchloroform and finally with just chloroform as described in Sambrook et al., supra. To 3.9 mL of pooled extracted DNA solution were added 0.4 mL NaOAc (3 M, pH 5), and 10 mL 100 percent ethanol. A white stringy precipitate was recovered with a yellow pipette tip, transferred into a new Eppendorf tube, washed once with 70 percent ethanol, and finally washed with 100 percent ethanol. The DNA was dried in vacuo for 1 minute and dissolved in 0.75 mL deionized water. A 20 µL aliquot was diluted to 1.0 mL and the OD 260 nm value was measured and recorded. The concentration of DNA in the original solution was calculated to be 0.30 mg/mL.

Oligonucleotides (oligos) were synthesized using phosphoramidite chemistry on a 380A DNA synthesizer (Applied Biosystems, Foster, Calif.) starting on 0.2 µM solid support columns. Protecting groups on the final products were removed by heating in concentrated ammonia solution at 55° C. for 12 hours. Crude mixtures of oligonucleotides (approximately 12 OD 260 nm units) were applied to 16 percent polyacrylamideurea gels and electrophoresed. DNA in the gels was visualized by short wave UV light. Bands were cut out and the DNA eluted by heating the gel pieces to 65° C. for 2 hours. Final purification was achieved by application of the eluted DNA solution onto C-18 Sep-Pac™ columns (Millipore) and elution of the bound oligonucleotide with a 60 percent methanol solution. The pure DNA was dissolved in deionized, distilled water (ddH$_2$O) and quantitated by measuring OD 260 nm.

A GeneAmp™ DNA amplification kit (Cetus Corp., Emeryville, Calif.) was used to clone the Hum4 $V_L$ germline gene by the polymerase chain reaction (PCR), which was set up according to the manufacturer's directions. A thermal cycler was used for the denaturation (94° C.), annealing (45° C.) and elongation (72° C.) steps. Each of the three steps in a cycle was carried out for 4 minutes; there was a total of 30 cycles.

Upstream of the regulatory sequences in the Hum4 $V_L$ germline gene, there is a unique Cla I restriction enzyme site. Therefore, the 5' end oligonucleotide for the PCR, called HUMVL(+) (FIG. 8), was designed to include this Cla I site.

FIG. 9 shows the human J4 (HJ4) amino acid and DNA sequences. The first two amino acids (Leu-Thr) complete the CDR3 region, the remainder make up the FR4 region. Glu is underlined in HJ4 because in CC49 J5 a somatic mutation had occured in this codon converting GAG (for Glu) to GTG (for Val). The (↓) indicates the slice site and the beginning of the intron between the J and Cκ exons. DNA sequences underlined in HJ4 represent parts of the sequence used for the 3' end PCR oligo.

FIG. 10 is the DNA and amino acid sequence of Hum4 $V_L$ in human/chimeric CC49H and CC83H. Specifically, the figure shows the entire DNA sequence of the Hum4 $V_L$ gene Cla I-Hind III segment in pRL1001, clone #2. A single base difference occured at position 3461 and is marked by an asterik (*). The corresponding amino acid sequences in the coding exons are shown. The site of the Leu Pro mutation in clone #7 is boxed. An arrow (↑) indicates the site of the single base deletion in clone #11. The coding strand is underlined to designate the sites used for hybridization of complementary oligonucleotide primers. In order the primers occur from the 5' end as follows: HUMLIN1(−); HUMLIN2(−); HUMLCDR1(−) and Hind III Cκ(−) (not shown).

Figure 11:
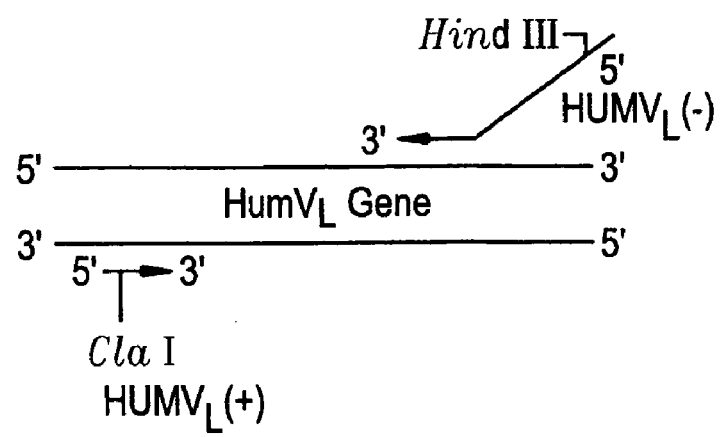
FIG. 11 illustrates a schematic representation of the human germline Subgroup IV $V_L$ gene (Hum4 $V_L$), as the target for the PCR.

The 3' end oligonucleotide, called HUMVL(−) (FIG. 8), contained a unique Hind III site; sufficient mouse intron sequence past the splicing site to permit an effective splice donor function; a human J4 sequence contiguous with the 3' end of the $V_L$ exon of Hum4 $V_L$ to complete the CDR3 and FR4 sequences of the $V_L$ domain (see FIGS. 9 and 10); nucleotides to encode a tyrosine residue at position 94 in CDR3; and 29 nucleotides close to the 3' end of the $V_L$ exon of Hum4 $V_L$ (shown underlined in the oligonucleotide HUMVL(−) in FIG. 8) to anneal with the human DNA target. In total, this 3' end oligonucleotide for the PCR was 98 bases long with a non-annealing segment (a "wagging tail") of 69 nucleotides. A schematic of the Hum4 $V_L$ gene target and the oligonucleotides used for the PCR are shown in FIG. 11. A 5' end oligo (HUMV$_L$(+)) and the 3'-end oligo (HUMV$_L$(−)) used to prime the elongation reactions for Taq polymerase and the target Hum4 $V_L$ gene are shown.

A PCR reaction was set up with 1 µg of total human DNA in a reaction volume of 100 µL. Primers HUMVL(−) and HUMVL(+) were each present at an initial concentration of 100 pmol. Prior to the addition of Taq polymerase (2.5 units/reaction) 100 µLs of mineral oil were used to overlay the samples. Control samples were set up as outlined below. The samples were heated to 95° C. for 3 minutes. When the PCR was complete, 20 µL samples were removed for analysis by agarose gel electrophoresis.

Based on the known size of the Hum4 $V_L$ DNA fragment to be cloned, and the size of the oligonucleotides used to target the gene, a product of 1099 bp was expected. A band corresponding to this size was obtained in the reaction (shown in lane 7, FIG. 12).

To prepare a plasmid suitable for cloning and subsequently expressing the Hum4 $V_L$ gene, the plasmid pSV2neo was obtained from ATCC and subsequently modified. pSV2neo was modified as set forth below (see FIG. 13).

The preparation of pSV2neo-101 was as follows. Ten micrograms of purified pSV2neo were digested with 40 units of Hind III at 37° C. for 1 hour. The linearized plasmid DNA was precipitated with ethanol, washed, dried and dissolved in 10 µL of water. Two microliters each of 10 mM dATP, dCTP, dGTP and dTTP were added, as well as 2 µL of 10× ligase buffer (Stratagene, La Jolla, Calif.). Five units (1 µL) of DNA polymerase I were added to make blunt the Hind III sticky ends. The reaction mixture was incubated at room temperature for 30 minutes. The enzyme was inactivated by heating the mixture to 65° C. for 15 minutes. The reaction mixture was then phenol extracted and ethanol precipitated into a pellet. The µL pellet was dissolved in 20 µL deionized, distilled water. A 2 pL aliquot (ca. 1 µg) was then added to a standard 20 µL ligation reaction, and incubated overnight at 4° C.

Competent *E. coli* DH1 cells (Invitrogen) were transformed with 1 µL and 10 µL aliquots of a ligation mix (Invitrogen, San Diego, Calif.) according to the manufacturer's directions. Ampicillin resistant colonies were obtained on LB plates containing 100 µg/mL ampicillin. Selected clones grown in 2.0 mL overnight cultures were prepared, samples of plasmid DNA were digested with Hind III and Bam HI separately, and a correct representative clone selected.

The resulting plasmid pSV2neo-101 was verified by size mapping and the lack of digestion with Hind III.

A sample of DNA (10 µg) from pSV2neo-101 mini-lysate was prepared by digesting with 50 units of Bam HI at 37° C. for 2 hours. The linearized plasmid was purified from a 4 percent polyacrylamide gel by electroelution. The DNA ends were made blunt by filling in the Bam HI site using dNTPs and Klenow fragment, as described earlier for the Hind III site of pSV2 neo-101.

Figure 14:
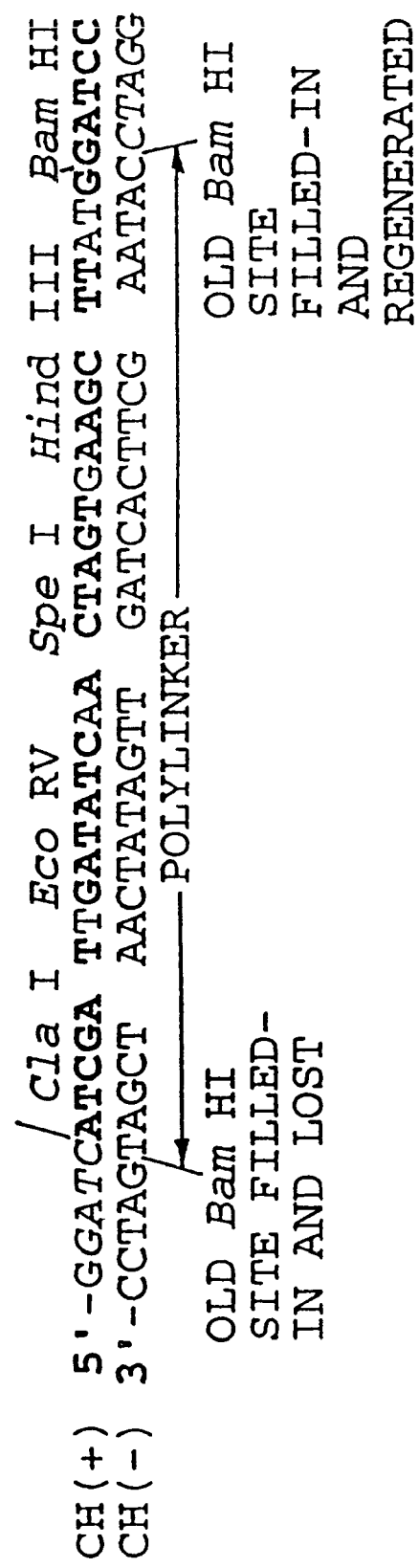
FIG. 14 illustrates a polylinker segment made by synthesizing two oligonucleotides: CH(+) and CH(−).

A polylinker segment containing multiple cloning sites was incorporated at the Bam HI site of pSV2neo-101 to create pSV2neo-102, as shown in FIG. 14. The arrow (←) indicates the direction of the Eco RI site in the vector. Note that the polylinker could be inserted in both orientations such that the Bam HI site on the left side could also be regenerated. The nucleotides used to fill-in the Bam HI site are shown in italics. The top synthetic oligo was called (CH(+) while the complimentary strand was CH(−). Equimolar amounts of two oligonucleotides, CH(+) and CH(−) (shown in FIG. 14) were annealed by heating for 3 minutes at 90° C. and cooling to 50° C. Annealed linker DNA and blunt ended pSV2neo-101 were added, in a 40:1 molar volume, to a standard 20 µL ligation reaction. *E. coli* DH1 (Invitrogen) was transformed with 0.5 µL and 5 µL aliquots of the ligation mixture (Invitrogen). Twelve ampicillin resistant colonies were selected for analysis of plasmid DNA to determine whether the linker had been incorporated.

A Hind III digest of mini-lysate plasmid DNA revealed linker incorporation in six of the clones. The plasmid DNA from several clones was sequenced, to determine the number of linker units that were blunt-end ligated to pSV2neo-101 as well as the relative orientation(s) with the linker. Clones for sequencing were selected on the basis of positive digestion with Hind III.

A Sequenase™ sequencing kit (United States Biochemical Corp, Cleveland, Ohio) was used to sequence the DNA. A primer, NEO102SEQ, was used for sequencing and is shown in FIG. 15. It is complementary to a sequence located upstream from the BamHI site in the vector. The Bam HI site where the polylinker was inserted in pSV2neo-101 is boxed. Between 3 µg and 5 µg of plasmid DNA isolated from *E. coli* mini-lysates were used for sequencing. The DNA was denatured and precipitated prior to annealing, as according to the manufacturer's instructions. Electrophoresis was carried out at 1500 volts; gels were dried prior to exposure to Kodak X-ray film. Data was processed using a DNASIS™ computer program (Hitachi).

Figure 16:
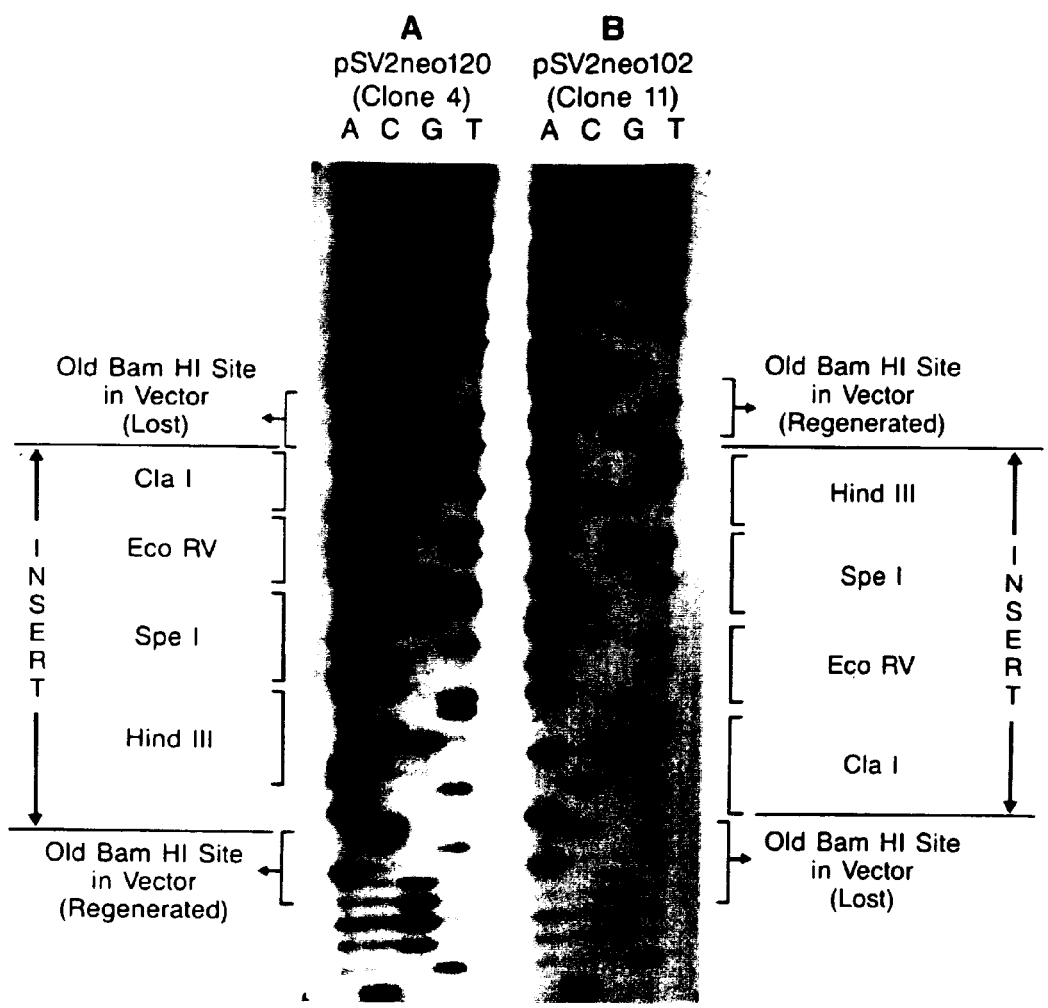
FIG. 16 illustrates an autoradigram depicting the DNA sequence of the polylinker region in pSV2neo-102.

From the DNA sequence data of 4 clones analyzed (see photograph of autoradiogram representing the sequence data of 2 of these clones—FIG. 16, reading the sequence (going up) is in the 5' to 3' direction of the (+) strand), compared to the expected sequence in FIG. 14, two clones having the desired orientation were obtained. In both cases a single 30-base linker unit was incorporated, but in opposite orientations. The panel A-sequence resulted in pSV2neo-120; and the panel B sequence resulted in pSV2neo-102. A representative clone was selected and designated pSV2neo-102.

A human Cκ gene was inserted into pSV2neo-102 to form pRL1000. The human Cκ DNA was contained in a 5.0 kb Hind III-Bam HI fragment (see Hieter et al. (1980), *Cell*, 22:197–207).

A 3 μg sample of DNA from a mini-lysate of pSV2neo-102 was digested with Bam HI and Hind III. The vector DNA was separated from the small Bam HI-Hind III linker fragment, generated in the reaction, by electrophoresis on a 3.75 percent DNA polyacrylamide gel. The desired DNA fragment was recovered by electroelution. A pBR322 clone containing the 5.0 kb Hind III-Bam HI fragment of the human Cκ gene (see Hieter et al., supra) was designated phumCκ. The 5.0 kb Hind III-Bam HI fragment was ligated with pSV2neo-102 and introduced into *E. coli* DH1 (Invitrogen). Ampicillin resistant colonies were screened and a clone containing the human Cκ gene was designated pRL1000.

Finally, pRL1000 clones were screened by testing mini-lysate plasmid DNA from *E. coli* with Hind III and Bam HI. A clone producing a plasmid which gave 2 bands, one at 5.8 kb (representing the vector) and the other at 5.0 kb (representing the human Cκ insert) was selected. Further characterization of pRL1000 was achieved by sequencing downstream from the Hind III site in the intron region of the human Cκ insert. The oligonucleotide used to prime the sequencing reaction was NEO102SEQ (see FIG. 15). Two hundred and seventeen bases were determined (see FIG. 17). A new oligonucleotide corresponding to the (−) strand near the Hind III site (shown in FIG. 17) was synthesized so that clones, containing the Hum4 $V_L$ gene that were cloned into the Cla I and Hind III sites in pRL1000 (see FIG. 13), could be sequenced.

A Cla I-Hind III DNA fragment containing Hum4 $V_L$ obtained by PCR was cloned into the plasmid vector pRL1000. DNA of pRL1000 and the Hum4 $V_L$ were treated with Cla I and Hind III and the fragments were gel purified by electrophoresis, as described earlier.

The pRL1000 DNA fragment and fragment containing Hum4 $V_L$ gene were ligated, and the ligation mixture used to transform *E. coli* DH1 (Invitrogen), following the manufacturer's protocol. Ampicillin resistant clones were screened for the presence of the Hum4 $V_L$ gene by restriction enzyme analysis and a representative clone designated pRL1001 (shown in FIG. 18). This is the expression vector to introduce the human anti-tumor L chain gene in Sp2/0 cells.

Figure 19:
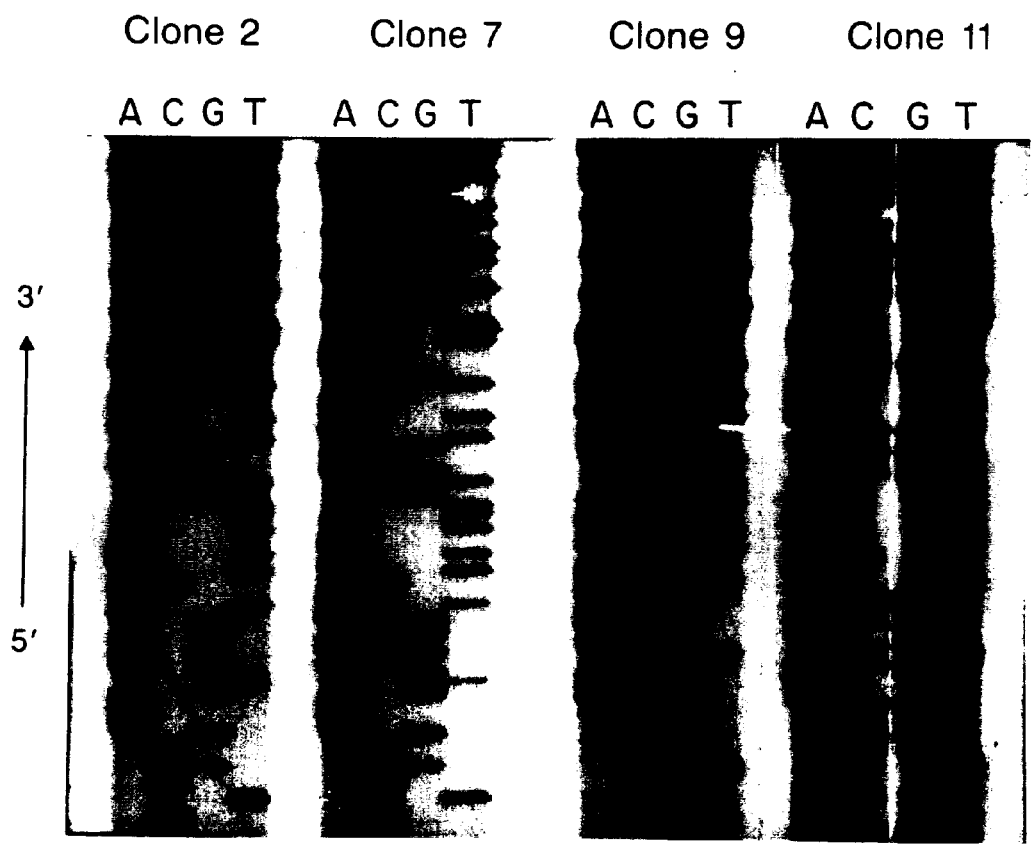
FIG. 19 illustrates an autoradiogram of DNA sequence for pRL1001 clones.

Four plasmids having the correct Cla I-Hind III restriction pattern were analyzed further by DNA sequencing of the insert region (see FIG. 19). Hind III Cκ (−) (shown by underlining on the plus strand to which it hybridizes in FIG. 17), HUMLIN1(−) (shown by underlining on the plus strand to which it hybridizes in FIG. 10), HUMLIN2(−) (shown by underlining on the plus strand to which it hybridizes in FIG. 10) and HUMLCDR1(−) (shown by underlining on the plus strand to which it hybridizes in FIG. 10) were used as the sequencing primers. Two out of the four plasmids analyzed had the expected sequence in the coding regions (FIG. 19, clones 2 and 9). The gel is read in the 5' to 3' direction on the (−) strand, from the Hind III Cκ (−) primer. Clones 2 and 9 were equivalent to the expected sequence, clone 7 had a single base base substitution (marked by *) and clone 11 had a single base deletion (marked by →).

Clone 2 was chosen and used for generating sufficient plasmid DNA for cell transformations and other analysis. This plasmid was used for sequencing through the Hum4 $V_L$, and the upstream region to the Cla I site. Only one change at nucleotide position 83 from a C to a G (FIG. 10) was observed, compared to a published sequence (Klobeck et al. (1985), supra). The DNA sequence data also indicates that the oligonucleotides used for PCR had been correctly incorporated into the target sequence.

A Biorad Gene Pulser™ apparatus was used to transfect Sp2/0 cells with linearized plasmid DNAs containing the light or heavy chain constructs. The Hum4 $V_L$ was introduced into Sp2/O cells along with corresponding heavy chains by the co-transfection scheme indicated in Table 1.

TABLE 1

| Cell Line | DNA Added | | |
|---|---|---|---|
| Designation | L Chain | H Chain | H Chain |
| MP1-44H | 20 μg | 15 μg | 0 μg |
| MP1-84H | 20 μg | 0 μg | 15 μg |

A total of $8.0 \times 10^6$ Sp2/0 cells were washed in sterile PBS buffer (0.8 mL at $1 \times 10^7$ viable cells/mL) and held on ice for 10 minutes. DNA of pRL1001, linearized at the Cla I site, and DNA of either p49 g1–2.3 or p83 g1–2.3, linearized at their respective Nde I sites, were added, in sterile PBS, to the cells (see protocol—Table 2) and held at 0° C. for a further 10 minutes. A single 200 volt, 960 μF electrical pulse lasting between 20 and 30 milliseconds was used for the electroporation. After holding the perturbed cells on ice for 5 minutes, 25 mL of RPMI medium with 10 percent fetal calf serum were introduced, and 1.0 mL samples aliquoted in a 24 well tissue culture plate. The cells were incubated at 37° C. in a 5 percent $CO_2$ atmosphere. After 48 hours, the media was exchanged with fresh selection media, now containing both 1 mg/mL Geneticin (G418) (Difco) and 0.3 μg/ml mycophenolic acid/gpt medium. Resistant cells were cultured for between 7 and 10 days.

Supernatants from wells having drug resistant colonies were tested on ELISA plates for activity against TAG-72. A roughly 10 percent pure TAG-72 solution prepared from LSI74T tumor xenograft cells was diluted 1:40 and used to coat flexible polyvinyl chloride microtitration plates (Dynatech Laboratories, Inc.). Wells were air-dried overnight, and blocked the next day with 1 percent BSA. Supernatant samples to be tested for anti-TAG-72 antibody were added to the washed wells and incubated for between 1 and 2 hours at 37° C. Alkaline phosphatase labeled goat anti-human IgG (diluted 1:250) (Southern Biotech Associates, Birmingham, Ala.) was used as the probe antibody. Incubation was for 1 hour. The substrate used was p-nitrophenylphosphate. Color development was terminated by the addition of 1.0 N NaOH. The plates were read spectrophotometrically at 405 nm and 450 nm, and the values obtained were 405 nm–450 nm.

Those samples producing high values in the assay were subcloned from the original 24 well plate onto 96 well plates. Plating was done at a cell density of half a cell per well (nominally 50 cells) to get pure monoclonal cell lines. Antibody producing cell lines were frozen down in media containing 10 percent DMSO.

Two cell lines were procured having the designations: MP1-44H and MP1-84H. MP1-44H has the chimeric CC49 g1 heavy chain with the Hum4 $V_L$ light chain; and MP1-84H has the chimeric CC83 g1 heavy chain with the Hum4 $V_L$ light chain.

A 1.0 L spinner culture of the cell line of the cell line MP1–44H was grown at 37° C. for 5 days for antibody production. The culture supernatant was obtained free of cells by centrifugation and filtration through a 0.22 micron filter apparatus. The clarified supernatant was passed over a Protein A cartridge (Nygene, N.Y.). Immunoglobulin was eluted using 0.1 M sodium citrate buffer, pH 3.0. The pH of the eluting fractions containing the antibody was raised to neutrality by the addition of Tris base, pH 9.0. The antibody-containing fractions were concentrated and passed over a Pharmacia Superose 12 HR 10/30 gel filtration column. A protein was judged to be homogeneous by SDS polyacrylamide gel electrophoresis. Isoelectric focusing further demonstrated the purity of MP1-44H.

The biological performance of the human composite antibody, MP1-44H, was evaluated by comparing immunohistochemistry results with two other anti-TAG-72 antibodies CC49 (ATCC No. HB 9459) and Ch44 (ATCC No. HB 9884). Sections of human colorectal tumor embedded in paraffin were tested with the three antibodies by methods familiar to those skilled in this art. All three antibodies gave roughly equivalent binding recognition of the tumor antigen present on the tumor tissue sample.

A further test of the affinity and biological integrity of the human composite antibody MP1-44H was a competition assay, based on cross-competing radioiodine-labeled versions of the antibody with CC49 and Ch44 in all combinations. From the data shown in FIG. 20, it is apparent that the affinity of all 3 antibodies is equivalent and can bind effectively to tumor antigen.

MP1-44H (ATCC HB 10426) and MP1-84H (ATCC HB 10427) were deposited at the American Type Culture Collection (ATCC). The contract with ATCC provides for permanent availability of the cell lines to the public on the issuance of the U.S. patent describing and identifying the deposit or the publications or upon the laying open to the public of any U.S. or foreign patent application, whichever comes first, and for availability of the cell line to one determined by the U.S. Commissioner of Patents and Trademarks to be entitled thereto according to 35 CFR §122 and the Commissioner's rules pursuant thereto (including 37 CFR §1.14 with particular reference to 886 OG 638). The assignee of the present application has agreed that if the cell lines on deposit should die or be lost or destroyed when cultivated under suitable conditions for a period of thirty (30) years or five (5) years after the last request, it will be promptly replaced on notification with viable replacement cell lines.

Example 2

Single-chain antibodies consist of a $V_L$, $V_H$ and a peptide linker joining the $V_L$ and $V_H$ domains to produce SCFVs. A single chain antibody, SCFV1, was constructed to have the Hum4 $V_L$ as V Domain 1 and CC49 $V_H$ as V Domain 2 (see FIG. 21).

The polypeptide linker which joins the two V domains was encoded by DNA introduced at the 3' end of the Hum4 $V_L$ DNA during a PCR. The oligonucleotides SCFV1a and SCFV2 were designed to obtain the DNA segment incorporating part of the yeast invertase leader sequence, the Hum4 $V_L$ and the SCFV linker.

The polypeptide linker for SCFV1 was encoded in oligonucleotide SCFV1b (see below). The underlined portions of the oligonucleotides SCFV1a and SCFV1b are complementary to sequences in the Hum4 $V_L$ and linker respectively. The sequences of SCFV1a and SCFV1b are as follows, with the hybridizing sequences underlined:

SCFV1a with the Hind III in bold:

5'-CTGCAAGCTTCCTTTTCCTTTTGGCTGGTTTTG

CAGCCAAAATATCTGCA<u>GACATCGTGATGACCCAGTC</u>-3'

SCFV1b with the Aat II site in bold:

5'-CGTAAGACGTCTAAGGAACGAAATTGGGCCAATTGTTCTGAGGA

<u>GACCGAACCTGACTCCTT</u>CACCTTGGTCCCTCCGCCG-3'

Figure 18:
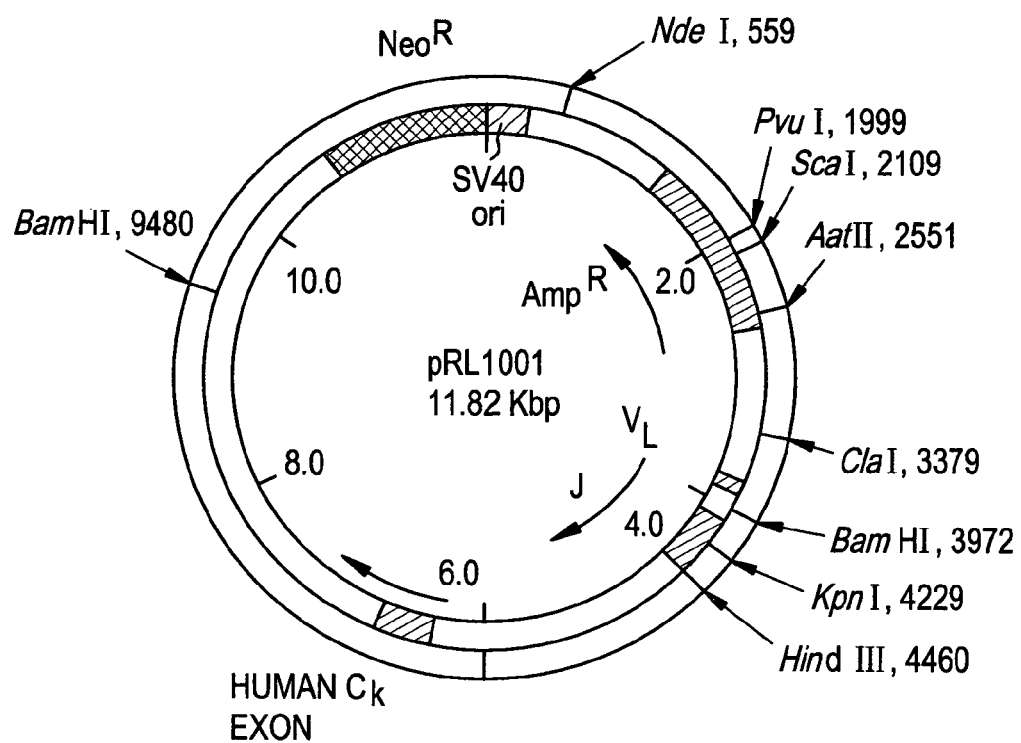
FIG. 18 illustrates the restriction enzyme map of pRL1001.

The target DNA in the PCR was pRL1001 (shown in FIG. 18). The PCR was performed pursuant to the teachings of Mullis et al., supra. A DNA fragment containing the Hum4 $V_L$-linker DNA component for the construction of SCFV1 was obtained and purified by polyacrylamide gel electrophoresis according to the teachings of Sambrook et al., supra.

p49 g1–2.3, containing CC49 $V_H$, was the target DNA in the PCR. PCR was performed according to the methods of Mullis et al., supra. The oligonucleotides used for the PCR of CC49 $V_H$ are as follows, with the hybridizing sequences underlined: SCFV1c, with the Aat II site in bold:

5'-<u>CTTAGACGTCCAGTTGCAGCAGTCTGACGC</u>-3'

SCFV1d, with the Hind III site in bold:

5'-GATC<u>AAGCTTCACTAGGAGACGGTGACTG-AGGTTCC</u>-3'

The purified Hum4 $V_L$-linker and $V_H$ DNA fragments were treated with Aat II (New England Biolabs, Beverly, Mass.) according to the manufacturer's protocol, and purified from a 5 percent polyacrylamide gel after electrophoresis. An equimolar mixture of the Aat II fragments was ligated overnight. The T4 DNA ligase was heat inactivated by heating the ligation reaction mixture at 65° C. for 10 minutes. Sodium chloride was added to the mixture to give a final concentration of 50 mM and the mixture was further treated with Hind III. A Hind III DNA fragment was isolated and purified from a 4.5 percent polyacrylamide gel and cloned into a yeast expression vector (see Carter et al. (1987), In: *DNA Cloning, A Practical Approach*, Glover (ed.) Vol III: 141–161). The sequence of the fragment, containing the contiguous SCFV1 construct, is set forth in FIG. 22.

The anti-TAG-72 SCFV1 described herein utilized the yeast invertase leader sequence (shown as positions −19 to −1 of FIG. 22), the Hum4 $V_L$ (shown as positions 1 to 113 of FIG. 22), an 18 amino acid linker (shown as positions 114 to 132 of FIG. 22) and CC49 $V_H$ (shown as positions 133 to 248 of FIG. 22).

The complete DNA and amino acid sequence of SCFV1 is given in FIG. 22. The oligonucleotides used to sequence the SCFV1 are set forth below.

TPI:
5'-CAATTTTTTGTTTGTATTCTTTTC-3'.

HUVKF3:
5'-CCTGACCGATTCAGTGGCAG-3'.

DC113:
5'-TCCAATCCATTCCAGGCCCTGTTCAGG-3'.

SUC2T:
5'-CTTGAACAAAGTGATAAGTC-3'.

Example 3

A plasmid, pCGS517 (FIG. 23), containing a prorennin gene was digested with Hind III and a 6.5 kb fragment was isolated. The plasmid pCGS517 has a triosephosphate isomerase promoter, invertase [SUC2] signal sequence, the prorennin gene and a [SUC2] terminator. The Hind III-digested SCFV1 insert obtained above (see FIG. 23) was ligated overnight with the Hind III fragment of pCGS517 using T4 DNA ligase (Stratagene, La Jolla, Calif.).

The correct orientation existed when the Hind III site of the insert containing part of the invertase signal sequence ligated to the vector DNA to form a gene with a contiguous signal sequence. E. coli DHI (Invitrogen) cells were transformed and colonies screened using a filter-microwave technique (see Buluwela, et al. (1989), Nucleic Acids Research, 17:452). From a transformation plate having several hundred colonies, 3 positive clones were obtained. Digesting the candidate plasmids with Sal I and Kpn I, each a single cutter, differentiated between orientations by the size of the DNA fragments produced. A single clone, PDYS-CFV1 (FIG. 23), had the correct orientation and was used for further experimentation and cloning. The probe used was derived from pRL1001, which had been digested with Kpn I and Cla I (see FIG. 18). The probe DNA was labeled with $^{32}$P a-dCTP using a random oligonucleotide primer labeling kit (Pharmacia LKB Biotechnology, Piscataway, N.J.).

The next step was to introduce the Bgl II-Sal 1 fragment from pDYSCFV1 into the same restriction sites of another vector (ca. 9 kb), which was derived from PCGS515 (FIG. 23), to give an autonomously replicating plasmid in S. cerevisiae.

DNA from the vector and insert were digested in separate reactions with Bgl II and Sal I using 10×buffer number 3 (50 MM Tris-HCI (pH 8.0), 100 mM NaCl, BRL). The DNA fragment from pDYSCFV1 was run in and electroeluted from a 5 percent polyacrylamide gel and the insert DNA was run and electroeluted from a 3.75 percent polyacrylamide gel. A standard ligation using T4 DNA ligase (Stratagene, La Jolla, Calif.) and a transformation using E. coli DH1 (Invitrogen) was carried out. Out of 6 clones selected for screening with Bgl II and Sal I, all 6 were correctly oriented, and one was designated pCGS515/SCFV1 (FIG. 23).

DNA sequencing of pCGS515/SCFVI DNA was done using a Sequenase™ kit (U.S. Biochemical, Cleveland, Ohio) using pCGS515/SCFV1 DNA. The results have been presented in FIG. 22 and confirm the sequence expected, based on the linker, the Hum4 $V_L$ and the CC49 $V_H$.

Transformation of yeast cells using the autonomously replicating plasmid pCGS515/SCFV1 was carried out using the lithium acetate procedures described in Ito et al. (1983), J. Bacteriol., 153:163–168; and Treco (1987), In: Curent Protocols in Molecular Biology, Ausebel et al. (eds), 2:13.71–13.7.6. The recipient strain of S. cerevisiae was CGY1284 having the genotype—MAT a (mating strain a), ura 3-52 (uracil auxotrophy), SSC1-1 (supersecreting 1), and PEP4$^+$ (peptidase 4 positive).

Transformed clones of CGY1284 carrying SCFV plasmids were selected by their ability to grow on minimal media in the absence of uracil. Transformed colonies appeared within 3 to 5 days. The colonies were transferred, grown and plated in YEPD medium. Shake flasks were used to provide culture supernatant with expressed product.

An ELISA procedure was used to detect biological activity of the SCFV1. The assay was set up such that the SCFV would compete with biotinylated CC49 (biotin-CC49) for binding to the TAG-72 antigen on the ELISA plate.

SCFV1 protein was partially purified from a crude yeast culture supernatant, using a Superose 12 gel filtration column (Pharmacia LKB Biotechnology), and found to compete with biotinylated CC49 in the competition ELISA. These results demonstrate that the SCFV1 had TAG-72 binding activity.

The SCFV1 protein was detected by a standard Western protocol (see Towbin et al. (1979), Proc. Natl. Acad. Sci., USA, 76:4350–4354). The detecting agent was biotinylated FAID14 (ATCC No. CRL 10256), an anti-idiotypic monoclonal antibody prepared from mice that had been immunized with CC49. A band was visualized that had an apparent molecular weight of approximately 26,000 daltons, the expected size of SCFV1. This result demonstrated that the SCFV1 had been secreted and properly processed.

Example 4

The following example demonstrates the cloning of human $V_H$ genes into a SCFV plasmid construct containing sequence coding for the Hum4 $V_L$ and a 25 amino acid linker called UNIHOPE.

A vector was prepared from plasmid pRW 83 containing a chloramphenicol resistance (Cam$^r$) gene for clone selection, and a penP gene with a penP promoter and terminator (see Mezes, et al. (1983), J. Biol. Chem., 258:11211–11218) and the pel B signal sequence (see Lei, et al. (1987), supra). The vector was designated Fragment A (see FIG. 24). The penP gene was removed with a Hind III/Sal I digest.

The penP promoter and pel B signal sequence were obtained by a PCR using pRW 83 as a template and oligonucleotides penP1 and penP2 as primers. The fragment was designated Fragment B (see FIG. 24). A Nco I enzyme restriction site was introduced at the 3' end of the signal sequence region by the penP2 oligonucleotide.

penP1:
5'-CGATAAGCTTGAATTCCATCACTTCC-3' penP2:
5'-GGCCATGGCTGGTTGGGCAGCGAGTAATAACAATCCAGCG GCT

GCCGTAGGCAATAGGTATTTCATCAAAATCGTCTCCCTCCGTTTGAA-3'

A SCFV comprised of a Hum4 $V_L$, a CC49 $V_H$, and an 18 amino acid linker (Lys Glu Ser Gly Ser Val Ser Ser Glu Gln Leu Ala Gln Phe Arg Ser Leu Asp) was obtained from pCGS515/SCFV1 by PCR using oligonucleotides penP3 and penP6. This fragment was designated Fragment D (see FIG. 24). A Bcl I site was introduced at the 3' end of the $V_H$ region by the penP6 oligonucleotide.

penP3:
5'-GCTGCCCAACCAGCCATGGCCGACATCGTGATGACCCAGTCTCC-3' penP6(-):
5'-CTCTTGATCACCAAGTGACTTTATGTAAGATGATGTTTTG ACG

GATTCATCGCAATGTTTTTATTTGCCGGAGACGGTGACTGAGGTTCC-3'

Fragments B and D were joined by PCR using oligonucleotides penP1 and penP6, following the procedures of Horton et al., supra. The new fragment was designated E (See FIG. 24).

Fragment C containing the penP termination codon was isolated by digesting pRW 83 with Bcl I and Sal I, and designated Fragment C. pRW 83 was isolated from *E. coli* strain GM161, which is DNA methylase minus or dam⁻. Plasmid PSCFV 31 (see FIG. 24) was created with a three part ligation Fragments A, C, and E.

The Nco I restriction enzyme site within the Camr gene and the Hind III site located at the 5' end of the penP promoter in pSCFV 31 were destroyed through a PCR DNA amplification using oligonucleotides Nco1.1 and Nco1.3(−) to generate an Eco RI-Nco I fragment and oligonucleotides Nco1.2 and Nco1.4c(−) to generate a Nco I to Eco RI fragment. These two fragments were joined by PCR-SOE using oligonucleotides Nco1.1 and Nco1.4c(−). The oligonucleotides are set forth below:

```
Nco1.1:
5'-TCCGGAATTCCGTATGGCAATGA-3'

Nco1.3(-):
5'-CTTGCGTATAATATTTGCCCATCGTGAAAACGGGGGC-3'

Nco1.2:
5'-ATGGGCAAATATTATACGCAAG-3'

Nco1.4c(-)
5'-CACTGAATTCATCGATGATAAGCTGTCAAACATGAG-3'
``` pSCFV 31 was digested with Eco RI and the larger fragment was isolated by polyacrylamide gel electrophoresis. To prevent self ligation, the DNA was dephosphorylated using calf intertinal alkaline phosphatase according to the teachings of Sambrook et al., supra.

A two part ligation of the larger pSCFV 31 digested fragment and the PCR-SOE fragment, described above, resulted in the creation of pSCFV 31b (see FIG. 25).

pSCFV 31b was digested with Nco I and Sal I and a fragment containing the Cam$^r$ gene was isolated.

The Hum4 $V_L$ was obtained by PCR DNA amplification using pCGS515/SCFV1 as a template and oligonucleotides 104BH1 and 104BH2(−) as primers.

```
104BH1:
5'-CAGCCATGGCCGACATCGTGATGACCCAGTCTCCA-3'

104BH2(-):
5'-AAGCTTGCCCCATGCTGCTTTAACGTTAGTTTTATCTGCTGG
AGACAGAGTGCCTTCTGCCTCCACCTTGGTCCCTCCGCCGAAAG-3'
```

The CC49 $V_H$ was obtained by PCR using p49 g1–2.3 (FIG. 5) as a template and oligonucleotides 104B3 and 104B4(−) as primers. A Nhe I enzyme restriction site was introduced just past the termination codon in the 3' end (before the Bcl I site) by oligonucleotide 104B4(−).

In the PCR which joined these two fragments using oligonucleotides 104BH1 and 104B4(−) as primers, a coding region for a 22 amino acid linker was formed.

A fragment C (same as above) containing the penP termination codon was isolated from pRW 83 digested with Bcl I and Sal I.

Plasmid pSCFV 33H (see FIG. 25) was created with a three part ligation of the vector, fragment C, and the SCFV fragment described above.

pSCFV 33H was digested with NcoI and NheI, and the DNA fragment containing the Cam$^r$ gene was isolated as a vector. Hum4 $V_L$ was obtained by PCR DNA amplification using pRL1001 (see FIG. 18) as a template and oligonucleotides UNIH1 and UNIH2(−) as primers. Oligonucleotides for the PCR were: UNIH1:
5'-CAGCCATGGCC GACATTGTGATGTCACAGTCTCC-3'

The Nco I site is in bold and the hybridizing sequence is underlined.

```
UNIH2(-)
5'-GAGGTCCGTAAGATCTGCCTCGCTACCTAGCAAA

AGGTCCTCAAGCTTGATCACCACCTTGGTCCCTCCGC-3'
```

The Hind III site is in bold.

The CC49 $V_H$ was obtained by a PCR using p49 g1–2.3 (see FIG. 6) as a template and oligonucleotides UNI3 and UNI4(−) as primers.

UNI3:
5'-AGCGAGGCAGATCTTACGGACCTCGAG GTTCAGTTGCAGCAGTCTGAC-3'.

The Xho I site is in bold and the hybridizing sequence is underlined.

UNI4(−):
5'-CATCGCTAGC TTTTTATGAGGAGACGGTGACTGAGGTTCC-3'.

The Nhe I site is in bold and the hybridizing sequence is underlined.

Oligonucleotides UNIH1 and UNI4(−) were used in the PCR-SOE amplification which joined the Hum4 $V_L$ and CC49 $V_H$ fragments and formed a coding region for a negatively charged fifteen amino acid linker. The DNA was digested with Nhe I and Nco I and ligated with the vector fragment from the Nco I-Nhe I digest of pSCFV 33H. The resultant plasmid was designated pSCFV UNIH (shown in FIG. 25).

With the construction of pSCFV UNIH, a universal vector for any SCFV was created with all the desired restriction enzyme sites in place.

pSCFV UNIH was digested with Hind III/Xho I, and the large DNA fragment containing the Cam$^r$ gene, Hum4 $V_L$ and CC49 $V_H$ was isolated.

A fragment coding for a 25 amino acid linker, was made by annealing the two oligonucleotides shown below. The

```
104B3:
5'-GTTAAAGCAGCATGGGCAAGCTTATGACTCAGTTGCAGCAGTCTGACGC-3'

104B4(-):
5'-CTCTTGATCACCAAGTGACTTTATGTAAGATGATGTTTTGACGGATTCATCGCTAGCTTTTTATTT

GCCATAATAAGGGGAGACGGTGACTGAGGTTCC-3'
``` linker UNIHOPE is based on 205C SCA™ linker (see Whitlow, (1990) *Antibody Engineering: New Technology and Application Implications*, IBC USA Conferences Inc, MA), but the first amino acid was changed from serine to leucine and the twenty-fifth amino acid were was changed from glycine to leucine, to accomodate the Hind III and Xho I restriction sites. The nucleotide sequence of the single chain portion of pSCFV Unihope H is shown in FIG. 26. Structural sequences are indicated by the amino acid sequence written above the DNA sequence. The symbols _ and _ indicate the beginning and end of a given segment. The amino acid sequence of the linker is boxed.

The nucleotide sequence encoding the linker UNIHOPE is set forth below:

UNIHOPE (FIG. 26):

```
UNIHOPE (FIG. 26):
5'-TATAAAGCTTAGTGCGGACGATGCGAAAAAGGATGCTGCGAAG

AAGGATGACGCTAAGAAAGACGATGCTAAAAAGGACCTCGAGTCTA-3'
```

UNIHOPE(-) (FIG. 26):

```
5'-TAGACTCGAGGTCCTTTTTAGCATCGTCTTTCTTAGCGTCAT
CCTTCTTCGCAGCATCCTTTTTCGCATCGTCCGCACTAAGCTTTATA-3'
```

Figure 27:
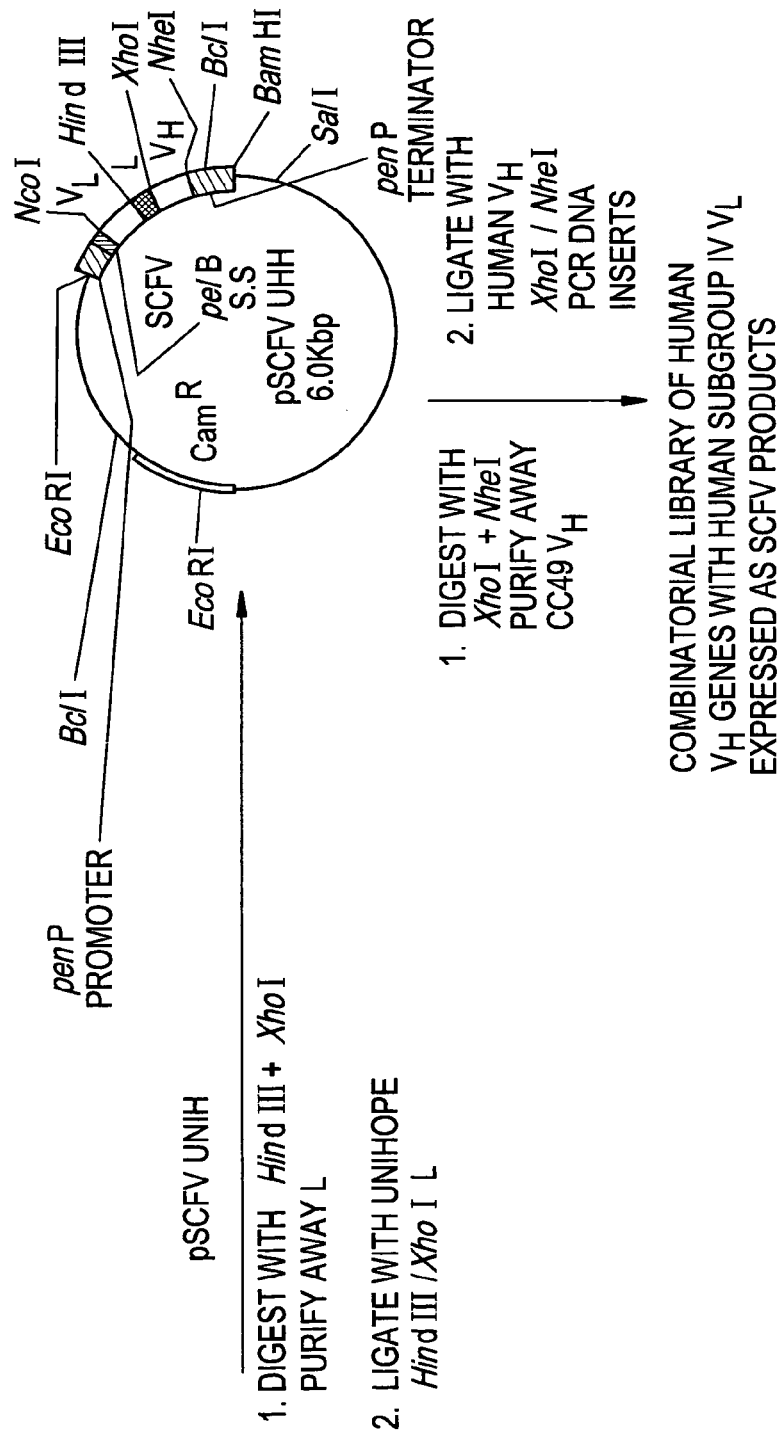
FIG. 27 shows the construction plasmid pSCFV UHH and a schematic of a combinatorial library of $V_H$ genes with Hum4 $V_L$.

The resulting strand was digested with Hind III/Xho I and ligated into the vector, thus generating the plasmid pSCFV UHH (shown in FIG. 27). Plasmid pSCFV UHH expresses a biologically active, TAG-72 binding SCFV consisting of the Hum4 $V_L$ and CC49 $V_H$. The expression plasmid utilizes the β-lactamase penP promoter, pectate lyase pelB signal sequence and the penP terminator region. Different immunoglobulin light chain variable regions can be inserted in the Nco I-Hind III restriction sites, different SCFV linkers can be inserted in the Hind III-Xho I sites and different immunoglobulin heavy chain variable regions can be inserted in the Xho I-Nhe I sites.

*E. coli* AGI (Stratagene) was transformed with the ligation mix, and after screening, a single chloramphenicol resistant clone, having DNA with the correct restriction map, was used for further work.

The DNA sequence and deduced amino acid sequence of the SCFV gene in the resulting plasmid are shown in FIG. 26.

*E. coli* AG1 containing pSCFV UHH were grown in 2 ml of LB broth with 20 μg/mL chloramphenicol (CAM 20). The culture was sonicated and assayed using a competition ELISA. The cells were found to produce anti-TAG-72 binding material. The competition assay was set up as follows: a 96 well plate was derivatized with a TAG-72 preparation from LS174T cells. The plate was blocked with 1% BSA in PBS for 1 hour at 31° C. and then washed 3 times. Twenty-five microliters of biotin CC49 (1/20,000 dilution of a 1 mg/mL solution) were added to the wells along with 25 μL of sample to be tested (competition step) and the plate was incubated for 30 minutes at 31° C. The relative amounts of TAG-72 bound to the plate, biotinylated CC49, streptavidin-alkaline phosphatase, and color development times were determined empirically in order not to have excess of either antigen or biotinylated CC49, yet have enough signal to detect competition by SCFV. Positive controls were CC49 at 5 μg/mL and CC49 Fab at 10 μL/mL. Negative controls were 1% BSA in PBS and/or concentrated LB. At the end of the competition step, unbound proteins were washed away.

Fifty microliters of a 1:1000 dilution of streptavidin conjugated with alkaline phosphatase (Southern Biotechnology Associates, Inc., Birmingham, Ala.) were added and the plate was incubated for 30 minutes at 31° C. The plate was washed 3 more times. Fifty microliters of a paranitrophenylphosphate solution (Kirkegaard & Perry Laboratories, Inc., Gaithersburg, Md.) were added and the color reaction was allowed to develop for a minimum of 20 minutes. The relative amount of SCFV binding was measured by optical density scanning at 405–450 nm using a microplate reader (Molecular Devices Corporation, Menlo Park, Calif.). Binding of the SCFV resulted in decreased binding of the biotinylated CC49 with a concomitant decrease in color development. The average value for triplicate test samples is shown in the table below:

| Sample (50 μL) (mixed 1:1 with CC49 Biotin) | OD 405 nm–OD 450 nm Value at 50 minutes |
|---|---|
| Sonicate *E. coli* AG1/pSCFVUHH clone 10 | 0.072 |
| Sonicate *E. coli* AG1/pSCFVUHH clone 11 | 0.085 |
| CC49 at 5 mg/mL | 0.076 |
| CC49 Fab at 10 mg/mL | 0.078 |
| LB (negative control) | 0.359 |

The data indicates that there was anti-TAG-72 activity present in the *E. coli* AGI/pSCFVUHH clone sonicate.

Example 5

The plasmid pSCFVUHH may be used to host other $V_H$ genes on Xho I-Nhe I fragments and test in a SCFV format, following the procedures set forth below. A schematic for this process is shown in FIG. 31.

Isolating Total RNA from Peripheral Blood Lymphocytes:

Blood from a normal, healthy donor is drawn into three 5 mL purple-cap Vacutainer tubes. Seven mL of blood are added to two 15 mL polypropylene tubes. An equal volume of lymphoprep (cat# AN5501, Accurate) is added and the solution is mixed by inversion. Both tubes are centrifuged at 1000 rpm and 18° C. for 20 minutes. The resulting white area near the top of the liquid (area not containing red blood cells) is removed from each sample and placed into two sterile polypropylene centrifuge tube. Ten mL of sterile PBS are added and the tube mixed by inversion. The samples are centrifuged at 1500 rpm and 18° C. for 20 minutes Total RNA is isolated from resulting pellet according to the RNAzol B Method (Chomczynski and Sacchi (1987), *Analytical Biochemistry*, 162:156–159). Briefly, the cell pellets are lysed in 0.4 mL RNAzol solution (cat#:CS-105, Cinna/Biotecx). RNA is solubilized by passing the cell pellet through a 1 mL pipet tip. Sixty μL of chloroform are added and the solution is shaken for 15 seconds. RNA solutions are then placed on ice for 5 minutes. Phases are separated by centrifugation at 12000×g and 4° C. for 15 minutes. The upper (aqueous) phases are transferred to fresh RNase-free microcentrifuge tubes. One volume of isopropanol is added and the samples placed at −20° C. for 1 hour. The samples are then placed on dry ice for 5 minutes and finally centrifuged for 40 seconds at 14,000×g and 4° C. The resulting supernatant is removed from each sample and the pellet is dissolved in 144 µL of sterile RNase-free water. Final molarity is brought to 0.2 in NaCl. The DNA is reprecipitated by adding 2 volumes of 100% ethanol, leaving on dry ice for 10 minutes, and centrifugation at 14,000 rpm and 4° C. for 15 minutes. The supernatants are then removed, the pellets washed with 75% ethanol and centrifuged for 8 minutes at 12000×g and 4° C. The ethanol is then removed and the pellets dried under vacuum. The resulting RNA is then dissolved in 20 sterile water containing 1 µl RNasin (cat#:N2511, Promega).

cDNA Synthesis:

cDNA synthesis is performed using a Gene Amp™ PCR kit (cat#: N808-0017 Perkin Elmer Cetus), RNasin™ (cat#: N2511, Promega), and AMV reverse transcriptase (cat#: M9004, Promega). The following protocol is used for each sample:

| Components | Amount |
|---|---|
| MgCl$_2$ solution | 4 µl |
| 10 × PCR buffer II | 2 µl |
| dATP | 2 µl |
| dCTP | 2 µl |
| dGTP | 2 µl |
| dTTP | 2 µl |
| 3' primer (random hexamers) | 1 µl |
| RNA sample | 2 µl |
| RNasin | 1 µl |
| AMV RT | 1.5 µl |

Samples are heated at 80° C. for 3 minutes then slowly cooled to 48° C. The samples are then centrifuged for 10 seconds. AMV reverse transcriptase is added to the samples which are then incubated for 30 minutes at 37° C. After incubation, 0.5 µl of each dNTP and 0.75 reverse transcriptase (cat#:109118, Boehringer Mannheim) are added. The samples are incubated for an additional 15 minutes at 37° C.

PCR Reaction:

Oligonucleotides are designed to amplify human $V_H$ genes by polymerase chain reaction. The 5' oligonucleotides are set forth below:

```
The 5'oligonucleotides are set forth below:
HVH 135:
5'-TATTCTCGAGGTGCA(AG)CTG(CG)TG(CG)
                                    AGTCTGG-3'

HVH2A:
5'-TATTCTCGAGGTCAA(CG)TT(AG)A(AG)
                                    GGAGTCTGG-3'

HVH46:
5'-TATTCTCGAGGTACAGCT(AG)CAG(CG)(AT)GTC
                                    (ACG) GG-3'

The 3'oligonucleotides are set forth below:
JH1245:
5'-TTATGCTAGCTGAGGAGAC(AG)GTGACCAGGG-3'

JH3:
5'-TTATGCTAGCTGAAGAGACGGTGACCATTG

JH6:
5'-TTATGCTAGCTGAGGAGACGGTGACCGTGG-3'
```

PCR reactions are performed with a GeneAmp™ PCR kit (cat#:N808-0017, Perkin Elmer Cetus). Components are listed below:

| Components | Amount |
|---|---|
| ddH$_2$O | 75 µl |
| 10 × buffer | 10 µl |
| dATP | 2 µl |
| dCTP | 2 µl |
| dGTP | 2 µl |
| dTTP | 2 µl |
| 1* Target DNA | 1 µl |
| 2* 5' primer | 2.5 µl |
| 3' primer | 2.0 µl |
| 3* AmpliTaq™ Polymerase | 1.3 µl |

| SUBSTANCE | Amount |
|---|---|
| DNA | 20 µl |
| NEB Buffer #2 | 4.5 µl |
| Nhe I | 2 µl |
| Xho I | 2 µl |
| ddH$_2$O | 16.5 µl |

Samples are incubated at 37° C. for one hour. After this incubation, an additional 1.5 µL Nhe I is added and samples are incubated an additional two hours at 37° C.

Purification of DNA:

After the restriction enzyme digest, DNA is run on a 5 percent polyacrylamide gel (Sambrook et al. (1989), supra). Bands of 390–420 bp in size are excised from the gel. DNA is electroeluted and ethanol precipitated according to standard procedures.

PCR products resulting from oligonucleotide combinations are pooled together: JH1245 with HVH135, HVH2A and HVH46; JH3 with HVH135, HVH2A and HVH46; JH6 with HVH135, HVH2A and HVH46. The volume of the resulting pools are reduced under vacuum to 50 microliters. The pools are then purified from a 4 percent polyacrylamide gel (Sambrook et al. (1989), supra) to isolate DNA fragments. Bands resulting at 390–420 bp are excised from the gel. The DNA from excised gel slices is electroeluted according to standard protocols set forth in Sambrook, supra.

Isolation of pSCFVUHH Xho I/Nhe I Vector Fragment

Approximately 5 µg in 15 µL of pSCFVUHH plasmid is isolated using the Magic Mini-prepT™ system (Promega). To this is added 5.4 µL OF 10× Buffer #2 (New England Biolabs), 45 units of Xho I (New England Biolabs), 15 units of Nhe I and 24 µL of ddH$_2$O. The reaction is allowed to proceed for 1 hour at 37° C. The sample is loaded on a 4% polyacrylamide gel, electrophoresed and purified by electroelution, as described earlier. The DNA pellet is dissolved in 20 µL of ddH$_2$O.

One hundred nanograms of pSCFVUHH digested with Xho I/Nhe I is ligated with a 1:1 molar ratio of purified human $V_H$ inserts digested with Xho I and Nhe I using T4 DNA ligase (Stratagene). Aliquots are used to transform competent E. coli AG1 cells (Stratagene) according to the supplier's instructions.

GVWP hydrophilic membranes (cat# GVWP14250, Millipore) are placed on CAM 20 LB agar plates (Sambrook et al., 1989). One membrane is added to each plate. Four hundred microliters of the E. coli AG1 transformation suspension from above are evenly spread over the surface of each membrane. The plates are incubated for 16 hours at 37° C.

Preparation of TAG-72-coated Membranes:

A 1% dilution of partially purified tumor associated glycoprotein-72 (TAG-72) produced in LS174 T-cells is prepared in TBS (cat# 28376, Pierce). Ten milliliters of the TAG dilution are placed in a petri plate (cat# 8-757-14, Fisher) for future use. Immobilon-P PVDF transfer membranes (cat# SE151103, Millipore) are immersed in methanol. The membranes are then rinsed three times in sterile double distilled water. After the final wash, the excess water is allowed to drain. Each of the membranes are placed in 10 milliliters of dilute TAG-72. The membranes are incubated at ambient temperature from 1 hour with gentle shaking. After incubation, the membranes are blocked with Western blocking solution (25 mM Tris, 0.15 M NaCl, pH 7.6; 1% BSA) for about 1 hour at ambient temperature.

Blocking solution is drained from the TAG membranes. With the side exposed to TAG-72 facing up, the membranes are placed onto fresh CAM 20 plates. Resulting air pockets are removed. The bacterial membranes are then added, colony side up, to a TAG membrane. The agar plates are incubated for 24 to 96 hours at ambient temperatures.

The orientation of the TAG-72 and bacterial membranes are marked with permanent ink. Both membranes are removed from the agar surface. The TAG-72 membrane is placed in 20 ml of Western antibody buffer (TBS in 0.05% Tween-20, cat# P-1379, Sigma Chemical Co.; 1% BSA, cat#3203, Biocell Laboratories) containing 0.2 ng of CC49-Biotin probe antibody. The bacterial membranes are replaced on the agar surface in their original orientation and set aside. CC49-Biotin is allowed to bind to the TAG membranes for 1 hour at 31° C. with gentle shaking. The membranes are then washed three times with TTBS (TBS, 0.05% Tween-20) for 5 minutes on an orbital shaker at 300 rpm. Streptavidin alkaline phosphatase (cat# 7100-04, Southern Biotechnology Associates) is added to Western antibody buffer to produce a 0.1% solution. The TAG-72 membranes are each immersed in 16 milliliters of the streptavidin solution and allowed to incubate for 30 minutes at 31° C. with gentle shaking. After incubation, the membranes are washed as previously described. A final wash is then performed using Western alkaline phosphate buffer (8.4 g NaCO$_3$, 0.203 g MgCl$_2$—H$_2$O, pH 9.8), for 2 minutes at 200 rpm at ambient temperature. To develop the membranes, Western blue stabilized substrate (cat# S384B, Promega) is added to each membrane surface. After 30 minutes at ambient temperatures, development of the membranes is stopped by rinsing the membranes three times with ddH$_2$O. The membranes are then photographed and clear zones are corelated with colonies on the hydrophilic membrane, set aside earlier. Colony(ies) are isolated for growth in culture and used to prepare plasmid DNA for sequencing characterization. Also, the protein product is isolated to evaluate specificity and affinity.

Identification of Hum4 V$_L$, Human V$_H$ Combinations Using pATDFLAG.

In a second assay system, Hum4 V$_L$-human V$_H$ combinations are discovered that bind to TAG-72 according to the schematic, supra, except for the following a different plasmid vector, pATDFLAG, was used (see below): at the assay step, IBI MII antibody is used as a probe to detect any Hum4 V$_L$-V$_H$ SCFV combinations that have bound to the hydrophobic membrane coated with TAG-72 and a sheep antimouse Ig antibody conjugated to horseradish peroxidase (Amersham, Arlington Heights, Ill.) is used to detect any binding of the MII antibody to TAG-72.

The plasmid pATDFLAG was generated from pSCF-VUHH (see FIG. 29) to incorporate a Flag-coding sequence 3' of any human V$_H$ genes to be expressed contiguously with Hum4 V$_L$. The plasmid PATDFLAG, when digested with Xho I and Nhe I and purified becomes the human V$_H$ discovery plasmid containing Hum4 V$_L$ in this SCFV format. The plasmid pATDFLAG was generated as follows. Plasmid pSCFVUHH treated with Xho I and Nhe I (isolated and described above) was used in a ligation reaction with the annealed FLAG and FLAGNC oligonucleotides. FLAGC:
5'-TCGAGACAATGTCGCTAGCGACTACAAG-GACGATGATGACAAATAAAAAC-3' FLAGNC:
5'-CTAGGTTTTTATTTGTCATCATCGTCCT-TGTAGTCGCTAGCGACATTGTC-3'

Equimolar amounts ($1 \times 10^{-10}$ moles of each of the oligonucleotides FLAGC and FLAGNC were mixed together using a ligation buffer (Stratagene). The sample is heated to 94° C. and is allowed to cool to below 35° C. before use in the ligation reaction below.

| Ligation Reaction to Obtain pATDFLAG | |
|---|---|
| COMPONENT | Amount |
| pSCFVUHH Xho I/Nhe I vector | 1.5 µl |
| ANNEALED FLAGC/FLAGNC | 0.85 µl |
| 10 × Ligation buffer | 2 µl |
| T4 DNA LIGASE | 1 µl |
| 10 MM ATP | 2 µl |
| ddH$_2$O | 12.65 µl |

This ligation reaction is carried out using the following components and amounts according the ligation protocol disclosed above. *E. coli* AG1 cells (Stratagene) are transformed with 3 µl of the above ligation reaction and colonies selected using CAM 20 plates. Clones having appropriate Nhe I, Xho I and Nhe I/Xho I restriction patterns are selected for DNA sequencing.

The oligonucleotide used to verify the sequence of the FLAG linker in pATDFLAG (see FIG. 28) is called PENPT-SEQ: 5'-CTTTATGTAAGATGATGTTTTG-3'. This oligonucleotide is derived from the non-coding strand of the penP terminator region. DNA sequencing is performed using Sequenase™ sequencing kit (U.S. Biochemical, Cleveland, Ohio) following the manufacturer's directions. The DNA and deduced amino acid sequences of the Hum4 V$_L$—UNI-HOPE linker—FLAG peptide of pATDFLAG is shown in FIG. 28.

Generation of pSC49FLAG

The CC49V$_H$ is inserted into the sites of Xho I-Nhe I PATDFLAG (see FIG. 29) and evaluated for biological activity with the purpose of serving as a positive control for the FLAG assay system to detect binding to TAG-72. The new plasmid, called pSC49FLAG (see FIG. 29) is generated as follows. The plasmid pATDFLAG (5 mg, purified from a 2.5 ml culture by the Magic Miniprep™ system (Promega) is treated with Xho I and Nhe I and the large vector fragment purified as described above for pSCFVUHH. The CC49 V$_H$ insert DNA fragment is obtained by PCR amplification from PSCFVUHH and oligonucleotides UNI3 as the 5' end oligonucleotide and SC49FLAG as the 3' end oligonucleotide. The resulting DNA and amino acid sequences of this SCFV antibody, with the FLAG peptide at the C-terminus, is shown in FIG. 30. The PCR reaction is carried out using 100 pmol each of the oligonucleotides, 0.1 ng of pSCFVUHH target DNA (uncut) and the standard protocol and reagents provided by Perkin Elmer Cetus. The DNA is first gel purfied, then treated with Xho I and Nhe I to generate sticky ends and purified from a 4% polyacrylamide gel and electroeluted as described earlier. The DNA vector (pATDFLAG treated with Xho I and Nhe I) and the insert (CC49 $V_H$ PCR product from pSCFVUHH treated with Xho I and Nhe I) are ligated in a 1:1 molar ratio, using 100 ng vector DNA (Stratagene kit) and used to transform *E. coli* AG1 competent cells (Stratagene) according to the manufacturer's directions. A colony with the correct plasmid DNA is picked as the pSC49FLAG clone.

Ligation of PATDFLAG Vector with PCR Amplified Human $V_H$ Inserts

The protocol for the ligation reaction is as follows:

| COMPONENT | Amount |
|---|---|
| DNA vector: pATDFLAG Xho I/Nhe I | 2.5 µl |
| Hum $V_H$ (X) DNA inserts: Xho I/Nhe I | 6 µl |
| 10 mM ATP (Stratagene) | 2 µl |
| 10 × buffer (Stratagene) | 2 µl |
| T4 DNA ligase (Stratagene) | 1 µl |
| ddH$_2$O | 6.5 µl |

DNA vector, ATP, 10× buffer and ddH$_2$O are combined. DNA insert and T4 DNA ligase are then added. Ligation reactions are placed in a 4 L beaker containing H$_2$O at 18° C. The temperature of the water is gradually reduced by refrigeration at 4° C. overnight. This ligation reaction generates pHum4 $V_L$-hum $V_H$ (X) (See FIG. 29).

Transformation of *E. coli* AG1 with pHum4 $V_L$-Hum $V_H$ (X) Ligation Mix

Transformation of pATDFLAG into competent *E. coli* AG1 cells (Stratagene) is achieved following the supplier's protocol.

IBI MII Anti-FLAG Antibody Plate Assay

The first three steps, preparation of TAG-coated membranes, plating of bacterial membranes, and assembly of TAG and bacterial membranes, are the same as those described in the CC49-Biotin Competition Plate Assay.

After the 24 hour incubation at ambient temperatures, the membranes are washed with TTBS three times at 250 rpm for four minutes. The MII antibody (cat# IB13010, International Biotechnologies, Inc.) is then diluted with TBS to a concentration ranging from 10.85 µg/ml to 0.03 µg/ml. Ten millilters of the diluted antibody are added to each membrane. The membranes are then incubated for 1 hour at ambient temperatures and shaken on a rotary shaker at 70 rpm. After incubation, the MII antibody is removed and the membranes are washed three times at 250 rpm and ambient temperatures for 5 minutes. The final wash is removed and 20 milliters of a 1:2000 dilution of sheep anti-mouse horseradish peroxidase linked whole antibody (cat# NA931, Amersham) is prepared with TBS and added to each membrane. The membranes are again incubated for 1 hour at ambient temperatures and 70 rpm. Following incubation, the membranes are washed three times at 250 rpm and ambient temperature for 5 minutes each. Enzygraphic Webs (cat# IB8217051, International Biotechnologies, Inc.) are used to develop the membranes, according to the manufacturer's instructions. The membranes are then photographed.

Instead of seeing a clear zone on the developed membrane for a positive Hum4 $V_L$-$V_H$ (X) clone producing an SCFV that binds to TAG-72, (as seen with the competition screening assay) in this direct FLAG—detecting assay, a blue-purple spot is indicative of a colony producing a SCFV that has bound to the TAG-72 coated membrane. The advantage of using the FLAG system is that any Hum4 $V_L$-$V_H$ SCFV combination that has bound to TAG-72 will be detected. Affinities can be measured by Scatchard analysis (Scatchard (1949), supra) and specificity by immunohistochemistry. These canidates could then be checked for binding to a specific epitope by using the competition assay, supra, and a competing antibody or mimetic, if desired.

The present invention is not to be limited in scope by the cell lines deposited since the deposited embodiment is intended as two illustrations of one aspect of the invention and all cell lines which are functionally equivalent are within the scope of the invention. Indeed, while this invention has been described in detail and with reference to specific embodiments thereof, it will be apparent to one skilled in the art that various changes and modifications could be made therein without departing from the spirit and scope of the appended claims.

Example 6

Hum4 $V_L$ may also be used as a source of framework regions (FRs) for grafting the complementarity determining regions (CDRs) of the light chain variable region of an antibody, such as the $V_L$ of the TAG-72-specific antibody, CC49. When Hum4 $V_L$ FRs are used in a humanized variable region construct (i.e. comprising non-human CDRs), the FRs may also be modified by replacing one or more of their amino acids with, e.g., murine, amino acids that may permit improvement in the functioning of the resulting antibody. Such an amino-acid-modified variable region is still considered a "humanized" region. An antibody or single chain antibody comprising a humanized light chain variable region having Hum4 $V_L$ FRs is herein termed a "humanized Hum4 $V_L$, $V_H$ antibody," i.e. any antibody or type of antibody in which the $V_L$(S) comprise (native or modified) Hum4 $V_L$ FRs and CDRs grafted thereon which are, or are derived from, non-human CDRs.

A humanized Hum4 $V_L$, $V_H$ antibody may use, as the heavy chain variable region(s) thereof, a $V_H$ which is entirely non-human, chimeric (partly human), humanized, or entirely human. Specifically in regard to aTAG-72 humanized Hum4 $V_L$, $V_H$ antibodies based on CC49, the $V_H$ of such an antibody may be an entirely murine CC49 $V_H$, a chimeric CC49 $V_H$, or a humanized CC49 $V_H$. The procedures set forth below describe production of an embodiment of the lattermost type of CC49-based aTAG-72 humanized Hum4 $V_L$, $V_H$ antibody: "HuCC49*" a humanized CC49 monoclonal humanized Hum4 $V_L$, $V_H$ antibody having CC49 $V_L$ CDRs grafted upon Hum4 $V_L$ FRs and having a humanized CC49 $V_H$ region.

The specific light chain FRs chosen for use in humanizing the CC49 $V_L$ are derived from the light chain FRs of the human MAb, LEN (the LEN light chain being a human k Subgroup IV light chain). This particular light chain was selected from among the human k Subgroup IV light chain sequences reported in Kabat et al., *Sequences of Proteins of Immunological Interest* (5th ed., 1991) (U.S. Department of Health and Human Services, NIH Publication No. 901-3242), based on the degree of similarity of its framework amino acid residues to certain framework residues of the native CC49 (nCC49) $V_L$—i.e. those residues potentially significant for maintenance of the combining site structure present in nCC49.

The decision as to which nCC49 amino acid residues were possibly significant, was itself based on study of a three-dimensional model of another antibody, McPC603, whose $V_L$ amino acids display identity to 95 of the 113 residues of the nCC49 $V_L$ (and identity to 69 of the 80 $V_L$ FR residues thereof). See E. A. Padlan, *Mol. Immunol.*, 31:169–217 (1994); however, the effects of specific amino acid residues and changes thereto are unpredictable. Based on this study, it was estimated that 43 of the nCC49 $V_L$ FR residues were possibly significant (see FIG. 32(A), asterisked residues), and the LEN $V_L$ was selected because its FR amino acids displayed identity in 36 of these 43 residues.

The same decision-making process was used to select the specific heavy chain FRs to be used in humanizing the nCC49 $V_H$. These FRs are derived from the heavy chain FRs of the human MAb, 21/28¢CL, which was chosen based on a three-dimensional model of the antibody, 36–71. The $V_H$ amino acids of 36–71 display identity to 84 of the 115 residues of the nCC49 $V_H$, and identity to 71 of the 87 FR residues thereof. (See Padlan, ibid.) Based on the study of 36–71, it was estimated that 40 of the nCC49 $V_H$ residues were possibly significant (see FIG. 32(B), asterisked residues), and the 21/28¢CL $V_L$ was then selected because its FR amino acids displayed identity in 28 of these 40 residues.

Of the 7 remaining, non-identical "possibly significant" residues of the LEN $V_L$ FRs, and the 12 of the 21/28¢CL $V_L$ FRs, these residues were replaced with the corresponding amino acids of CC49 $V_L$ and CC49 $V_H$, respectively, so as to retain in the final, humanized antibody, all of the residues estimated as being "possibly significant." Thus, the humanized MAb, HuCC49*, was designed to comprise: 1) a humanized $V_L$ comprising the three $V_L$ CDRs of nCC49 and the residue-modified $V_L$ FRs of the human MAb, LEN; and 2) a humanized $V_H$ comprising the three $V_H$ CDRs of nCC49 and the residue-modified $V_H$ FRs of the human MAb, 21/28¢CL. (See FIG. 32 which sets forth the humanization protocols for the CC49 $V_L$ and $V_H$ regions.)

Based on the resulting humanization protocols, nucleotide sequences were deduced from the amino acid sequence of each of the humanized $V_L$ and $V_H$ regions. The projected sequences were then refined by choosing codons for high frequency usage in the murine system and also by eliminating—with the help of the programs FOLD and MAPSORT, (Devereux et al., *Nucl. Acids Res.*, 12:387–395 (1984))—any self-annealing regions or any internal sites for the restriction endonucleases which were to be used for inserting the sequences into the appropriate vectors. The refined nucleotide sequences are shown in FIG. 33.

For the generation of humanized $V_H$- and $V_L$-coding sequences, two sets of four 121- to 126-base-pair-long oligonucleotides were synthesized. The four overlapping oligomers of a given set (depicted by long arrows in FIG. 33) encompassed the entire refined nucleotide sequence of the humanized $V_H$ or $V_L$ gene on alternating strands. Double-stranded coding sequences were generated from the overlapping oligomers and then amplified, by the polymerase chain reaction (PCR), according to the following procedures.

First, four 20-base-pair-long amplification end primers were purchased (Midland Certified Reagent Co., Midland, Tex.) or synthesized (using a model 8700 DNA synthesizer Milligen/Bioresearch, Burlington, Vt.), and then these end primers were chromatographically purified (on Oligo-Pak columns from Milligen/Bioresearch). The sequences of these end primers were:

1. 5¢ $V_H$, coding: 5¢-CTAAGCTTCCACCATGGAG[?]-3¢;

2. 3¢ $V_H$, noncoding: 5¢-ATGGGCCCGTAGTTTTGGCG-3¢;

3. 5¢ $V_L$, coding: 5¢-GCAAGCTTCCACCATGGATA-3¢; and 4. 3¢ $V_L$, noncoding: 5¢-AGCCGCGGCCCGTTTCAGTT-3¢.

Both of the 5¢-primers carry a HindIII site, while the 3¢ $V_H$ primer has an ApaI site and the 3¢ $V_L$ primer carries a SacII site at the flank.

PCR was carried out separately for each of the $V_L$ and $V_H$ coding sequences (data not shown), according to standard PCR reaction procedures. (Daugherty et al., *Nucl. Acids, Res.*, 19:2471–2476 (1991).) To a final volume of 50 ml of PCR buffer—containing 2.5 mM of each of the dNTPs and 2.5 units of Taq DNA polymerase (Perkin Elmer Cetus, Norwalk, Conn.)—1 pmol each of the four overlapping oligomers and 50 pmol each of the two end primers were added. Three cycles of denaturation (1 min at 94° C.), annealing (2 min at 55° C.), and polymerization (2 min at 70° C.) were followed by 17 additional cycles of denaturation (1 min at 94° C.), annealing (2 min at 55° C.), and polymerization (1 min at 72° C.). This was followed by a final primer extension for 15 min at 72° C.

The DNA was extracted with phenol/chloroform and precipitated with ethanol. The amplified DNA was gel purified either as such or after treatment with the appropriate restriction endonucleases. Then the purified, PCR-generated copies of the DNA sequence encoding the humanized $V_L$ were cloned in the vector, pBluescript SK$^+$ (Stratagene, La Jolla, Calif.), while those for the humanized $V_H$ were separately cloned in the vector pCRIII (a TA cloning vector designed for cloning PCR products, from Invitrogen, San Diego, Calif.) thereby generating pBSHuCC49*$V_L$ and pTAHuCC49*$V_H$, respectively. Each of the humanized variable regions was sequenced to check the fidelity of the PCR products.

After the fidelity of the PCR products was checked, eukaryotic expression vectors bearing genes comprising these variable region-encoding DNA sequences were constructed as illustrated in FIG. 34. The expression vectors bear a gene for a selectable marker. This gene for the selectable marker is driven by the 5¢ long terminal repeat derived from M-MSV, while the human cytomegalovirus (HCMV) immediate early promoter drives the "target" gene, i.e. the HuCC49* light or heavy chain gene construct. A multiple cloning site is located immediately 3¢ to the HCMV promoter.

For the light chain of HuCC49*, pLNCXCC49Huk—an expression construct of the cCC49 light chain—was used as a source of DNA encoding the human k constant region. Taking advantage of an internal SacII site and a ClaI site located 3¢ to the constant region DNA, a SacII/ClaI fragment encoding the human k constant region was excised therefrom. This fragment, together with the humanized $V_L$-encoding HindIII/SacII fragment excised from pBSHuCC49*$V_L$, was inserted directionally, by three-way ligation, between HindIII and ClaI sites in the retroviral expression construct pLNCX II, a retroviral vector. This vector is essentially the vector pLNCX, (Miller et al., *Biotechniques*, 7:980–989 (1989)), obtained from Dr. D. Miller (Fred Hutchinson Cancer Research Center, Seattle, Wash.) and modified by destroying an EcoRI site in the backbone of the vector while retaining another EcoRI site located 45 base pairs 5¢ to the neomycin resistance gene therein. pLNCX II is hereinafter referred to as pLNCX. Insertion of these two DNA fragments into pLNCX as indicated resulted in formation of pLNCXHuCC49HuK. (See FIG. 34(A).)

For the heavy chain construct, an ApaI/ClaI DNA fragment encoding a human g1 constant region was excised from pLHCXCC49HuG$_1$—an expression construct of the cCC49 heavy chain—by taking advantage of an ApaI site in the C$_H$1 domain of the human g1 and a ClaI site located 3¢ to the g1 heavy chain. A HindIII/ApaI fragment encoding the humanized V$_H$ region was obtained from the construct pTAHuCC49*VH. Again, three-way ligation was used to directionally clone the two DNA fragments between the HindIII and ClaI sites of an expression vector, pLgpCX II. pLgpCX II is a retroviral vector derived from pLNCX II by replacing a 1.2-kb BamHI fragment carrying the neomycin resistance gene with a 0.7-kb BglII/BamHI fragment carrying the Ecogpt gene which had been excised from the vector pEE6HCMVgpt, (White et al., *Protein Eng.*, 1:499–505 (1987)). The Ecogpt gene encodes xanthine-guanine phosphoribosyltransferase which confers resistance to mycophenolic acid in mammalia cells grown in culture medium supplemented with xanthine. pLgpCX II is hereinafter referred to as pLgpCX. Insertion of these two DNA fragments into pLgpCX as indicated resulted in formation of pLgpCXHuCC49HuG$_1$. (See FIG. 34(B).)

In order to express the HuCC49* MAb itself, the pLNCXHuCC49HuK and pLgpCXHuCC49HuG$_1$ expression vector constructs were sequentially transfected into host cells as follows.

First, the expression construct, pLNCXHuCC49HuK, was electroporated into SP2/0 murine myeloma cells (of the SP2/0-Ag14 cell line, obtained as a gift from Dr. S. Morrison, University of California, Los Angeles), using the Cell-Porator system (GIBCO BRL, Gaithersburg, Md.). Electroporation was carried out as previously described (Slavin-Chiorini et al., *Int. J. Cancer*, 53:97–103 (1993)), with minor modifications. Briefly, 40 mg of the PvuI linearized DNA was added to a polypropylene electroporation chamber containing 1×10$^7$ cells suspended in 1 ml of serum-free DMEM supplemented with 4.5 g/liter glucose. The cell/DNA mixture was placed in an ice-water bath and pulsed at 650 V/cm for 13 msec at a capacitance setting of 1600 mF. After keeping the cells on ice for 10 min, they were diluted in complete RPMI-1640 medium [RPMI-1640 containing 15% (v/v) heat-inactivated fetal calf serum, 2 mM L-glutamine, 1 mM sodium pyruvate, and 50 mg gentamicin/ml] and distributed in 24-well tissue culture plates (Costar, Cambridge, Mass.) at 1×10$^5$ cells/wells. After incubation at 37° C. in a 5% CO$_2$ incubator for 48 h, the medium was replaced with selection medium.

Selection medium consisted of complete RPMI-1640 containing 700 mg/ml of active G418 (GIBCO BRL). After 2 weeks of selection in medium supplemented with G418, approximately 20% of the wells showed cell growth. Tissue culture supernatants from approximately 50% of the wells with cell growth were positive for human k chain reactivity, indicating that these cells were expressing the k light chain of HuCC49*.

Second, the expression construct pLgpCXHuCC49HuG$_1$, was electroporated into a HuCC49* k chain-producing transfectant using the above-described procedure. However, after electroporation and incubation, the medium was instead replaced with a selection medium consisting of complete RPMI-1640 containing 1 mg/ml mycophenolic acid (Sigma Chemical Co., St. Louis, Mo.), 250 mg/ml xanthine, and 15 mg/ml hypoxanthine (GIBCO BRL). After selection in this mycophenolic acid-containing medium, supernatants from two transfectants were reactive with a protein extract of TAG-72-positive LS-174T human colon carcinoma xenografts, indicating that these cells were expressing a whole aTAG-72 antibody.

In addition, no reactivity was observed to a protein extract of TAG-72-negative A375 human melanoma xenografts (the A375 human melanoma cell line being obtained from Dr. S. Aaronson, National Cancer Institute, NIH, Bethesda, Md.), thereby indicating that these two transfectants were expressing an antibody specific for TAG-72. The transfectant that secreted a higher titer of TAG-72-reactive Ig was cloned by limiting dilution, and the subclone that produced the highest titer—designated HuCC49*—was adapted for growth in serum- and protein-free medium (PFHM-II, Gibco BRL).

In order to assess the purity of the HuC49* antibody, and to characterize its mobility relative to that of chimeric CC49 (cCC49), SDS-PAGE analysis was performed under reducing and non-reducing conditions. Quantities of the HuCC49* antibody sufficient for these analyses were obtained by growing the above-selected HuCC49* clone in protein-free hybridoma medium PFHM-II (Gibco BRL), followed by isolation from the tissue culture supernatants via protein G affinity chromatography and concentration of the harvested antibody as follows: 1) the tissue culture supernatants were applied to a recombinant protein G (Gibco BRL) agarose column; 2) the bound protein was eluted from the column using 0.1 M glycine hydrochloride buffer, pH 2.6; 3) the pH of the eluted material was immediately adjusted to 7.0 using 1.0 M Tris buffer, pH 8.0; 4) the pH 7.0 material was dialyzed against phosphate-buffered saline (PBS), pH 7.4; and 5) the dialyzed material was concentrated using an immersible-CX-30 ultrafilter (Millipore, Bedford, Mass.).

The HuCC49* protein concentration was determined using a Bio-Rad Microassay procedure, (M. M. Bradform, *Anal. Biochem.*, 72:248–254 (1976)), or by the method of Lowry et al. (*J. Biol. Chem.*, 193:265–275 (1951)). Approximately 1 mg of HuCC49* was recovered per ml of the tissue culture supernatants. cCC49 was purified from tissue culture supernatant using high-performance liquid chromatography and the protein concentration was likewise determined.

PAGE analyses of cCC49 and HuCC49* were performed on precast 4–20% SDS-polyacrylamide Tris-glycine gels (Novex, San Diego, Calif.) with and without denaturation with 2-mercaptoethanol. Proteins on the gel were visualized by staining with Coomassie Brilliant blue R250 according to the method of U.K. Laemmli (*Nature* (London), 227:680–685 (1970)).

Figure 35A:
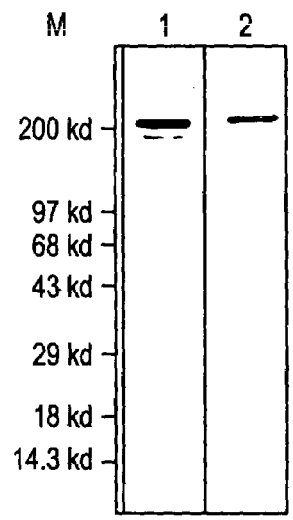
FIG. 35 illustrates SDS-PAGE analyses of purified HuCC49* and cCC49 under non-reducing (A) and reducing (B) conditions.

The gel profiles under non-reducing conditions showed that the HuCC49* MAb (FIG. 35(A), lane 2) has virtually identical mobility to that of cCC49 (FIG. 35(A), lane 1), which has a molecular mass of approximately 160 kDa. Under reducing conditions, the HuCC49* MAb (FIG. 35(B), lane 2) yielded two protein bands of approximately 25–28 and 50–55 kDa. This is consistent with the molecular masses of the heavy and light chains of cCC49 (FIG. 35(B), lane 1).

In order to better characterize HuCC49* relative to cCC49 and nCC49, purified HuCC49*, cCC49, and nCC49 were obtained and radio-labeled for use in further analysis by PAGE, HPLC, and immunoreactivity studies (the development and reactivity of nCC49 has been previously described by Kuroki et al., *Cancer Res.*, 48:4588–4596 (1988)). Thus, these three antibodies were labeled with Na$^{125}$I or Na$^{131}$I using the Iodo-Gen (Pierce, Rockford, Ill.)

method of Colcher et al. (*Cancer Res.*, 43:736–742 (1983)). The iodination protocol resulted in $^{125}$I-labeled cCC49, 125I-labeled nCC49, and $^{131}$I-labeled HuCC49* with specific activities of 2–5 mCi/mg.

These three radioiodinated antibodies were evaluated by SDS-PAGE analysis under non-reducing and reducing conditions. The radioiodinated MAbs were detected by autoradiography using Kodak XAR X-ray film (Rochester, N.Y.) and Lightning Plus intensifying screens (E.I. DuPont deNemours & Co., Wilmington, Del.). Molecular weight profiles, similar to those described for the unlabeled purified MAbs, were observed.

The integrity of each of the radioiodinated CC49 molecules was then evaluated by HPLC size-exclusion chromatography. The HPLC analyses were performed using a Sepherogel-TSK 2000 SW, 0.75×30 cm column (Beckman Instruments, Inc., Berkeley, Calif.) equilibrated in 67 mM sodium phosphate containing 100 mM KCl, pH 6.8. Samples (250,000 cpm in 25 ml) were applied and eluted from the column at a flow rate of 0.5 ml/min. The radioactivity was measured in a flow-through gamma scintillation counter (Model 170; Beckman Instruments, Inc.). Each of $^{131}$I-labeled HuCC49*, $^{125}$I-labeled cCC49, and $^{125}$I-labeled nCC49 eluted from the column at 29 min. as a distinct species (see FIGS. 36(A) and (B): data not shown for $^{125}$I-labeled nCC49).

Finally, the immunoreactivities of the radiolabeled antibodies were assessed by a modification of a method previously described by Schott et al. (*Cancer Res.*, 52:6413–5417 (1982)), using bovine submaxillary mucin (BSM). BSM was immobilized onto solid support gel beads (Reacti-Gel HW65F from Pierce, Rockford, Ill.) as detailed by Jonson et al. (*Cancer Res.*, 46:850–857 (1986)), at a ratio of 2 mg BSM to 1 ml of wet-packed gel, and the TAG-72-positive BSM beads were used to perform the radioimmuno-reactivity assay. 50 ml of wet-packed BSM beads was placed in each tube of (multiple sets of) three pairs of 1.5 ml microfuge tubes. The radiolabeled antibodies were diluted to 23 nCi in 1 ml of 1% bovine serum albumin (BSA) in PBS. The radiolabeled antibodies were then added to the duplicate tubes, counted in a gamma scintillation counter, and incubated for 2 h at room temperature with end-over-end rotation. The BSM beads were then pelleted at 800'g for 5 min, and the beads in each tube were washed twice with 1 ml of 1% BSA in PBS. The radioactivity remaining in each tube was measured and the total percent bound to the BSM beads was calculated. The percent bound for each of the radiolabeled Ig forms was greater than 85, while the percent bound for a nonspecific antibody was typically <10%. Approximately 85% of the $^{131}$I-labeled HuCC49* and 90% of the $^{125}$I-labeled cCC49 MAbs bound to BSM beads, thus indicating the immunoreactivity of the HuCC49* and cCC49 MAbs.

Next, the relative affinity constants ($K_a$) of HuCC49*, and cCC49 and nCC49, were determined using a competition radioimmunoassay (RIA) technique. Competition RIAs were performed using $^{125}$I-labeled nCC49 as the radiolabeled antibody and BSM as the target antigen, according to the method of Hand et al. (*Cancer Immunol. Immunother.*, 35:165–174 (1992)). In these RIAs, $^{125}$I-labeled nCC49 was used to compete for the binding of each of the three unlabeled competitor antibodies bound to the TAG-72-positive BSM. The percentage of radiolabeled MAb bound to antigen (% bound), compared to a buffer control was calculated.

Figure 37:
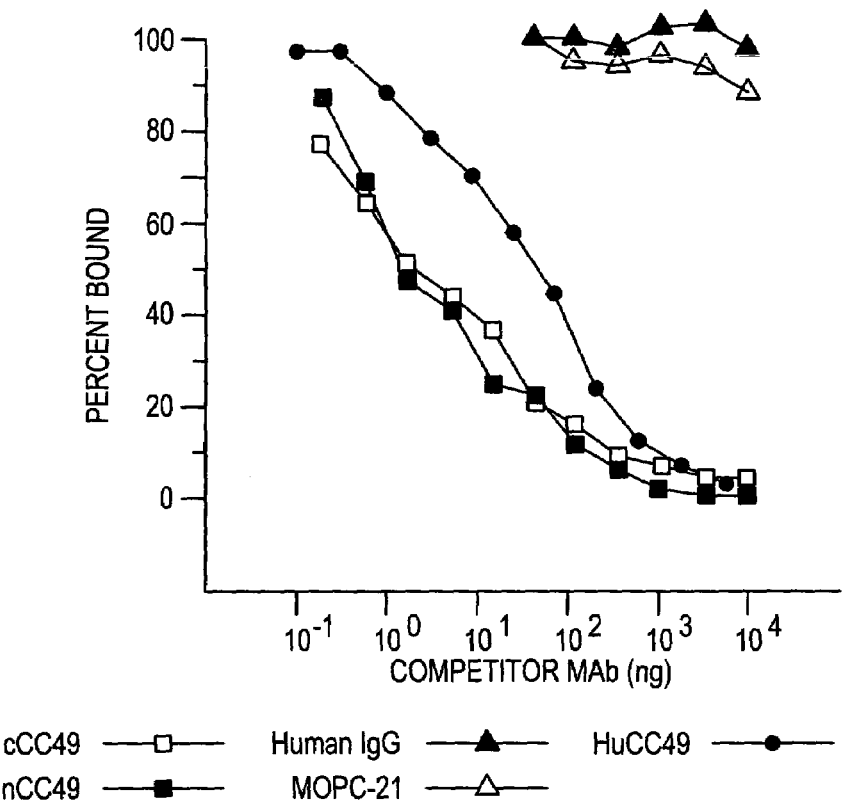
FIG. 37 shows the reactivity of HuCC49*, cCC49, and nCC49 in a competition RIA against $^{125}$I-labeled nCC49 bound to BSM-immobilized TAG-72.

As shown in FIG. 37, all three CC49 MAbs were able to completely inhibit the binding of the $^{125}$I-labeled nCC49 to TAG-72, although the level of competition observed with the HuCC49* MAb differed from that of the nCC49 and cCC49 MAbs. Approximately 45 mg of the HuCC49* was required for 50% competition, as compared with 1.5 and 2.0 mg of the nCC49 and cCC49 MAbs, respectively. No competition was observed when control murine IgG (MOPC-21, an IgG$_1$ murine myeloma protein obtained from Organon Technika, Durham, N.C.) and control human IgG (purified IgG obtained from Jackson Immuno-Research, West Grove, Pa.) were used as competitors.

The $K_a$s of HuCC49*, cCC49, and nCC49 were determined using the method of G. Scatchard (*Ann. NY Acad. Sci.*, 51:660–668 (1949)). The relative affinity constant of the cCC49 MAb was found to be $1.2 \times 10^8$ M$^{-1}$ and that of the nCC49 MAb was found to be $1.8 \times 10^8$ M$^{-1}$, while the $K_a$ of HuCC49* was $6.0 \times 10^7$ M$^{-1}$, i.e. approximately 2- to 3-fold less than those of the nCC49 and cCC49 MAbs, respectively.

Studies were then initiated to compare the plasma clearance and biodistribution of HuCC49* with that of cCC49. It has previously been shown that the pharmacokinetics of nCC49 and cCC49 in mice differ greatly, with cCC49 clearing more rapidly. This has been shown to affect in vivo tumor targeting. Thus, HuCC49* and cCC49 were compared in pharmacokinetics and in vivo targeting studies as follows. Each of 5 athymic (nu/nu) mice received one i.v. injection containing a mixture of 0.94 mCi/mouse of $^{125}$I-labeled cCC49 and 0.98 mCi/mouse of $^{131}$I-labeled HuCC49*. Blood samples were collect at specified time intervals via the tail vein into 10-ml capillary tubes (Drummon, Broomall, Pa.). The amount of $^{131}$I and $^{125}$I in the plasma was determined and normalized to account for differences in the rates of decay of the radionuclides. The percentage of the injected dose of each radionuclide remaining the plasma was then calculated.

Figure 38:
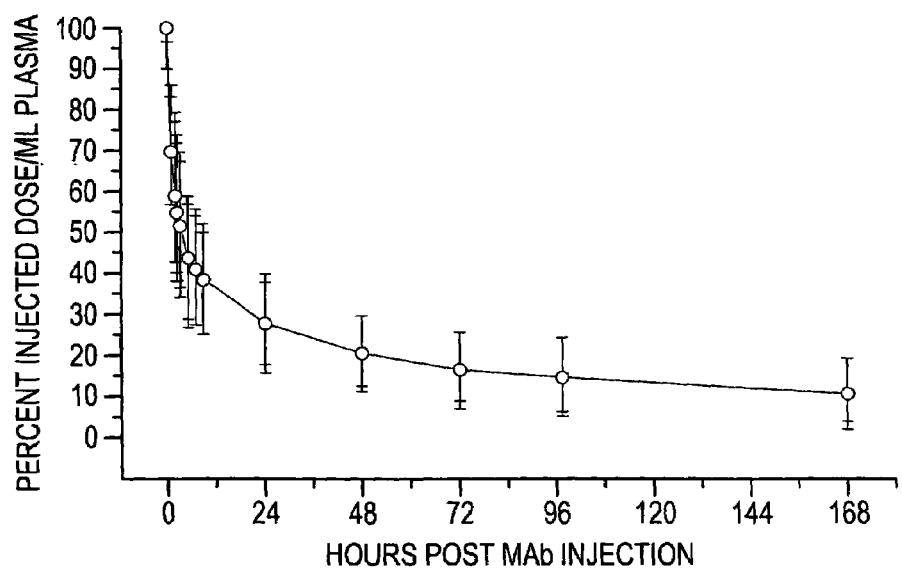
FIG. 38 shows the clearance of radioiodinated HuCC49* and cCC49 MAbs from the serum of mice.

The data from this experiment was used to determine the half-lives of the antibodies in plasma, using a curve-fitting program. The $t_{1/2}$a and $t_{1/2}$b of HuCC49* were 4.2 and 149 h, respectively. These values are comparable to the $t_{1/2}$a and $t_{1/2}$b values for cCC49, i.e. 4.7 and 139 h, respectively. Statistical analysis was also performed on this plasma clearance data using a 2-tailed paired Student's t test with n=5 and 4 degrees of freedom. FIG. 38 shows that both MAbs have similar blood clearance patterns with approximately 74% of the radiolabeled MAb dose clearing the blood at 24 h and 83% by 72 h.

Experiments were then conducted to assess the biodistribution of these antibodies in order to compare the ability of HuCC49* to localize to human tumor xenografts with that of cCC49. The biodistribution of the HuCC49* MAb was compared with that of the cCC49 MAb as follows. Female athymic (nu/nu) mice bearing TAG-72-positive tumor xenografts were produced according a method previously described by Colcher et al. (*Cancer Res.*, 43:736–742 (1983)), using cells from the LS-174T human colon adenocarcinoma cell line (described by Rutzki et al., *In Vitro*, 12:180–191 (1976)) which was obtained from the American Type Culture Collection (Rockville, Md.).

These tumor-bearing mice were injected in the tail vein with a mixture containing approximately 0.94 mCi/mouse of $^{125}$I-labeled cCC49 and 0.98 mCi/mouse of $^{131}$I-labeled HuCC49*. Blood, tumor, and all major organs were collected and weighted (5 mice per time point). Radioactivity was measured in a gamma scintillation counter and radioactive decay was counted. The percentage of the injected dose per gram (% ID/g) for each organ was determined and the radiolocalization indices (% ID/g in tumor divided by the % ID/g in normal tissue) were calculated. Statistical analysis was also done for the biodistribution data using a 2-tailed paired Student's t test with n=5 and 4 degrees of freedom.

No statistically significant difference was observed between the % ID/g of either MAb to tumors or tissues collected at any time point (Table 2). Both antibodies showed tumor localization by 24 h; by 96 h, when there was <2% of the injected dose per ml of blood, the % ID/g in tumor was 22.6% for HuCC49* and 19.5% for cCC49 (Table 2). No specific uptake of either radiolabeled antibody was observed in any normal tissue tested. As shown in Table 3, the radiolocalization indices (RIs) (% ID/g in tumor divided by the % ID/g in normal tissue) of the two MAbs were not appreciably different for any tumor:normal tissue ratio. Thus, these data indicate that the HuCC49* and cCC49 MAbs have similar tumor-targeting properties.

TABLE 2

Radiolocalization of $^{131}$I-Labeled HuCC49* and $^{125}$I-Labeled CCC49 in Athymic Mice Bearing LS-174T Tumors (% ID/g)[a]

| Antibody, Organ | % ID/g | | | | |
|---|---|---|---|---|---|
| | 24 h | 48 h | 72 h | 96 h | 168 h |
| HuCC49* | | | | | |
| Tumor | 15.4 ± 7.2[b] | 22.8 ± 17.1 | 16.1 ± 12.8 | 22.6 ± 5.3 | 12.9 ± 12.4 |
| Blood | 5.1 ± 1.4 | 4.1 ± 2.9 | 2.2 ± 1.8 | 1.6 ± 0.8 | 0.8 ± 0.7 |
| Liver | 3.3 ± 1.6 | 2.7 ± 0.9 | 1.5 ± 0.8 | 1.6 ± 0.2 | 0.6 ± 0.3 |
| Spleen | 5.7 ± 3.9 | 4.7 ± 0.9 | 2.7 ± 1.6 | 4.6 ± 0.8 | 3.3 ± 2.5 |
| Kidneys | 1.5 ± 0.4 | 1.1 ± 0.4 | 0.8 ± 0.5 | 0.6 ± 0.1 | 0.4 ± 0.2 |
| Lungs | 2.0 ± 0.3 | 2.0 ± 1.2 | 1.0 ± 0.7 | 1.0 ± 0.4 | 0.4 ± 0.3 |
| cCC49 | | | | | |
| Tumor | 16.1 ± 7.5 | 23.4 ± 19.0 | 14.9 ± 12.0 | 10.5 ± 6.0 | 12.3 ± 11.3 |
| Blood | 4.5 ± 1.6 | 3.6 ± 2.8 | 1.7 ± 1.4 | 1.1 ± 0.7 | 0.6 ± 0.4 |
| Liver | 3.8 ± 1.8 | 3.0 ± 0.8 | 1.4 ± 0.9 | 1.3 ± 0.2 | 0.4 ± 0.3 |
| Spleen | 8.5 ± 5.5 | 6.7 ± 1.2 | 3.5 ± 2.5 | 7.5 ± 2.7 | 4.8 ± 3.8 |
| Kidneys | 1.6 ± 0.4 | 1.0 ± 0.5 | 0.6 ± 0.4 | 0.4 ± 0.1 | 0.3 ± 0.1 |
| Lungs | 2.1 ± 0.3 | 1.9 ± 1.2 | 0.8 ± 0.5 | 0.8 ± 0.4 | 0.4 ± 0.2 |

[a]Athymic mice (5 per group) bearing LS-174T human colon carcinoma xenografts were injected i.v. with a mixture containing approximately 10 mCi of each radiolabeled MAb, and sacrificed at the indicated times.
[b]Values represent the mean % ID/g ± SD of samples from 5 mice.

TABLE 3

Radiolocalization of $^{131}$I-Labeled HuCC49* and $^{125}$I-Labeled cCC49 in Athymic Mice Bearing LS-174T Tumors (Radiolocalization Index)[a]

| Antibody, Organ | Radiolocalization Index[b] | | | | |
|---|---|---|---|---|---|
| | 24 h | 48 h | 72 h | 96 h | 168 h |
| HuCC49* | | | | | |
| Blood | 3.1 ± 1.1[c] | 6.8 ± 4.1 | 8.6 ± 3.7 | 16.7 ± 5.5 | 24.7 ± 23.6 |
| Liver | 5.4 ± 3.3 | 9.2 ± 7.4 | 9.2 ± 3.9 | 14.1 ± 3.9 | 21.8 ± 14.3 |
| Spleen | 3.6 ± 2.7 | 5.3 ± 4.5 | 5.4 ± 2.9 | 5.0 ± 1.6 | 5.1 ± 5.1 |
| Kidneys | 10.2 ± 4.8 | 19.5 ± 8.6 | 18.2 ± 5.5 | 37.7 ± 3.2 | 30.6 ± 20.4 |
| Lungs | 7.7 ± 3.1 | 11.4 ± 4.3 | 14.6 ± 3.2 | 25.5 ± 7.3 | 36.6 ± 27.6 |
| cCC49 | | | | | |
| Blood | 3.8 ± 1.4 | 9.1 ± 7.0 | 12.1 ± 7.1 | 21.0 ± 6.9 | 27.3 ± 23.8 |
| Liver | 4.7 ± 2.6 | 8.2 ± 6.6 | 9.3 ± 2.6 | 14.6 ± 3.9 | 25.8 ± 17.0 |
| Spleen | 2.4 ± 1.6 | 3.5 ± 2.5 | 4.4 ± 2.4 | 2.9 ± 1.4 | 3.6 ± 3.4 |
| Kidneys | 10.2 ± 4.7 | 20.4 ± 8.0 | 21.5 ± 5.3 | 46.1 ± 7.5 | 40.6 ± 26.9 |
| Lungs | 7.9 ± 3.5 | 11.9 ± 4.4 | 16.0 ± 3.7 | 26.6 ± 9.1 | 32.2 ± 22.7 |

[a]Athymic mice (5 per group) bearing LS-174T human colon carcinoma xenografts were injected i.v. with a mixture containing approximately 1.0 µCi of each radiolabeled MAb, and sacrificed at the indicated times.
[b]The radiolocalization index is the ratio of the % ID/g of the tumor tissue to the % ID/g of the normal tissue.
[c]Values represent the radiolocalization index ±SD of samples from 5 mice.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

SEQUENCE LISTING

<160> NUMBER OF SEQ ID NOS: 78

<210> SEQ ID NO 1
<211> LENGTH: 70
<212> TYPE: DNA
<213> ORGANISM: Artificial Sequence
<220> FEATURE:
<221> NAME/KEY: Primer SCFV1a
<222> LOCATION: 1..70
<223> OTHER INFORMATION: Oligonucleotide for incorporating part of the yeast invertase leader sequence into DNA encoding SCFV1

<400> SEQUENCE: 1
ctgcaagctt cctttcctt ttggctggtt ttgcagccaa aatatctgca gacatcgtga    60
tgacccagtc                                                          70

<210> SEQ ID NO 2
<211> LENGTH: 81
<212> TYPE: DNA
<213> ORGANISM: Artificial Sequence
<220> FEATURE:
<221> NAME/KEY: Primer SCFV1b
<222> LOCATION: 1..81
<223> OTHER INFORMATION: Oligonucleotide for incorporating the SCFV linker coding sequence into DNA encoding SCFV1
<220> FEATURE:
<221> NAME/KEY: SCFV linker DNA
<222> LOCATION: 9..62
<223> OTHER INFORMATION: DNA sequence encoding the SCFV linker present in SCFV1

<400> SEQUENCE: 2
cgtaagacgt ctaaggaacg aaattgggcc aattgttctg aggagaccga acctgactcc    60
ttcaccttgg tccctccgcc g                                             81

<210> SEQ ID NO 3
<211> LENGTH: 30
<212> TYPE: DNA
<213> ORGANISM: Artificial Sequence
<220> FEATURE:
<221> NAME/KEY: Primer SCFV1c
<222> LOCATION: 1..30
<223> OTHER INFORMATION: Oligonucleotide for amplifying CC49 VH

<400> SEQUENCE: 3
cttagacgtc cagttgcagc agtctgacgc                                    30

<210> SEQ ID NO 4
<211> LENGTH: 37
<212> TYPE: DNA
<213> ORGANISM: Artificial Sequence
<220> FEATURE:
<221> NAME/KEY: Primer SCFV1d
<222> LOCATION: 1..36
<223> OTHER INFORMATION: Oligonucleotide for amplifying CC49 VH

<400> SEQUENCE: 4
gatcaaggct tcactaggag acggtgactg aggttcc                            37

<210> SEQ ID NO 5
<211> LENGTH: 24
<212> TYPE: DNA
<213> ORGANISM: Artificial Sequence

```
<220> FEATURE:
<221> NAME/KEY: Primer TPI
<222> LOCATION: 1..24
<223> OTHER INFORMATION: Oligonucleotide used to sequence DNA encoding
      SCFV1

<400> SEQUENCE: 5 caatttttg tttgtattct tttc                                            24

<210> SEQ ID NO 6
<211> LENGTH: 20
<212> TYPE: DNA
<213> ORGANISM: Artificial Sequence
<220> FEATURE:
<221> NAME/KEY: Primer HUVKF3
<222> LOCATION: 1..20
<223> OTHER INFORMATION: Oligonucleotide used to sequence DNA encoding
      SCFV1

<400> SEQUENCE: 6
cctgaccgat tcagtggcag                                                20

<210> SEQ ID NO 7
<211> LENGTH: 27
<212> TYPE: DNA
<213> ORGANISM: Artificial Sequence
<220> FEATURE:
<221> NAME/KEY: Primer DC113
<222> LOCATION: 1..27
<223> OTHER INFORMATION: Oligonucleotide used to sequence DNA encoding
      SCFV1

<400> SEQUENCE: 7
tccaatccat tccaggccct gttcagg                                        27

<210> SEQ ID NO 8
<211> LENGTH: 20
<212> TYPE: DNA
<213> ORGANISM: Artificial Sequence
<220> FEATURE:
<221> NAME/KEY: Primer SUC2T
<222> LOCATION: 1..20
<223> OTHER INFORMATION: Oligonucleotide used to sequence DNA encoding
      SCFV1

<400> SEQUENCE: 8
cttgaacaaa gtgataagtc                                                20

<210> SEQ ID NO 9
<211> LENGTH: 26
<212> TYPE: DNA
<213> ORGANISM: Artificial Sequence
<220> FEATURE:
<221> NAME/KEY: Primer penP1
<222> LOCATION: 1..26
<223> OTHER INFORMATION: Oligonucleotide for amplifying the penP
      promoter - pel B signal sequence of plasmid pRW83

<400> SEQUENCE: 9
cgataagctt gaattccatc acttcc                                         26

<210> SEQ ID NO 10
<211> LENGTH: 90
<212> TYPE: DNA
<213> ORGANISM: Artificial Sequence
```

```
<220> FEATURE:
<221> NAME/KEY: Primer penP2
<222> LOCATION: 1..90
<223> OTHER INFORMATION: Oligonucleotide for amplifying the penP
      promoter - pel B signal sequence of plasmid pRW83

<400> SEQUENCE: 10
ggccatggct ggttgggcag cgagtaataa caatccagcg gctgccgtag gcaataggta      60
tttcatcaaa atcgtctccc tccgtttgaa                                       90

<210> SEQ ID NO 11
<211> LENGTH: 44
<212> TYPE: DNA
<213> ORGANISM: Artificial Sequence
<220> FEATURE:
<221> NAME/KEY: Primer penP3
<222> LOCATION: 1..44
<223> OTHER INFORMATION: Forward oligonucleotide primer for amplifying
      DNA encoding a Hum4VL-linker-CC49VH SCFV from pCGS515/SCFV1

<400> SEQUENCE: 11
gctgcccaac cagccatggc cgacatcgtg atgacccagt ctcc                       44

<210> SEQ ID NO 12
<211> LENGTH: 90
<212> TYPE: DNA
<213> ORGANISM: Artificial Sequence
<220> FEATURE:
<221> NAME/KEY: Primer penP6(-)
<222> LOCATION: 1..90
<223> OTHER INFORMATION: Reverse oligonucleotide primer for amplifying
      DNA encoding a Hum4VL-linker-CC49VH SCFV from pCGS515/SCFV1

<400> SEQUENCE: 12
ctcttgatca ccaagtgact ttatgtaaga tgatgttttg acggattcat cgcaatgttt      60
ttatttgccg gagacggtga ctgaggttcc                                       90

<210> SEQ ID NO 13
<211> LENGTH: 23
<212> TYPE: DNA
<213> ORGANISM: Artificial Sequence
<220> FEATURE:
<221> NAME/KEY: Primer Nco1.1
<222> LOCATION: 1..23
<223> OTHER INFORMATION: Forward oligonucleotide primer for destroying
      the Nco I site within the Camr gene in plasmid pSCFV31

<400> SEQUENCE: 13
tccggaattc cgtatggcaa tga                                              23

<210> SEQ ID NO 14
<211> LENGTH: 37
<212> TYPE: DNA
<213> ORGANISM: Artificial Sequence
<220> FEATURE:
<221> NAME/KEY: Primer Nco1.3(-)
<222> LOCATION: 1..37
<223> OTHER INFORMATION: Reverse oligonucleotide primer for destroying
      the Nco I site within the Camr gene in plasmid pSCFV31

<400> SEQUENCE: 14
cttgcgtata atatttgccc atcgtgaaaa cggggggc                              37

<210> SEQ ID NO 15
<211> LENGTH: 22
<212> TYPE: DNA
<213> ORGANISM: Artificial Sequence
```

<220> FEATURE:
<221> NAME/KEY: Primer Nco1.2
<222> LOCATION: 1..22
<223> OTHER INFORMATION: Forward oligonucleotide primer for destroying
the Hind III site at the 5' end of the penP promoter in plasmid
pSCFV31

<400> SEQUENCE: 15
atgggcaaat attatacgca ag                                            22

<210> SEQ ID NO 16
<211> LENGTH: 36
<212> TYPE: DNA
<213> ORGANISM: Artificial Sequence
<220> FEATURE:
<221> NAME/KEY: Primer Nco1.4c(-)
<222> LOCATION: 1..36
<223> OTHER INFORMATION: Reverse oligonucleotide primer for destroying
the Hind III site at the 5' end of the penP promoter in plasmid
pSCFV31

<400> SEQUENCE: 16
cactgaattc atcgatgata agctgtcaaa catgag                             36

<210> SEQ ID NO 17
<211> LENGTH: 35
<212> TYPE: DNA
<213> ORGANISM: Artificial Sequence
<220> FEATURE:
<221> NAME/KEY: Primer 104BH1
<222> LOCATION: 1..35
<223> OTHER INFORMATION: Forward oligonucleotide primer for amplifying
DNA encoding Hum4VL from plasmid pCGS515/SCFV1

<400> SEQUENCE: 17
cagccatggc cgacatcgtg atgacccagt ctcca                              35

<210> SEQ ID NO 18
<211> LENGTH: 86
<212> TYPE: DNA
<213> ORGANISM: Artificial Sequence
<220> FEATURE:
<221> NAME/KEY: Primer 104BH2(-)
<222> LOCATION: 1..86
<223> OTHER INFORMATION: Reverse oligonucleotide primer for amplifying
DNA encoding Hum4VL from plasmid pCGS515/SCFV1

<400> SEQUENCE: 18
aagcttgccc catgctgctt taacgttagt tttatctgct ggagacagag tgccttctgc   60
ctccaccttg gtccctccgc cgaaag                                        86

<210> SEQ ID NO 19
<211> LENGTH: 50
<212> TYPE: DNA
<213> ORGANISM: Artificial Sequence
<220> FEATURE:
<221> NAME/KEY: Primer 104B3
<222> LOCATION: 1..50
<223> OTHER INFORMATION: Forward oligonucleotide primer for amplifying
DNA encoding CC49 VH from plasmid p49g1-2.3

<400> SEQUENCE: 19
gttaaagcag catggggcaa gcttatgact cagttgcagc agtctgacgc               50

<210> SEQ ID NO 20
<211> LENGTH: 99
<212> TYPE: DNA
<213> ORGANISM: Artificial Sequence

```
<220> FEATURE:
<221> NAME/KEY: Primer 104B4(-)
<222> LOCATION: 1..99
<223> OTHER INFORMATION: Reverse oligonucleotide primer for amplifying
      DNA encoding CC49 VH from plasmid p49g1-2.3

<400> SEQUENCE: 20
ctcttgatca ccaagtgact ttatgtaaga tgatgttttg acggattcat cgctagcttt      60
ttatttgcca taataagggg agacggtgac tgaggttcc                             99

<210> SEQ ID NO 21
<211> LENGTH: 34
<212> TYPE: DNA
<213> ORGANISM: Artificial Sequence
<220> FEATURE:
<221> NAME/KEY: Primer UNIH1
<222> LOCATION: 1..34
<223> OTHER INFORMATION: Forward oligonucleotide primer for amplifying
      DNA encoding Hum4VL from plasmid pRL1001

<400> SEQUENCE: 21
cagccatggc cgacattgtg atgtcacagt ctcc                                  34

<210> SEQ ID NO 22
<211> LENGTH: 72
<212> TYPE: DNA
<213> ORGANISM: Artificial Sequence
<220> FEATURE:
<221> NAME/KEY: Primer UNIH2(-)
<222> LOCATION: 1..72
<223> OTHER INFORMATION: Reverse oligonucleotide primer for amplifying
      DNA encoding Hum4VL from plasmid pRL1001

<400> SEQUENCE: 22
gaggtccgta agatctcgcc tcgctaccta gcaaaaggtc ctcaagcttg atcaccacct      60
tggtccctcc gc                                                          72

<210> SEQ ID NO 23
<211> LENGTH: 48
<212> TYPE: DNA
<213> ORGANISM: Artificial Sequence
<220> FEATURE:
<221> NAME/KEY: Primer UNI3
<222> LOCATION: 1..48
<223> OTHER INFORMATION: Forward oligonucleotide primer for amplifying
      DNA encoding CC49 VH from plasmid p49g1-2.3

<400> SEQUENCE: 23
agcgaggcag atcttacgga cctcgaggtt cagttgcagc agtctgac                   48

<210> SEQ ID NO 24
<211> LENGTH: 40
<212> TYPE: DNA
<213> ORGANISM: Artificial Sequence
<220> FEATURE:
<221> NAME/KEY: Primer UNI4(-)
<222> LOCATION: 1..40
<223> OTHER INFORMATION: Reverse oligonucleotide primer for amplifying
      DNA encoding CC49 VH from plasmid p49g1-2.3

<400> SEQUENCE: 24
catcgctagc tttttatgag gagacggtga ctgaggttcc                            40

<210> SEQ ID NO 25
<211> LENGTH: 89
<212> TYPE: DNA
<213> ORGANISM: Artificial Sequence
```

```
<220> FEATURE:
<221> NAME/KEY: Primer UNIHOPE
<222> LOCATION: 1..89
<223> OTHER INFORMATION: Oligonucleotide encoding the (+) strand of the
      linker UNIHOPE

<400> SEQUENCE: 25
tataaagctt agtgcggacg atgcgaaaaa ggatgctgcg aagaaggatg acgctaagaa      60
agacgatgct aaaaaggacc tcgagtcta                                        89

<210> SEQ ID NO 26
<211> LENGTH: 89
<212> TYPE: DNA
<213> ORGANISM: Artificial Sequence
<220> FEATURE:
<221> NAME/KEY: Primer UNIHOPE(-)
<222> LOCATION: 1..89
<223> OTHER INFORMATION: Oligonucleotide encoding the (-) strand of the
      linker UNIHOPE

<400> SEQUENCE: 26
tagactcgag gtcctttta gcatcgtctt tcttagcgtc atccttcttc gcagcatcct      60
ttttcgcatc gtccgcacta agctttata                                       89

<210> SEQ ID NO 27
<211> LENGTH: 30
<212> TYPE: DNA
<213> ORGANISM: Artificial Sequence
<220> FEATURE:
<221> NAME/KEY: Primer HVH135
<222> LOCATION: 1..30
<223> OTHER INFORMATION: Forward oligonucleotide primer for amplifying
      human VH genes

<400> SEQUENCE: 27
tattctcgag gtgcarctgs tgsagtctgg                                       30

<210> SEQ ID NO 28
<211> LENGTH: 30
<212> TYPE: DNA
<213> ORGANISM: Artificial Sequence
<220> FEATURE:
<221> NAME/KEY: Primer HVH2A
<222> LOCATION: 1..30
<223> OTHER INFORMATION: Forward oligonucleotide primer for amplifying
      human VH genes

<400> SEQUENCE: 28
tattctcgag gtcaasttra rggagtctgg                                       30

<210> SEQ ID NO 29
<211> LENGTH: 30
<212> TYPE: DNA
<213> ORGANISM: Artificial Sequence
<220> FEATURE:
<221> NAME/KEY: Primer HVH46
<222> LOCATION: 1..30
<223> OTHER INFORMATION: Forward oligonucleotide primer for amplifying
      human VH genes

<400> SEQUENCE: 29
tattctcgag gtacagctrc agswgtcvgg                                       30

<210> SEQ ID NO 30
<211> LENGTH: 30
<212> TYPE: DNA
<213> ORGANISM: Artificial Sequence
```

```
<220> FEATURE:
<221> NAME/KEY: Primer JH1245
<222> LOCATION: 1..30
<223> OTHER INFORMATION: Reverse oligonucleotide primer for amplifying
      human VH genes

<400> SEQUENCE: 30
ttatgctagc tgaggagacr gtgaccaggg                                          30

<210> SEQ ID NO 31
<211> LENGTH: 30
<212> TYPE: DNA
<213> ORGANISM: Artificial Sequence
<220> FEATURE:
<221> NAME/KEY: Primer JH3
<222> LOCATION: 1..30
<223> OTHER INFORMATION: Reverse oligonucleotide primer for amplifying
      human VH genes

<400> SEQUENCE: 31
ttatgctagc tgaagagacg gtgaccattg                                          30

<210> SEQ ID NO 32
<211> LENGTH: 30
<212> TYPE: DNA
<213> ORGANISM: Artificial Sequence
<220> FEATURE:
<221> NAME/KEY: Primer JH6
<222> LOCATION: 1..30
<223> OTHER INFORMATION: Reverse oligonucleotide primer for amplifying
      human VH genes

<400> SEQUENCE: 32
ttatgctagc tgaggagacg gtgaccgtgg                                          30

<210> SEQ ID NO 33
<211> LENGTH: 50
<212> TYPE: DNA
<213> ORGANISM: Artificial Sequence
<220> FEATURE:
<221> NAME/KEY: Primer FLAGC
<222> LOCATION: 1..50
<223> OTHER INFORMATION: Forward oligonucleotide primer for generating
      plasmid pATDFLAG from plasmid pSCFVUHH

<400> SEQUENCE: 33
tcgagacaat gtcgctagcg actacaagga cgatgatgac aaataaaaac                    50

<210> SEQ ID NO 34
<211> LENGTH: 50
<212> TYPE: DNA
<213> ORGANISM: Artificial Sequence
<220> FEATURE:
<221> NAME/KEY: Primer FLAGNC
<222> LOCATION: 1..50
<223> OTHER INFORMATION: Reverse oligonucleotide primer for generating
      plasmid pATDFLAG from plasmid pSCFVUHH

<400> SEQUENCE: 34
ctaggttttt atttgtcatc atcgtccttg tagtcgctag cgacattgtc                    50

<210> SEQ ID NO 35
<211> LENGTH: 22
<212> TYPE: DNA
<213> ORGANISM: Artificial Sequence
```

```
<220> FEATURE:
<221> NAME/KEY: Primer PENPTSEQ
<222> LOCATION: 1..22
<223> OTHER INFORMATION: Oligonucleotide primer for verifying the
      sequence of the FLAG linker in pATDFLAG

<400> SEQUENCE: 35
ctttatgtaa gatgatgttt tg                                             22

<210> SEQ ID NO 36
<211> LENGTH: 20
<212> TYPE: DNA
<213> ORGANISM: Artificial Sequence
<220> FEATURE:
<221> NAME/KEY: Primer 5 VH, coding
<222> LOCATION: 1..20
<223> OTHER INFORMATION: Forward oligonucleotide primer for generating
      DNA encoding a humanized VH

<400> SEQUENCE: 36
ctaagcttcc accatggagn                                                20

<210> SEQ ID NO 37
<211> LENGTH: 20
<212> TYPE: DNA
<213> ORGANISM: Artificial Sequence
<220> FEATURE:
<221> NAME/KEY: Primer 3 VH, noncoding
<222> LOCATION: 1..20
<223> OTHER INFORMATION: Reverse oligonucleotide primer for generating
      DNA encoding a humanized VH

<400> SEQUENCE: 37
atgggcccgt agttttggcg                                                20

<210> SEQ ID NO 38
<211> LENGTH: 20
<212> TYPE: DNA
<213> ORGANISM: Artificial Sequence
<220> FEATURE:
<221> NAME/KEY: Primer 5 VL, coding
<222> LOCATION: 1..20
<223> OTHER INFORMATION: Forward oligonucleotide primer for generating
      DNA encoding a humanized VL

<400> SEQUENCE: 38
gcaagcttcc accatggata                                                20

<210> SEQ ID NO 39
<211> LENGTH: 20
<212> TYPE: DNA
<213> ORGANISM: Artificial Sequence
<220> FEATURE:
<221> NAME/KEY: Primer 3 VL, noncoding
<222> LOCATION: 1..20
<223> OTHER INFORMATION: Reverse oligonucleotide primer for generating
      DNA encoding a humanized VL

<400> SEQUENCE: 39
agccgcggcc cgtttcagtt                                                20

<210> SEQ ID NO 40
<211> LENGTH: 982
<212> TYPE: DNA
<213> ORGANISM: Mus musculus
```

-continued

```
<220> FEATURE:
<221> NAME/KEY: VHaTAG germline coding sequence part 1
<222> LOCATION: 384..428
<220> FEATURE:
<221> NAME/KEY: Intron
<222> LOCATION: 429..508
<220> FEATURE:
<221> NAME/KEY: VHaTAG germline coding sequence part 2
<222> LOCATION: 509..813

<400> SEQUENCE: 40
```

| | | |
|---|---|---|
| ccttctcttc ctccaccacc aaatccacca tttgtaaatc aacatgttaa catatcacag | 60 | |
| agtggagcaa cagaatcagg gcaaaaatat gctgagagat ttatccctgt cgttacaacc | 120 | |
| aaagcatctg tctagaattc ataaaaactt tatgggatac atttcctcag agaggaatag | 180 | |
| gatttggacc tgacgatcct gctgcccgag ccatgtgatg acagttcttc tccagttgaa | 240 | |
| ctaggtcctt atctaagaaa tgcactgctc atgaatatgc aaatcacccg agtctatggc | 300 | |
| agtaaataca gagatgttca taccataaaa acaatatatg atcagtgtct tctccgctat | 360 | |

```
ccctggacac actgactcta acc atg gaa tgg agc tgg gtc ttt ctc ttc ttc    413
                             Met Glu Trp Ser Trp Val Phe Leu Phe Phe
                              1               5                  10 ctg tca gta act aca g gtaaggggct caccatttcc aaatctaaag tggagtcagg    469
Leu Ser Val Thr Thr
                15 gcctgaggtg acaaagatat cacctttggc tttccacag gt gtc cac tcc cag gtt    525
                                                Gly Val His Ser Gln Val
                                                                    20 cag ctg cag cag tct gac gct gag ttg gtg aaa cct ggg gct tca gtg    573
Gln Leu Gln Gln Ser Asp Ala Glu Leu Val Lys Pro Gly Ala Ser Val
         25                  30                  35 aag ata tcc tgc aag gct tct ggc tac acc ttc act gac cat gct att    621
Lys Ile Ser Cys Lys Ala Ser Gly Tyr Thr Phe Thr Asp His Ala Ile
 40                  45                  50 cac tgg gtg aag cag aag cct gaa cag ggc ctg gaa tgg att gga tat    669
His Trp Val Lys Gln Lys Pro Glu Gln Gly Leu Glu Trp Ile Gly Tyr
         55                  60                  65 att tct ccc gga aat ggt gat att aag tac aat gag aag ttc aag ggc    717
Ile Ser Pro Gly Asn Gly Asp Ile Lys Tyr Asn Glu Lys Phe Lys Gly
 70                  75                  80                  85 aag gcc aca ctg act gca gac aaa tcc tcc agc act gcc tac atg cag    765
Lys Ala Thr Leu Thr Ala Asp Lys Ser Ser Ser Thr Ala Tyr Met Gln
             90                  95                 100 ctc aac agc ctg aca tct gag gat tct gca gtg tat ttc tgt aaa aga    813
Leu Asn Ser Leu Thr Ser Glu Asp Ser Ala Val Tyr Phe Cys Lys Arg
        105                 110                 115
```

| | | |
|---|---|---|
| cacagtgttg taaccacatc ctgagtgtgt cagaaatcct gggggagcag aaagatacac | 873 | |
| tgggactgag aagacagaaa aattaatcct tagacttgct cagaaatcgt aattttgaat | 933 | |
| gcctatttat ttcatcttgc tcacacacct atattgcttt tgtaagctt | 982 | |

```
<210> SEQ ID NO 41
<211> LENGTH: 451
<212> TYPE: DNA
<213> ORGANISM: Mus musculus
<220> FEATURE:
<221> NAME/KEY: CC46 VH coding sequence
<222> LOCATION: 49..450
```

```
<400> SEQUENCE: 41
atatgatcag tgtcttctcc gctatccctg gacacactga ctctaacc atg gaa tgg        57
                                                      Met Glu Trp
                                                       1 agc tgg gtc ttt ctc ttc ttc ctg tca gta act aca ggt gtc cac tcc        105
Ser Trp Val Phe Leu Phe Phe Leu Ser Val Thr Thr Gly Val His Ser
 5               10                  15 caa ttt cag cta cag cag tct gac gct gag ttg gtg aga cct ggg gct        153
Gln Phe Gln Leu Gln Gln Ser Asp Ala Glu Leu Val Arg Pro Gly Ala
 20                  25                  30                  35 tca gtg aag att tcc tgc aag gct tct ggc tac acc ttc act gac cat        201
Ser Val Lys Ile Ser Cys Lys Ala Ser Gly Tyr Thr Phe Thr Asp His
                 40                  45                  50 gct att cac tgg gtg aag cag aag cct gaa cag ggc ctg gaa tgg att        249
Ala Ile His Trp Val Lys Gln Lys Pro Glu Gln Gly Leu Glu Trp Ile
                     55                  60                  65 gga tat ttt tct ccc gga aat ggt gat att aag tac aat gag aag ttc        297
Gly Tyr Phe Ser Pro Gly Asn Gly Asp Ile Lys Tyr Asn Glu Lys Phe
             70                  75                  80 aag ggc aag gcc aca ctg act gca gac aaa tcc tcc agc act gcc tac        345
Lys Gly Lys Ala Thr Leu Thr Ala Asp Lys Ser Ser Ser Thr Ala Tyr
 85                  90                  95 atg cag ttc aac agc ctg aca tct gag gac tct gca gtg tat ttc tgt        393
Met Gln Phe Asn Ser Leu Thr Ser Glu Asp Ser Ala Val Thr Phe Cys
100                 105                 110                 115 acg ggc ggc tac ggg ttt gct ttc tgg ggc caa ggg act ctg gtc act        441
Thr Gly Gly Tyr Gly Phe Ala Phe Trp Gly Gln Gly Thr Leu Val Thr
                    120                 125                 130 gtc tct gca g                                                          451
Val Ser Ala <210> SEQ ID NO 42
<211> LENGTH: 865
<212> TYPE: DNA
<213> ORGANISM: Mus musculus
<220> FEATURE:
<221> NAME/KEY: CC49 VH coding sequence part 1
<222> LOCATION: 384..428
<220> FEATURE:
<221> NAME/KEY: Intron
<222> LOCATION: 429..508
<220> FEATURE:
<221> NAME/KEY: CC49 VH coding sequence part 2
<222> LOCATION: 509..864

<400> SEQUENCE: 42
ccttctcttc ctccaccacc aaatccacca tttgtaaatc aacatgttaa catatcacag       60
agtggagcaa cagaatcagg gcaaaaatat gctgagagat ttttccctgt cgttacaacc      120
aaagcatctg tctagaattc ataaaaactt tatgggatac atttcctcag agaggaatag      180
gatttggacc tgacgatcct gctgcccgag ccatgtgatg acagttcttc tccagttgaa      240
ctaggtcctt atctaagaaa tgcactgctc atgaatatgc aaatcacccg agtctatggc      300
agtaaataca gagatgttca taccataaaa acaatatgtg atcagtgtct ctccgctat       360 ccctggacac actgactcta acc atg gaa tgg agc tgg gtc ttt ctc ttc ttc      413
                         Met Glu Trp Ser Trp Val Phe Leu Phe Phe
                          1               5                  10 ctg tca gta act aca g gtaaggggct caccatttcc aaatctaaag tggagtcagg      469
Leu Ser Val Thr Thr
                 15
```

-continued

```
gcctgaggtg acaaagatgt cacctttggc tgtccacag gt gtc cac tcc cag gtt      525
                                             Gly Val His Ser Gln Val
                                                               20 cag ttg cag cag tct gac gct gag ttg gtg aaa cct ggg gct tca gtg        573
Gln Leu Gln Gln Ser Asp Ala Glu Leu Val Lys Pro Gly Ala Ser Val
        25                  30                  35 aag att tcc tgc aag gct tct ggc tac acc ttc act gac cat gca att        621
Lys Ile Ser Cys Lys Ala Ser Gly Tyr Thr Phe Thr Asp His Ala Ile
    40                  45                  50 cac tgg gtg aaa cag aac cct gaa cag ggc ctg gaa tgg att gga tat        669
His Trp Val Lys Gln Asn Pro Glu Gln Gly Leu Glu Trp Ile Gly Tyr
55                  60                  65 ttt tct ccc gga aat gat gat ttt aaa tac aat gag agg ttc aag ggc        717
Phe Ser Pro Gly Asn Asp Asp Phe Lys Tyr Asn Glu Arg Phe Lys Gly
70                  75                  80                  85 aag gcc aca ctg act gca gac aaa tcc tcc agc act gcc tac gtg cag        765
Lys Ala Thr Leu Thr Ala Asp Lys Ser Ser Ser Thr Ala Tyr Val Gln
            90                  95                  100 ctc aac agc ctg aca tct gag gat tct gca gtg tat ttc tgt aca aga        813
Leu Asn Ser Leu Thr Ser Glu Asp Ser Ala Val Tyr Phe Cys Thr Arg
        105                 110                 115 tcc ctg aat atg gcc tac tgg ggt caa gga acc tca gtc acc gtc tcc        861
Ser Leu Asn Met Ala Tyr Trp Gly Gln Gly Thr Leu Val Thr Val Ser
    120                 125                 130 tca g                                                                  865
Ser
```

<210> SEQ ID NO 43
<211> LENGTH: 862
<212> TYPE: DNA
<213> ORGANISM: Mus musculus
<220> FEATURE:
<221> NAME/KEY: CC83 VH coding sequence part 1
<222> LOCATION: 374..428
<220> FEATURE:
<221> NAME/KEY: Intron
<222> LOCATION: 429..508
<220> FEATURE:
<221> NAME/KEY: CC83 VH coding sequence part 2
<222> LOCATION: 509..861

<400> SEQUENCE: 43

```
ccttctcttc ctccaccacc aaatccacca tttgtaaatc aacatgttaa catatcacag        60
agtggagcaa cagaatcagg gcaaaaatat gctgagagat ttatccctgt cgttacaacc       120
aaagcatctg tctagaattc ataaaaactt tatgggatac atttcctcag agaggaatag       180
gatttggacc tgacgatcct gctgcccgag ccatgtgatg acagttcttc tccagttgaa       240
ctaggtcctt atctaagaaa tgcactgctc atgaatatgc aaatcacccg agtctatggc       300
agtaaataca gagatgttca taccataaaa acaatatatg atcagtgtct tctccgctat       360
ccctggacac actgactcta acc atg gaa tgg agc tgg gtc ttt ctc ttc ttc      413
                          Met Glu Trp Ser Trp Val Phe Leu Phe Phe
                           1               5                  10 ctg tca gta act aca g gtaaggggct caccatttcc aaatctaaag tggagtcagg      469
Leu Ser Val Thr Thr
            15 gcctgaggtg acaaagatat cacctttggc tttccacag gt gtc cac tcc cag gtt      525
                                             Gly Val His Ser Gln Val
                                                               20 cag ttg cag cag tct gac gct gag ttg gtg aaa cct ggg gct tca gtg        573
Gln Leu Gln Gln Ser Asp Ala Glu Leu Val Lys Pro Gly Ala Ser Val
        25                  30                  35
```

```
aag att tcc tgc aag gct tct ggc tac acc ttc act gac cat gct att        621
Lys Ile Ser Cys Lys Ala Ser Gly Tyr Thr Phe Thr Asp His Ala Ile
        40                  45                  50 cac tgg gtg aag cag aag cct gaa cag ggc ctg gaa tgg att gga tat        669
His Trp Val Lys Gln Lys Pro Glu Gln Gly Leu Glu Trp Ile Gly Tyr
55                  60                  65 att tct ccc gga aat gat gat att aag tac aat gag aag ttc aag ggc        717
Ile Ser Pro Gly Asn Asp Asp Ile Lys Tyr Asn Glu Lys Phe Lys Gly
70                  75                  80                  85 aag gcc aca ctg act gca gac aaa tcc tcc agt act gcc tac atg caa        765
Lys Ala Thr Leu Thr Ala Asp Lys Ser Ser Ser Thr Ala Tyr Met Gln
                90                  95                 100 ctc aac agc ctg aca tct gag gat tct gca gtg tat ttc tgt aga aga        813
Leu Asn Ser Leu Thr Ser Glu Asp Ser Ala Val Thr Phe Cys Arg Arg
            105                 110                 115 tcc ttc tac ggc aac tgg ggc caa ggc acc acc ctc aca gtc tcc tca g      862
Ser Phe Tyr Gly Asn Trp Gly Gln Gly Thr Thr Leu Thr Val Ser Ser
            120                 125                 130

<210> SEQ ID NO 44
<211> LENGTH: 430
<212> TYPE: DNA
<213> ORGANISM: Mus musculus
<220> FEATURE:
<221> NAME/KEY: CC92 VH coding sequence
<222> LOCATION: 28..429

<400> SEQUENCE: 44
ctatccctgg acacactgac tctaacc atg gaa tgg agc tgg gtc ttt ctc ttc       54
                                Met Glu Trp Ser Trp Val Phe Leu Phe
                                  1               5 ttc ctg tca gta act aca ggt gtc cac tcc cag gtt caa ctg cag cag        102
Phe Leu Ser Val Thr Thr Gly Val His Ser Gln Val Gln Leu Gln Gln
10                  15                  20                  25 tct gac gct gag ttg gtg aaa cct ggg gct tca gtg aag ata tcc tgc        150
Ser Asp Ala Glu Leu Val Lys Pro Gly Ala Ser Val Lys Ile Ser Cys
                30                  35                  40 aag gct tct ggc tac acc ttc act gac cat gct att cac tgg gtg aag        198
Lys Ala Ser Gly Tyr Thr Phe Thr Asp His Ala Ile His Trp Val Lys
            45                  50                  55 cag aaa cct gaa cag ggc ctg gaa tgg att gga tat att tct ccc gga        246
Gln Lys Pro Glu Gln Gly Leu Glu Trp Ile Gly Tyr Ile Ser Pro Gly
        60                  65                  70 aat gat gat att aag tac aat gag aag ttc aag ggt aag gcc aca ctg        294
Asn Asp Asp Ile Lys Tyr Asn Glu Lys Phe Lys Gly Lys Ala Thr Leu
    75                  80                  85 act gca gac aaa ccc tcc aac act gtc tac atg cag ctc aac agc ctg        342
Thr Ala Asp Lys Pro Ser Asn Thr Val Tyr Met Gln Leu Asn Ser Leu
90                  95                 100                 105 acc tct gag gat tct gca gtg tat ttc tgt aca aga tct cta tcc ggg        390
Thr Ser Glu Asp Ser Ala Val Tyr Phe Cys Thr Arg Ser Leu Ser Gly
                110                 115                 120 aac tcc tgg ggc cag ggc acc act ctc aca gtc tcc tca g                  430
Asn Ser Trp Gly Gln Gly Thr Thr Leu Thr Val Ser Ser
            125                 130

<210> SEQ ID NO 45
<211> LENGTH: 117
<212> TYPE: PRT
<213> ORGANISM: Mus musculus
<220> FEATURE:
<221> NAME/KEY: VHaTAG
<222> LOCATION: 1..117
```

```
<400> SEQUENCE: 45

Met Glu Trp Ser Trp Val Phe Leu Phe Phe Leu Ser Val Thr Thr Gly
1               5                   10                  15

Val His Ser Gln Val Gln Leu Gln Gln Ser Asp Ala Glu Leu Val Lys
            20                  25                  30

Pro Gly Ala Ser Val Lys Ile Ser Cys Lys Ala Ser Gly Tyr Thr Phe
        35                  40                  45

Thr Asp His Ala Ile His Trp Val Lys Gln Lys Pro Glu Gln Gly Leu
    50                  55                  60

Glu Trp Ile Gly Tyr Ile Ser Pro Gly Asn Gly Asp Ile Lys Tyr Asn
65                  70                  75                  80

Glu Lys Phe Lys Gly Lys Ala Thr Leu Thr Ala Asp Lys Ser Ser
                85                  90                  95

Thr Ala Tyr Met Gln Leu Asn Ser Leu Thr Ser Glu Asp Ser Ala Val
                100                 105                 110

Thr Phe Cys Lys Arg
            115

<210> SEQ ID NO 46
<211> LENGTH: 134
<212> TYPE: PRT
<213> ORGANISM: Mus musculus
<220> FEATURE:
<221> NAME/KEY: CC46 VH
<222> LOCATION: 1..134

<400> SEQUENCE: 46

Met Glu Trp Ser Trp Val Phe Leu Phe Phe Leu Ser Val Thr Thr Gly
1               5                   10                  15

Val His Ser Gln Phe Gln Leu Gln Gln Ser Asp Ala Glu Leu Val Arg
            20                  25                  30

Pro Gly Ala Ser Val Lys Ile Ser Cys Lys Ala Ser Gly Tyr Thr Phe
        35                  40                  45

Thr Asp His Ala Ile His Trp Val Lys Gln Lys Pro Glu Gln Gly Leu
    50                  55                  60

Glu Trp Ile Gly Tyr Phe Ser Pro Gly Asn Gly Asp Ile Lys Tyr Asn
65                  70                  75                  80

Glu Lys Phe Lys Gly Lys Ala Thr Leu Thr Ala Asp Lys Ser Ser
                85                  90                  95

Thr Ala Tyr Met Gln Phe Asn Ser Leu Thr Ser Glu Asp Ser Ala Val
                100                 105                 110

Thr Phe Cys Thr Gly Gly Tyr Gly Phe Ala Phe Trp Gly Gln Gly Thr
            115                 120                 125

Leu Val Thr Val Ser Ala
        130

<210> SEQ ID NO 47
<211> LENGTH: 134
<212> TYPE: PRT
<213> ORGANISM: Mus musculus
<220> FEATURE:
<221> NAME/KEY: CC49 VH
<222> LOCATION: 1..134
```

-continued

```
<400> SEQUENCE: 47

Met Glu Trp Ser Trp Val Phe Leu Phe Phe Leu Ser Val Thr Thr Gly
1               5                   10                  15

Val His Ser Gln Val Gln Leu Gln Gln Ser Asp Ala Glu Leu Val Lys
            20                  25                  30

Pro Gly Ala Ser Val Lys Ile Ser Cys Lys Ala Ser Gly Tyr Thr Phe
        35                  40                  45

Thr Asp His Ala Ile His Trp Val Lys Gln Asn Pro Glu Gln Gly Leu
    50                  55                  60

Glu Trp Ile Gly Tyr Phe Ser Pro Gly Asn Asp Asp Phe Lys Tyr Asn
65                  70                  75                  80

Glu Arg Phe Lys Gly Lys Ala Thr Leu Thr Ala Asp Lys Ser Ser Ser
                85                  90                  95

Thr Ala Tyr Val Gln Leu Asn Ser Leu Thr Ser Glu Asp Ser Ala Val
            100                 105                 110

Thr Phe Cys Thr Arg Ser Leu Asn Met Ala Tyr Trp Gly Gln Gly Thr
        115                 120                 125

Ser Val Thr Val Ser Ser
    130

<210> SEQ ID NO 48
<211> LENGTH: 133
<212> TYPE: PRT
<213> ORGANISM: Mus musculus
<220> FEATURE:
<221> NAME/KEY: CC83 VH
<222> LOCATION: 1..133

<400> SEQUENCE: 48

Met Glu Trp Ser Trp Val Phe Leu Phe Phe Leu Ser Val Thr Thr Gly
1               5                   10                  15

Val His Ser Gln Val Gln Leu Gln Gln Ser Asp Ala Glu Leu Val Lys
            20                  25                  30

Pro Gly Ala Ser Val Lys Ile Ser Cys Lys Ala Ser Gly Tyr Thr Phe
        35                  40                  45

Thr Asp His Ala Ile His Trp Val Lys Gln Lys Pro Glu Gln Gly Leu
    50                  55                  60

Glu Trp Ile Gly Tyr Ile Ser Pro Gly Asn Asp Asp Ile Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Leu Asn Ser Leu Thr Ser Glu Asp Ser Ala Val
            100                 105                 110

Thr Phe Cys Arg Arg Ser Phe Tyr Gly Asn Trp Gly Gln Gly Thr Thr
        115                 120                 125

Leu Thr Val Ser Ser
    130

<210> SEQ ID NO 49
<211> LENGTH: 134
<212> TYPE: PRT
<213> ORGANISM: Mus musculus
<220> FEATURE:
<221> NAME/KEY: CC92 VH
<222> LOCATION: 1..134
```

<400> SEQUENCE: 49

```
Met Glu Trp Ser Trp Val Phe Leu Phe Phe Leu Ser Val Thr Thr Gly
1               5                   10                  15

Val His Ser Gln Val Gln Leu Gln Gln Ser Asp Ala Glu Leu Val Lys
            20                  25                  30

Pro Gly Ala Ser Val Lys Ile Ser Cys Lys Ala Ser Gly Tyr Thr Phe
        35                  40                  45

Thr Asp His Ala Ile His Trp Val Lys Gln Lys Pro Glu Gln Gly Leu
    50                  55                  60

Glu Trp Ile Gly Tyr Ile Ser Pro Gly Asn Asp Asp Ile Lys Tyr Asn
65                  70                  75                  80

Glu Lys Phe Lys Gly Lys Ala Thr Leu Thr Ala Asp Lys Pro Ser Asn
            85                  90                  95

Thr Val Tyr Met Gln Leu Asn Ser Leu Thr Ser Glu Asp Ser Ala Val
            100                 105                 110

Thr Phe Cys Thr Arg Ser Leu Ser Gly Asn Ser Trp Gly Gln Gly Thr
        115                 120                 125

Thr Leu Thr Val Ser Ser
        130
```

<210> SEQ ID NO 50
<211> LENGTH: 423
<212> TYPE: DNA
<213> ORGANISM: Artificial Sequence
<220> FEATURE:
<221> NAME/KEY: B17X2 VH coding sequence
<222> LOCATION: 7..423
<223> OTHER INFORMATION: DNA encoding the heavy chain variable region of the anti-N-acetylglucosamine antibody, B17X2

<400> SEQUENCE: 50

```
gaattc atg gaa aaa ctt tgg ttc ttg ctt ctg ctg ctg acc atc cct        48
       Met Glu Lys Leu Trp Phe Leu Leu Leu Leu Leu Thr Ile Pro
       1               5                   10 tca tgg gtc ttg tcc cag atc acc ttg aag gag tct ggt cct acn ctg      96
Ser Trp Val Leu Ser Gln Ile Thr Leu Lys Glu Ser Gly Pro Thr Leu
15                  20                  25                  30 gtg aaa ccc aca cag acc ctc acg ctg acc tgc acc ttc tct ggg ttc     144
Val Lys Pro Thr Gln Thr Leu Thr Leu Thr Cys Thr Phe Ser Gly Phe
                35                  40                  45 tca ctc agc act cat gga gtg ggt gtg ggc tgg atc cgt nnn nnc cca     192
Ser Leu Ser Thr His Gly Val Gly Val Gly Trp Ile Arg Xaa Xaa Pro
            50                  55                  60 gga aag gcc ctg gag tgg ctt gca ctc att tat tgg gat gat gat aag     240
Gly Lys Ala Leu Glu Trp Leu Ala Leu Ile Tyr Trp Asp Asp Asp Lys
        65                  70                  75 cgc tac agc cca tct ctg aag agc agg ctc acc atc acc aag gac acc     288
Arg Tyr Ser Pro Ser Leu Lys Ser Arg Leu Thr Ile Thr Lys Asp Thr
    80                  85                  90 tcc aaa aac cag gtg atc ctt aca atg acc aac atg gac cct gtg gac     336
Ser Lys Asn Gln Val Ile Leu Thr Met Thr Asn Met Asp Pro Val Asp
95                  100                 105                 110 aca gcc aca tat tat tgt gca cac ggg ctg cca tct atg gtt aag aac     384
Thr Ala Thr Tyr Tyr Cys Ala His Gly Leu Pro Ser Met Val Lys Asn
                115                 120                 125 tgg ggc caa ggg acc acg gtc acc gtc tcc tca ggg agt                  423
Trp Gly Gln Gly Thr Thr Val Thr Val Ser Ser Gly Ser
            130                 135
```

<210> SEQ ID NO 51
<211> LENGTH: 139
<212> TYPE: PRT
<213> ORGANISM: Artificial Sequence
<220> FEATURE:
<221> NAME/KEY: B17X2 VH
<222> LOCATION: 1..139
<223> OTHER INFORMATION: Heavy chain variable region of the
      anti-N-acetylglucosamine antibody, B17X2

<400> SEQUENCE: 51

```
Met Glu Lys Leu Trp Phe Leu Leu Leu Leu Thr Ile Pro Ser Trp
1               5                   10                  15

Val Leu Ser Gln Ile Thr Leu Lys Glu Ser Gly Pro Thr Leu Val Lys
            20                  25                  30

Pro Thr Gln Thr Leu Thr Leu Thr Cys Thr Phe Ser Gly Phe Ser Leu
        35                  40                  45

Ser Thr His Gly Val Gly Val Gly Trp Ile Arg Xaa Xaa Pro Gly Lys
    50                  55                  60

Ala Leu Glu Trp Leu Ala Leu Ile Tyr Trp Asp Asp Asp Lys Arg Tyr
65                  70                  75                  80

Ser Pro Ser Leu Lys Ser Arg Leu Thr Ile Thr Lys Asp Thr Ser Lys
                85                  90                  95

Asn Gln Val Ile Leu Thr Met Thr Asn Met Asp Pro Val Asp Thr Ala
            100                 105                 110

Thr Tyr Tyr Cys Ala His Gly Leu Pro Ser Met Val Lys Asn Trp Gly
        115                 120                 125

Gln Gly Thr Thr Val Thr Val Ser Ser Gly Ser
    130                 135
```

<210> SEQ ID NO 52
<211> LENGTH: 1954
<212> TYPE: DNA
<213> ORGANISM: Mus musculus
<220> FEATURE:
<221> NAME/KEY: J-H germline genes
<222> LOCATION: 1..1954
<223> OTHER INFORMATION: Murine J-H germline genes obtained from pNP9

<400> SEQUENCE: 52

```
ggatcctggc cagcattgcc gctaggtccc tctcttctat gctttctttg tccctcactg    60
gcctccatct gagataatcc tggagcccta gccaaggatc atttattgtc agggggtctaa  120
tcattgttgt cacaatgtgc ctggtttgct tactggggcc aagggactct ggtcactgtc   180
tctgcaggtg agtcctaact tctcccattc taaatgcatg ttgggggggat tctgagcctt   240
caggaccaag attctctgca aacgggaatc aagattcaac ccctttgtcc caaagttgag    300
acatgggtct gggtcaggga ctctctgcct gctggtctgt ggtgacatta gaactgaagt    360
atgatgaagg atctgccaga actgaagctt gaagtctgag gcagaatctt gtccagggtc    420
tatcggactc ttgtgagaat tagggggctga cagttgatgg tgacaatttc agggtcagtg   480
actgtcaggt ttctctgagg tgaggctgga atataggtca ccttgaagac taaagagggg    540
tccagggggct tttctgcaca ggcagggaac agaatgtgga caatgactt gaatggttga    600
ttcttgtgtg acaccaagaa ttggcataat gtctgagttg cccaagggtg atcttagcta    660
aaaacccact attgtgatta ctatgctatg gactactggg gtcaaggaac ctcagtcacc    720
gtctcctcag gtaagaatgg cctctccagg tctttatttt taacgtttgt tatggagttt   780
tctgagcatt gcagactaat cttggatatt tgccctgagg gagccggctg agagaagttg    840
```

```
ggaaataaat ctgtctaggg atctcagagc ctttaggaca gattatctcc acatctttga      900
aaaactaaga atctgtgtga tggtgttggt ggagtccctg atgatgggga tagggacttt      960
ggaggctcat ttgagggaga tgctaaaaca atcctatggc tggagggata gttggggctg     1020
tagttggaga ttttcagttt ttagaatgaa gtattagctg caatacttca aggaccacct     1080
ctgtgacaac cattttatac agtatccagg catagggaca aaaagtggag tggggcactt     1140
tctttagatt tgtgaggaat gttccacact agattgttta aaacttcatt tgttggaagg     1200
agctgtctta gtgattgagt caagggagaa aggcatctag cctcggtctc aaaagggtag     1260
ttgctgtcta gagaggtctg gtggagcctg caaaagtcca gctttcaaag gaacacagaa     1320
gtatgtgtat ggaatattag aagatgttgc ttttactctt aagttggttc ctaggaaaaa     1380
tagttaaata ctgtgacttt aaaatgtgag agggttttca agtactcatt tttttaaatg     1440
tccaaaattt ttgtcaatca atttgaggtc ttgtttgtgt agaactgaca ttacttaaag     1500
tttaaccgag gaatgggagt gaggctctct catacccctat tcagaactga cttttaacaa    1560
taataaatta agtttaaaat attttttaaat gaattgagca atgttgagtt gagtcaagat    1620
ggccgatcag aaccggaaca cctgcagcag ctggcaggaa gcaggtcatg tgcaaggct      1680 atttggggaa gggaaaataa aaccactagg taaacttgta gctgtggttt aagaagtgg     1740 ttttgaaaca ctctgtccag ccccaccaaa ccgaaagtcc aggctgagca aaacaccacc    1800
tgggtaattt gcatttctaa aataagttga ggattcagcc gaaactggag aggtcctctt     1860
ttaacttatt gagttcaacc ttttaatttt agcttgagta gttctagttt ccccaaactt     1920
aagtttatcg acttctaaaa tgtatttaga attc                                 1954
```

<210> SEQ ID NO 53
<211> LENGTH: 26
<212> TYPE: DNA
<213> ORGANISM: Artificial Sequence
<220> FEATURE:
<221> NAME/KEY: HUMVL(+)
<222> LOCATION: 1..26
<223> OTHER INFORMATION: Forward oligonucleotide primer for
     amplification of the Hum4 VL germline gene

<400> SEQUENCE: 53
gaagagtatc gataaaattt attgag                                            26

<210> SEQ ID NO 54
<211> LENGTH: 98
<212> TYPE: DNA
<213> ORGANISM: Artificial Sequence
<220> FEATURE:
<221> NAME/KEY: HUMVL(-)
<222> LOCATION: 1..98
<223> OTHER INFORMATION: Reverse oligonucleotide primer for
     amplification of the Hum4 VL germline gene

<400> SEQUENCE: 54
cattaagctt agaaaagtgt acttacgttt gatcaccacc ttggtccctc cgccgaaagt      60
gagaggataa ctataatatt gctgacagta ataaactg                              98

<210> SEQ ID NO 55
<211> LENGTH: 55
<212> TYPE: DNA
<213> ORGANISM: Homo sapiens
<220> FEATURE:
<221> NAME/KEY: HJ4 coding sequence
<222> LOCATION: 1..55
<223> OTHER INFORMATION: Human J4 DNA sequence

<400> SEQUENCE: 55

```
ctc act ttc ggc gga ggg acc aag gtg gag atc aaa cgt aagtgcactt      49
Leu Thr Phe Gly Gly Gly Thr Lys Val Glu Ile Lys Arg
1               5                   10 tcctaa                                                              55
```

<210> SEQ ID NO 56
<211> LENGTH: 13
<212> TYPE: PRT
<213> ORGANISM: Artificial Sequence
<220> FEATURE:
<221> NAME/KEY: HJ4
<222> LOCATION: 1..13
<223> OTHER INFORMATION: Human J4 region

<400> SEQUENCE: 56

```
Leu Thr Phe Gly Gly Gly Thr Lys Val Glu Ile Lys Arg
1               5                   10
```

<210> SEQ ID NO 57
<211> LENGTH: 1088
<212> TYPE: DNA
<213> ORGANISM: Homo sapiens
<220> FEATURE:
<221> NAME/KEY: Hum4 VL coding sequence part 1
<222> LOCATION: 448..495
<220> FEATURE:
<221> NAME/KEY: Intron
<222> LOCATION: 496..715
<220> FEATURE:
<221> NAME/KEY: Hum4 VL coding sequence part 2
<222> LOCATION: 716..1068

<400> SEQUENCE: 57

```
atcgataaaa tttattgaga atttgtttat tatgattaac agaggtaaaa gccagtatat     60
tactgattaa tataggtaaa aggcagttaa gaaattggga atgctttctc ttctgctttc    120
ttctacgatg cacaaggcgt tcacatttta tgcccctatg aaaattacta ggctgtccta    180
gtcattagat ctttcagcag tttgtagttt tagagcttct aagttgactt ctgtcttttc    240
tattcataca attacacatt ctgtgatgat atttttggct cttgatttac attgggtact    300
ttcacaaccc actgctcatg aaatttgctt ttgtactact ggttgttttt gcataggccc    360
ctccaggcca cgaccaggtg tttggatttt ataaacgggc cgtttgcatt gtgaactgag    420
ctacaacagg caggcagggg cagcaag atg gtg ttg cag acc cag gtc ttc att    474
                               Met Val Leu Gln Thr Gln Val Phe Ile
                                 1               5 tct ctg ttg ctc tgg atc tct g gtgaggaatt aaaaagtgcc acagtctttt       526
Ser Leu Leu Leu Trp Ile Ser
 10              15 cagagtaata tctgtgtaga ataaaaaaa attaagatat agttggaaat aatgactatt     586
tccaatatgg atccaattat ctgctgactt ataatactac tagaaagcaa atttaaatga    646
catatttcaa ttatatctga dacagcgtgt ataagtttat gtataatcat tgtccattac    706 tgactacag gt ccc tac ggg gac atc gtg atg acc cag tct cca gac tcc     756
         Gly Ala Tyr Gly Asp Ile Val Met Thr Gln Ser Pro Asp Ser
                 20                  25                  30 ctg gct gtg tct ctg ggc gag agg gcc acc atc aac tgc aag tcc agc      804
Leu Ala Val Ser Leu Gly Glu Arg Ala Thr Ile Asn Cys Lys Ser Ser
         35                  40                  45 cag agt gtt tta tac agc tcc aac aat aag aac tac tta gct tgg tac      852
Gln Ser Val Leu Tyr Ser Ser Asn Asn Lys Asn Tyr Leu Ala Trp Tyr
     50                  55                  60
```

```
cag cag aaa cca gga cag cct cct aag ctg ctc att tac tgg gca tct    900
Gln Gln Lys Pro Gly Gln Pro Pro Lys Leu Leu Ile Tyr Trp Ala Ser
         65                  70                  75 acc cgg gaa tcc ggg gtc cct gac cga ttc agt ggc agt ggg tct ggg    948
Thr Arg Glu Ser Gly Val Pro Asp Arg Phe Ser Gly Ser Gly Ser Gly
 80                  85                  90 aca gat ttc act ctc acc atc agc agc ctg cag gct gaa gat gtg gca    996
Thr Asp Phe Thr Leu Thr Ile Ser Ser Leu Gln Ala Glu Asp Val Ala
 95                 100                 105                 110 gtt tat tac tgt cag caa tat tat agt tat cct ctc act ttc ggc gga   1044
Val Tyr Tyr Cys Gln Gln Tyr Tyr Ser Tyr Pro Leu Thr Phe Gly Gly
             115                 120                 125 ggg acc aag gtg gtg aaa aaa cgt aagtacactt ttctaagctt              1088
Gly Thr Lys Val Val Ile Lys Arg
            130
```

```
<210> SEQ ID NO 58
<211> LENGTH: 134
<212> TYPE: PRT
<213> ORGANISM: Homo sapiens
<220> FEATURE:
<221> NAME/KEY: Hum4 VL
<222> LOCATION: 1..134

<400> SEQUENCE: 58

Met Val Leu Gln Thr Gln Val Phe Ile Ser Leu Leu Leu Trp Ile Ser
 1               5                  10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
         35                  40                  45

Val Leu Tyr Ser Ser Asn Asn Lys Asn Tyr Leu Ala Trp Tyr Gln Gln
     50                  55                  60

Lys Pro Gly Gln Pro Pro Lys Leu Leu Ile Tyr Trp Ala Ser Thr Arg
 65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Tyr Tyr Ser Tyr Pro Leu Thr Phe Gly Gly Gly Thr
         115                 120                 125

Lys Val Val Ile Lys Arg
            130
```

```
<210> SEQ ID NO 59
<211> LENGTH: 40
<212> TYPE: DNA
<213> ORGANISM: Artificial Sequence
<220> FEATURE:
<221> NAME/KEY: Primer CH(+)
<222> LOCATION: 1..40
<223> OTHER INFORMATION: Forward oligonucleotide primer for inserting
      DNA encoding a polylinker into plasmid pSV2neo-101 to create
      plasmid pSV2neo-102

<400> SEQUENCE: 59
ggatcatcga ttgatatcaa ctagtgaagc ttatggatcc                          40
```

```
<210> SEQ ID NO 60
<211> LENGTH: 40
<212> TYPE: DNA
<213> ORGANISM: Artificial Sequence
```

```
<220> FEATURE:
<221> NAME/KEY: Primer CH(-)
<222> LOCATION: 1..40
<223> OTHER INFORMATION: Reverse oligonucleotide primer for inserting
      DNA encoding a polylinker into plasmid pSV2neo-101 to create
      plasmid pSV2neo-102

<400> SEQUENCE: 60
ggatccataa gcttcactag ttgatatcaa tcgatgatcc                              40

<210> SEQ ID NO 61
<211> LENGTH: 93
<212> TYPE: DNA
<213> ORGANISM: Artificial Sequence
<220> FEATURE:
<221> NAME/KEY: Primer NEO102SEQ
<222> LOCATION: 4..24
<223> OTHER INFORMATION: Primer for sequencing plasmids pSV2neo-102
      and pRL1000

<400> SEQUENCE: 61
gaggaggtta gggtttatga ggacacagag gagcttcctg gggatccaga catgataaga       60
tacattgatg agtttggaca aaccacaact aga                                    93

<210> SEQ ID NO 62
<211> LENGTH: 258
<212> TYPE: DNA
<213> ORGANISM: Artificial Sequence
<220> FEATURE:
<221> NAME/KEY: Oligonucleotide Hind IIIC?(-) complementary sequence
<222> LOCATION: 53..80
<223> OTHER INFORMATION: DNA sequence complementary to the
      oligonucleotide primer, Hind IIICk(-), used to sequence versions
      of plasmid pRL1000 containing the Hum4 VL coding sequence

<400> SEQUENCE: 62
cttcctgggg atcatcgatt gatatcaact agttgaagct ttttttttt cagtgctatt        60 taattatttc aatatcctct catcaaatgt atttaaataa caaaagctca accaaaaaga      120
aagaaatatg taattctttc agagtaaaaa tcacacccat gacctggcca ctgagggctt      180
gatcaattca ctttgaattt ggcattaaat accattaagg tatattaact gattttaaaa      240
taagatatat tcgtgacc                                                    258

<210> SEQ ID NO 63
<211> LENGTH: 836
<212> TYPE: DNA
<213> ORGANISM: Artificial Sequence
<220> FEATURE:
<221> NAME/KEY: SCFV1 coding sequence
<222> LOCATION: 20..799
<223> OTHER INFORMATION: DNA sequence encoding the single chain
      anti-TAG-72 antibody SCFV1
<220> FEATURE:
<221> NAME/KEY: Leader coding sequence
<222> LOCATION: 20..76
<223> OTHER INFORMATION: DNA sequence encoding yeast invertase leader
      sequence
<220> FEATURE:
<221> NAME/KEY: Hum4 VL coding sequence
<222> LOCATION: 77..406
<223> OTHER INFORMATION: DNA sequence encoding human kappa subgroup 4
      light chain variable region of SCFV1
<220> FEATURE:
<221> NAME/KEY: Linker coding sequence
<222> LOCATION: 407..460
<223> OTHER INFORMATION: DNA sequence encoding the 18-amino acid VL-VH
      linker of single chain antibody SCFV1
```

```
<220> FEATURE:
<221> NAME/KEY: CC49 VH coding sequence
<222> LOCATION: 460..799
<223> OTHER INFORMATION: DNA sequence encoding the murine CC49 heavy
      chain variable region of SCFV1

<400> SEQUENCE: 63
aaaaactata agctccatg atg ctt ttg caa gct ttc ctt ttc ctt ttg gct         52
                    Met Leu Leu Gln Ala Phe Leu Phe Leu Leu Ala
                     1               5                  10 ggt ttt gca gcc aaa ata tct gca gac atc gtg atg acc cag tct cca         100
Gly Phe Ala Ala Lys Ile Ser Ala Asp Ile Val Met Thr Gln Ser Pro
            15                  20                  25 gac tcc ctg gct gtg tct ctg ggc gag agg gcc acc atc aac tgc aag         148
Asp Ser Leu Ala Val Ser Leu Gly Glu Arg Ala Thr Ile Asn Cys Lys
        30                  35                  40 tcc agc cag agc aag gtt tta tac agc tcc aac aat aag aac tac tta gct    196
Ser Ser Gln Ser Val Leu Tyr Ser Ser Asn Asn Lys Asn Tyr Leu Ala
    45                  50                  55 tgg tac cag cag aaa cca gga cag cct cct aag ctc ctc att tac tgg         244
Trp Tyr Gln Gln Lys Pro Gly Gln Pro Pro Lys Leu Leu Ile Tyr Trp
 60                  65                  70                  75 gca tct acc cgg gaa tcc ggg gtc cct gac cga ttc agt ggc agc ggg         292
Ala Ser Thr Arg Glu Ser Gly Val Pro Asp Arg Phe Ser Gly Ser Gly
                80                  85                  90 tct ggg aca gat ttc act ctc acc atc agc agc ctg cag gct gaa gat         340
Ser Gly Thr Asp Phe Thr Leu Thr Ile Ser Ser Leu Gln Ala Glu Asp
            95                 100                 105 gtg gca gtt tat tac tgt cag caa tat tat agt tat cct ctc act ttc         388
Val Ala Val Tyr Tyr Cys Gln Gln Tyr Tyr Ser Tyr Pro Leu Thr Phe
        110                 115                 120 ggc gga ggg acc aag gtg aag gag tca ggt tcg gtc tcc tca gaa caa         436
Gly Gly Gly Thr Lys Val Lys Glu Ser Gly Ser Val Ser Ser Glu Gln
    125                 130                 135 ttg gcc caa ttt cgt tcc tta gac gtc cag ttg cag cag tct gac gct         484
Leu Ala Gln Phe Arg Ser Leu Asp Val Gln Leu Gln Gln Ser Asp Ala
140                 145                 150                 155 gag ttg gtg aaa cct ggg gct tca gtg aag aat tcc tgc aag gct tct         532
Glu Leu Val Lys Pro Gly Ala Ser Val Lys Asn Ser Cys Lys Ala Ser
                160                 165                 170 ggc tac acc ttc act gac cat gca att cac tgg gtg aaa cag aac cct         580
Gly Tyr Thr Phe Thr Asp His Ala Ile His Trp Val Lys Gln Asn Pro
            175                 180                 185 gaa cag ggc ctg gaa tgg att gga tat ttt tct ccc gga aat gat gat         628
Glu Gln Gly Leu Glu Trp Ile Gly Tyr Phe Ser Pro Gly Asn Asp Asp
        190                 195                 200 ttt aaa tac aat gag agg ttc aag ggc aag gcc aca ctg act gca gac         676
Phe Lys Tyr Asn Glu Arg Phe Lys Gly Lys Ala Thr Leu Thr Ala Asp
    205                 210                 215 aaa tcc tcc agc act gcc tac gtg cag ctc aac agc ctg aca tct gag         724
Lys Ser Ser Ser Thr Ala Tyr Val Gln Leu Asn Ser Leu Thr Ser Glu
220                 225                 230                 235 gat tct gca gtg tat ttc tgt aca aga tcc ctg aat atg gcc tac tgg         772
Asp Ser Ala Val Tyr Phe Cys Thr Arg Ser Leu Asn Met Ala Tyr Trp
                240                 245                 250 ggt caa gga acc tca gtc acc gtc tcc tagtgaagct tggaacacca              819
Gly Gln Gly Thr Ser Val Thr Val Ser
            255                 260 cacaaaccat atccaaa                                                      836
```

```
<210> SEQ ID NO 64
<211> LENGTH: 260
<212> TYPE: PRT
<213> ORGANISM: Artificial Sequence
<220> FEATURE:
<221> NAME/KEY: SCFV1
<222> LOCATION: 1..260
<223> OTHER INFORMATION: Single chain anti-TAG-72 antibody, SCFV1
<220> FEATURE:
<221> NAME/KEY: Leader sequence
<222> LOCATION: 1..19
<223> OTHER INFORMATION: Invertase leader sequence from yeast
<220> FEATURE:
<221> NAME/KEY: Hum4 VL
<222> LOCATION: 20..129
<223> OTHER INFORMATION: Human kappa subgroup 4 light chain variable
      region in SCFV1
<220> FEATURE:
<221> NAME/KEY: Linker
<222> LOCATION: 130..147
<223> OTHER INFORMATION: 18-amino acid VL-VH linker in SCFV1
<220> FEATURE:
<221> NAME/KEY: CC49 VH
<222> LOCATION: 148..260
<223> OTHER INFORMATION: Murine CC49 heavy chain variable region in
      SCFV1

<400> SEQUENCE: 64

Met Leu Leu Gln Ala Phe Leu Phe Leu Leu Ala Gly Phe Ala Ala Lys
1               5                   10                  15

Ile Ser Ala Asp Ile Val Met Thr Gln Ser Pro Asp Ser Leu Ala Val
            20                  25                  30

Ser Leu Gly Glu Arg Ala Thr Ile Asn Cys Lys Ser Ser Gln Ser Val
        35                  40                  45

Leu Tyr Ser Ser Asn Asn Lys Asn Tyr Leu Ala Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Leu Gln Ala Glu Asp Val Ala Val Tyr Tyr
            100                 105                 110

Cys Gln Gln Tyr Tyr Ser Tyr Pro Leu Thr Phe Gly Gly Gly Thr Lys
        115                 120                 125

Val Lys Glu Ser Gly Ser Val Ser Ser Glu Gln Leu Ala Gln Phe Arg
    130                 135                 140

Ser Leu Asp Val Gln Leu Gln Gln Ser Asp Ala Glu Leu Val Lys Pro
145                 150                 155                 160

Gly Ala Ser Val Lys Ile Ser Cys Lys Ala Ser Gly Tyr Thr Phe Thr
                165                 170                 175

Asp His Ala Ile His Trp Val Lys Gln Asn Pro Glu Gln Gly Leu Glu
            180                 185                 190

Trp Ile Gly Tyr Phe Ser Pro Gly Asn Asp Asp Phe Lys Tyr Asn Glu
        195                 200                 205

Arg Phe Lys Gly Lys Ala Thr Leu Thr Ala Asp Lys Ser Ser Ser Thr
    210                 215                 220

Ala Tyr Val Gln Leu Asn Ser Leu Thr Ser Glu Asp Ser Ala Val Tyr
225                 230                 235                 240

Phe Cys Thr Arg Ser Leu Asn Met Ala Tyr Trp Gly Gln Gly Thr Ser
                245                 250                 255

Val Thr Val Ser
            260
```

<210> SEQ ID NO 65
<211> LENGTH: 1330
<212> TYPE: DNA
<213> ORGANISM: Artificial Sequence
<220> FEATURE:
<221> NAME/KEY: pSCFVUHH SCFV coding sequence
<222> LOCATION: 293..1114
<223> OTHER INFORMATION: DNA in plasmid pSCFVUHH, encoding a Hum4
    VL-linker-CC49 VH single chain anti-TAG-72 antibody
<220> FEATURE:
<221> NAME/KEY: Signal sequence coding sequence
<222> LOCATION: 293..358
<223> OTHER INFORMATION: DNA encoding the pelB signal sequence for
    the single chain anti-TAG-72 antibody expressed from plasmid
    pSCFVUHH
<220> FEATURE:
<221> NAME/KEY: Hum4 VL coding sequence
<222> LOCATION: 359..697
<223> OTHER INFORMATION: DNA encoding the human kappa subgroup 4 light
    chain variable region in the single chain anti-TAG-72 antibody
    expressed from plasmid pSCFVUHH
<220> FEATURE:
<221> NAME/KEY: Linker coding sequence
<222> LOCATION: 698..772
<223> OTHER INFORMATION: DNA encoding a 25-amino acid UNIHOPE Hum4
    VL-CC49 VH linker
<220> FEATURE:
<221> NAME/KEY: CC49 VH coding sequence
<222> LOCATION: 773..1114
<223> OTHER INFORMATION: DNA encoding the murine CC49 heavy chain
    variable region in the single chain anti-TAG-72 antibody expressed
    from plasmid pSCFVUHH

<400> SEQUENCE: 65

```
ctcatgtttg acagcttatc atcgatgaat tccatcactt ccctccgttc atttgtcccc      60
ggtggaaacg aggtcatcat ttccttccga aaaacggtt gcatttaaat cttacatatg     120
taatactttc aaagactaca tttgtaagat ttgatgtttg agtcggctga agatcgtac     180 gtaccaatta ttgtttcgtg attgttcaag ccataacact gtagggatag tggaaagagt    240
gcttcatctg gttacgatca atcaaatatt caaacggagg gagacgattt tg atg aaa    298
                                                            Met Lys
                                                              1 tac cta ttg cct acg gca gcc gct gga ttg tta tta ctc gct gcc caa       346
Tyr Leu Leu Pro Thr Ala Ala Ala Gly Leu Leu Leu Leu Ala Ala Gln
            5                   10                  15 cca gcc atg gcc gac atc gtg atg acc cag tct cca gac tcc ctg gct       394
Pro Ala Met Ala Asp Ile Val Met Thr Gln Ser Pro Asp Ser Leu Ala
        20                  25                  30 gtg tct ctg ggc gag agg gcc acc atc aac tgc aag tcc agc cag agt       442
Val Ser Leu Gly Glu Arg Ala Thr Ile Asn Cys Lys Ser Ser Gln Ser
 35                  40                  45                  50 gtt tta tac agc tcc aac aat aag aac tac tta gct tgg tac cag cag       490
Val Leu Tyr Ser Ser Asn Asn Lys Asn Tyr Leu Ala Trp Tyr Gln Gln
                55                  60                  65 aaa cca gga cag cct cct aag ctg ctc att tac tgg gca tct acc cgg       538
Lys Pro Gly Gln Pro Pro Lys Leu Leu Ile Tyr Trp Ala Ser Thr Arg
            70                  75                  80 gaa tcc ggg gtc cct gac cga ttc agt ggc agc ggg tct ggg aca gat       586
Glu Ser Gly Val Pro Asp Arg Phe Ser Gly Ser Gly Ser Gly Thr Asp
        85                  90                  95 ttc act ctc acc atc agc agc ctg cag gct gaa gat gtg gca gtt tat       634
Phe Thr Leu Thr Ile Ser Ser Leu Gln Ala Glu Asp Val Ala Val Tyr
    100                 105                 110 tac tgt cag caa tat tat agt tat cct ctc act ttc ggc gga ggg acc       682
Tyr Cys Gln Gln Tyr Tyr Ser Tyr Pro Leu Thr Phe Gly Gly Gly Thr
115                 120                 125                 130
```

-continued

```
aag gtg gtg atc aag ctt agt gcg gac gat gcg aaa aag gat gct gcg    730
Lys Val Val Ile Lys Leu Ser Ala Asp Asp Ala Lys Lys Asp Ala Ala
            135                 140                 145 aag aag gat gac gct aag aaa gac gat gct aaa aag gac ctc cag gtt    778
Lys Lys Asp Asp Ala Lys Lys Asp Asp Ala Lys Lys Asp Leu Gln Val
        150                 155                 160 cag ttg cag cag tct gct gag ttg gtg aaa cct ggg gct tca gtg aag    826
Gln Leu Gln Gln Ser Ala Glu Leu Val Lys Pro Gly Ala Ser Val Lys
    165                 170                 175 att tcc tgc aag gct tct ggc tac acc ttc act gac cat gca att cac    874
Ile Ser Cys Lys Ala Ser Gly Tyr Thr Phe Thr Asp His Ala Ile His
180                 185                 190 tgg gtg aaa cag aac cct gaa cag ggc ctg gaa tgg att gga tat ttt    922
Trp Val Lys Gln Asn Pro Glu Gln Gly Leu Glu Trp Ile Gly Tyr Phe
195                 200                 205                 210 tct ccc gga aat gat gat ttt aaa tac aat gag agg ttc aag ggc aag    970
Ser Pro Gly Asn Asp Asp Phe Lys Tyr Asn Glu Arg Phe Lys Gly Lys
            215                 220                 225 gcc aca ctg act gca gac aaa tcc tcc agc act gcc tac gtg cag ctc   1018
Ala Thr Leu Thr Ala Asp Lys Ser Ser Ser Thr Ala Tyr Val Gln Leu
        230                 235                 240 aac agc ctg aca tct gag gat tct gca gtg tat ttc tct aca aga tcc   1066
Asn Ser Leu Thr Ser Glu Asp Ser Ala Val Tyr Phe Cys Thr Arg Ser
    245                 250                 255 ctg aat atg gcc tac tgg ggt caa gga acc tca gtc acc gtc tcc tca   1114
Leu Asn Met Ala Tyr Trp Gly Gln Gly Thr Ser Val Thr Val Ser Ser
260                 265                 270 taaaagcta gcgatgaatc cgtcaaaaca tcatcttaca taaagtcact tggtgatcaa   1174
gctcatatca ttgtccggca atggtgtggg cttttttttgt tttctatctt taaagatcat   1234
gtgaaggaaa aaacgggaaa atcggtctgc gggaaaggac cgggttttttg tcgaaatcat   1294 aggcgaatgg gttggattgt gacaaaattc ggatcc                            1330
```

<210> SEQ ID NO 66
<211> LENGTH: 274
<212> TYPE: PRT
<213> ORGANISM: Artificial Sequence
<220> FEATURE:
<221> NAME/KEY: pSCFVUHH SCFV
<222> LOCATION: 1..274
<223> OTHER INFORMATION: The Hum4 VL-linker-CC49 VH single chain
      anti-TAG-72 antibody expressed from plasmid pSCFVUHH
<220> FEATURE:
<221> NAME/KEY: Signal sequence coding sequence
<222> LOCATION: 1..22
<223> OTHER INFORMATION: The pelB signal sequence for the single chain
      anti-TAG-72 antibody expressed from plasmid pSCFVUHH
<220> FEATURE:
<221> NAME/KEY: Hum4 VL
<222> LOCATION: 23..135
<223> OTHER INFORMATION: The human kappa subgroup 4 light chain variable
      region in the single chain anti-TAG-72 antibody expressed from
      plasmid pSCFVUHH
<220> FEATURE:
<221> NAME/KEY: Linker
<222> LOCATION: 136..160
<223> OTHER INFORMATION: The 25-amino acid UNIHOPE Hum4 VL-CC49 VH
      linker
<220> FEATURE:
<221> NAME/KEY: CC49 VH
<222> LOCATION: 161..274
<223> OTHER INFORMATION: The murine CC49 heavy chain variable region in
      the single chain anti-TAG-72 antibody expressed from plasmid
      pSCFVUHH -continued

```
<400> SEQUENCE: 66

Met Lys Tyr Leu Leu Pro Thr Ala Ala Ala Gly Leu Leu Leu Leu Ala
1               5                   10                  15

Ala Gln Pro Ala Met Ala Asp Ile Val Met Thr Gln Ser Pro Asp Ser
            20                  25                  30

Leu Ala Val Ser Leu Gly Glu Arg Ala Thr Ile Asn Cys Lys Ser Ser
        35                  40                  45

Gln Ser Val Leu Tyr Ser Ser Asn Asn Lys Asn Tyr Leu Ala Trp Tyr
    50                  55                  60

Gln Gln Lys Pro Gly Gln Pro Pro Lys Leu Leu Ile Tyr Trp Ala Ser
65                  70                  75                  80

Thr Arg Glu Ser Gly Val Pro Asp Arg Phe Ser Gly Ser Gly Ser Gly
                85                  90                  95

Thr Asp Phe Thr Leu Thr Ile Ser Ser Leu Gln Ala Glu Asp Val Ala
            100                 105                 110

Val Tyr Tyr Cys Gln Gln Tyr Tyr Ser Tyr Pro Leu Thr Phe Gly Gly
        115                 120                 125

Gly Thr Lys Val Val Ile Lys Leu Ser Ala Asp Ala Lys Lys Asp
    130                 135                 140

Ala Ala Lys Lys Asp Asp Ala Lys Lys Asp Ala Lys Lys Asp Leu
145                 150                 155                 160

Gln Val Gln Leu Gln Gln Ser Ala Glu Leu Val Lys Pro Gly Ala Ser
                165                 170                 175

Val Lys Ile Ser Cys Lys Ala Ser Gly Tyr Thr Phe Thr Asp His Ala
        180                 185                 190

Ile His Trp Val Lys Gln Asn Pro Glu Gln Gly Leu Glu Trp Ile Gly
    195                 200                 205

Tyr Phe Ser Pro Gly Asn Asp Asp Phe Lys Tyr Asn Glu Arg Phe Lys
    210                 215                 220

Gly Lys Ala Thr Leu Thr Ala Asp Lys Ser Ser Ser Thr Ala Tyr Val
225                 230                 235                 240

Gln Leu Asn Ser Leu Thr Ser Glu Asp Ser Ala Val Tyr Phe Cys Thr
                245                 250                 255

Arg Ser Leu Asn Met Ala Tyr Trp Gly Gln Gly Thr Ser Val Thr Val
        260                 265                 270

Ser Ser

<210> SEQ ID NO 67
<211> LENGTH: 1028
<212> TYPE: DNA
<213> ORGANISM: Artificial Sequence
<220> FEATURE:
<221> NAME/KEY: FLAG peptide coding sequence
<222> LOCATION: 784..813
<223> OTHER INFORMATION: DNA in plasmid pATDFLAG, encoding the FLAG
      peptide adapter

<400> SEQUENCE: 67
ctcatgtttg acagcttatc atcgatgaat tccatcactt ccctccgttc atttgtcccc      60
ggtggaaacg aggtcatcat ttccttccga aaaacggtt gcatttaaat cttacatatg     120
taatactttc aaagactaca tttgtaagat ttgatgtttg agtcggctga agatcgtac     180 gtaccaatta ttgtttcgtg attgttcaag ccataacact gtagggatag tggaaagagt     240
gcttcatctg gttacgatca atcaaatatt caaacggagg gagacgattt tg atg aaa     298
                                                            Met Lys
                                                            1
```

```
tac cta ttg cct acg gca gcc gct gga ttg tta tta ctc gct gcc caa         346
Tyr Leu Leu Pro Thr Ala Ala Ala Gly Leu Leu Leu Ala Ala Gln
         5                  10                  15 cca gcc atg gcc gac atc gtg atg acc cag tct cca gac tcc ctg gct         394
Pro Ala Met Ala Asp Ile Val Met Thr Gln Ser Pro Asp Ser Leu Ala
 20                  25                  30 gtg tct ctg ggc gag agg gcc acc atc aac tgc aag tcc agc cag agt         442
Val Ser Leu Gly Glu Arg Ala Thr Ile Asn Cys Lys Ser Ser Gln Ser
 35                  40                  45                  50 gtt tta tac agc tcc aac aat aag aac tac tta gct tgg tac cag cag         490
Val Leu Tyr Ser Ser Asn Asn Lys Asn Tyr Leu Ala Trp Tyr Gln Gln
                 55                  60                  65 aaa cca gga cag cct cct aag ctg ctc att tac tgg gca tct acc cgg         538
Lys Pro Gly Gln Pro Pro Lys Leu Leu Ile Tyr Trp Ala Ser Thr Arg
             70                  75                  80 gaa tcc ggg gtc cct gac cga ttc agt ggc agc ggg tct ggg aca gat         586
Glu Ser Gly Val Pro Asp Arg Phe Ser Gly Ser Gly Ser Gly Thr Asp
         85                  90                  95 ttc act ctc acc atc agc agc ctg cag gct gaa gat gtg gca gtt tat         634
Phe Thr Leu Thr Ile Ser Ser Leu Gln Ala Glu Asp Val Ala Val Tyr
 100                 105                 110 tac tgt cag caa tat tat agt tat cct ctc act ttc ggc gga ggg acc         682
Tyr Cys Gln Gln Tyr Tyr Ser Tyr Pro Leu Thr Phe Gly Gly Gly Thr
115                 120                 125                 130 aag gtg gtg atc aag ctt agt gcg gac gat gcg aaa aag gat gct gcg         730
Lys Val Val Ile Lys Leu Ser Ala Asp Asp Ala Lys Lys Asp Ala Ala
                 135                 140                 145 aag aag gat gac gct aag aaa gac gat gct aaa aag gac ctc cag             775
Lys Lys Asp Asp Ala Lys Lys Asp Asp Ala Lys Lys Asp Leu Gln
             150                 155                 160 acaatgtc gct agc gac tac aag gac gat gat gac aaa taaaaacct              822
         Ala Ser Asp Tyr Lys Asp Asp Asp Asp Lys
          1               5                  10 agcgatgaat ccgtcaaaac atcatcttac ataaagtcac ttggtgatca agctcatatc       882
attgtccggc aatggtgtgg gctttttttg ttttcatctt taaagatcat gtgaaggaaa       942
aaacgggaaa atcggtctgc gggaaaggac cgggttttgg tcgaaatcat aggcgaatgg       1002
gttggattgt gacaaaattc ggatcc                                            1028
```

<210> SEQ ID NO 68
<211> LENGTH: 10
<212> TYPE: PRT
<213> ORGANISM: Artificial Sequence
<220> FEATURE:
<221> NAME/KEY: FLAG peptide
<222> LOCATION: 1..10
<223> OTHER INFORMATION: The FLAG peptide adapter

<400> SEQUENCE: 68

Ala Ser Asp Tyr Lys Asp Asp Asp Asp Lys
 1               5                  10

<210> SEQ ID NO 69
<211> LENGTH: 1359
<212> TYPE: DNA
<213> ORGANISM: Artificial Sequence
<220> FEATURE:
<221> NAME/KEY: pSC49FLAG SCFV coding sequence
<222> LOCATION: 293..1144
<223> OTHER INFORMATION: DNA in plasmid pSC49FLAG, encoding a Hum4
      VL-linker-CC49 VH single chain anti-TAG-72 antibody

```
<220> FEATURE:
<221> NAME/KEY: Signal sequence coding sequence
<222> LOCATION: 293..358
<223> OTHER INFORMATION: DNA encoding the pelB signal sequence for the
      single chain anti-TAG-72 antibody expressed from plasmid pSC49FLAG
<220> FEATURE:
<221> NAME/KEY: Hum4 VL coding sequence
<222> LOCATION: 359..697
<223> OTHER INFORMATION: DNA encoding the human kappa subgroup 4 light
      chain variable region in the single chain anti-TAG-72 antibody
      expressed from plasmid pSC49FLAG
<220> FEATURE:
<221> NAME/KEY: Linker coding sequence
<222> LOCATION: 698..772
<223> OTHER INFORMATION: DNA encoding a 25-amino acid UNIHOPE Hum4
      VL-CC49 VH linker
<220> FEATURE:
<221> NAME/KEY: CC49 VH coding sequence
<222> LOCATION: 773..1114
<223> OTHER INFORMATION: DNA encoding the murine CC49 heavy chain
      variable region in the single chain anti-TAG-72 antibody expressed
      from plasmid pSC49FLAG
<220> FEATURE:
<221> NAME/KEY: FLAG peptide coding sequence
<222> LOCATION: 1121..1144
<223> OTHER INFORMATION: DNA encoding the FLAG peptide adapter

<400> SEQUENCE: 69
ctcatgtttg acagcttatc atcgatgaat tccatcactt ccctccgttc atttgtcccc      60
ggtggaaacg aggtcatcat ttccttccga aaaaacggtt gcatttaaat cttacatatg     120
taatactttc aaagactaca tttgtaagat ttgatgtttg agtcggctga agatcgtac      180 gtaccaatta ttgtttcgtg attgttcaag ccataacact gtagggatag tggaaagagt     240
gcttcatctg gttacgatca atcaaatatt caaacggagg gagacgattt tg atg aaa    298
                                                           Met Lys
                                                             1 tac cta ttg cct acg gca gcc gct gga ttg tta tta ctc gct gcc caa       346
Tyr Leu Leu Pro Thr Ala Ala Ala Gly Leu Leu Leu Leu Ala Ala Gln
            5                  10                  15 cca gcc atg gcc gac atc gtg atg acc cag tct cca gac tcc ctg gct       394
Pro Ala Met Ala Asp Ile Val Met Thr Gln Ser Pro Asp Ser Leu Ala
         20                  25                  30 gtg tct ctg ggc gag agg gcc acc atc aac tgc aag tcc agc cag agt       442
Val Ser Leu Gly Glu Arg Ala Thr Ile Asn Cys Lys Ser Ser Gln Ser
 35                  40                  45                  50 gtt tta tac agc tcc aac aat aag acc tac tta gct tgg tac cag cag       490
Val Leu Tyr Ser Ser Asn Asn Lys Thr Tyr Leu Ala Trp Tyr Gln Gln
                 55                  60                  65 aaa cca gga cag cct cct aag ctg ctc att tac tgg gca tct acc cgg       538
Lys Pro Gly Gln Pro Pro Lys Leu Leu Ile Tyr Trp Ala Ser Thr Arg
             70                  75                  80 gaa tcc ggg gtc cct gac cga ttc agt ggc agc ggg tct ggg aca gat       586
Glu Ser Gly Val Pro Asp Arg Phe Ser Gly Ser Gly Ser Gly Thr Asp
 85                  90                  95 ttc act ctc acc atc agc agc ctg cag gct gaa gat gtg gca gtt tat       634
Phe Thr Leu Thr Ile Ser Ser Leu Gln Ala Glu Asp Val Ala Val Tyr
            100                 105                 110 tac tgt cag caa tat tat agt tat cct ctc act ttc ggc gga ggg acc       682
Tyr Cys Gln Gln Tyr Tyr Ser Tyr Pro Leu Thr Phe Gly Gly Gly Thr
115                 120                 125                 130 aag gtg gtg atc aag ctt agt gcg gac gat gcg aaa aag gat gct gcg       730
Lys Val Val Ile Lys Leu Ser Ala Asp Asp Ala Lys Lys Asp Ala Ala
                135                 140                 145
```

-continued

```
aag aag gat gac gct aag aaa gac gat gct aaa aag gac ctc cag gtt      778
Lys Lys Asp Asp Ala Lys Lys Asp Asp Ala Lys Lys Asp Leu Gln Val
            150                 155                 160 cag ttg cag cag tct gct gag ttg gtg aaa cct ggg gct tca gtg aag      826
Gln Leu Gln Gln Ser Ala Glu Leu Val Lys Pro Gly Ala Ser Val Lys
        165                 170                 175 att tcc tgc aag gct tct ggc tac acc ttc act gac cat gca att cac      874
Ile Ser Cys Lys Ala Ser Gly Tyr Thr Phe Thr Asp His Ala Ile His
    180                 185                 190 tgg gtg aaa cag aac cct gaa cag ggc ctg gaa tgg att gga tat ttt      922
Trp Val Lys Gln Asn Pro Glu Gln Gly Leu Glu Trp Ile Gly Tyr Phe
195                 200                 205                 210 tct ccc gga aat gat gat ttt aaa tac aat gag agg ttc aag ggc aag      970
Ser Pro Gly Asn Asp Asp Phe Lys Tyr Asn Glu Arg Phe Lys Gly Lys
                215                 220                 225 gcc aca ctg act gca gac aaa tcc tcc agc act gcc tac gtg cag ctc     1018
Ala Thr Leu Thr Ala Asp Lys Ser Ser Ser Thr Ala Tyr Val Gln Leu
            230                 235                 240 aac agc ctg aca tct gag gat tct gca gtg tat ttc tgt aca aga tcc     1066
Asn Ser Leu Thr Ser Glu Asp Ser Ala Val Tyr Phe Cys Thr Arg Ser
        245                 250                 255 ctg aat atg gcc tac tgg ggt caa gga acc tca gtc acc gtc tcc tca     1114
Leu Asn Met Ala Tyr Trp Gly Gln Gly Thr Ser Val Thr Val Ser Ser
    260                 265                 270 gct agc gac tac aag gac gat gat gac aaa taaaaaccta gcgatgaatc       1164
Ala Ser Asp Tyr Lys Asp Asp Asp Asp Lys
275                 280 cgtcaaaaca tcatcttaca taaagtcact tggtgatcaa gctcatatca ttgtccggca   1224
atggtgtggg cttttttttgt tttcatcttt aaagatcatg tgaaggaaaa aacgggaaaa   1284
tcggtctgcg ggaaaggacc gggttttttgt cgaaatcata ggcgaatggg ttggattgtg   1344
acaaaattcg gatcc                                                    1359
```

<210> SEQ ID NO 70
<211> LENGTH: 284
<212> TYPE: PRT
<213> ORGANISM: Artificial Sequence
<220> FEATURE:
<221> NAME/KEY: pSC49FLAG SCFV
<222> LOCATION: 1..284
<223> OTHER INFORMATION: The Hum4 VL-linker-CC49 VH single chain
      anti-TAG-72 antibody expressed from plasmid pSC49FLAG
<220> FEATURE:
<221> NAME/KEY: Signal sequence coding sequence
<222> LOCATION: 1..22
<223> OTHER INFORMATION: The pelB signal sequence for the single
      chain anti-TAG-72 antibody expressed from plasmid pSC49FLAG
<220> FEATURE:
<221> NAME/KEY: Hum4 VL coding sequence
<222> LOCATION: 23..135
<223> OTHER INFORMATION: The human kappa subgroup 4 light chain variable
      region in the single chain anti-TAG-72 antibody expressed from
      plasmid pSC49FLAG
<220> FEATURE:
<221> NAME/KEY: Linker coding sequence
<222> LOCATION: 136..160
<223> OTHER INFORMATION:The 25-amino acid UNIHOPE Hum4 VL-CC49 VH linker
<220> FEATURE:
<221> NAME/KEY: CC49 VH coding sequence
<222> LOCATION: 161..274
<223> OTHER INFORMATION: The murine CC49 heavy chain variable region in
      the single chain anti-TAG-72 antibody expressed from plasmid
      pSC49FLAG
<220> FEATURE:
<221> NAME/KEY: FLAG peptide
<222> LOCATION: 277..284
<223> OTHER INFORMATION: The FLAG peptide adapter

```
<400> SEQUENCE: 70

Met Lys Tyr Leu Leu Pro Thr Ala Ala Ala Gly Leu Leu Leu Leu Ala
1               5                   10                  15

Ala Gln Pro Ala Met Ala Asp Ile Val Met Thr Gln Ser Pro Asp Ser
            20                  25                  30

Leu Ala Val Ser Ser Gly Glu Arg Ala Thr Ile Asn Cys Lys Ser Ser
            35                  40                  45

Gln Ser Val Leu Tyr Ser Ser Asn Asn Lys Asn Tyr Leu Ala Trp Tyr
        50                  55                  60

Gln Gln Lys Pro Gly Gln Pro Pro Lys Leu Leu Ile Tyr Trp Ala Ser
65                  70                  75                  80

Thr Arg Glu Ser Gly Val Pro Asp Arg Phe Ser Gly Ser Gly Ser Gly
                85                  90                  95

Thr Asp Phe Thr Leu Thr Ile Ser Ser Leu Gln Ala Glu Asp Val Ala
            100                 105                 110

Val Tyr Tyr Cys Gln Gln Tyr Tyr Ser Tyr Pro Leu Thr Phe Gly Gly
            115                 120                 125

Gly Thr Lys Val Val Ile Lys Leu Ser Ala Asp Ala Lys Lys Asp
        130                 135                 140

Ala Ala Lys Lys Asp Asp Ala Lys Lys Asp Asp Ala Lys Lys Asp Leu
145                 150                 155                 160

Gln Val Gln Leu Gln Gln Ser Ala Glu Leu Val Lys Pro Gly Ala Ser
                165                 170                 175

Val Lys Ile Ser Cys Lys Ala Ser Gly Tyr Thr Phe Thr Asp His Ala
            180                 185                 190

Ile His Trp Val Lys Gln Asn Pro Glu Gln Gly Leu Glu Trp Ile Gly
        195                 200                 205

Tyr Phe Ser Pro Gly Asn Asp Asp Phe Lys Tyr Asn Glu Arg Phe Lys
        210                 215                 220

Gly Lys Ala Thr Leu Thr Ala Asp Lys Ser Ser Ser Thr Ala Tyr Val
225                 230                 235                 240

Gln Leu Asn Ser Leu Thr Ser Glu Asp Ser Ala Val Tyr Phe Cys Thr
                245                 250                 255

Arg Ser Leu Asn Met Ala Tyr Trp Gly Gln Gly Thr Ser Val Thr Val
            260                 265                 270

Ser Ser Ala Ser Asp Tyr Lys Asp Asp Asp Lys
        275                 280

<210> SEQ ID NO 71
<211> LENGTH: 113
<212> TYPE: PRT
<213> ORGANISM: Mus musculus
<220> FEATURE:
<221> NAME/KEY: Murine CC49 VL
<222> LOCATION: 1..113

<400> SEQUENCE: 71

Asp Ile Val Met Ser Gln Ser Pro Ser Ser Leu Pro Val Ser Val Gly
1               5                   10                  15

Glu Lys Val Thr Leu Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60
```

```
Pro Asp Arg Phe Thr Gly Ser Gly Ser Gly Thr Asp Phe Thr Leu Ser
65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys

<210> SEQ ID NO 72
<211> LENGTH: 113
<212> TYPE: PRT
<213> ORGANISM: Homo sapiens
<220> FEATURE:
<221> NAME/KEY: LEN VL
<222> LOCATION: 1..113

<400> SEQUENCE: 72

Asp Ile Val Met Thr Gln Ser Pro Asp Ser Leu Ala Val Ser Leu Gly
1               5                   10                  15

Glu Arg Ala Thr Ile Asn Cys Xaa Xaa Xaa Xaa Xaa Xaa Xaa Xaa Xaa
            20                  25                  30

Xaa Xaa Xaa Xaa Xaa Xaa Xaa Xaa Trp Tyr Gln Gln Lys Pro Gly Gln
        35                  40                  45

Pro Pro Lys Leu Leu Ile Tyr Xaa Xaa Xaa Xaa Xaa Xaa Xaa Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Xaa Xaa
                85                  90                  95

Xaa Xaa Xaa Xaa Xaa Xaa Phe Gly Gln Gly Thr Lys Leu Glu Ile
            100                 105                 110

Lys

<210> SEQ ID NO 73
<211> LENGTH: 113
<212> TYPE: PRT
<213> ORGANISM: Artificial Sequence
<220> FEATURE:
<221> NAME/KEY: HuCC49 VL
<222> LOCATION: 1..113
<223> OTHER INFORMATION: Humanized CC49 light chain variable region with
      Hum4 VL FRs
<220> FEATURE:
<221> NAME/KEY: LEN FR1
<222> LOCATION: 1..23
<223> OTHER INFORMATION: Human LEN light chain variable region FR1
<220> FEATURE:
<221> NAME/KEY: CC49 VL CDR1
<222> LOCATION: 24..40
<223> OTHER INFORMATION: Murine CC49 light chain variable region CDR1
<220> FEATURE:
<221> NAME/KEY: LEN FR2
<222> LOCATION: 41..55
<223> OTHER INFORMATION: Human LEN light chain variable region FR2
<220> FEATURE:
<221> NAME/KEY: CC49 VL CDR2
<222> LOCATION: 56..62
<223> OTHER INFORMATION: Murine CC49 light chain variable region CDR2
<220> FEATURE:
<221> NAME/KEY: LEN FR3
<222> LOCATION: 63..94
<223> OTHER INFORMATION: Human LEN light chain variable region FR3
<220> FEATURE:
<221> NAME/KEY: CC49 VL CDR3
<222> LOCATION: 95..103
<223> OTHER INFORMATION: Murine CC49 light chain variable region CDR3
```

-continued

```
<220> FEATURE:
<221> NAME/KEY: LEN FR4
<222> LOCATION: 104..113
<223> OTHER INFORMATION: Human LEN light chain variable region FR4

<400> SEQUENCE: 73

Asp Ile Val Met Ser Gln Ser Pro Asp Ser Leu Ala Val Ser Leu Gly
1               5                   10                  15

Glu Arg Val Thr Leu Asn Cys Lys Ser Gln Ser Leu Leu Tyr Ser
                20                  25                  30

Gly Asn Gln Lys Asn Tyr Leu Ala Trp Tyr Gln Lys Pro Gly Gln
            35                  40                  45

Ser Pro Lys Leu Leu Ile Tyr Trp Ala Ser Ala Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys

<210> SEQ ID NO 74
<211> LENGTH: 115
<212> TYPE: PRT
<213> ORGANISM: Mus musculus
<220> FEATURE:
<221> NAME/KEY: Murine CC49 VH
<222> LOCATION: 1..115

<400> SEQUENCE: 74

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
                20                  25                  30

Ala Ile His Trp Val Lys Gln Asn Pro Glu Gln Gly Leu Glu Trp Ile
            35                  40                  45

Gly Tyr Phe Ser Pro Gly Asn Asp Asp Phe Lys Tyr Asn Glu Arg Phe
        50                  55                  60

Lys Gly Lys Ala Thr Leu Thr Ala Asp Lys Ser Ser Ser Thr Ala Tyr
65                  70                  75                  80

Val Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser
        115

<210> SEQ ID NO 75
<211> LENGTH: 115
<212> TYPE: PRT
<213> ORGANISM: Homo sapiens
<220> FEATURE:
<221> NAME/KEY: Human 21/28'CL VH
<222> LOCATION: 1..115
```

-continued

```
<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Xaa Xaa
            20                  25                  30

Xaa Xaa Xaa Trp Val Arg Gln Ala Pro Gly Gln Arg Leu Glu Trp Met
        35                  40                  45

Gly Xaa Xaa Xaa Xaa Xaa Xaa Xaa Xaa Xaa Xaa Xaa Xaa Xaa Xaa Xaa
    50                  55                  60

Xaa Xaa Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Xaa Xaa Xaa Xaa Xaa Xaa Trp Gly Gln Gly Thr Leu Val Thr
            100                 105                 110

Val Ser Ser
        115

<210> SEQ ID NO 76
<211> LENGTH: 115
<212> TYPE: PRT
<213> ORGANISM: Artificial Sequence
<220> FEATURE:
<221> NAME/KEY: HuCC49 VH
<222> LOCATION: 1..115
<223> OTHER INFORMATION: Humanized CC49 heavy chain variable region with
      21/28'CL VH FRs
<220> FEATURE:
<221> NAME/KEY: 21/28'CL FR1
<222> LOCATION: 1..30
<223> OTHER INFORMATION: Human 21/28'CL heavy chain variable region FR1
<220> FEATURE:
<221> NAME/KEY: CC49 VH CDR1
<222> LOCATION: 31..35
<223> OTHER INFORMATION: Murine CC49 heavy chain variable region CDR1
<220> FEATURE:
<221> NAME/KEY: 21/28'CL FR2
<222> LOCATION: 36..49
<223> OTHER INFORMATION: Human 21/28'CL heavy chain variable region FR2
<220> FEATURE:
<221> NAME/KEY: CC49 VH CDR2
<222> LOCATION: 50..66
<223> OTHER INFORMATION: Murine CC49 heavy chain variable region CDR2
<220> FEATURE:
<221> NAME/KEY: 21/28'CL FR3
<222> LOCATION: 67..98
<223> OTHER INFORMATION: Human 21/28'CL heavy chain variable region FR3
<220> FEATURE:
<221> NAME/KEY: CC49 VH CDR3
<222> LOCATION: 99..104
<223> OTHER INFORMATION: Murine CC49 heavy chain variable region CDR3
<220> FEATURE:
<221> NAME/KEY: 21/28'CL FR4
<222> LOCATION: 105..115
<223> OTHER INFORMATION: Human 21/28'CL heavy chain variable region FR4

<400> SEQUENCE: 76

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Gly Gln Arg Leu Glu Trp Ile
        35                  40                  45

Gly Tyr Phe Ser Pro Gly Asn Asp Asp Phe Lys Tyr Asn Glu Arg Phe
    50                  55                  60
```

```
Lys Gly Lys Ala Thr Leu Thr Ala Asp Thr Ser Ala Ser Thr Ala Tyr
 65                  70                  75                  80

Val Glu Leu Ser Ser Leu Arg Ser Glu Asp Thr Ala Val Tyr Phe Cys
                 85                  90                  95

Thr Arg Ser Leu Asn Met Ala Tyr Trp Gly Gln Gly Thr Leu Val Thr
            100                 105                 110

Val Ser Ser
        115

<210> SEQ ID NO 77
<211> LENGTH: 424
<212> TYPE: DNA
<213> ORGANISM: Artificial Sequence
<220> FEATURE:
<221> NAME/KEY: HuCC49 VL coding sequence
<222> LOCATION: 14..412
<223> OTHER INFORMATION: DNA encoding a humanized CC49 light chain
      variable region with Hum4 VL FRs

<400> SEQUENCE: 77
gcaagcttcc acc atg gat agc cag gcc cag gtg ctc atg ctc ctg ctg        49
            Met Asp Ser Gln Ala Gln Val Leu Met Leu Leu Leu
             1               5                  10 ctg tgg gtg agc ggc aca tgc ggc gac atc gtg atg agc cag tct cca       97
Leu Trp Val Ser Gly Lys Cys Gly Asp Ile Val Met Ser Gln Ser Pro
        15                  20                  25 gac tcc ctg gcc gtg tcc ctg ggc gag agg gtg act ctg aat tgc aag      145
Asp Ser Leu Ala Val Ser Leu Gly Glu Arg Val Thr Leu Asn Cys Lys
 30                  35                  40 tcc agc cag tcc ctg ctc tat agc gga aat cag aag aac tat ctc gcc      193
Ser Ser Gln Ser Leu Leu Tyr Ser Gly Asn Gln Lys Asn Tyr Leu Ala
 45                  50                  55                  60 tgg tat cag cag aaa cca ggg cag agc cct aaa ctg ctg att tac tgg      241
Trp Tyr Gln Gln Lys Pro Gly Gln Ser Pro Lys Leu Leu Ile Tyr Trp
                 65                  70                  75 gca tcc gct agg gaa tcc ggc gtg cct gat cgc ttc agc ggc agc gga      289
Ala Ser Ala Arg Glu Ser Gly Val Pro Asp Arg Phe Ser Gly Ser Gly
            80                  85                  90 tct ggg aca gac ttc act ctg aca atc agc agc gtg cag gca gaa gac      337
Ser Gly Thr Asp Phe Thr Leu Thr Ile Ser Ser Val Gln Ala Glu Asp
        95                 100                 105 gtg gca gtc tat tat tgt cag cag tat tat agc tat ccc ctc aca ttc      385
Val Ala Val Tyr Tyr Cys Gln Gln Tyr Tyr Ser Tyr Pro Leu Thr Phe
    110                 115                 120 ggc gct ggc acc aag ctg gaa ctg aaa cgggccgcgg ct                    424
Gly Ala Gly Thr Lys Leu Glu Leu Lys
125                 130

<210> SEQ ID NO 78
<211> LENGTH: 434
<212> TYPE: DNA
<213> ORGANISM: Artificial Sequence
<220> FEATURE:
<221> NAME/KEY: HuCC49 VH coding sequence
<222> LOCATION: 14..419
<223> OTHER INFORMATION: DNA encoding a humanized CC49 heavy chain
      variable region with 21/28'CL VH FRs

<400> SEQUENCE: 78
ctaagcttcc acc atg gag tgg tcc tgg gtc ttc ctc ttc ttc ctg tcc        49
            Met Glu Trp Ser Trp Val Phe Leu Phe Phe Leu Ser
             1               5                  10
```

-continued

```
gtg act act gga gtg cac tcc cag gtc cag ctg gtg cag tcc ggc gct      97
Val Thr Thr Gly Val His Ser Gln Val Gln Leu Val Gln Ser Gly Ala
        15                  20                  25 gag gtg gtg aaa cct ggg gct tcc gtg aag att tcc tgc aag gca agc     145
Glu Val Val Lys Pro Gly Ala Ser Val Lys Ile Ser Cys Lys Ala Ser
        30                  35                  40 ggc tac acc ttc act gat cac gca atc cac tgg gtg aaa cag aat cct    193
Gly Tyr Thr Phe Thr Asp His Ala Ile His Trp Val Lys Gln Asn Pro
45                  50                  55                  60 gga cag cgc ctg gag tgg att gga tat ttc tct ccc gga aac gat gat    241
Gly Gln Gly Leu Glu Trp Ile Gly Tyr Phe Ser Pro Gly Asn Asp Asp
                65                  70                  75 ttt aag tac aat gag agg ttc aag ggc aag gcc aca ctg act gca gac    289
Phe Lys Tyr Asn Glu Arg Phe Lys Gly Lys Ala Thr Leu Thr Ala Asp
            80                  85                  90 aca tct gcc agc act gcc tac gtg gag ctc tcc agc ctg aga tcc gag    337
Thr Ser Ala Ser Thr Ala Tyr Val Glu Leu Ser Ser Leu Arg Ser Glu
        95                  100                 105 gat act gca gtg tac ttc tgc aca aga tcc ctg aat atg gcc tac tgg    385
Asp Thr Ala Val Tyr Phe Cys Thr Arg Ser Leu Asn Met Ala Tyr Trp
    110                 115                 120 gga cag gga acc ctg gtc acc gtc tcc agc gccaaaacta cgggcccat       434
Gly Gln Gly Thr Leu Val Thr Val Ser Ser
125                 130
```

What is claimed is:

1. A nucleic acid sequence which encodes a humanized or composite anti-TAG-72 antibody or anti-TAG-72 antibody fragment which comprises a CDR-grafted light chain having light chain CDRs of a murine anti-TAG-72 antibody grafted onto a human subgroup IV kappa light chain, and a CDR-grafted heavy chain having heavy chain CDRs of a murine anti-TAG-72 antibody, wherein the murine anti-TAG-72 antibody is selected from the group consisting of CC49 (ATCC No. HB 9459), CC83 (ATCC No. HB 9453), CC46 (ATCC No. HB 9458) CC92 (ATCC No. HB 9454), CC30 (ATCC NO. HB 9457) and CC11 (ATCC No. HB 9455).

2. A vector comprising a nucleic acid sequence which encodes a humanized or composite anti-TAG-72 antibody or anti-TAG-72 antibody fragment which comprises a CDR-grafted light chain having light chain CDRs of a murine anti-TAG-72 antibody grafted onto a human subgroup IV kappa light chain, and/or a CDR-grafted heavy chain having heavy chain CDRs of a murine anti-TAG-72 antibody, wherein the murine anti-TAG-72 antibody is selected from the group consisting of CC49 (ATCC No. HB 9459), CC83 (ATCC No. HB 9453), CC46 (ATCC No. HB 9458), CC92 (ATCC No. HB 9454), CC30 (ATCC NO. HB 9457), and CC11 (ATCC No. HB 9455).

3. The vector according to claim 2, wherein said vector comprises a selection marker that is effective in a eukaryotic or prokaryotic cell.

4. The vector according to claim 3, wherein the selection marker is a drug resistant selection marker.

5. The vector according to claim 2, wherein the vector is a viral expression vector.

6. The vector according to claim 2, wherein the vector further comprises a nucleic acid sequence encoding a peptide linker, a nucleic acid molecule capable of directing the expression of genes to which they are operatively linked, and/or a restriction fragment.

* * * * *

UNITED STATES PATENT AND TRADEMARK OFFICE
CERTIFICATE OF CORRECTION

PATENT NO. : 7,179,899 B2
APPLICATION NO. : 10/255478
DATED : February 20, 2007
INVENTOR(S) : Mezes et al.

It is certified that error appears in the above-identified patent and that said Letters Patent is hereby corrected as shown below:

On the Cover:

In (56) Other Publications, "Marsh et al," should be --Marsh et al.,--.

In (56) Other Publications, "Polke et al," should be --Polke et al.,--.

In the Specification:

Column 1, Line 10, "6,495,137." should be --6,497,137,--.

Column 1, Line 11, "The applicants herein claim" should be --which claims--.

Column 1, Line 16, "al." should be --al., and which is now abandoned;--.

Column 1, Line 17, "present application" should be --and which--.

Column 1, Line 20, "Ser. No. Ser. No." should be --Ser. No.--.

Column 3, Line 34, "TAG-72." should be --TAG 72. As it is customary in the art, the term "Hum4 $V_L$" which is itself derived from the designation of a protein - $i.e.$ the variable domain of a light chain belonging to Subgroup IV of the class of human κ light chains – can indicate this protein and/or the gene(s) or DNA sequence(s) which encode it.--.

Column 4, Lines 31-32, "FIG. 2...and CC92 $V_H$." should be --Figure 2, $i.e.$ Figures 2A-2G illustrate the nucleotide sequences of $V_H$ αTAG (SEQ ID NO: 40), CC46 $V_H$ (SEQ ID NO: 41), CC49 $V_H$ (SEQ ID NO: 42), CC83 $V_H$ (SEQ ID NO: 43) and CC92 $V_H$ (SEQ ID NO: 44).--.

Column 4, Lines 33-34, "FIG. 3...and CC92 $V_H$." should be --Figure 3, $i.e.$ Figures 3A-3E illustrate the amino acid sequences of $V_H$ αTAG (SEQ ID NO: 45), CC46 $V_H$ (SEQ ID NO: 46), CC49 $V_H$ (SEQ ID NO: 47), CC83 $V_H$ (SEQ ID NO: 48) and CC92 $V_H$ (SEQ ID NO: 49).--.

Column 4, Lines 35-36, "FIG. 4...antibody B17X2." should be --Figure 4, Figures 4A-4B illustrate the $V_H$ nucleotide (SEQ ID NO: 50) and amino acid (SEQ ID NO: 51) sequences of antibody B17X2.--.

UNITED STATES PATENT AND TRADEMARK OFFICE
CERTIFICATE OF CORRECTION

| | | |
|---|---|---|
| PATENT NO. | : 7,179,899 B2 | |
| APPLICATION NO. | : 10/255478 | |
| DATED | : February 20, 2007 | |
| INVENTOR(S) | : Mezes et al. | |

It is certified that error appears in the above-identified patent and that said Letters Patent is hereby corrected as shown below:

Column 4, Lines 37-38, "FIG. 5...from pNP9." should be --Figure 5, *i.e.* Figures 5A-5B illustrate the mouse germline J-H genes (SEQ ID NO: 52) from pNP9.--.

Column 4, Lines 41-42, "FIG. 8...and HUMVL (-)." should be --Figure 8, Figures 8A-8B illustrate the entire sequence of HUMVL(+) (SEQ ID NO: 53) and HUMVL (-) (SEQ ID NO: 54).--.

Column 4, Lines 43-44, "FIG. 9...amino acid sequence." should be --Figure 9 illustrates the human J4 (HJ4) nucleotide sequence (SEQ ID NO: 55) and amino acid sequence (SEQ ID NO: 56). The underlined DNA sequence represents a part of the sequence used for the 3' terminal PCR primer, HUMVL (-).--.

Column 4, Lines 45-46, "FIG. 10...ClaI-HindIII segment." should be --Figure 10, *i.e.* Figures 10A-10E illustrate the nucleotide sequences (SEQ ID NO: 57), and the amino acid sequences (SEQ ID NO: 58) of Hum4 $V_L$, *Cla*I-*Hin*dIII segment.--.

Column 4, Lines 47-50, "FIG. 11...target for the PCR." should be --Figure 11 illustrates a schematic representation of the human germline Subgroup IV $V_L$ gene (Hum4 $V_L$), as a target for the PCR referring to this gene as the "human germline Subgroup IV gene (Hum4 $V_L$)." The arrowheads shown on the PCR primers indicate the direction of synthesis.--.

Figure 12:
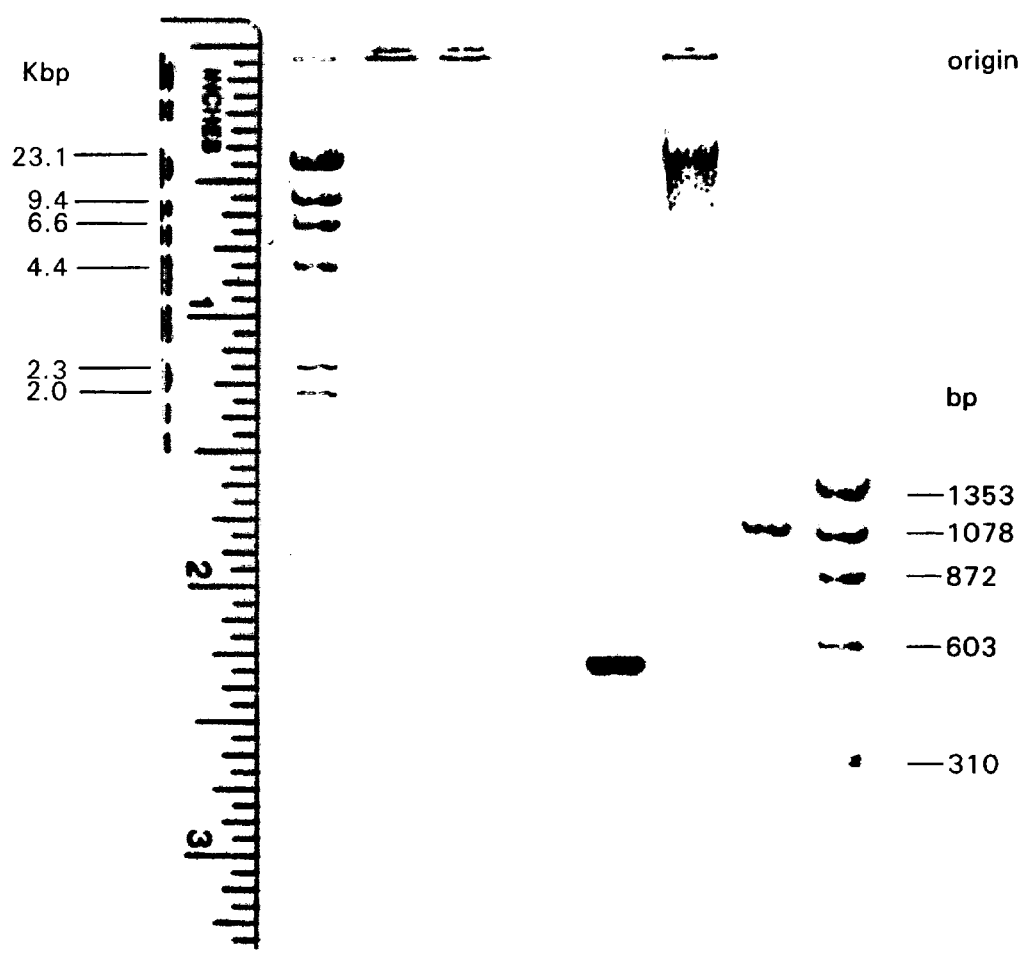
FIG. 12 shows the results of an agarose gel electrophoresis of a PCR reaction to obtain the Hum4 $V_L$ gene.

Column 4, Lines 51-52, "FIG. 12...the Hum4 $V_L$ gene." should be --Figure 12 shows the results of an agarose gel electrophoresis of a PCR reaction to obtain the Hum 4 $V_L$ gene, as visualized by ethidium bromide under long wavelength UV light. Lane 1: λ *Hin*dIII standard; Lane 2: no *Taq* polymerase control; Lane 3: no primers added; Lane 4: no human DNA template; Lane 5: GENEAMP kit positive control; Lane 6: 3μg human DNA with primers and *Taq* polymerase; Lane 7: same as Lane 6, but with 1μg human DNA; Lane 8: ΦX174-H*ae*III DNA standard.--.

Figure 13A:
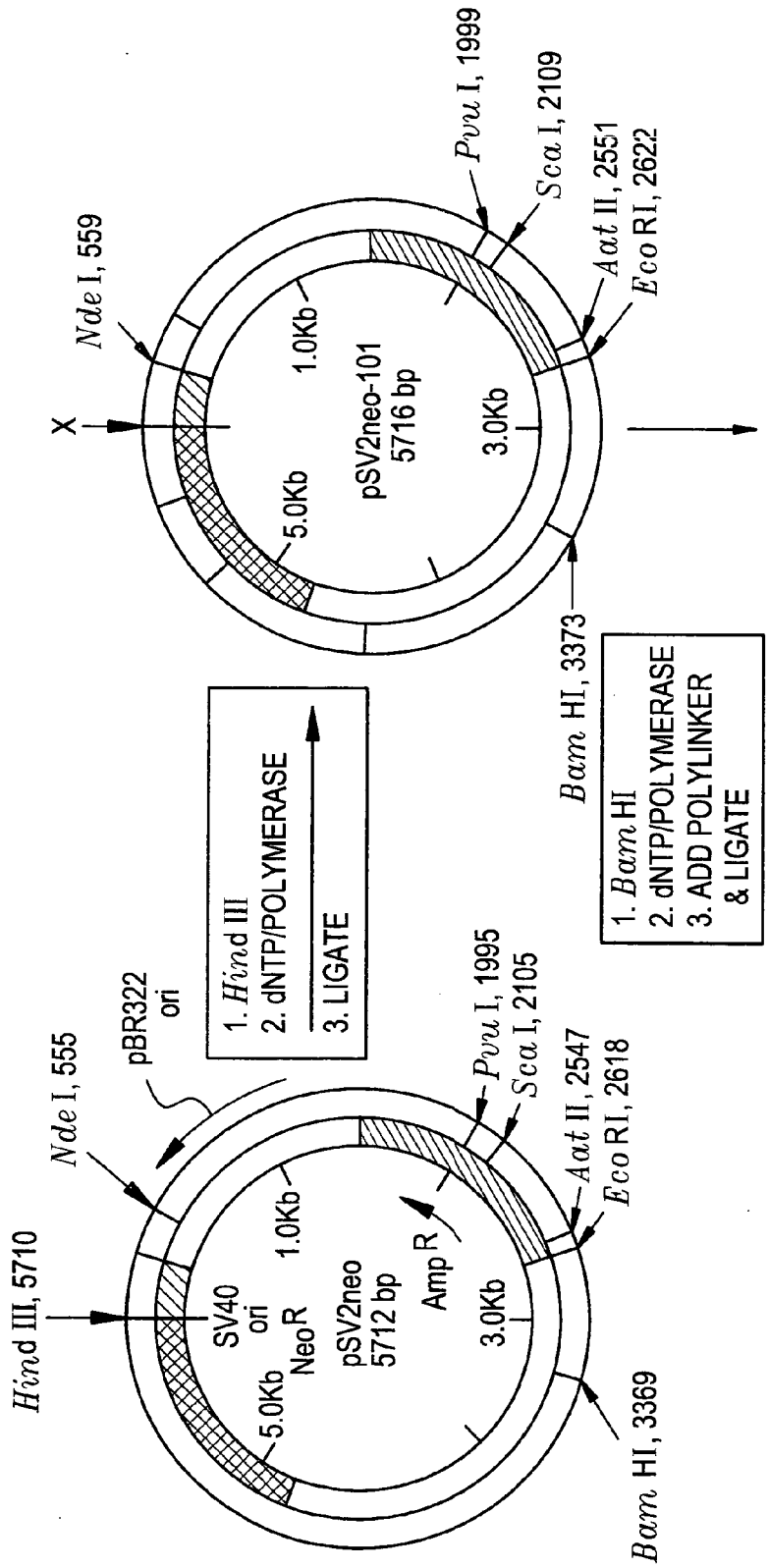
FIG. 13 illustrates the restriction enzyme maps of pRL1000, and precursor plasmids pSV2neo, pSV2neo-101 and pSV2neo-102. "X" indicates where the HindIII site of pSV2neo has been destroyed.
Figure 13B:
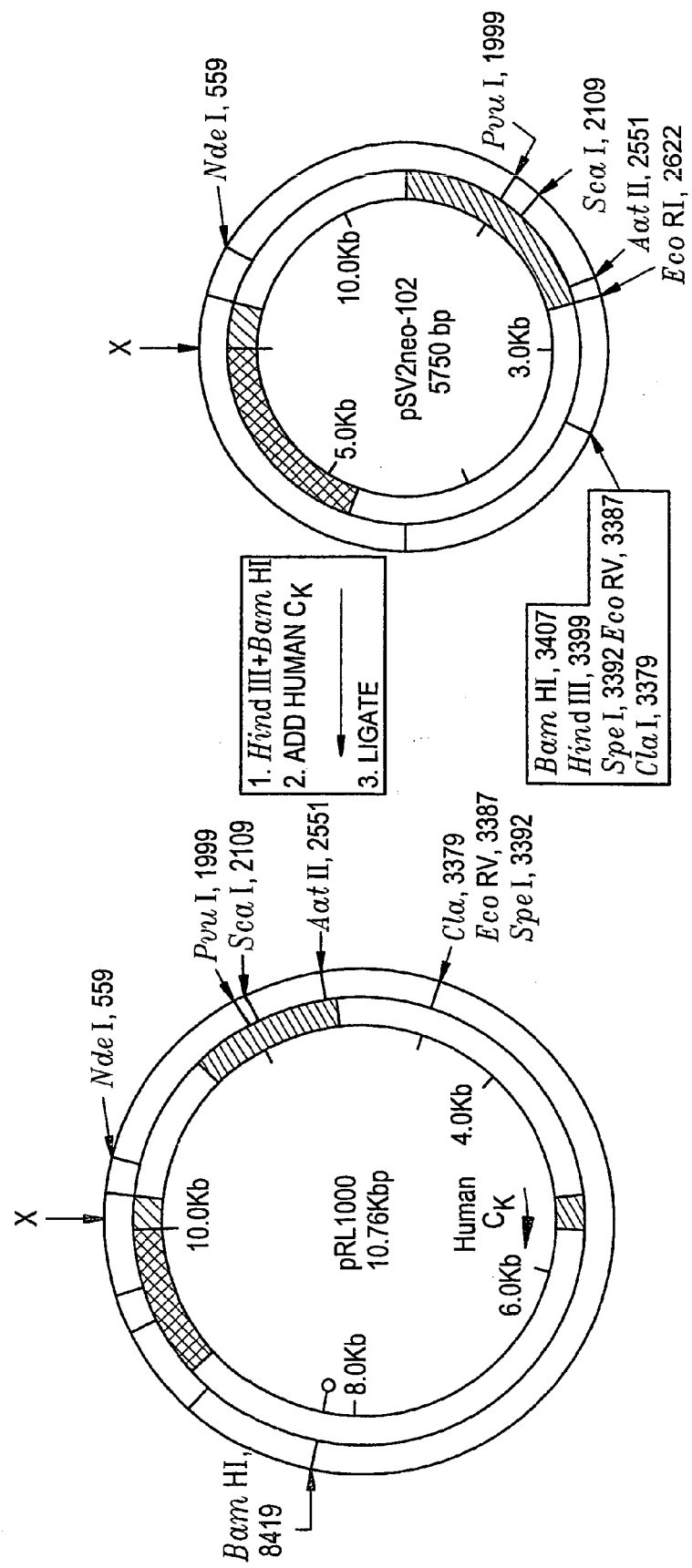

Column 4, Lines 52-56, "FIG. 13...has been destroyed." should be --Figure 13, *i.e.* Figures 13A-13B illustrate the restriction enzyme maps of pRL1000, and precursor plasmids pSV2neo, pSV2neo-101 and pSW2neo-102. "X" indicates where the *Hin*dIII site of pSV2neo has been destroyed.--.

UNITED STATES PATENT AND TRADEMARK OFFICE
CERTIFICATE OF CORRECTION

PATENT NO. : 7,179,899 B2
APPLICATION NO. : 10/255478
DATED : February 20, 2007
INVENTOR(S) : Mezes et al.

It is certified that error appears in the above-identified patent and that said Letters Patent is hereby corrected as shown below:

Column 4, Lines 57-58, "FIG. 14...oligonucleotides: CH(+) and CH(-)." should be --Figure 14 illustrates a polylinker segment made by synthesizing two oligonucleotides: CH(+) (SEQ ID NO:59) and CH(-) (SEQ ID NO:60).--.

Column 4, Lines 59-61, "FIG. 15...of pSV2neo-102." should be --Figure 15 illustrates a primer, NEO102SEQ (SEQ ID NO:6I), used for sequencing plasmid DNA from several clones of pSV2neo-102. The primer is underlined; the boxed *Bam*HI sequence indicates the site where the polylinker was inserted in pSV2neo-101.--.

Column 4, Lines 62-63, "FIG. 16...of pSV2neo-102." should be --Figure 16 illustrates an autoradiogram depicting the DNA sequence of the polylinker region both in pSV2neo-102, where the (+) strand of the polylinker DNA is inserted in the plasmid's sense strand, and in pSV2neo-120, where the (-) strand of the polylinker DNA is inserted in the plasmid's sense strand.--.

Column 4, Lines 64-65, "FIG. 17...of pRL1000." should be --Figure 17 illustrates a partial nucleotide sequence segment (SEQ ID NO:62) of pRL1000-, reading the (+) strand from the primer NEO102SEQ. Sequence data past the *Hin*dIII site is from the human Ck *Hin*dIII-*Bam*HI insert.--.

Figure 20A:
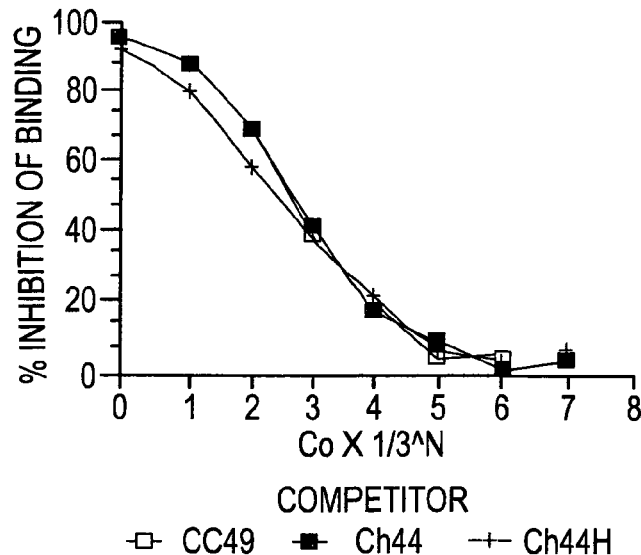
FIG. 20 illustrates a competition assay for binding to TAG-using a composite Hum4 $V_L$, $V_H\alpha$TAG antibody.
Figure 20B:
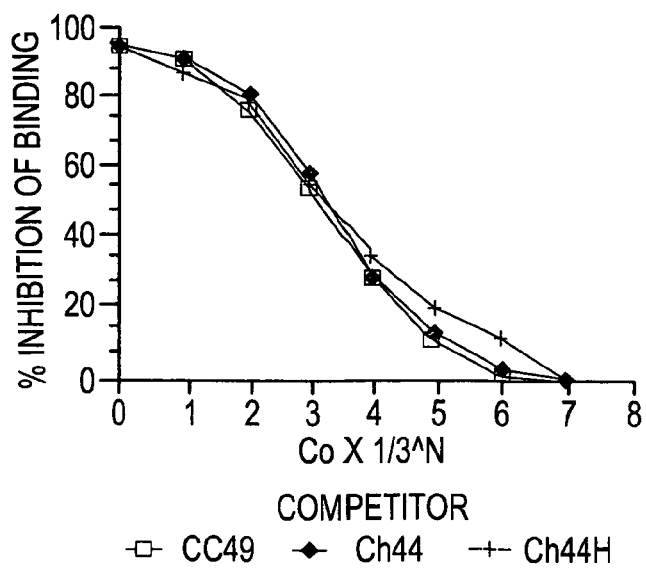

Column 5, Lines 3-4, "FIG. 20...Hum4 $V_L$, $V_H$ αTAG antibody." should be --Figure 20, *i.e.* Figures 20A-20C illustrate a competition assay for binding to TAG-using a composite Hum4 $V_L$, $V_H$αTAG antibody.--.

Figure 21:
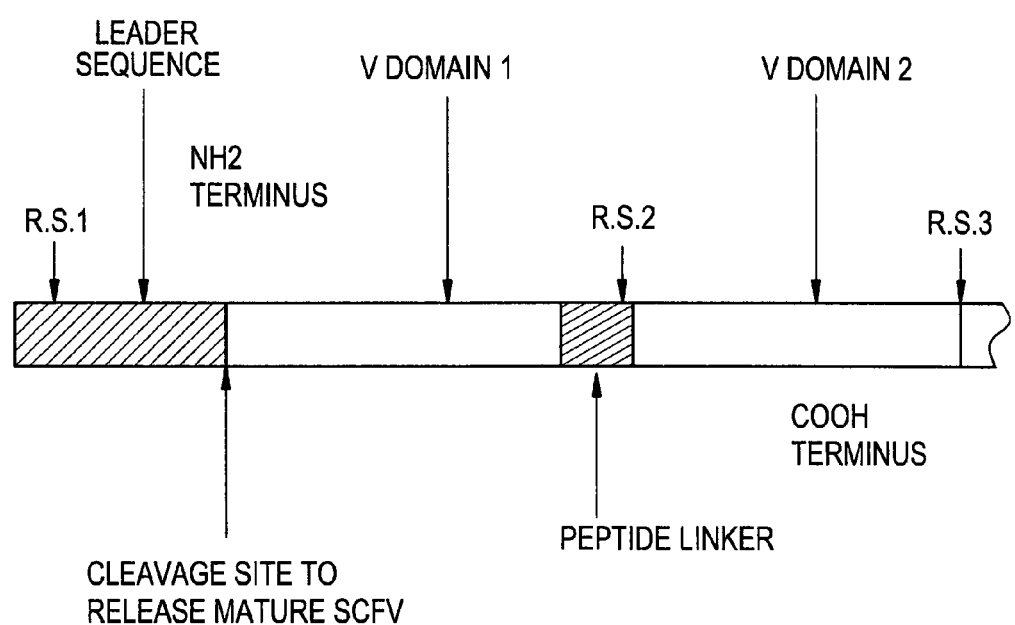
FIG. 21 illustrates a general DNA construction of a single chain, composite Hum4 $V_L$, $V_H\alpha$TAG.

Column 5, Lines 4-5, "FIG. 21...Hum4 $V_L$, $V_H$ αTAG." should be --Figure 21, illustrates a general DNA construction of a single chain, composite Hum4 $V_L$, $V_H$αTAG antibody.--.

Column 5, Lines 6-7, "FIG. 22...of SCFV1." should be --Figure 22, *i.e.* Figures 22A-22C illustrate the nucleotide sequence (SEQ ID NO:63) and amino acid sequence (SEQ ID NO:64) of SCFV1.--.

Figure 23A:
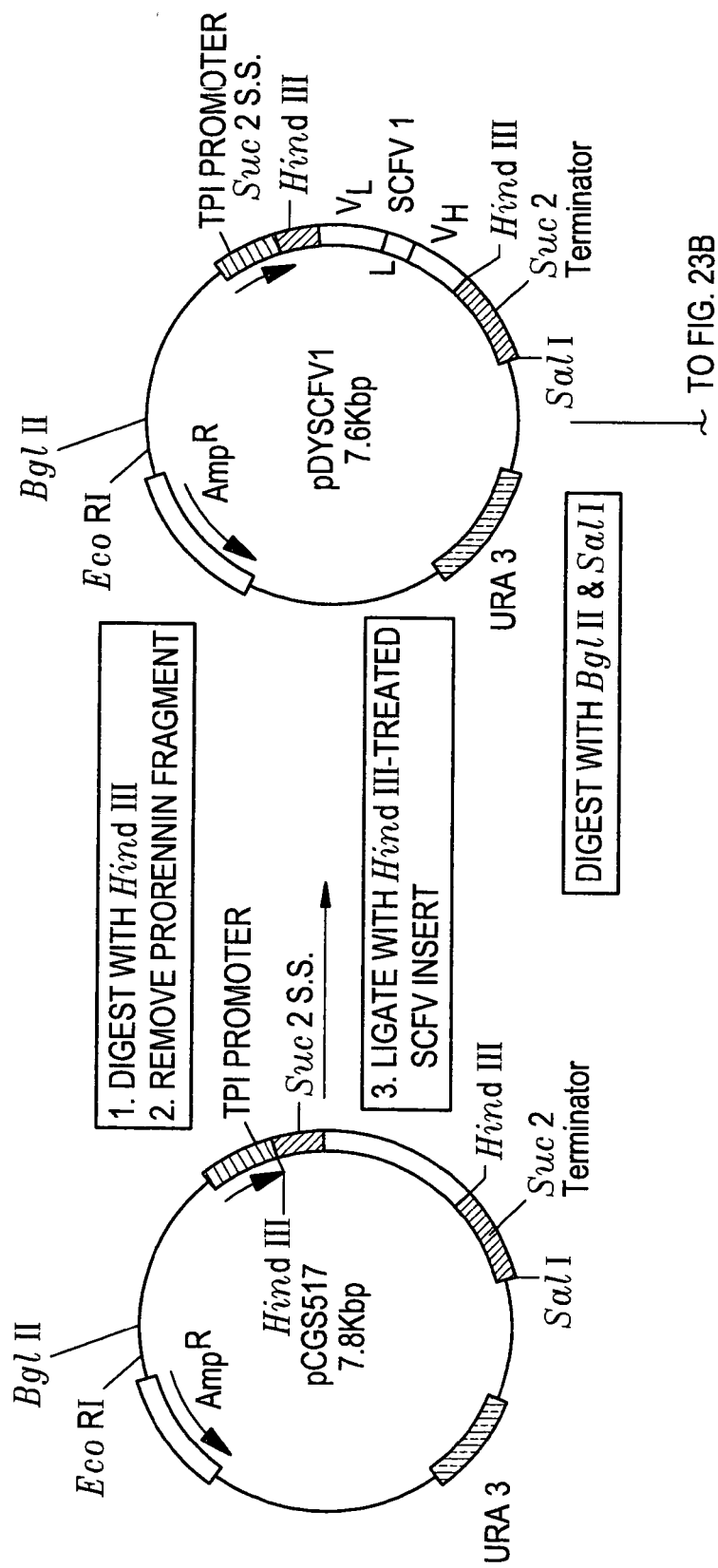
FIG. 23 shows the construction of plasmid pCGS515/SCFV1.
Figure 23B:
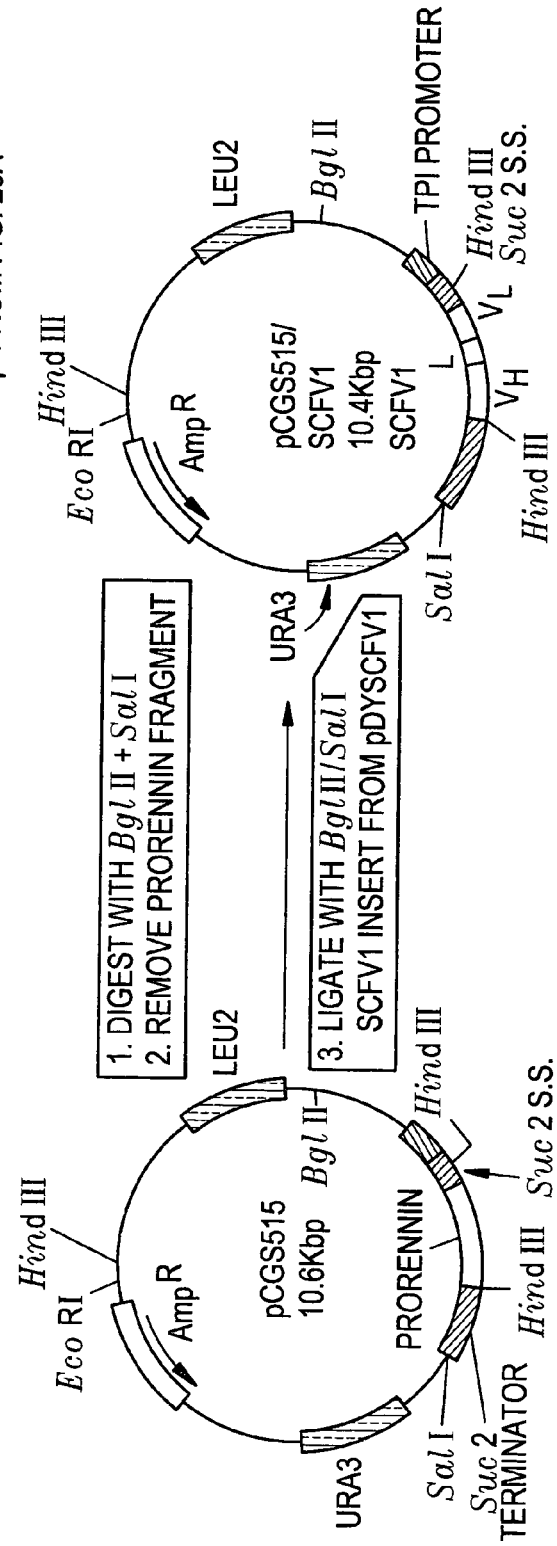

Column 5, Lines 8-9, "FIG. 23...pCGS515/SCFV1." should be --Figure 23, *i.e.* Figures 23A-23B illustrate the construction of plasmid pCGS515/SCFV1.--.

Figure 24A:
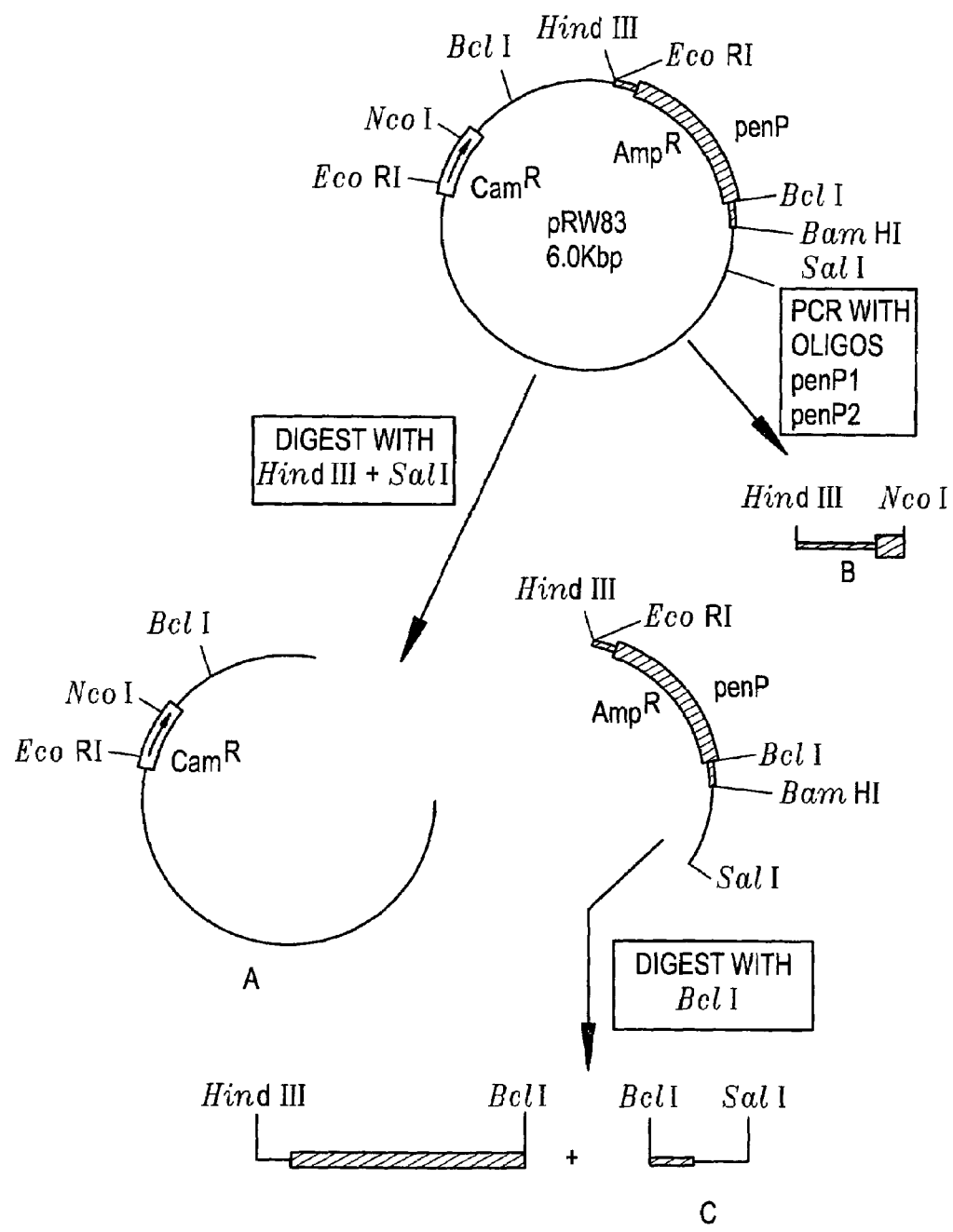
FIG. 24 shows the construction of plasmid pSCFV31.
Figure 24B:
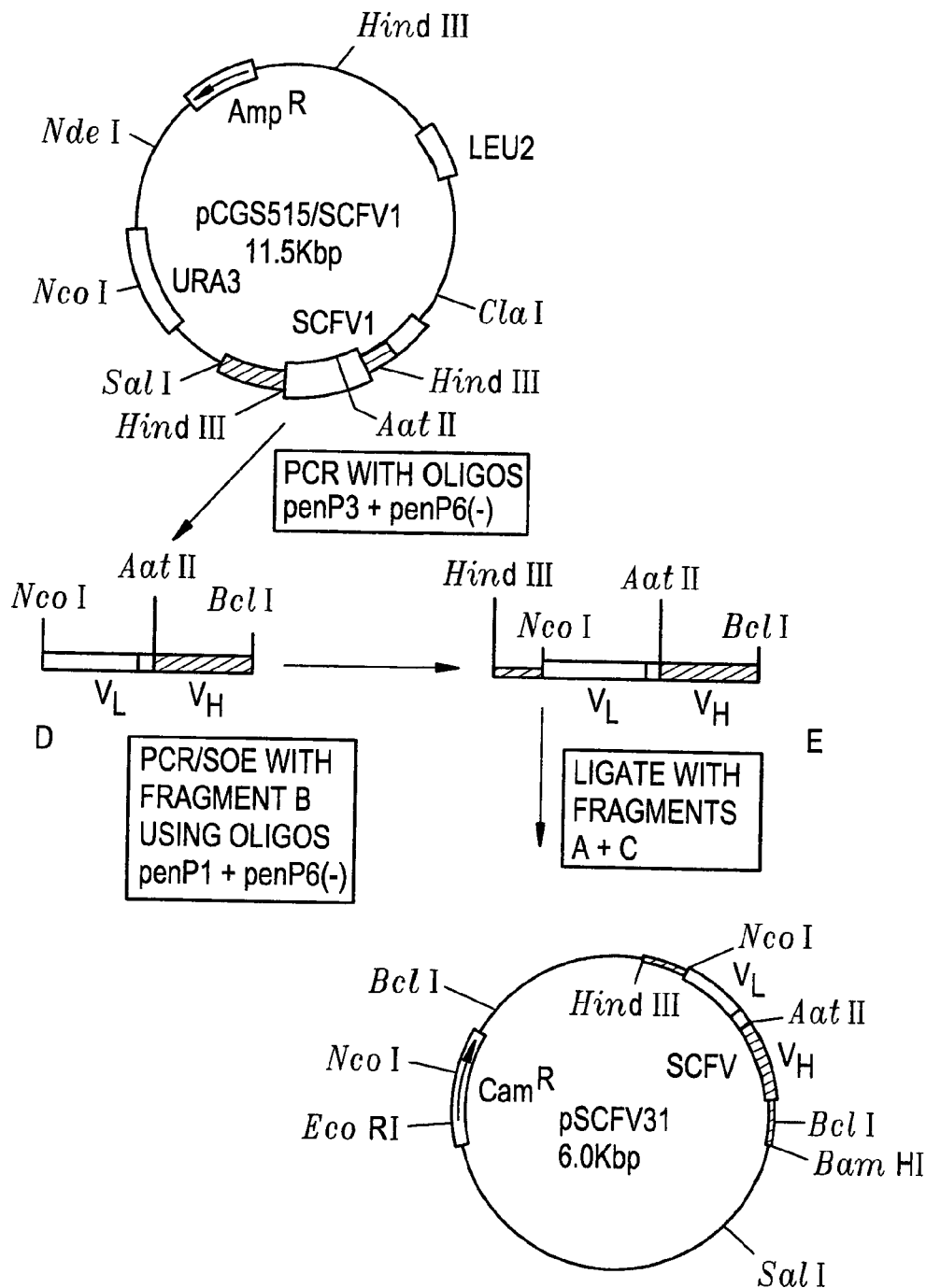

Column 5, Line 10, "FIG. 24...plasmid pSCFV31." should be --Figure 24, *i.e.* Figures 24A-24B show the construction of plasmid pSCFV31.--.

UNITED STATES PATENT AND TRADEMARK OFFICE
CERTIFICATE OF CORRECTION

| | | |
|---|---|---|
| PATENT NO. | : 7,179,899 B2 | |
| APPLICATION NO. | : 10/255478 | |
| DATED | : February 20, 2007 | |
| INVENTOR(S) | : Mezes et al. | |

Figure 25A:
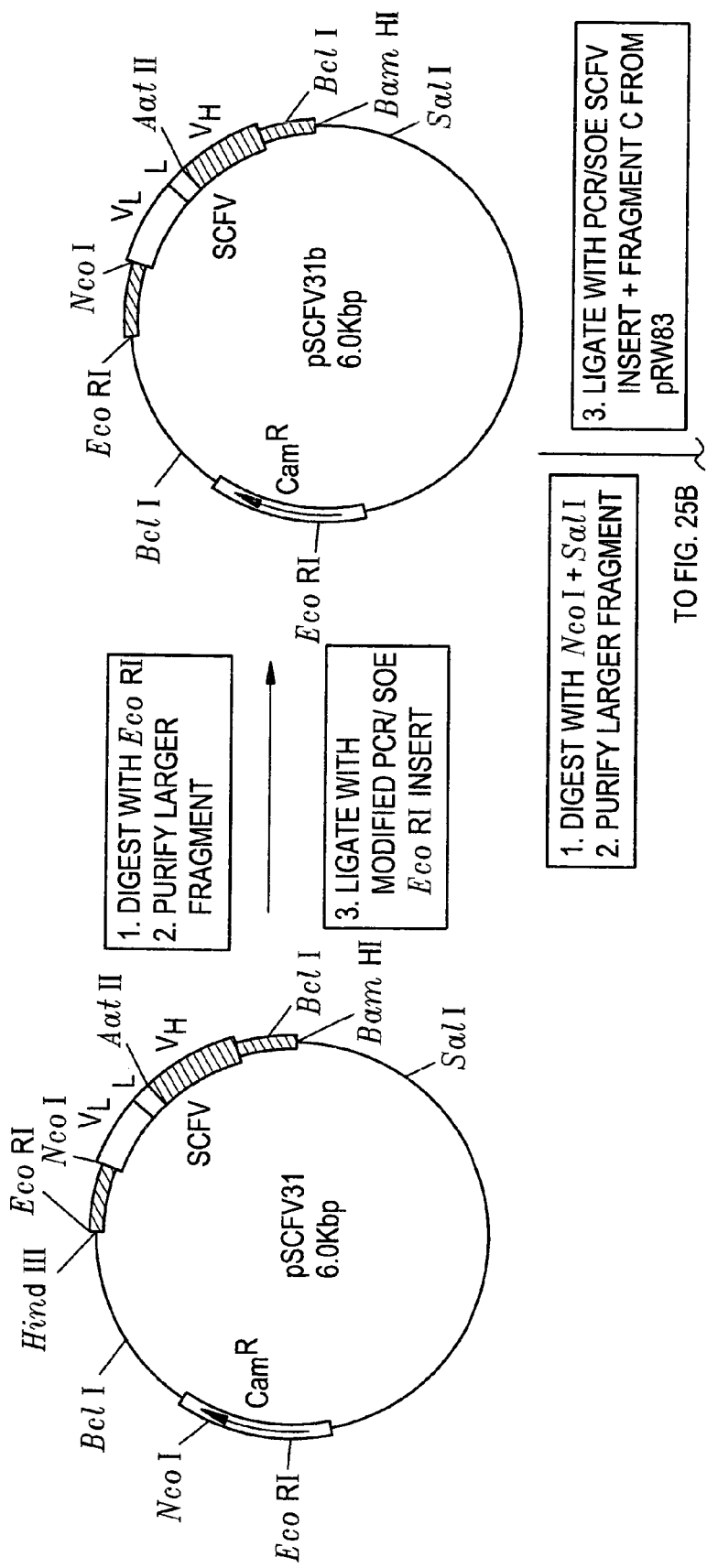
FIG. 25 shows the construction of E. coli SCFV expression plasmids containing Hum4 $V_L$.

It is certified that error appears in the above-identified patent and that said Letters Patent is hereby corrected as shown below:

Column 5, Lines 11-12, "FIG. 25...containing Hum4 $V_L$." should be --Figure 25, *i.e.* Figures 25A-25B illustrate the construction of *E. coli* SCFV expression plasmids containing Hum4 $V_L$.--.

Column 5, Lines 13-15, "FIG. 26...present in pSCFVUHH." should be --Figure 26, *i.e.* Figures 26A-26D show the DNA sequence (SEQ ID NO:65) and amino acid sequence (SEQ ID NO:66) of Hum4 $V_L$ -CC49$V_H$ SCFV present in pSCFVUHH.--.

Column 5, Lines 19-20, "FIG. 28...adapter in pATDFLAG." should be --Figure 28, *i.e.* Figures 28A-28C illustrate the nucleotide sequence (SEQ ID NO:67) of FLAG peptide adapter (SEQ ID NO:68) in pATDFLAG.--.

Column 5, Lines 23-24, "FIG. 30...of pSC49FLAG." should be --Figure 30, *i.e.* Figures 30A-30D illustrate the nucleotide (SEQ ID NO:69) and amino acid (SEQ ID NO:70) of pSC49FLAG.--.

Figure 31A:
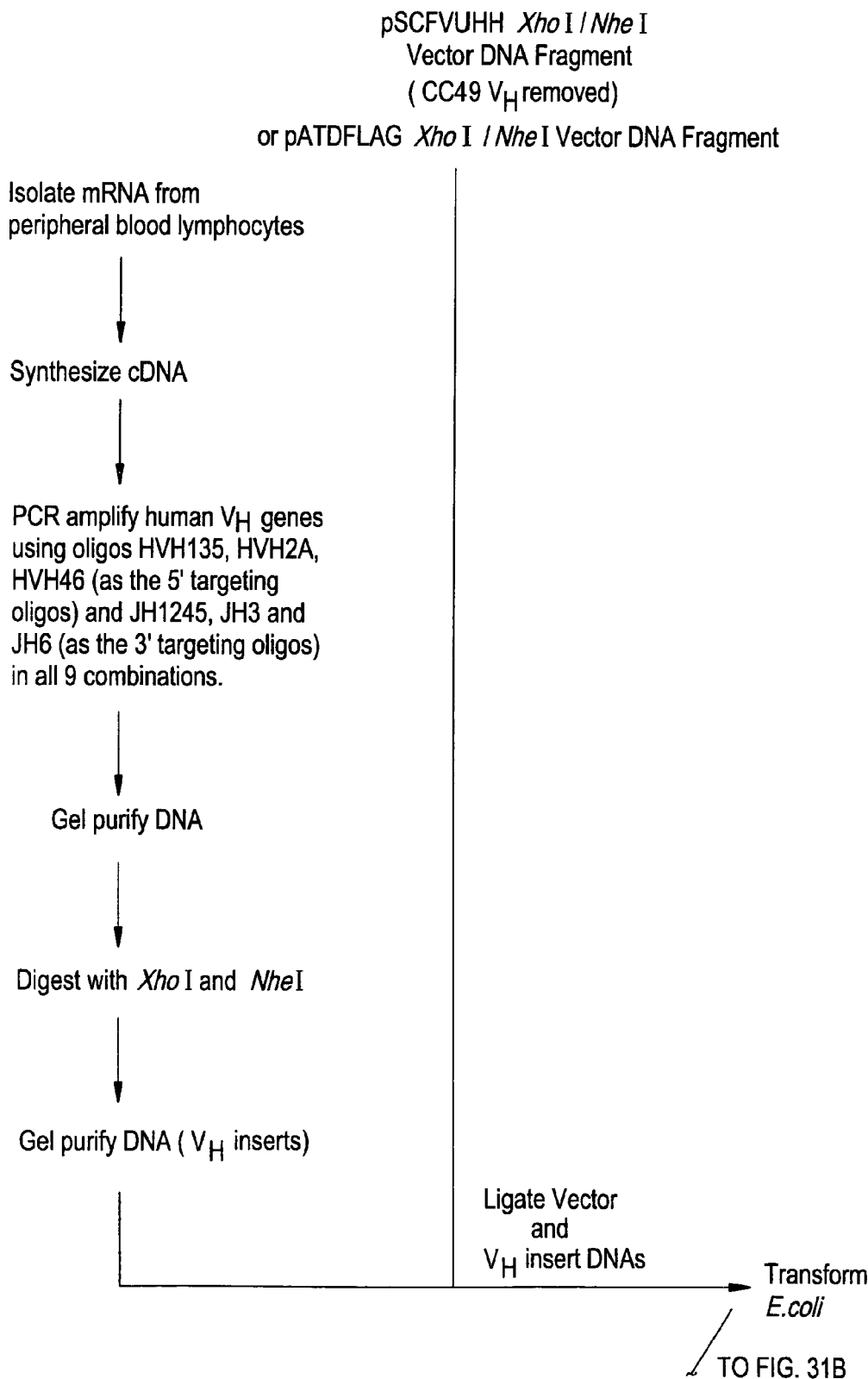
FIG. 31 shows the flow diagram for the discovery of HUM4 $V_L$-$V_H$ combinations that compete with prototype TAG-binding antibodies or mimetics.

Column 5, Lines 25-27, "FIG. 31...antibodies of mimetics." should be --Figure 31, *i.e.* Figures 31A-31B show the flow diagram for the discovery of HUM4 $V_L$-$V_H$ combinations that compete with prototype TAG-binding antibodies or mimetics.--.

Column 5, Lines 28-30, "FIG. 32...derived from CC49." should be --Figure 32, *i.e.* Figures 32A-32B illustrate the "humanization" protocols used in Example 6 to produce the humanized antibody variable regions derived from CC49. Figure 32A presents the amino acid sequences of the native CC49 $V_L$ (SEQ ID NO:71), the $V_L$ framework regions (SEQ ID NO:72) of human MAb LEN, and the humanized version of CC49 $V_L$ (SEQ ID NO:73) (HuCC49) derived from nCC49 and LEN. Figure 32B presents the amino acid sequences of the native CC49 $V_H$ (SEQ ID NO:74), the $V_H$ framework regions (SEQ ID NO:75) of human MAb 21/28'CL, and the humanized version of CC49 $V_H$ (SEQ ID NO:76) (HuCC49) derived from nCC49 and 21/28'CL. Framework residues deemed important for maintaining the combining-site structure of CC49, as based on the known structures of the antigen-binding regions of McPC603 (for $V_L$) and 36-71 (for $V_H$), are marked with an asterisk.--.

UNITED STATES PATENT AND TRADEMARK OFFICE
CERTIFICATE OF CORRECTION

PATENT NO. : 7,179,899 B2
APPLICATION NO. : 10/255478
DATED : February 20, 2007
INVENTOR(S) : Mezes et al.

It is certified that error appears in the above-identified patent and that said Letters Patent is hereby corrected as shown below:

Column 5, Lines 31-32, "FIG. 33...variable regions genes." should be --Figure 33, *i.e.* Figures 33A-33B illustrate the nucleotide sequences of the humanized CC49 (HuCC49*) $V_L$ (SEQ ID NO:77), and $V_H$ (SEQ ID NO:78) variable regions genes, respectively, at nucleotides 74-412 and nucleotides 70-415. Lowercase letters indicate sequences that do not encode the variable region domains or their leader peptides.--.

Figure 34A:
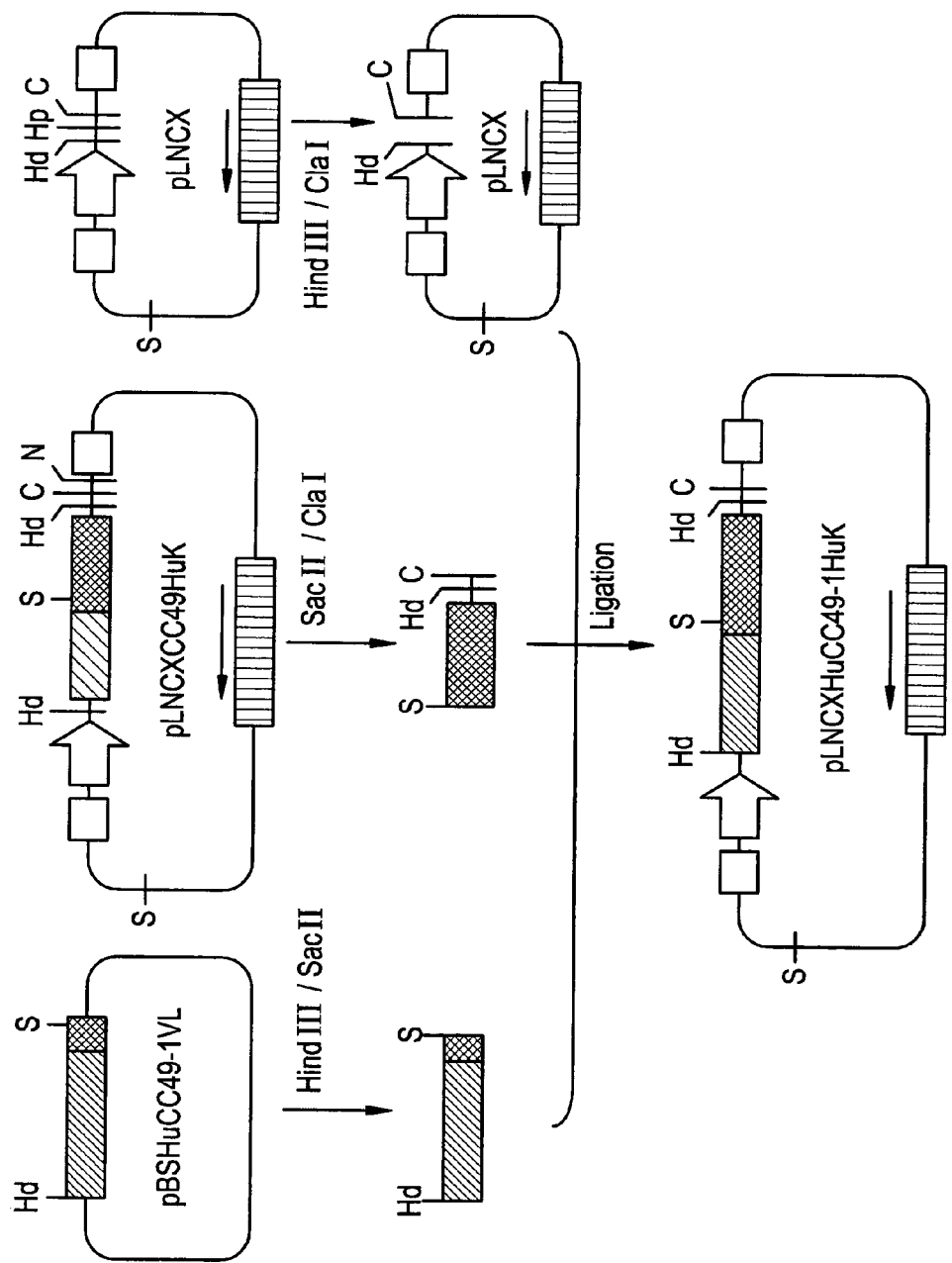
FIG. 34 is a schematic illustration of the process used in Example 6 to form the eukaryotic expression constructs of the humanized light (A) and heavy (B) chains of HuCC49*.
Figure 34B:
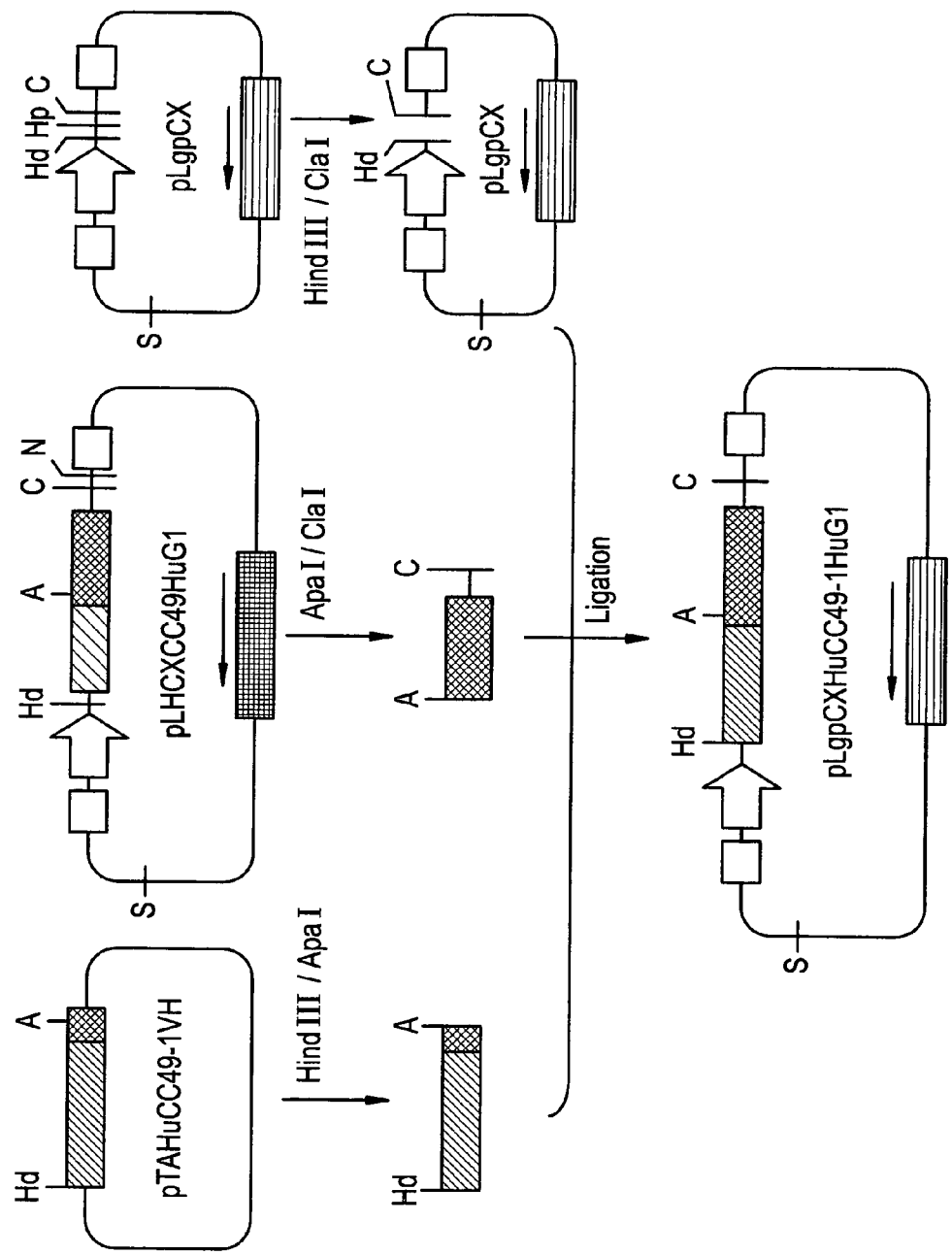

Column 5, Lines 33-35, "FIG. 34...chains of HuCC49*." should be --Figure 34, *i.e.* Figures 34A-34B present a schematic illustration of the process used in Example 6 to form the eukaryotic expression constructs of the humanized light (A) and heavy (B) chains of HuCC49*. Thin lines represent sequences derived from the prokaryotic vectors pBR322, pBluescript $SK^+$, or pCR II. Thick lines depict human K or γ1 constant regions. Densely hatched boxes represent the humanized variable regions, while sparsely hatched boxes indicate murine variable regions. Boxes with vertical, horizontal, or vertical-horizontal cross bars show neomycin, mycophenolic acid, or hygromycin resistance genes, and thin arrows show their transcriptional direction.--.

Figure 35B:
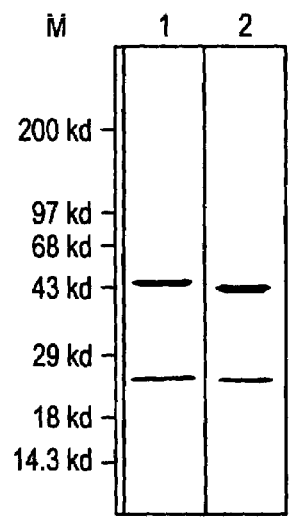

Column 5, Lines 36-38, "FIG. 35...and reducing (B) conditions." should be --Figure 35, *i.e.* Figures 35A-35B illustrate SDS-PAGE analyses of purified HuCC49* (1) and cCC49 (2) under non-reducing (A) and reducing (B) conditions. Numbers beneath the "M" represent sizes of molecular weight markers.--.

Figure 36A:
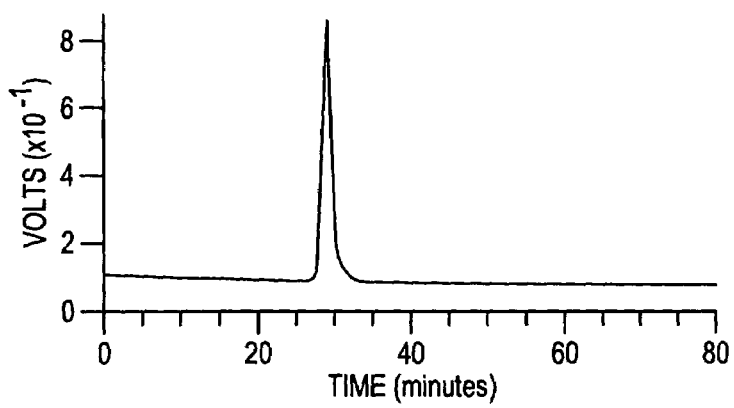
FIG. 36 illustrates HPCL analyses of (A) radioiodinated HuCC49* ($^{131}$I-labeled) and (B) radioiodinated cCC49 ($^{125}$I-labeled) MAbs.
Figure 36B:
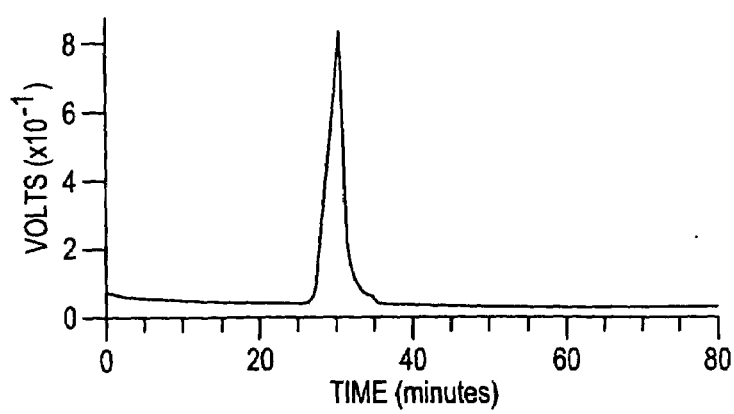

Column 5, Lines 39-41, "FIG. 36...and reducing (B) conditions." should be --Figure 36, *i.e.* Figures 36A-36B illustrate HPLC analyses of (A) radioiodinated HuCC49* ($^{131}$I-labeled) and (B) radioiodinated cCC49 ($^{125}$I-labeled) MAbs.--.

Column 5, Lines 42-44, "FIG. 37...TAG-72." should be --Figure 37 shows the reactivity of HuCC49* (closed circles), cCC49 (open squares), and nCC49 (closed squares) in a competition RIA against $^{125}$I-labeled nCC49 bound to BSM-immobilized TAG-72. The controls were human IgG (closed triangles) and MOPC-21 (open triangles).--.

Column 5, Line 45, "TAG-72." should be --TAG-72. The controls were human IgG (closed triangles) and MOPC-21 (open triangles).--.

Column 6, Line 17, "Kabat et al (1991)." should be --Kabat et al. (1991)--.

Column 6, Line 61, "will at least about" should be --will be at least about--.

UNITED STATES PATENT AND TRADEMARK OFFICE
CERTIFICATE OF CORRECTION

PATENT NO.        : 7,179,899 B2
APPLICATION NO. : 10/255478
DATED              : February 20, 2007
INVENTOR(S)      : Mezes et al.

It is certified that error appears in the above-identified patent and that said Letters Patent is hereby corrected as shown below:

Column 7, Line 26, "aTAG" should be --αTAG--.

Column 8, Line 40, "Ck" should be --$C_k$--.

Column 8, Line 61, "(see FIGS 2. and 3)." should be --(see Figures 2A-G and 3A-E).--.

Column 9, Line 9, "FIG. 2 shows" should be --Figures 2A-G show--.

Column 9, Line 44, "163:95-109." should be --163:95-109).--.

Column 9, Line 51, "FIG. 3" should be --Figures 3A-E--.

Column 9, Line 53, "FIG. 4" should be --Figures 4A-B--.

Column 9, Line 53, "amino residues" should be --amino acid residues--.

Column 9, Line 54, "FIG. 3" should be --Figures 3A-E--.

Column 9, Line 55, "FIG. 4" should be --Figures 4A-B--.

Column 10, Line 6, "immunoglobilin" should be --immunoglobulin--.

Column 12, Line 11, "complementarily" should be --complementarity--.

Column 12, Line 21, "768);" should be --768;--.

Column 12, Line 29, "hydribidize" should be --hybridize--.

Column 12, Line 38, "homologs" should be --homolog--.

Column 12, Line 67, "sequences" should be --sequence--.

Column 14, Line 26, "See" should be --(See--.

Column 15, line 1, "permissable" should be --permissible--.

Column 15, Line 16, "polynucleotidemediated" should be --polynucleotide-mediated--.

UNITED STATES PATENT AND TRADEMARK OFFICE
CERTIFICATE OF CORRECTION

PATENT NO. : 7,179,899 B2
APPLICATION NO. : 10/255478
DATED : February 20, 2007
INVENTOR(S) : Mezes et al.

It is certified that error appears in the above-identified patent and that said Letters Patent is hereby corrected as shown below:

Column 15, Line 28, "ie." should be --i.e.--.

Column 15, Line 43, "host cell are grown" should be --host cells are grown--.

Column 15, Line 52, "1072." should be --1072).--.

Column 15, Line 64, "Uses While it is possible" should be separated on two lines of text; it should be
--Uses
While it is possible--.

Column 18, Line 58, "Hum4 $V_L$" should be --Hum4 $V_L$, $V_H$--.

Column 19, Line 4, "Conjugates of a composite" should be --Conjugates of composite--.

Column 19, Line 28, "$^{311}$I" should be --$^{131}$I--.

Column 19, Line 28, "$^{105}$Rh $^{47}$Sc" should be --$^{105}$Rh, $^{47}$Sc--.

Column 19, Line 43, "(RIGS)." should be --(RIGS (Neoprobe Corp., Dublin, OH)).--.

Column 19, Line 51, "Neoprobe™ scanner, commercially available from Neoprobe Corporation, Columbus, Ohio." should be --NEOPROBE scanner (Neoprobe Corp., Dublin, OH), commercially available from Neoprobe Corporation, Dublin, OH.--.

Column 20, Line 8, "(see FIG 5)." should be --(see Figures 5A-B).--.

Column 20, Line 14, "et. al." should be --et al.--.

Column 20, Line 15, "Vacutainer" should be --VACUTAINER--.

Column 20, Line 16, "anticoagulant) were filled" should be --anticoagulant) (Becton, Dickinson & Co., East Rutherford, NJ) were filled--.

Column 20, Line 20, "erythrocycte" should be --erythrocyte--.

UNITED STATES PATENT AND TRADEMARK OFFICE
CERTIFICATE OF CORRECTION

PATENT NO. : 7,179,899 B2
APPLICATION NO. : 10/255478
DATED : February 20, 2007
INVENTOR(S) : Mezes et al.

It is certified that error appears in the above-identified patent and that said Letters Patent is hereby corrected as shown below:

Column 20, Line 22, "6.5 minutes The" should be --6.5 minutes. The--.

Column 20, Line 60, "Sep-Pac™ columns (Millipore)" should be --SEP-PAC columns (Waters Corp., Milford, MA)--.

Column 20, line 64, "GeneAmp™" should be --GENEAMP--.

Column 21, Line 8, "(FIG. 8)" should be --(Figure 8A)--.

Column 21, Line 19, "FIG. 10 is" should be --Figures 10A-E present--.

Column 21, Line 24, "asterik" should be --asterisk--.

Column 21, Line 25, "Leu Pro" should be --Leu-Pro--.

Column 21, Line 33, "(FIG. 8)" should be --(Figure 8B)--.

Column 21, Line 38, "(see FIGS. 9 and 10);" should be --(see Figures 9 and 10A-E);--.

Column 21, Line 41, "FIG. 8)" should be --Figures 8B)--.

Column 21, Line 47, "(HUMV$_L$(+))" should be --(HUMVL(+))--.

Column 21, Line 48, "HUMV$_L$(-))" should be --(HUMVL(-))--.

Column 21, Line 67, "(see FIG. 13)." should be --(see Figures 13A-B).--.

Column 22, Line 13, "The μL pellet was dissolved" should be --The pellet was dissolved--.

Column 22, Line 14, "2 pL" should be --2 μL--.

Column 22, Line 34, "pSV2 neo-101" should be --pSV2neo-101--.

Column 22, Line 43, "(CH(+)" should be --CH(+)--.

UNITED STATES PATENT AND TRADEMARK OFFICE
CERTIFICATE OF CORRECTION

PATENT NO. : 7,179,899 B2
APPLICATION NO. : 10/255478
DATED : February 20, 2007
INVENTOR(S) : Mezes et al.

It is certified that error appears in the above-identified patent and that said Letters Patent is hereby corrected as shown below:

Column 22, Line 43, "complimentary" should be --complementary--.

Column 22, Line 60, "Sequenase™" should be --SEQUENASE--.

Column 23, Line 4, "DNASIS™" should be --DNASIS--.

Column 23, Line 5, "(Hitachi)." should be --(Hitachi Software Engineering Co., Ltd., Yokohama, Japan).--.

Column 23, Line 47, "(see FIG. 13)," should be --(see Figures 13A-B),--.

Column 24, Line 1, "in FIG. 10)," should be --in Figures 10A-E),--.

Column 24, Line 4, "hybridizesin FIG. 10)" should be --hybridizes in Figures 10A-E--.

Column 24, Line 16, "(FIG. 10)" should be --(Figures 10A-E)--.

Column 24, Line 21, "Biorad Gene Pulser™" should be --BIO-RAD GENE PULSER--.

Column 24, Line 21, "apparatus was" should be --apparatus (Bio-Rad Laboratories, Inc., Richmond, CA) was--.

Column 24, Line 49, "Geneticin" should be --GENETICIN--.

Column 24, Line 49, "(Difco)" should be --(Life Technologies, Inc., Chagrin Falls, OH (obtained from Difco Laboratories, Ltd., now Becton, Dickinson and Co., Franklin Lakes, NJ))--.

Column 25, Line 9, "g1" should be --$\gamma 1$--.

Column 25, Line 10, "g1" should be --$\gamma 1$--.

Column 25, Line 39, "FIG. 20," should be --Figures 20A-C,--.

Column 25, Line 44, "(ATCC)." should be --(ATCC, P.O. Box 1549, Manassas, VA 20108).--.

UNITED STATES PATENT AND TRADEMARK OFFICE
CERTIFICATE OF CORRECTION

PATENT NO. : 7,179,899 B2
APPLICATION NO. : 10/255478
DATED : February 20, 2007
INVENTOR(S) : Mezes et al.

It is certified that error appears in the above-identified patent and that said Letters Patent is hereby corrected as shown below:

Column 26, Line 18, "-3' " should be -- -3' (SEQ ID NO: 1)--.

Column 26, Line 25, "-3' " should be --3' (SEQ ID NO: 2)--.

Column 26, Line 38, "5'-CTTAGACGTCCAGTTGCAGCAGTCTGACGC-3'" should be --5'-CTTAGACGTCCAGTTGCAGCAGTCTGACGC-3' (SEQ ID NO: 3)--.

Column 26, Line 41, "5'-GATCAAGCTTCACTAGGAGACGGTGACTG-AGGTTCC-3'" should be --5'-GATCAAGCTTCACTAGGAGACGGTGACTG-AGGTTCC-3' (SEQ ID NO: 4)--.

Column 26, Line 58, "in FIG. 22." should be --in Figures 22A-C.--.

Column 26, Line 61, "of FIG. 22)," should be --of Figures 22A-C),--.

Column 26, Line 62, "of FIG. 22)," should be --of Figures 22A-C),--.

Column 26, Line 63, "of FIG. 22)" should be --of Figures 22A-C)--.

Column 26, Line 64, "of FIG. 22)." should be --of Figures 22A-C).--.

Column 26, Line 66, "in FIG. 22." should be --in Figures 22A-C.--.

Column 27, Line 3, "-3'." should be -- -3' (SEQ ID NO: 5).--.

Column 27, Line 6, "-3'." should be -- -3' (SEQ ID NO: 6).--.

Column 27, Line 8, "-3'." should be -- -3' (SEQ ID NO: 7).--.

Column 27, Line 11, "-3'." Should be -- -3' (SEQ ID NO: 8).--.

Column 27, Line 20, "(see FIG. 23)" should be --(see Figures 23A-B)--.

Column 27, Line 26, "DHI" should be --DH1--.

Column 27, Line 32, "PDYSCFV1 (FIG. 23)," should be --pDYSCFV1 (Figures 23A-B)--.

UNITED STATES PATENT AND TRADEMARK OFFICE
CERTIFICATE OF CORRECTION

PATENT NO. : 7,179,899 B2
APPLICATION NO. : 10/255478
DATED : February 20, 2007
INVENTOR(S) : Mezes et al.

It is certified that error appears in the above-identified patent and that said Letters Patent is hereby corrected as shown below:

Column 27, Line 39, "Sal 1 fragment" should be --Sal I fragment--.

Column 27, Line 41, "PCGS515 (FIG. 23)," should be --pCGS515 (Figures 23A-B).--.

Column 27, Line 46, "Tris-HCI" should be --Tris-HCl--.

Column 27, Line 54, "(FIG. 23)." should be --(Figures 23A-B).--.

Column 27, Line 54, "pCGS515/SCFVI" should be --pCGS515/SCFV1--.

Column 27, Line 55, "Sequenase™" should be --SEQUENASE--.

Column 27, Line 57, "in FIG. 22 and" should be --in Figures 22A-C and--.

Column 27, Line 59, "autonomosly" should be --autonomously--.

Column 27, Line 62, "Curent" should be --Current--.

Column 27, Line 63, "Ausebel" should be --Ausubel--.

Column 28, Line 12, "Superose" should be --SUPEROSE--.

Column 28, Line 37, "(see FIG. 24)." should be --(see Figures 24A-B).--.

Column 28, Line 42, "(see FIG. 24)." should be --(see Figures 24A-B).--.

Column 28, Line 47, "-3'" should be -- -3' (SEQ ID NO: 9)--.

Column 28, Line 51, "-3'" should be -- -3' (SEQ ID NO: 10)--.

Column 28, Line 55, "ASP) was obtained" should be --ASP (residues 130-147 of SEQ ID NO: 64)) was obtained--.

Column 28, Line 58, "(see FIG. 24)." should be --(see Figures 24A-B).--.

Column 28, Line 62, "-3'" should be -- -3' (SEQ ID NO: 11)--.

UNITED STATES PATENT AND TRADEMARK OFFICE
CERTIFICATE OF CORRECTION

PATENT NO. : 7,179,899 B2
APPLICATION NO. : 10/255478
DATED : February 20, 2007
INVENTOR(S) : Mezes et al.

It is certified that error appears in the above-identified patent and that said Letters Patent is hereby corrected as shown below:

Column 28, Line 66, "-3'" should be -- -3' (SEQ ID NO: 12)--.

Column 29, Line 4, "(See FIG. 24)." should be --(see Figures 24A-B).--.

Column 29, Line 9, "Plasmid PSCFV" should be --pSCFV--.

Column 29, Line 9, "(see FIG. 24)" should be --(see Figures 24A-B)--.

Column 29, Line 11, "Camr" should be --Cam$^r$--.

Column 29, Line 22, "-3'" should be -- -3' (SEQ ID NO: 13)--.

Column 29, Line 25, "-3'" should be -- -3' (SEQ ID NO: 14)--.

Column 29, Line 27, "-3'" should be -- -3' (SEQ ID NO: 15)--.

Column 29, Line 29, "Ncol.4c(-)" should be --Ncol.4c(-):--.

Column 29, Line 30, "-3'" should be -- -3' (SEQ ID NO: 16)--.

Column 29, Line 35, "intertinal alkaline" should be --intestinal alkaline--.

Column 29, Line 39, "(see FIG. 25)." should be --(see Figures 25A-B).--.

Column 29, Line 48, "-3'" should be -- -3' (SEQ ID NO: 17)--.

Column 29, Line 51, "-3'" should be -- -3' (SEQ ID NO: 18)--.

Column 29, Line 54, "(FIG. 5)" should be --(Figure 6)--.

Column 29, Line 61, "-3'" should be -- -3' (SEQ ID NO: 19)--.

Column 29, Line 66, "-3'" should be -- -3' (SEQ ID NO: 20)--.

Column 30, Line 7, "(see FIG. 25)" should be --(see Figures 25A-B)--.

UNITED STATES PATENT AND TRADEMARK OFFICE
CERTIFICATE OF CORRECTION

| | |
|---|---|
| PATENT NO. | : 7,179,899 B2 |
| APPLICATION NO. | : 10/255478 |
| DATED | : February 20, 2007 |
| INVENTOR(S) | : Mezes et al. |

It is certified that error appears in the above-identified patent and that said Letters Patent is hereby corrected as shown below:

Column 30, Line 17, "5'-CAGCCATGGCC GACATTGTGATGTCACAGTCTCC-3'" should be -- 5'-CAGCCATGGCC GACATTGTGATGTCACAGTCTCC-3' (SEQ ID NO: 21)--.

Column 30, Line 25, "-3'" should be -- -3' (SEQ ID NO: 22)--.

Column 30, Line 33, "5'-AGCGAGGCAGATCTTACGGACCTCGAG GTTCAGTTGCAGCAGTCTGAC-3'." should be --5'-AGCGAGGCAGATCTTACGGACCTCGAGGTTCAGTTGCAGCAGTCTGAC-3' (SEQ ID NO: 23).--.

Column 30, Line 39, "5'-CATCGCTAGC TTTTTATGAGGAGACGGTGACTGAGGTTCC-3'." should be --5'-CATCGCTAGCTTTTTATGAGGAGACGGTGACTGAGGTTCC-3' (SEQ ID NO: 24).--.

Column 30, Line 49, "(shown in FIG. 25)." should be --(shown in Figures 25A-B).--.

Column 31, Line 1, "SCA™ linker" should be --SCA linker--.

Column 31, Line 3, "Inc, MA)," should be --Inc., MA),--.

Column 31, line 5, "acid were was" should be --acid was--.

Column 31, Line 9, "in FIG. 26." should be --in Figures 26A-D.--.

Column 31, Line 11, "_and_" should be --← and →--.

Column 31, Line 16, "(FIG. 26)" should be --(Figures 26A-D)--.

Column 31, Line 21, "-3'" should be -- -3' (SEQ ID NO: 25)--.

Column 31, Line 23, "(FIG. 26)" should be --(Figures 26A-D--.

Column 31, Line 27, "-3'" should be -- -3' (SEQ ID NO: 26)--.

Column 31, Line 40, "AGI" should be --AG1--.

UNITED STATES PATENT AND TRADEMARK OFFICE
CERTIFICATE OF CORRECTION

PATENT NO. : 7,179,899 B2
APPLICATION NO. : 10/255478
DATED : February 20, 2007
INVENTOR(S) : Mezes et al.

It is certified that error appears in the above-identified patent and that said Letters Patent is hereby corrected as shown below:

Column 32, Line 5, "paranitrophenylphosphate" should be --para-nitrophenylphosphate--.

Column 32, Line 30, "AGI" should be --AG1--.

Column 32, Line 37, "FIG. 31." should be --Figures 31A-B.--.

Column 32, Line 41, "Vacutainer tubes." should be --VACUTAINER tubes (Becton, Dickinson & Co., East Rutherford, NJ).--.

Column 32, Line 43, "lymphoprep (cat# AN 5501, Accurate)" should be --LYMPHOPREP (Nycomed Pharma AS, Oslo, Norway (obtained as cat# AN5501 from Accurate Chemical & Scientific Corp., Westbury, NY))--.

Column 32, Line 48, "tube." should be --tubes.--.

Column 32, Line 50, "20 minutes Total" should be --20 minutes. Total--.

Column 32, Line 53, "RNAzol B Method" should be --RNAzol B (Molecular Research Center, Inc., Cincinnati, OH) Method--.

Column 32, Line 55, "RNAzol solution (cat#:CS-105, Cinna/Biotecx)." should be --RNAzol solution (Molecular Research Center, Inc., Cincinnati, OH (obtained as cat# CS-105 from Cinna/Biotecx Laboratories, Int'l., Inc., Friendswood, TX)).--.

Column 33, Line 11, "RNasin (cat#:N2511, Promega)." should be --RNASIN (cat# N2511, Promega, Corp., Madison, WI).--.

Column 33, Line 13, "Gene Amp™" should be --GENEAMP"--.

Column 33, Line 14, "RNasin" should be --RNASIN--.

Column 33, Line 15, "AMV reverse transcriptase (cat#: M9004, Promega)." should be -- AMV reverse transcriptase (Seikagaku America, Inc., Ijamsville, MD (obtained as cat# M9004 from Promega)).--.

UNITED STATES PATENT AND TRADEMARK OFFICE
CERTIFICATE OF CORRECTION

PATENT NO.       : 7,179,899 B2
APPLICATION NO.  : 10/255478
DATED            : February 20, 2007
INVENTOR(S)      : Mezes et al.

It is certified that error appears in the above-identified patent and that said Letters Patent is hereby corrected as shown below:

Column 33, Line 29, "RNasin" should be --RNASIN--.

Column 33, Line 34, "transcriptase is added" should be --transcriptase (Seikagaku America, Inc., Ijamsville, MD) is added--.

Column 33, Line 47, "The 5' oligonucleotides are set forth below:" should be deleted.

Column 33, Line 48, "-3'" should be -- -3' (SEQ ID NO: 27)--.

Column 33, Line 52, "-3'" should be -- -3' (SEQ ID NO: 28)--.

Column 33, Line 56, "-3'" should be -- -3' (SEQ ID NO: 29)--.

Column 33, Line 58, "-3'" should be -- -3' (SEQ ID NO: 30)--.

Column 33, Line 61, "5' -TTATGCTAGCTGAAGAGACGGTGACCATTG" should be --5'-TTATGCTAGCTGAAGAGACGGTGACCATTG (SEQ ID NO: 31)--.

Column 33, Line 64, "-3'" should be -- -3' (SEQ ID NO: 32)--.

Column 33, Line 65, "Geneamp™" should be --GENEAMP--.

Column 34, Line 13, "AmpliTaq™" should be --AMPLITAQ Polymerase (Roche Molecular Systems, Inc., Branchburg, NJ)--.

Column 34, Line 49, "Magic Mini-prepT™ system (Promega)." should be --MAGIC MINIPREP system (plasmid DNA isolation system, Promega Corp., Madison, WI).--.

Column 34, Line 64, "GVWP hydrophilic membranes (cat# GVWP14250, Millipore)" should be --GVWP hydrophilic membranes (PVDF membranes, cat# GVWP14250, Millipore Corp., Bedford, MA)--.

Column 35, Line 9, "Immobilon-P" should be --IMMOBILON-P--.

Column 36, Line 6, "PATDFLAG" should be --pATDFLAG--.

Column 36, Line 14, "-3' FLAGNC:" should be -- -3' (SEQ ID NO: 33) FLAGNC:--.

UNITED STATES PATENT AND TRADEMARK OFFICE
CERTIFICATE OF CORRECTION

PATENT NO. : 7,179,899 B2
APPLICATION NO. : 10/255478
DATED : February 20, 2007
INVENTOR(S) : Mezes et al.

It is certified that error appears in the above-identified patent and that said Letters Patent is hereby corrected as shown below:

Column 36, Line 16, "-3'" should be -- -3' (SEQ ID NO: 34)--.

Column 36, Line 17, "(1x10$^{-10}$ moles" should be --(1 x 10$^{-10}$ moles)--.

Column 36, Line 35, "according the ligation" should be --according to the ligation--.

Column 36, Line 42, "(see FIG. 28)" should be --(see Figures 28A-C)--.

Column 36, Line 43, "-3." should be -- -3' (SEQ ID NO: 35).--.

Column 36, Line 46, "Sequenase™" should be --SEQUENASE--.

Column 36, Line 50, "in FIG. 28." should be --(in Figures 28A-C).--.

Column 36, Line 54, "PATDFLAG" should be --pATDFLAG--.

Column 36, Line 59, "Magic Miniprep™ system (Promega) is" should be --MAGIC MINIPREP system (plasmid DNA isolation system, Promega Corp., Madison, WI) is--.

Column 36, Line 63, "PSCFVUHH" should be --pSCFVUHH--.

Column 36, Line 67, "in FIG 30." should be --in Figures 30A-D.--.

Column 37, Line 4, "purfied" should be --purified--.

Column 37, Line 14, "PATDFLAG" should be --pATDFLAG--.

Column 37, Line 33, "hum" should be --Hum--.

Column 37, Line 50, "millilters" should be --milliliters--.

Column 37, Line 56, "milliters" should be --milliliters--.

Column 37, Line 63, "Biotechnologies, Inc.)" should be --Biotechnologies, Inc., New Haven, CT (now Eastman Kodak Co., Rochester, NY))--.

Column 38, Line 9, "canidates" should be --candidates--.

UNITED STATES PATENT AND TRADEMARK OFFICE
CERTIFICATE OF CORRECTION

PATENT NO. : 7,179,899 B2
APPLICATION NO. : 10/255478
DATED : February 20, 2007
INVENTOR(S) : Mezes et al.

It is certified that error appears in the above-identified patent and that said Letters Patent is hereby corrected as shown below:

Column 38, Line 45, "aTAG-72" should be --αTAG-72--.

Column 38, Line 50, "aTAG-72" should be --αTAG-72--.

Column 38, Line 51, ""HuCC49*"" should be --"HuCC49*" (ATCC HB-12404, deposited September 26, 1997 in the ATCC)--.

Column 39, Line 17, "21/28¢" should be --21/28'--.

Column 39, Line 24, "21/28¢" should be --21/28'--.

Column 39, Line 28, "21/28¢" should be --21/28'--.

Column 39, Line 38, "21/28¢" should be --21/28'--.

Column 39, Line 38, "FIG. 32" should be --Figures 32A-B--.

Column 39, Line 51, "FIG. 33." should be --Figures 33A-B--.

Column 39, Line 55, "FIG. 33)" should be --Figures 33A-B)--.

Column 40, Line 1, "(on Oligo-Pak columns from Milligen/Bioresearch)." should be --(on OLIGO-PAK columns (Millipore Corp., Bedford, MA) obtained from Milligen/Bioresearch).--.

Column 40, Line 5, "5¢ $V_H$, coding: 5¢-CTAAGCTTCCACCATGGAG[?]-3¢;" should be --5' $V_H$, coding: 5'-CTAAGCTTCCACCATGGAGN-3' (SEQ ID NO:36);--.

Column 40, Line 6, "3¢ $V_H$, noncoding: 5¢-ATGGGCCCGTAGTTTTGGCG-3¢;" should be --3' $V_H$, noncoding: 5'- ATGGGCCCGTAGTTTTGGCG -3' (SEQ ID NO:37);--.

Column 40, Line 8, "5¢ $V_L$, coding: 5¢-GCAAGCTTCCACCATGGATA-3¢;" should be --5' $V_L$, coding: 5'- GCAAGCTTCCACCATGGATA -3' (SEQ ID NO:38);--.

UNITED STATES PATENT AND TRADEMARK OFFICE
CERTIFICATE OF CORRECTION

PATENT NO. : 7,179,899 B2
APPLICATION NO. : 10/255478
DATED : February 20, 2007
INVENTOR(S) : Mezes et al.

It is certified that error appears in the above-identified patent and that said Letters Patent is hereby corrected as shown below:

Column 40, Line 9, "3¢ $V_L$, noncoding: 5¢-AGCCGCGGCCCGTTTCAGTT-3¢." should be --3' $V_L$, noncoding: 5'- AGCCGCGGCCCGTTTCAGTT -3' (SEQ ID NO:39).--.

Column 40, Line 11, "5¢" should be --5'--.

Column 40, Line 11, "3¢" should be --3'--.

Column 40, Line 12, "3¢" should be --3'--.

Column 40, Line 35, "pCRIII" should be --pCRII--.

Column 40, Line 45, "FIG. 34." should be --Figures 34A-B.--.

Column 40, Line 47, "5¢" should be --5'--.

Column 40, Line 51, "3¢" should be --3'--.

Column 40, Line 57, "3¢" should be --3'--.

Column 41, Line 2, "5¢" should be --5'--.

Column 41, Line 8, "g1" should be --γ1--.

Column 41, Line 11, "g1" should be --γ1--.

Column 41, Line 12, "g1" should be --γ1--.

Column 41, Line 12, "3¢" should be --3'--.

Column 41, Line 24, "mammalia" should be --mammalian--.

Column 41, Line 36, "Cell-Porator" should be --CELL-PORATOR--.

Column 41, Line 37, "(GIBCO BRL)" should be --(Life Technologies, Inc., Rockville, MD (obtained from Gibco BRL, Gaithersburg, MD))--.

UNITED STATES PATENT AND TRADEMARK OFFICE
CERTIFICATE OF CORRECTION

PATENT NO. : 7,179,899 B2
APPLICATION NO. : 10/255478
DATED : February 20, 2007
INVENTOR(S) : Mezes et al.

It is certified that error appears in the above-identified patent and that said Letters Patent is hereby corrected as shown below:

Column 42, Line 7, "aTAG-72" should be --αTAG-72--.

Column 42, Line 17, "(PFHM-II, Gibco BRL)." should be --(PFHM-II, Gibco BRL (now Invitrogen Corp., Carlsbad, CA)).--.

Column 42, Line 18, "HuC49*" should be --HuCC49*--.

Column 42, Line 35, "immersible-CX-30" should be --immersible CX-30--.

Column 42, Line 67, "Iodo-Gen" should be --IODO-GEN--.

Column 43, Line 3, "125I-labeled" should be --$^{125}$I-labeled--.

Column 43, Line 8, "(Rochester, N.Y.)" should be --(Eastman Kodak Co., Rochester, NY)--.

Column 43, Line 9, "deN-emours" should be -- deNemours--.

Column 43, Line 28, "-5417" should be -- -6417--.

Column 43, Line 41, "800'g" should be --800xg--.

Column 44, Line 25, "were collect" should be --were collected--.

Column 44, Line 29, "remaining the plasma" should be --remaining in the plasma--.

Column 44, Line 48, "according a method" should be --according to a method--.

Column 44, Line 53, "(Rockville, Md.)." should be --(10801 University Boulevard, Manassas, VA 20110-2209).--.

Column 46, Line 9, "CCC49" should be --cCC49--.

UNITED STATES PATENT AND TRADEMARK OFFICE
CERTIFICATE OF CORRECTION

PATENT NO. : 7,179,899 B2
APPLICATION NO. : 10/255478
DATED : February 20, 2007
INVENTOR(S) : Mezes et al.

It is certified that error appears in the above-identified patent and that said Letters Patent is hereby corrected as shown below:

In the Claims:

Column 113, Line 41, ") CC92" should be --), CC92--.

Column 113, Line 48, "and/or" should be --a--.

Signed and Sealed this

Twenty-fifth Day of August, 2009

David J. Kappos
*Director of the United States Patent and Trademark Office*